(12) United States Patent
Almeida et al.

(10) Patent No.: US 10,106,782 B2
(45) Date of Patent: Oct. 23, 2018

(54) HIGH-TITER HCV FULL-LENGTH GENOTYPE 2B INFECTIOUS CELL CULTURE SYSTEMS AND APPLICATIONS THEREOF

(71) Applicant: Hvidovre Hospital, Hvidovre (DK)

(72) Inventors: Santseharay Ramirez Almeida, Hvidovre (DK); Yiping Li, Hvidovre (DK); Judith M. Gottwein, Frederiksberg C (DK); Jens Bukh, Præstø (DK)

(73) Assignee: HVIDOVRE HOSPITAL, Hvidovre (DK)

( * ) Notice: Subject to any disclaimer, the term of this patent is extended or adjusted under 35 U.S.C. 154(b) by 0 days.

(21) Appl. No.: 14/906,521

(22) PCT Filed: Jul. 28, 2014

(86) PCT No.: PCT/DK2014/050231
§ 371 (c)(1),
(2) Date: Jan. 20, 2016

(87) PCT Pub. No.: WO2015/014369
PCT Pub. Date: Feb. 5, 2015

(65) Prior Publication Data
US 2016/0194612 A1 Jul. 7, 2016

(30) Foreign Application Priority Data

Jul. 29, 2013 (DK) .................................. 2013 70418

(51) Int. Cl.
*C12N 7/00* (2006.01)
*C07K 14/005* (2006.01)
*C12Q 1/70* (2006.01)

(52) U.S. Cl.
CPC .............. *C12N 7/00* (2013.01); *C07K 14/005* (2013.01); *C12Q 1/707* (2013.01); *C12N 2770/24221* (2013.01); *C12N 2770/24222* (2013.01); *C12N 2770/24251* (2013.01)

(58) Field of Classification Search
None
See application file for complete search history.

(56) References Cited

U.S. PATENT DOCUMENTS

| | | | |
|---|---|---|---|
| 8,454,974 B2 | 6/2013 | Scheel et al. | |
| 8,506,969 B2 | 8/2013 | Gottwein et al. | |
| 8,563,706 B2 | 10/2013 | Scheel et al. | |
| 8,569,472 B2 | 10/2013 | Gottwein et al. | |
| 8,618,275 B2 | 12/2013 | Jensen et al. | |
| 8,663,653 B2 | 3/2014 | Gottwein et al. | |
| 8,772,022 B2 | 7/2014 | Gottwein et al. | |
| 8,846,891 B2 | 9/2014 | Prento et al. | |
| 9,382,517 B2 * | 7/2016 | Li | C12N 7/00 |
| 9,388,389 B2 | 7/2016 | Scheel et al. | |
| 2009/0252755 A1 | 10/2009 | Bukh et al. | |
| 2010/0093841 A1 | 4/2010 | Gottwein et al. | |
| 2016/0244729 A1* | 8/2016 | Li | C12N 7/00 |

FOREIGN PATENT DOCUMENTS

| | | |
|---|---|---|
| WO | WO 2006/096459 A2 | 9/2006 |
| WO | WO 2008/125119 A1 | 10/2008 |
| WO | WO 2010/017818 A1 | 2/2010 |
| WO | WO 2010/022727 A1 | 3/2010 |
| WO | WO 2011/038737 A1 | 4/2011 |
| WO | WO 2013/139339 A1 | 9/2013 |
| WO | WO 2013/139340 A1 | 9/2013 |
| WO | WO 2015/014369 A1 | 2/2015 |
| WO | WO 2015/058772 A2 | 4/2015 |
| WO | WO 2015/158353 A1 | 10/2015 |
| WO | WO 2015/179204 A1 | 11/2015 |

OTHER PUBLICATIONS

Murayama et al. Production of infectious chimeric hepatitis C virus genotype 2b harboring minimal regions of JFH-1. J Virol. Feb. 2012;86(4):2143-52. (Year: 2012).*
Altschul, Stephen F. et al., "Protein database searches for multiple alignments" Proc. Natl. Acad. Sci., Jul. 1990, pp. 5509-5513, vol. 87.
Altschul, Stephen F. et al., "Basic Local Alignment Search Tool" J. Mol. Biol., 1990, pp. 403-410, vol. 215.
Bukh, Jens et al., "Challenge Pools of Hepatitis C Virus Genotypes 1-6 Prototype Strains: Replication Fitness and Pathogenicity in Chimpanzees and Human Liver—Chimeric Mouse Models" J Infect. Dis., May 2010, pp. 1381-1389, vol. 201.
Engle, Ronald E. et al., "Development of a TaqMan Assay for the Six Major Genotypes of Hepatitis C Virus: Comparison With Commercial Assays" Journal of Medical Virology, 2008, pp. 72-79, vol. 80.
Gottwein, Judith M. et al., "Development and Characterization of Hepatitis C Virus Genotype 1-7 Cell Culture Systems: Role of CD81 and Scavenger Receptor Class B Type I and Effect of Antiviral Drugs" Hepatology, 2009, pp. 364-377, vol. 49, No. 2.
Li, Yi-Ping et al., "Non-genotype-specific role of the hepatitis C virus 5' untranslated region in virus production and in inhibition by interferon" Virology, 2011, pp. 222-234, vol. 421.
Li, Yi-Ping et al., "Robust full-length hepatitis C virus genotype 2a and 2b infectious cultures using mutations identified by a systematic approach applicable to patient strains" PNAS, May 2012, pp. E1101-E1110, vol. 109, No. 18.

(Continued)

*Primary Examiner* — Michelle S Horning
(74) *Attorney, Agent, or Firm* — Knobbe Martens Olson & Bear LLP

(57) ABSTRACT

The present invention relates to nucleic acid sequences that encode hepatitis C viruses (HCV) of genotype 2b that are useful in the fundamental research of HCV as well as in the search of a vaccine against HCV. In particular the present invention relates to nucleic acid sequences that comprises HCVs, which are capable of expressing said virus when transfected into cells and are capable of infectivity in vivo.

Figure 2:
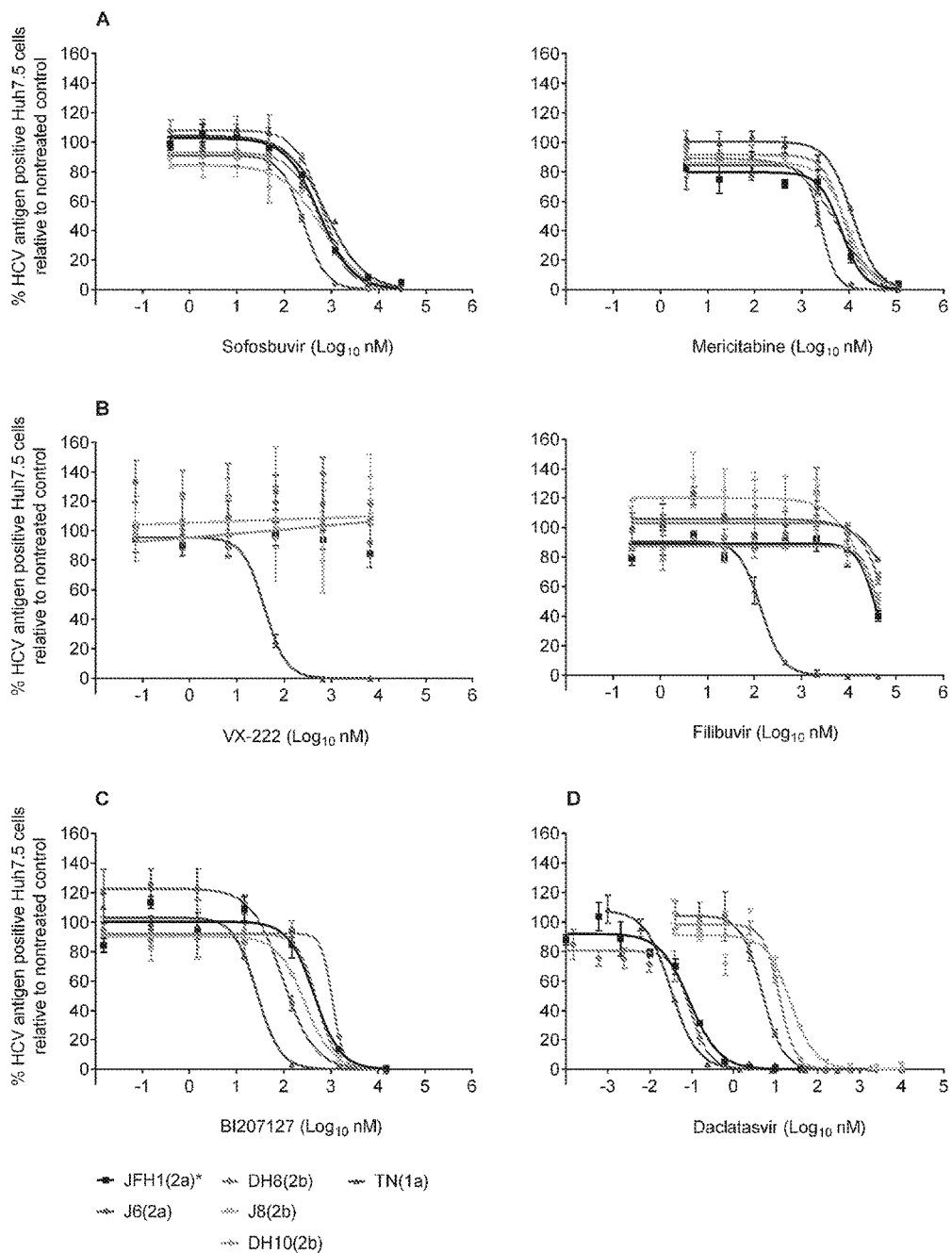

9 Claims, 16 Drawing Sheets
Specification includes a Sequence Listing.

(56) References Cited

OTHER PUBLICATIONS

Li, Yi-Ping et al., "Highly efficient full-length hepatitis C virus genotype 1 (strain TN) infectious culture system" PNAS, Nov. 27, 2012, pp. 19757-19762, vol. 109, No. 48.
Lindenbach, Brett D. et al., "Complete Replication of Hepatitis C Virus in Cell Culture" Science, Jul. 22, 2005, pp. 623-626, vol. 309.
Murayama, Asako et al., "The NS3 Helicase and NS5B-to-$3_1$X Regions Are Important for Efficient Hepatitis C Virus Strain JFH-1 Replication in Huh7 Cells" Journal of Virology, Aug. 2007, pp. 8030-8040, vol. 81, No. 15.
Murayama, Asako et al., "RNA Polymerase Activity and Specific RNA Structure Are Required for Efficient HCV Replication in Cultured Cells" PloS Pathogens, Apr. 2010, pp. 1-11, vol. 6, Issue 4.
Okamoto, Hiroaki et al., "Nucleotide sequence of the genomic RNA of hepatitis C virus isolated from a human carrier: comparison with reported isolates for conserved and divergent regions" Journal of General Virology, 1991, pp. 2697-2704, vol. 72.
Okamoto, Hiroaki et al., "Full-Length Sequence of a Hepatitis C Virus Genome Having Poor Homology to Reported Isolates: Comparative Study of Four Distinct Genotypes" Virology, 1992, pp. 331-341, vol. 188.
Ramirez, Santseharay et al., "Highly Efficient Infectious Cell Culture of Three Hepatitis C Virus Genotype 2b Strains and Sensitivity to Lead Protease, Nonstructural Protein 5A, and Polymerase Inhibitors" Hepatology, 2014, pp. 395-407, vol. 59.
Scheel, Troels K.H. et al., "Recombinant HCV Variants With NS5A From Genotypes 1-7 Have Different Sensitivities to an NS5A Inhibitor but Not Interferon-α" Gastroenterology, 2011, pp. 1032-1042, vol. 140.
Wakita, Takaji et al., "Production of infectious hepatitis C virus in tissue culture from a cloned viral genome" Nat Med., 2005, pp. 791-796, vol. 11, No. 7.
Yanagi, Masayuki et al., "Hepatitis C Virus: An Infectious Molecular Clone of a Second Major Genotype (2a) and Lack of Viability of Intertypic 1a and 2a Chimeras" Virology, 1999, pp. 250-263, vol. 262.
International Search Report for PCT/DK2014/050231 dated Oct. 20,2014.
Akazawa, Daisuke et al., "Production and characterization of HCV particles from serum-free culture" Vaccine, 2011, pp. 4821-4828, vol. 29.
Akazawa, Daisuke et al., "Neutralizing Antibodies Induced by Cell Culture-Derived Hepatitis C Virus Protect Against Infection in Mice" Gastroenterology, 2013, pp. 447-455, vol. 145.
Bukh, Jens et al., "A milestone for hepatitis C virus research: A virus generated in cell culture is fully viable in vivo" PNAS, Mar. 2006, pp. 3500-3501, vol. 103, No. 10.
Chen, N. et al., "Oxymatrine inhibits target cell infection in the HCVcc system" Chinese Journal of Hepatology, Jan. 2016, pp. 40-45, vol. 24, No. 1—Abstract.
Date, Tomoko et al., "Novel Cell Culture-Adapted Genotype 2a Hepatitis C Virus Infectious Clone" Journal of Virology, Oct. 2012, pp. 10805-10820, vol. 86, No. 19.
Gottwein, Judith M. et al., "Combination Treatment with Hepatitis C Virus Protease and NS5A Inhibitors Is Effective against Recombinant Genotype 1a, 2a, and 3a Viruses" Antimicrobial Agents and Chemotherapy, Mar. 2013, pp. 1291-1303, vol. 57, No. 3.
Houghton, Michael et al., "An Inactivated Hepatitis C Virus Vaccine on the Horizon?" Editorials, 2013, pp. 285-288.
Kolykhalov, Alexander A. et al., "Transmission of Hepatitis C by Intrahepatic Inoculation with Transcribed RNA" Science, Jul. 1997, pp. 570-574, vol. 277.
Kuiken, Carla et al., "A Comprehensive System for Consistent Numbering of HCV Sequences, Proteins and Epitopes" Hepatology, Nov. 2006, pp. 1355-1361, vol. 44, No. 5.
Li, Yi-Ping et al., "Protease inhibitors differentially inhibit novel HCV 5'UTR-NS5A genotype 3-6 recombinants" Article intended for submission to Gastroenterology.
Li, Yi-Ping et al., "MicroRNA-122 antagonism against hepatitis C virus genotypes 1-6 and reduced efficacy by host RNA insertion or mutations in the HCV 5' UTR" PNAS, Mar. 2011, pp. 4991-4996, vol. 108, No. 12.
Li, Yi-Ping et al., "Differential Sensitivity of 5'UTR-NS5A Recombinants of Hepatitis C Virus Genotypes 1-6 to Protease and NS5A Inhibitors" Gastroenterology, 2014, pp. 812-821.e4, vol. 146.
Li, Yi-Ping et al., "Efficient infectious cell culture systems of the hepatitis C virus prototype strains HCV- 1 and H77" JVI-02877-14R1, Oct. 2014.
Mathiesen, Christian K. et al., "Production and characterization of high-titer serum-free cell culture grown hepatitis C virus particles of genotype 1-6" Virology, 2014, pp. 190-208, vol. 458-459.
Morris, David L. et al., "Adipose Tissue Macrophages Function As Antigen-Presenting Cells and Regulate Adipose Tissue $CD4^+$ T Cells in Mice" Diabetes, Aug. 2013, pp. 2762-2772, vol. 62.
Ramirez, Santseharay et al., "Highly Efficient Infectious Cell Culture of Three HCV Genotype 2b Strains and Sensitivity to Lead Protease, NS5A, and Polymerase Inhibitors" submitted to Hepatology on Jun. 12, 2013.
Shiokawa, Mai et al., "Novel Permissive Cell Lines for Complete Propagation of Hepatitis C Virus" Journal of Virology, May 2014, pp. 5578-5594, vol. 88, No. 10.
Yao, Xiangjie et al., "Baculovirus Mediated Production of Infectious Hepatitis C Virus in Human Hepatoma Cells Stably Expressing T7 RNA Polymerase" Mol Biotechnol, 2008, pp. 186-194, vol. 40.
Database UniParc, Nov. 28, 2012, XP-002699169.
Scheel, Troels K. H. et al., "Development of JFH1-based cell culture systems for hepatitis C virus genotype 4a and evidence for cross-genotype neutralization" PNAS, Jan. 2008, pp. 997-1002, vol. 105, No. 3.
GenBank: AF009606.1, "Hepatitis C virus subtype 1a polyprotein gene, complete cds.", Jun. 18, 2009.
GenBank: BAD73984.1, "polyprotein, Partial [Hepatitis C virus subtype 1B]", Oct. 17, 2008.
GenBank: GU814266.1, "Synthetic construct Hepatitis C virus ED43 polyprotein gene, complete cds." May 4, 2010.

* cited by examiner

Figure 1
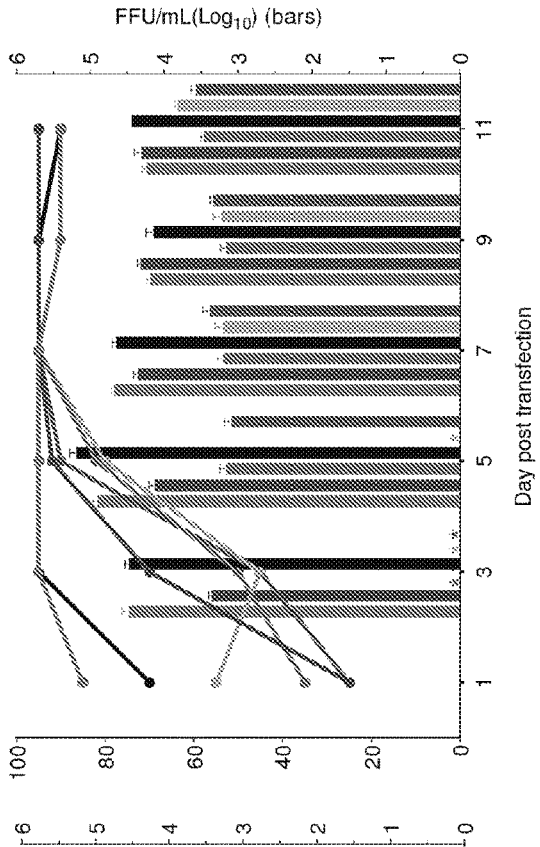
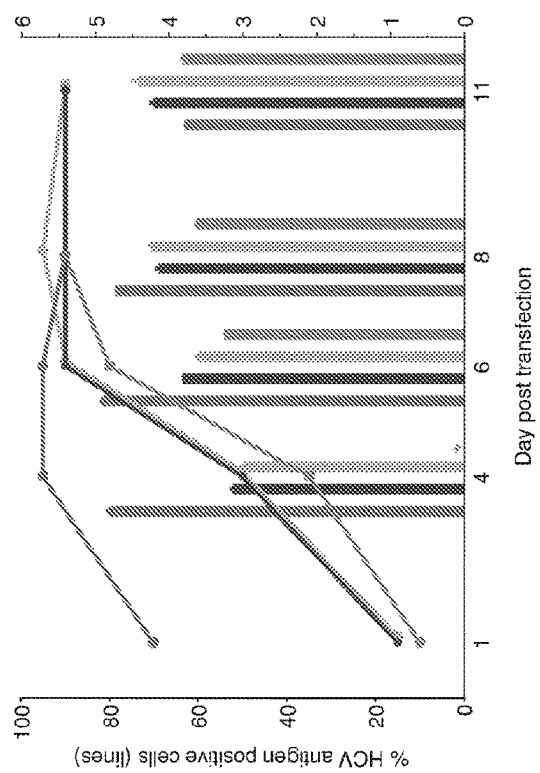

| | | Nucleotide Position | Forward Sequence 5'-3' | Reverse Sequence 5'-3' |
|---|---|---|---|---|
| cDNA synthesis | | 9471 | - | GCAAACCCTAGCTACACTCCATAG |
| 1st Round PCR | | 57-9467 | ACTGTCTTCACGCAGAAAGCGTCTAGCCAT | CGGCAAACCCTAGCTACACTCC |
| Nested PCR | 1 | 66-1310 | ACCCAGAAAGCGTCTAGCCATGGGCGTTAGT | ATGGCATGGGACATGATG |
| | 2 | 576-1699 | CCRGGATATCCTTGGCC | TCAACAGCTCTGGCTGCCC |
| | 3 | 1310-2458 | ATGGCATGGGACATGATG | GTGGACGTGCAGTACCT |
| | 4 | 2235-3304 | AAGGYGCGGATGTATG | CCCAATGGAGAAGAAGG |
| | 5 | 2883-3845 | TGGTGGCTGTCCTACATGCTG | CAACCCTCAARGGATCATC |
| | 6 | 3756-4829 | CGAAACGCTGATGTCATTCC | AACGTAGAGGGAGAACTGGG |
| | 7 | 4614-5790 | CTCGACGTCTCCGTTATACCA | CCATCTCTTGAACATCATG |
| | 8 | 5553-6615 | GGCCTCYTACACACAGGCC | ATTTGGAGGGTGGCAGCGT |
| | 9 | 6481-7438 | CCATGAAAATAACRGGCCCG | TGACTCCGGTCACTCCACTGG |
| | 10 | 7261-8392 | AACCACCCACTGTCCTAGGY | CAGAAGAATCCATATATCAGGC |
| | 11[a] | 8236-9467 | CCTATGGGTTCCAATACTCTCC | CGGCAAACCCTAGCTACACTCC |

| Gene | 5A | 5A | 5A | 5A | 5A | 5A | 5B | 5B | 5B | 5B | 5B |
|---|---|---|---|---|---|---|---|---|---|---|---|
| Recombinant | 7297 | 7476 | 7615 | 7641 | 7657 | 8080 | 8832 | 8903 | 9312 | 9343 | |
| H77 reference | 7297 | 7455 | 7584 | 7591 | 7657 | 8024 | 8766 | 8837 | 9246 | 9277 | |
| DH10consensus | C | G | A | G | T | A | A | C | A | A | |
| DH10-LSG | | | | | | | | | | | |
| Transfection 1  1st | · | · | · | A/g | · | · | · | · | · | G | |
| 2nd | · | · | · | A | · | · | · | · | · | G | |
| 3rd | · | · | · | A | · | · | · | · | · | G | |
| 4th | · | · | · | A | · | · | · | · | · | G | |
| Transfection 2  2nd | C/T | G/T | T | · | C/G | · | · | T | G | G | |
| DH10-LSG +mutations | | | | | | | | | | | |
| G351S/Y792N/A992V/I1824V/ N1931S/ V1951A/D2434N  1st | · | · | · | A | · | · | · | · | · | G | |
| 2nd | · | · | · | A | · | A/G | · | · | · | G | |
| G351S/Y792N/A992V/I1824V/ N1931T/ V1951A/D2434N  1st | · | · | · | A | · | · | A/g | · | · | G | |
| 2nd | · | · | · | A | · | · | A/G | · | · | G | |
| Recombinant aa | 2319 | 2379 | 2426 | 2434 | 2439 | 2583 | 2831 | 2854 | 2991 | 3001 | |
| H77 reference | 2319 | 2372 | 2408 | 2415 | 2417 | 2561 | 2809 | 2832 | 2969 | 2979 | |
| Change | T-I | D-Y | D-V | D-N | I-T/S | I-V | · | · | R-G | D-G | |

Figure 7 (continued)

| Target | Clinical Development | Drug Names | EC₅₀ (nM) | | | | | |
|---|---|---|---|---|---|---|---|---|
| | | | JFH1 (2a)* | J6 (2a) | DH8 (2b) | J8 (2b) | DH10 (2b) | TN (1a) |
| NS3 | Licensed | Telaprevir (VX-950) | 493 | 458 | 894 | 179 | 893 | 109 |
| | | Boceprevir (Sch503034) | 588 | 1123 | 981 | 146 | 2069 | 128 |
| | Phase 3 | Vaniprevir (MK7009) | 88 | 129 | 219 | 122 | 778 | 16 |
| | | Simeprevir (TMC435) | 96 | 266 | 71 | 9 | 53 | 33 |
| | | Faldaprevir (BI-201335) | 89 | 123 | 190 | 176 | 706 | 19 |
| | | Asunaprevir (BMS650032) | 159 | 899 | 1474 | 444 | 3284 | 64 |
| | Phase 2 | MK-5172 | 12 | 7 | 18 | 8 | 24 | 1.3 |
| NS5A | Phase 3 | Daclastavir (BMS-790052) | 0.09 | 5 | 0.09 | 23 | 12 | 0.032 |
| NS5B | Phase 3 | Sofosbuvir (PSI-7977, GS-7977) | 558 | 256 | 650 | 615 | 607 | 774 |
| | Phase 2 | Mericitabine (PSI-6130, RG7128) | 6931 | 2611 | 5483 | 9255 | 7987 | 11928 |
| | | Filibuvir (PF-00868554) | ni | ni | ni | ni | ni | 138 |
| | | VX-222 | ni | ni | ni | ni | ni | 38 |
| | | BI207127 | 449 | 97 | 1089 | 282 | 510 | 28 |

Figure 11

HIGH-TITER HCV FULL-LENGTH GENOTYPE 2B INFECTIOUS CELL CULTURE SYSTEMS AND APPLICATIONS THEREOF

CROSS REFERENCE TO RELATED APPLICATIONS

This application is a U.S. National Phase Application of PCT International Application Number PCT/DK2014/050231, filed on Jul. 28, 2014, designating the United States of America and published in the English language, which is an International Application of and claims the benefit of priority to Danish Patent Application No. PA 2013 70418, filed on Jul. 29, 2013. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG36-008APC.txt, the date of creation of the ASCII text file is Jan. 14, 2016, and the size of the ASCII text file is 609 KB.

TECHNICAL FIELD OF THE INVENTION

The present invention relates to nucleic acid sequences that encode hepatitis C viruses (HCV) of genotype 2b that are useful in the fundamental research of HCV as well as in the search of drug candidates and a vaccine against HCV. In particular the present invention relates to nucleic acid sequences that comprises HCV, which are capable of expressing said virus when transfected into cells and/or are capable of infectivity in vivo.

BACKGROUND OF THE INVENTION

Hepatitis C is one of the most widespread infectious diseases in the world. About 180 million people are infected with hepatitis C virus (HCV) worldwide with a yearly incidence of 3-4 million.

While the acute phase of infection is mostly asymptomatic, the majority of acutely infected individuals develops chronic hepatitis and is at increased risk of developing liver cirrhosis and hepatocellular carcinoma.

Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and post-translationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 7 major HCV genotypes (genotypes 1-7) have been identified, which differ by 31-33% at the nucleotide level and deduced amino acid level.

In addition, there are numerous subtypes (a, b, c, etc.), which differ by 20-25% on the nucleotide and deduced amino acid level.

Since its discovery in 1989, research on HCV has been hampered by the lack of appropriate cell culture systems allowing for research on the complete viral life cycle as well as new therapeutics and vaccines.

In 2001, a genotype 2a isolate (JFH1) was described, which subsequently was found to yield high RNA titers in the replicon system without adaptive mutations.

A major breakthrough occurred in 2005, when formation of infectious viral particles was reported after transfection of RNA transcripts from the JFH1 full-length consensus cDNA clone into Huh7 cells.

At the same time, it was demonstrated that the intragenotypic 2a/2a recombinant genome (J6/JFH1), in which the structural genes (Core, E1, E2), p7 and NS2 of JFH1 were replaced by the respective genes of clone J6CF, produced infectious viral particles in Huh7.5 cells (a cell line derived from bulk Huh7 cells) with an accelerated kinetic.

Cell culture derived J6/JFH viruses were apparently fully viable in vivo.

To facilitate HCV research and obtain basic knowledge for better and individualized treatment, the present inventors have aimed at developing culture systems for other HCV patient isolates.

Hence, improved and alternative HCV genomes of all genotypes, which are capable of expressing said virus when transfected into cells and are capable of infectivity in vivo, would be advantageous.

SUMMARY OF THE INVENTION

An object of the present invention relates to nucleotide sequences that encode HCV that are useful in the fundamental research of HCV as well as in the search of drug candidates and a vaccine against HCV.

In particular, it is an object of the present invention to provide nucleotide sequences of HCV of genotype 2b which are capable of expressing said virus when transfected into cells and are capable of infectivity in vivo.

Thus, one aspect of the present invention relates to an isolated nucleic acid molecule which encodes a human hepatitis C virus wherein the hepatitis C virus is derived from genotype 2b, comprising the mutations F1468L in NS3, A1676S in NS4A, and D3001G in NS5B.

A further aspect of the present invention relates to an isolated nucleic acid molecule which encodes a human hepatitis C virus wherein the hepatitis C virus is derived from genotype 2b with specific mutations that allow growth without the mutations F1468L in NS3, A1676S in NS4A, and D3001G in NS5B.

Another aspect of the invention relates to an isolated nucleic acid molecule which encodes a human hepatitis C virus of genotype 2b, wherein the strain is J8cc-HT (SEQ ID NO:14).

Yet another aspect of the present invention relates to an isolated nucleic acid molecule which encodes a human hepatitis C virus of genotype 2b, wherein the strain is J8_LSG/STAT (SEQ ID NO:15).

Another aspect of the present invention relates to an isolated nucleic acid molecule which encodes a human hepatitis C virus of genotype 2b that has an open reading frame (ORF) nucleic acid sequence with 90% sequence identity to SEQ ID NO:56.

A further aspect of the present invention relates to the isolated nucleic acid molecule of the present invention, which is strain DH10_LSG (SEQ ID NO:10), DH8_LSG (SEQ ID NO:2) or strain DH8cc (SEQ ID NO:8).

Another aspect of the present invention relates to the isolated nucleic acid molecule of the present invention, further comprising one or more mutations selected from the group consisting of F772C, W864R, A1208T, I1968V, E2263V, H2922R, M292L, L612M, G1154A, N1217Y, Q1763R, I2440T, G351S, Y792N, A992V, I1824V, N1931T, V1951A, D2434N, N1931S, N534T, V1951A, I2440T, L3021F, L884P, I2439S, I2439T, L3021F, W2429R, L758S, A1790T, G351S, Y792N, A992V, V1951A, D2434N, G1154A, and A1208T.

Yet another aspect of the present invention relates to a composition comprising a nucleic acid molecule of the present invention suspended in a suitable amount of a pharmaceutical acceptable diluent or excipient.

Another aspect of the present invention relates to a cassette vector for cloning viral genomes, comprising, inserted therein, the nucleic acid sequence according of the present invention and having an active promoter upstream thereof.

An aspect of the present invention relates to a cell comprising the nucleic, the composition or the cassette vector of the present invention.

Another aspect of the present invention relates to a method for producing a hepatitis C virus particle, comprising culturing a cell of the present invention to allow the cell to produce the virus.

Another aspect of the present invention relates to a method for producing a cell, which replicates human hepatitis C virus and produces a virus particle comprising introducing a nucleic acid molecule of the present invention into a cell.

Another aspect of the present invention relates to a method for screening an anti-hepatitis C virus substance, comprising culturing at least one selected from the group consisting of a cell comprising the nucleic acids of the present invention, a cell of the present invention and the hepatitis C virus particle obtainable from the method of the present invention together with a hepatitis C virus permissive cell, and detecting the replicating RNA or the virus particles in the resulting culture.

BRIEF DESCRIPTION OF THE FIGURES

FIG. 1 shows transfection of Huh7.5 cells with RNA transcripts of full-length genotype 2b recombinants DH8, J8, and DH10. The different 2b recombinants contained F1468L/A1676S/D3001G (LSG) and additional adaptive mutations as indicated. Panels A and B represent two independent transfection experiments; J65'UTR-NS2/JFH1 was included as control. Graphs show percentage of Core/NS5A antigen positive cells (left y axis) and HCV infectivity titers in collected supernatants (right y axis: Log 10 FFU/ml, mean of triplicate infections±SEM is shown) at the analyzed days (x axis); supernatants from day 1 were not analyzed. Stars indicate infectivity titers below the assay limit of detection (2.5 and 2.7 Log 10 FFU/mL in A and B, respectively).

FIG. 2 shows concentration-response curves for genotype 1a, 2a, and 2b full-length viruses treated with NS5B polymerase inhibitors and NS5A inhibitor Daclatasvir. Values represent the means of triplicates and SEM (bars). *J6core-NS2/JFH1 recombinant8. In the different graphs, each curve corresponds to a single virus, following the color code as shown at the bottom of the figure. Panel A: Nucleoside/tide analogs (NI) Sofosbuvir (nucleotide) and Mericitabine (nucleoside). Panel B: Non-nucleotide analogs (NNI) VX-222 and Filibuvir (thumb II inhibitors). Note that for isolates JFH1, J6, DH8, J8, and DH10 a concentration-response curve could not be generated, since the viruses were not inhibited at non-cytotoxic concentrations of Filibuvir and VX-222. Panel C: NNI BI207127 (thumb I inhibitor). Panel D: NS5A inhibitor Daclatasvir. For this drug, data was generated in three independent experiments (one including J6 and JFH1, another TN, and a third J8, DH8, and DH10).

FIG. 3 shows concentration-response curves for genotype 1a, 2a, and 2b full-length viruses treated with lead protease inhibitors (PIs). Values represent the means of triplicates and SEM (bars). *J6core-NS2/JFH1 recombinant. In the different graphs, each curve corresponds to a single virus, following the color code indicated. Panel A: licensed PIs Telaprevir and Boceprevir. Panel B: phase III PIs Vaniprevir, Simeprevir, Asunaprevir, and Faldaprevir. Panel C: phase 2 PI MK-5172.

FIG. 4 shows concentration-response curves for J8 full-length viruses with and without adaptive mutations in the NS3/protease domain, treated with lead protease inhibitors. Values represent the means of triplicates and SEM (bars). Solid lines refer to the original J8 polyclonal virus with adaptive mutations in NS3 (J8cc 5th passage) and dashed-lines represent J8 without protease adaptive mutations (J8_LSG/STAT 2nd passage). The EC50 values (nM) of the corresponding drug for the two viruses are indicated in the individual graphs. Panel A: licensed PIs Telaprevir and Boceprevir. Panel B: phase III PIs Vaniprevir, Simeprevir, and Asunaprevir. Panel C: phase 2 PI MK-5172.

FIG. 5 shows primers Used for ORF Analysis of Recovered 2b Cell Culture Viruses by Direct Sequencing. Primer sequences are shown in 5'-3' sense. Nucleotide positions include primer sequences and are numbered according to J8CF sequence (JQ745651). a: amplicon 11 was obtained by semi-nested PCR. The primer sequences are listing in the sequence listing as SEQ ID NOs 31-55.

FIG. 6 shows characterization of DH8 Full-Length Viruses. Changes in nucleotide and amino acid positions identified in direct sequencing of the ORF are listed; the corresponding H77 (AF009606) reference number is also given. The original nucleotide for DH8CF is shown at the top and engineered mutations are shown in shadings (LSG is shown in dark shading). Dots indicate identity with DH8CF. All positions with coding and non-coding changes are shown. When a determined position has a change, two capital letters separated by a slash indicate a nucleotide quasispecies (50/50) population, whereas a capital letter separated from a lowercase letter indicates a dominant/minor detection; when the change consist of more than 1 residue, the two residues are separated by a dash. For each of the reported positions the respective HCV gene is given and abbreviations are used for non-structural genes NS4A (4A), NS4B (4B), NS5A (5A) and NS5B (5B). (a): viruses collected from different time points after passage were mixed to generate a stock for antiviral treatments. b: recombinant named DH8cc. ud: under the limit of detection of infectivity titration assay, nd: not done.

FIG. 7 shows characterization of DH10 Full-Length Viruses. Changes in nucleotide and amino acid positions identified in direct sequencing of the ORF are listed; the corresponding H77 (AF009606) reference number is also given. The original nucleotide for DH10 consensus is shown at the top and engineered mutations are shown in shadings (LSG is shown in dark shading). Dots indicate identity with DH10 consensus. All positions with coding and non-coding changes are shown. When a determined position has a change, two capital letters separated by a slash indicates a nucleotide quasispecies (50/50) population, whereas a capital letter separated from a lowercase letter indicates a dominant/minor detection; when the change consist of more than 1 residue, the two residues are separated by a dash. For each of the reported positions the respective HCV gene is given and abbreviations are used for non-structural genes NS4A (4A), NS4B (4B), NS5A (5A) and NS5B (5B). Nucleotide 6121 changed to G and C in transfection 1 and 2, respectively corresponding to amino acid S and T. (a): viruses collected from different time points after passage were mixed to generate an homogeneous pool that was used as a stock for antiviral treatments.

Figure 8:
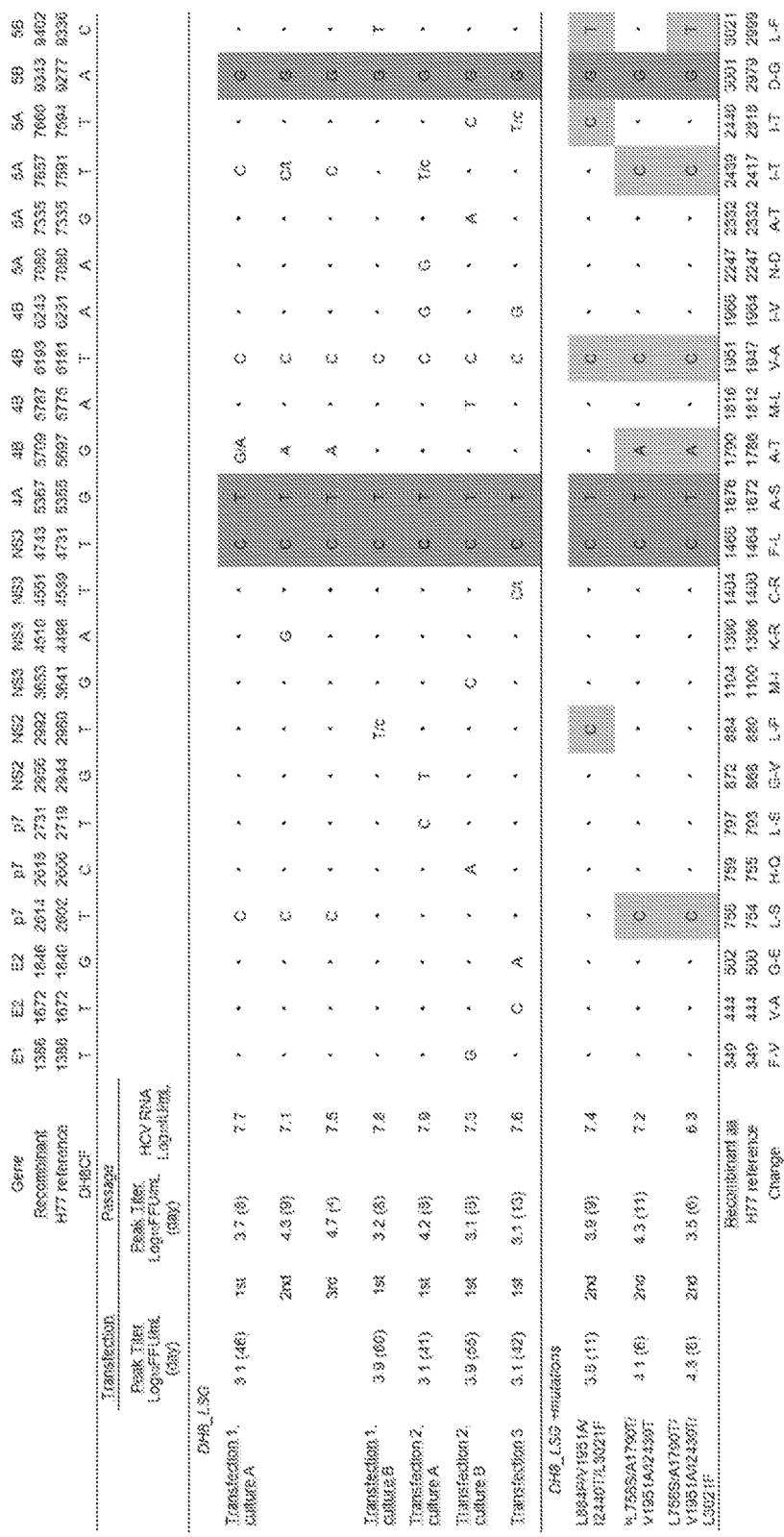

FIG. 8 shows characterization of DH8 Full-Length Viruses. Changes at indicated nt and aa positions identified in direct ORF sequencing are listed; the corresponding H77 (AF009606) reference number is also given. All dominant coding changes are shown; minor and 50/50 changes are depicted only at positions where dominant changes in other genomes were found; for an overview of all changes see FIG. 6. The associated HCV gene is indicated. The original DH8CF sequence is shown at the top and engineered mutations are shown in light shadings (LSG in dark shading). Dots indicate identity with DH8CF. (a): viruses collected from different time points after passage were mixed to generate stock for antiviral treatment assays. b: recombinant named DH8cc.

Figure 9:
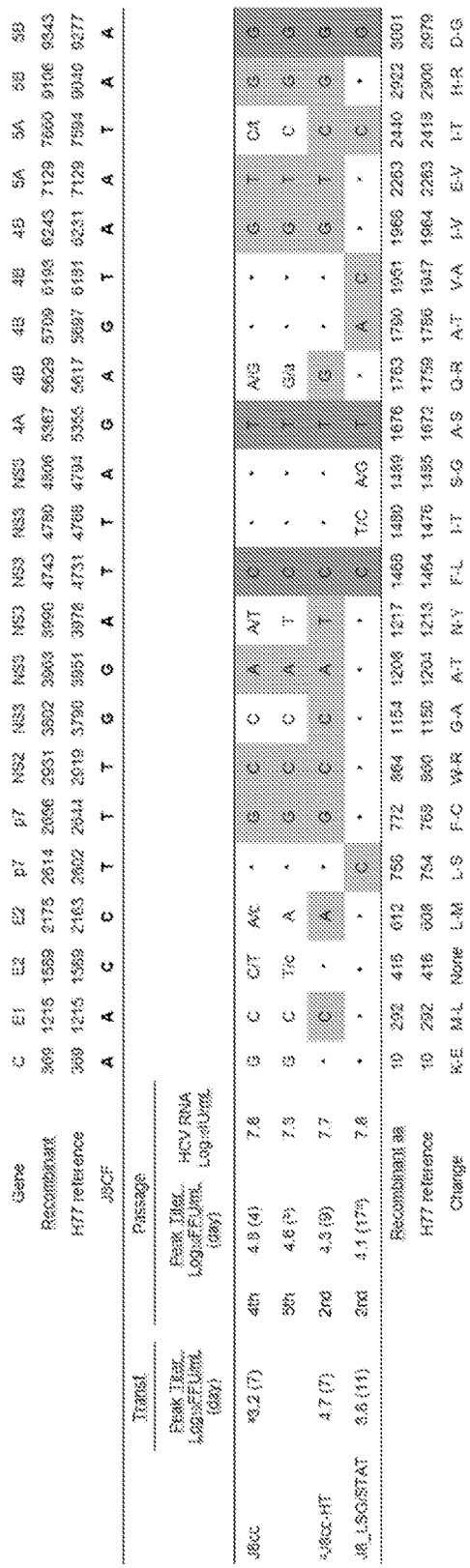

FIG. 9 shows characterization of J8 Full-Length Viruses. Changes at indicated nt and aa positions identified in direct ORF sequencing are listed; the corresponding H77 (AF009606) reference number is also given. All nucleotide changes are shown. The associated HCV gene is indicated. The original J8CF sequence is shown at the top and engineered mutations are shown in light shadings (LSG in dark shading). Dots indicate identity with J8CF a: data from J8cc. (b): viruses collected from different time points after passage were mixed to generate stock for antiviral treatments. c: recombinant and recovered viruses contain non-coding mutation, A5324G. d: viruses harvested at this time point were used in treatment assays.

Figure 10:
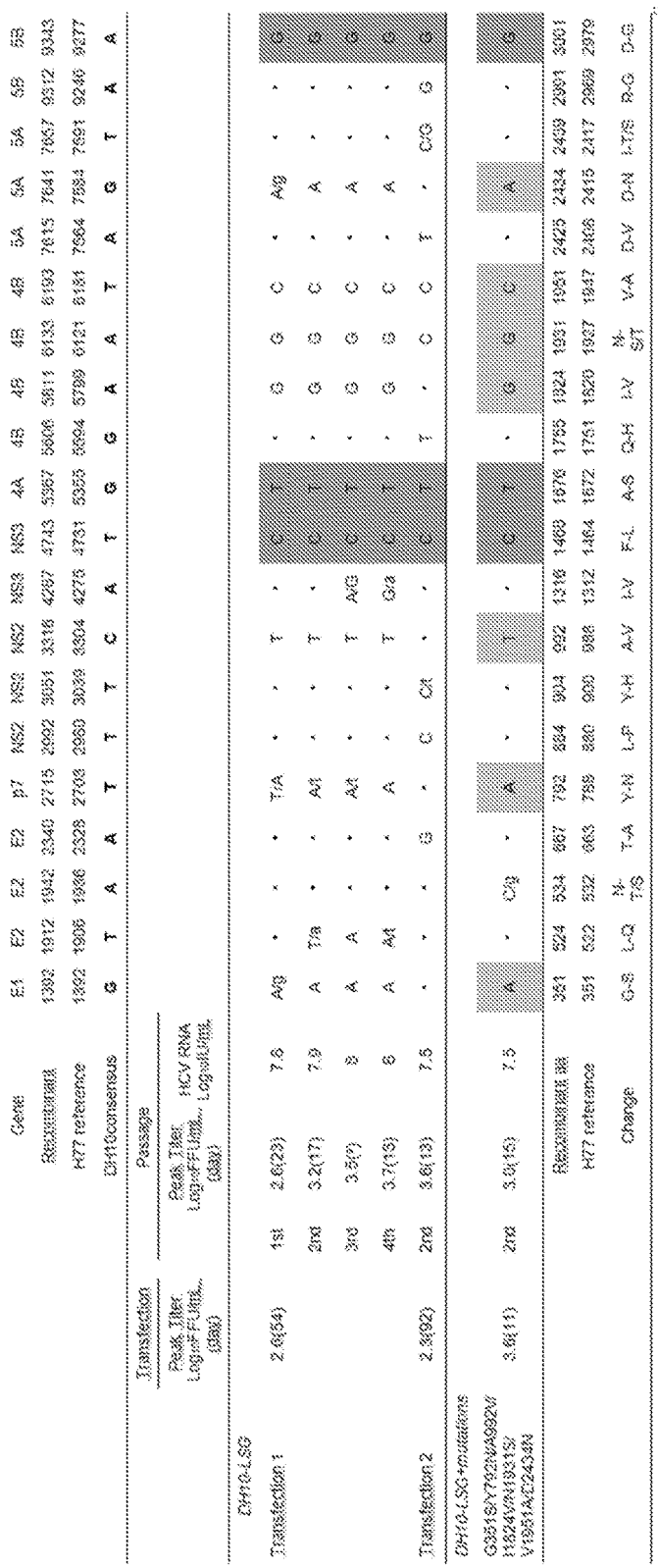

FIG. 10 shows characterization of DH10 Full-Length Viruses. Changes at indicated nt and aa positions identified in direct ORF sequencing are listed; the corresponding H77 (AF009606) reference number is also given. All dominant coding changes are shown; minor and 50/50 changes are depicted only at positions where dominant changes in other genomes were found; for an overview of all changes see FIG. 7. The associated HCV gene is indicated. The original DH10 consensus sequence is shown at the top and engineered mutations are shown in light shadings (LSG in dark shading). Dots indicate identity with DH10 consensus. Nucleotide 6121 changed to G and C in transfection 1 and 2, respectively, corresponding to amino acid S and T. (a): viruses collected from different time points after passage were mixed to generate stock for antiviral treatments.

Figure 3:
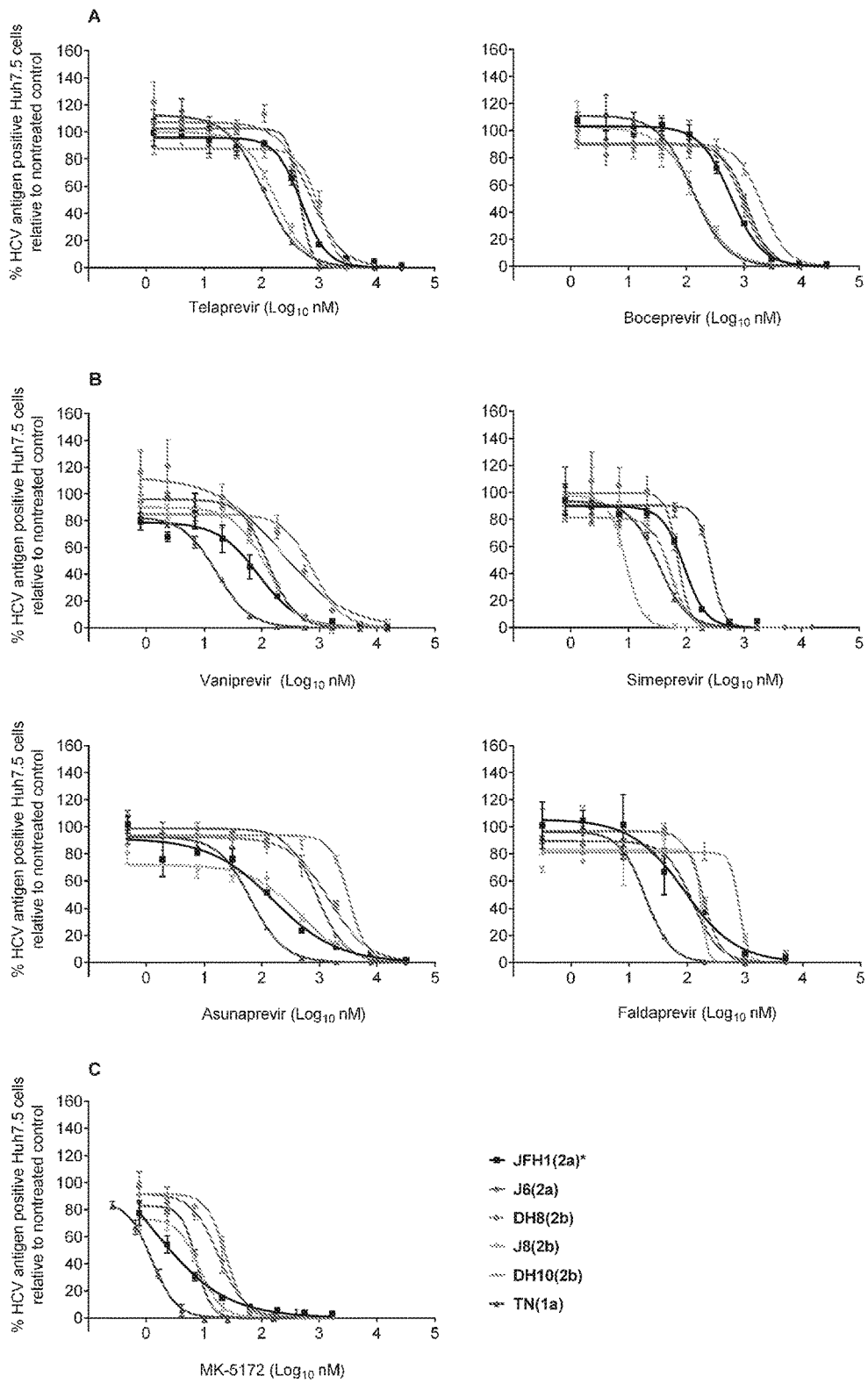
Figure 4:
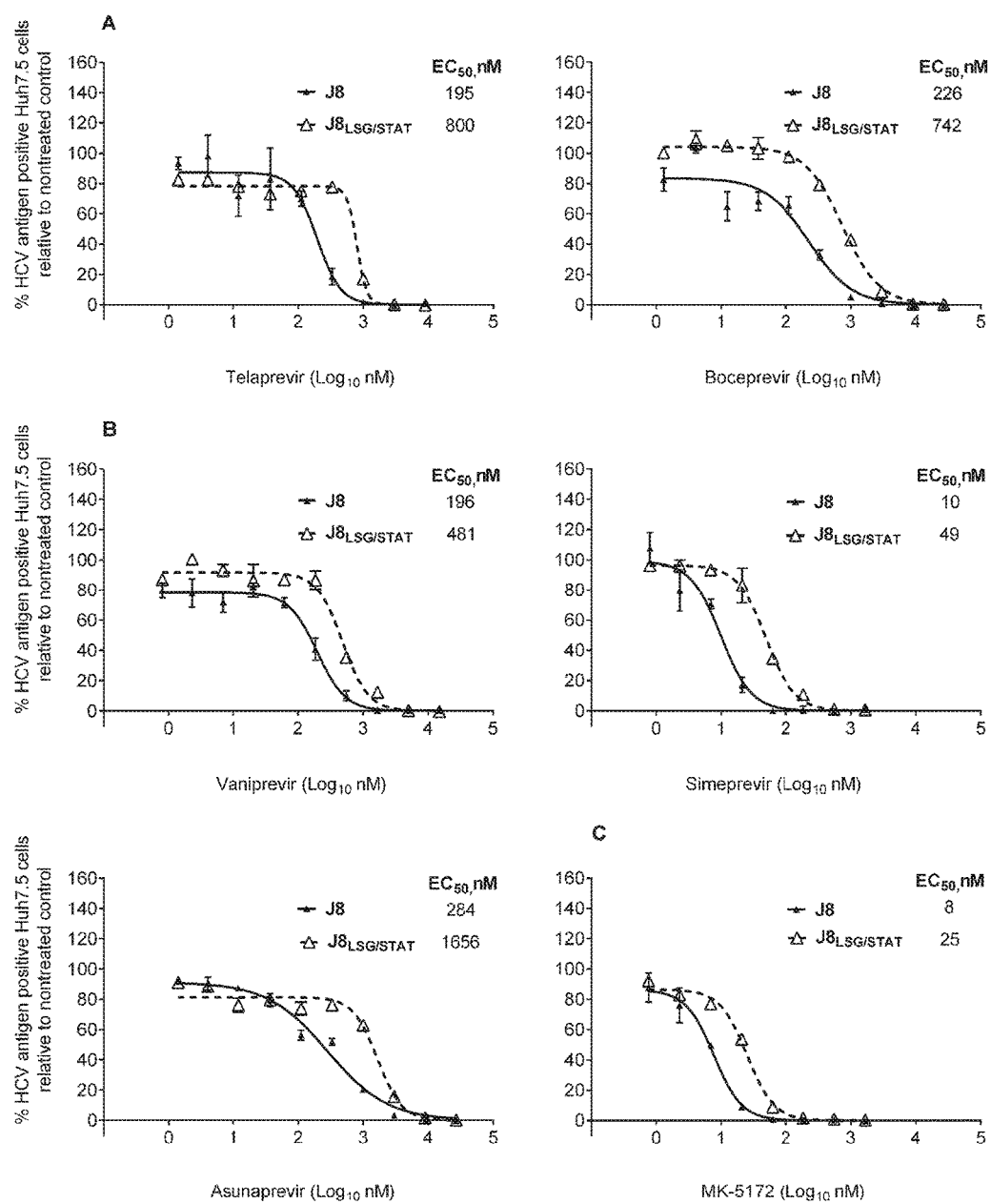

FIG. 11 shows median EC50 Values Obtained in Treatment Assays of HCV Genotype 1a, 2a, and 2b Full-Length Viruses for Different Protease, NS5A, and Polymerase DAAs. EC50 values were obtained from the sigmoidal dose-response curves shown in FIGS. 2 and 3. Ni: not inhibited. a: J6core-NS2/JFH1 recombinant.

DETAILED DESCRIPTION OF THE INVENTION

The present invention advantageously provides hepatitis C virus (HCV) of genotype 2b nucleotide sequences capable of replication, expression of functional HCV proteins, and infection in vivo and in vitro for development of antiviral therapeutics and diagnostics.

Nucleic Acid Molecules (cDNA Clones and RNA Transcripts)

The present invention is directed towards an isolated nucleic acid molecule which encodes a human hepatitis C virus of genotype 2b, wherein said molecule is capable of expressing said virus when transfected into cells, comprises at least one adaptive mutation in the amino acid sequence of NS3, which is F1464L, comprises at least one adaptive mutation in the amino acid sequence of NS4A which is A1672S, and comprises at least one adaptive mutation in the amino acid sequence of NS5B which is D2979G according to the H77 reference sequence with GenBank accession number AF009606.

In one embodiment of the present invention is the isolated nucleic acid molecule capable of infectivity in vivo.

The adaptive mutations as shown above means that in the case of F1464L is phenylalanine at amino acid position 1464 changed to Leucine.

The original amino acids F1464, A1672, and D2979 (H77 reference numbers) at LSG positions are highly conserved across all HCV genotypes.

Thus, one aspect of the present invention relates to an isolated nucleic acid molecule which encodes a human hepatitis C virus wherein the hepatitis C virus is derived from genotype 2b, comprising the mutations F1468L in NS3, A1676S in NS4A, and D3001G in NS5B.

The terms "isolate" and "strain" are used herein interchangeably.

In another preferred embodiment of the present invention the hepatitis C virus is of genotype 2b and is isolate J8cc corresponding to GenBank accession number JQ745652.

The adaptive LSG mutations of isolate J8cc are F1468L/A1676S/D3001G corresponding to F1464L/A1672S/D2979G according to the H77 reference sequence with GenBank accession number AF009606. The work has been published as Li et al., Proc Natl Acad Sci USA. 2012 May 1; 109(18):E1101-10. Also see Author Summary in Proc Natl Acad Sci USA on page 6806 (volume 109, number 18).

The present inventors have identified a wide variety of recombinants that generated different virus viability.

These recombinants are described in the examples of the present application and are disclosed in the sequence listing as SEQ ID NO: 1-15 (nucleic acid sequences) and SEQ ID NO: 16-30 (amino acid sequences).

One aspect of the present invention relates to the isolated nucleic acid molecule J8cc-HT (SEQ ID NO:14) corresponding to genbank number KF420338.

Another aspect of the present invention relates to the isolated nucleic acid molecule J8_LSG/STAT (SEQ ID NO:15) corresponding to genbank number KF420339.

Another aspect of the present invention relates to an isolated nucleic acid molecule that has an open reading frame (ORF) nucleic acid sequence with 90% sequence identity to SEQ ID NO:56.

Another aspect of the present invention relates to the isolated nucleic acid molecule DH10_LSG (SEQ ID NO:10).

Another aspect of the present invention relates to the isolated nucleic acid molecule DH8_LSG (SEQ ID NO:2).

Another aspect of the present invention relates to the isolated nucleic acid molecule DH8cc (SEQ ID NO:8).

A further aspect of the present invention relates to the DH8 consensus clone of SEQ ID NO: 1.

In an embodiment of the present invention are these sequences isolated nucleic acid sequences and amino acid sequence, respectively.

Thus relates one aspect of the present invention to the DH8 consensus clone of SEQ ID NO: 16.

Another aspect of the present invention relates to the isolated amino acid molecule J8cc-HT (SEQ ID NO:29) corresponding to genbank number KF420338.

Another aspect of the present invention relates to the isolated amino acid molecule J8_LSG/STAT (SEQ ID NO:30) corresponding to genbank number KF420339.

Another aspect of the present invention relates to an isolated amino acid molecule that has an open reading frame (ORF)amino acid sequence with 90% sequence identity to SEQ ID NO:56.

Another aspect of the present invention relates to the isolated amino acid molecule DH10_LSG (SEQ ID NO:25).

Another aspect of the present invention relates to the isolated amino acid molecule DH8_LSG (SEQ ID NO:17).

Another aspect of the present invention relates to the isolated amino acid molecule DH8cc (SEQ ID NO:23).

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100).

In one embodiment the two sequences are the same length.

In another embodiment the two sequences are of different length and gaps are seen as different positions.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

An embodiment of the present invention thus relates to sequences of the present invention that has some degree of sequence variation.

One embodiment relates to J8cc-HT (SEQ ID NO: 14) in which the nucleic acid molecule comprises the nucleic acid sequence with a sequence identity of at least 80% to that of SEQ ID NO: 14.

In another embodiment, the nucleic acid comprises a sequence sharing at least 85% identity with that set forth in SEQ ID NO: 14, such as 90% identity, 91% identity, 92% identity, 93% identity, 94% identity, 95% identity, 96% identity, 97% identity, 98% identity, or 99% identity.

Another embodiment relates to J8_LSG/STAT (SEQ ID NO: 15) in which the nucleic acid molecule comprises the nucleic acid sequence with a sequence identity of at least 80% to that of SEQ ID NO: 15.

In another embodiment, the nucleic acid comprises a sequence sharing at least 85% identity with that set forth in SEQ ID NO: 15, such as 90% identity, 91% identity, 92% identity, 93% identity, 94% identity, 95% identity, 96% identity, 97% identity, 98% identity, or 99% identity.

Yet another embodiment relates to DH8_LSG (SEQ ID NO: 2) in which the nucleic acid molecule comprises the nucleic acid sequence with a sequence identity of at least 80% to that of SEQ ID NO: 2.

In another embodiment, the nucleic acid comprises a sequence sharing at least 85% identity with that set forth in SEQ ID NO: 2, such as 90% identity, 91% identity, 92% identity, 93% identity, 94% identity, 95% identity, 96% identity, 97% identity, 98% identity, or 99% identity.

A further embodiment relates to DH10_LSG (SEQ ID NO: 10) in which the nucleic acid molecule comprises the nucleic acid sequence with a sequence identity of at least 80% to that of SEQ ID NO 10.

In another embodiment, the nucleic acid comprises a sequence sharing at least 85% identity with that set forth in SEQ ID NO: 10, such as 90% identity, 91% identity, 92% identity, 93% identity, 94% identity, 95% identity, 96% identity, 97% identity, 98% identity, or 99% identity.

A further embodiment relates to DH8cc (SEQ ID NO: 8) in which the nucleic acid molecule comprises the nucleic acid sequence with a sequence identity of at least 80% to that of SEQ ID NO 8.

In another embodiment, the nucleic acid comprises a sequence sharing at least 85% identity with that set forth in SEQ ID NO: 8, such as 90% identity, 91% identity, 92% identity, 93% identity, 94% identity, 95% identity, 96% identity, 97% identity, 98% identity, or 99% identity.

Several of the sequences of the present invention have been submitted to genbank:

DH8CF (SEQ ID NOs 1 and 16) and corresponds to KF420335

DH8cc (SEQ ID NOs 8 and 23) corresponds to KF420336

DH8-LSG+L884P/V1951A/I2440T/L3021F (SEQ ID NOs 7 and 22) corresponds to KF420337 (also known as DH8-LSG-PATF)

J8cc-HT (SEQ ID NOs 14 and 29) corresponds to KF420338

J8-LSG/STAT (SEQ ID NOs 15 and 30) corresponds to KF420339

DH10-LSG+G351S/Y792N/A992V/I1824V/N1931S/V1951A/D2434N (SEQ ID NOs and 28) corresponds to KF420340 and is also known as DH10cc.

It should be noted that while several of the sequences in the present application (SEQ ID NOs: 1-15 and 31-55) are DNA sequences, the present invention contemplates the corresponding RNA sequence, and DNA and RNA complementary sequences as well.

Thus, in cases where a DNA sequence is mentioned refers such DNA sequence also to the RNA equivalent i.e. with Ts exchanged with Us as well as their complimentary sequences.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to the sequences of the present invention.

Various modifications for example of the 5' and 3' UTR are also contemplated by the invention.

In another embodiment, the nucleic acid further comprises a reporter gene, which, in one embodiment, is a gene encoding neomycin phosphotransferase, *Renilla* luciferase, secreted alkaline phosphatase (SEAP), *Gaussia* luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA.

Thus, where particular sequences of nucleic acids of the invention are set forth, both DNA and corresponding RNA are intended, including positive and negative strands thereof.

In a further embodiment, the nucleic acid sequences or the nucleic acid sequences with any mutation described in this document is obtained by any other means than what is described above.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

Thus, in one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventors here report adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use, is characterized in that it contains one, several or all of the nucleic acid exchanges listed below and/or one or several or all of the following amino acid exchanges.

One embodiment of the present invention relates to adaptive mutations, wherein the adaptive mutation is a mutation that can be observed by clonal or direct sequencing of recovered replicating genomes of the sequences of the present invention.

Thus in a further embodiment, the present invention relates to nucleic acid molecules according to the present invention, wherein said molecule comprises one or more adaptive mutations in p7, NS2, NS3, NS4A, NS4B, NS5A or NS5B singly or in combination.

In the context of the present invention the term "adaptive mutation" is meant to cover mutations identified in passaged viruses that provide the original and any other HCV sequence the ability to grow efficiently in culture. Furthermore all introductions of mutations into the sequences described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins.

This also includes other HCV genomes with adaptive mutations, all of them, combinations of them or individual mutations that grow in culture.

It should be understood that any feature and/or aspect discussed above in connection with the mutations according to the invention apply by analogy to both single mutations and any combination of the mutations.

In another embodiment all the amino acid changes observed herein are provided by the present application. The skilled addressee can easily obtain the same amino acid change by mutating another base of the codon and hence all means of obtaining the given amino acid sequence is intended.

Examples of such adaptive mutations disclosed in the present examples are F772C, W864R, A1208T, I1968V, E2263V, H2922R, M292L, L612M, G1154A, N1217Y, Q1763R, I2440T, G351S, Y792N, A992V, I1824V, N1931T, V1951A, D2434N, N1931S, N534T, V1951A, I2440T, L3021F, L884P, I2439S, I2439T, L3021F, W2429R, L758S, A1790T, G351S, Y792N, A992V, V1951A, D2434N, G1154A, and A1208T.

Thus, one embodiment of the present invention relates to an isolated nucleic acid molecule of the present invention, further comprising one or more mutations selected from the group consisting of F772C, W864R, A1208T, I1968V, E2263V, H2922R, M292L, L612M, G1154A, N1217Y, Q1763R, I2440T, G351S, Y792N, A992V, I1824V, N1931T, V1951A, D2434N, N1931S, N534T, V1951A, I2440T, L3021F, L884P, I2439S, I2439T, L3021F, W2429R, L758S, A1790T, G351S, Y792N, A992V, V1951A, D2434N, G1154A, and A1208T.

A further aspect of the present invention relates to an isolated nucleic acid molecule which encodes a human hepatitis C virus wherein the hepatitis C virus is derived from genotype 2b with specific mutations that allow growth without the mutations F1468L in NS3, A1676S in NS4A, and D3001G in NS5B.

Such isolated nucleic acid molecule which encodes a human hepatitis C virus wherein the hepatitis C virus is derived from genotype 2b would comprise one or more mutations selected from the group consisting of F772C, W864R, A1208T, I1968V, E2263V, H2922R, M292L, L612M, G1154A, N1217Y, Q1763R, I2440T, G351S, Y792N, A992V, I1824V, N1931T, V1951A, D2434N, N1931S, N534T, V1951A, I2440T, L3021F, L884P, I2439S, I2439T, L3021F, W2429R, L758S, A1790T, G351S, Y792N, A992V, V1951A, D2434N, G1154A, and A1208T.

In one embodiment is one or more of the above mentioned mutations inserted into DH8CF (SEQ ID NO: 1) with or without LSG mutations.

Titer

To determine the efficiency of the developed system, HCV RNA titers are determined in IU/ml (international units/ml) with Taq-Man Real-Time-PCR and infectious titers are determined with a focus forming unit assay.

The infectious titers are determined as TCID50/ml (median tissue culture infectious close/ml) or FFU/ml (focus forming unites/ml); in such method, infectivity titers are determined by infection of cell culture replicates with serial dilutions of virus containing supernatants and, following immuno-stainings for HCV antigens, counting of HCV-antigen positive cell foci.

HCV RNA titers and infectivity titers can be determined extracellularly, in cell culture supernatant (given as IU and TCID50 or FFU per ml, respectively) or intracellularly, in lysates of pelleted cells (given as IU and TCID50 or FFU related to a the given cell number or culture plate wells, which was lysed).

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ TCID50/ml or above following transfection and/or subsequent viral passage, such as a titer of at least $10^3$ TCID50/ml, such as a titer of at least $10^4$ TCID50/ml, such as a titer of at least $10^5$ TCID50/ml, such as a titer of at least $10^6$ TCID50/ml, such as a titer of at least $10^7$ TCID50/ml, such as a titer of at least $10^8$ TCID50/ml, such as a titer of at least $10^9$ TCID50/ml or such as a titer of at least $10^{10}$ TCID50/ml.

In another embodiment, the present invention relates to a nucleic acid molecule according to the invention, wherein said molecule is capable of generating a HCV infectivity titer of at least $10^2$ FFU/ml or above following transfection and/or subsequent viral passage, such as a titer of at least $10^3$ FFU/ml, such as a titer of at least $10^4$ FFU/ml, such as a titer of at least $10^5$ FFU/ml, such as a titer of at least $10^6$ FFU/ml, such as a titer of at least $10^7$ FFU/ml, such as a titer of at least $10^8$ FFU/ml, such as a titer of at least $10^9$ FFU/ml or such as a titer of at least $10^{10}$ FFU/ml.

It is of course evident to the skilled addressee that the titers described here are obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response.

Adjuvants include, but are not limited to, complete Freund's adjuvant, incomplete Freund's adjuvant, saponin, mineral gels such as aluminum hydroxide, surface active substances such as lysolecithin, pluronicpolyols, polyanions, peptides, oil or hydrocarbon emulsions, keyhole limpet hemocyanins, dinitrophenol, and potentially useful human adjuvants such as BCG (bacilleCalmette-Guerin) and *Corynebacterium parvmm*.

Preferably, the adjuvant is pharmaceutically acceptable.

Thus relates one embodiment of the present invention to a composition comprising a nucleic acid molecule according to the present invention suspended in a suitable amount of a pharmaceutical acceptable diluent or excipient.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus relates one embodiment of the present invention to a cell comprising the nucleic acid according to the present invention, the composition of present invention or the cassette vector of the present invention.

Another embodiment of the present invention relates to a method for producing a cell, which replicates human hepatitis C virus and produces a virus particle comprising introducing a nucleic acid molecule of the present invention into a cell.

In a preferred embodiment is the cell is a Huh7.5 cell.

Another embodiment of the present invention relates to a cell obtainable by the methods of the present invention.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein such as a hepatitis C virus infected cell obtainable by any of the methods described.

In one embodiment, the hepatocyte cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9 and the low-density lipid receptor.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV, which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

In one embodiment the introduced mutations attenuates the virus in vivo.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

In one embodiment, the method further comprises isolating infectious HCV. In another embodiment, the method further comprises freezing aliquots of said infectious HCV.

According to this aspect of the invention, and in one embodiment, the HCV is infectious following thawing of said aliquots, and in another embodiment, the HCV is infectious following repeated freeze-thaw cycles of said aliquots.

A further embodiment of the present invention relates to a method for in vitro producing a hepatitis C virus-infected cell comprising culturing a cell according to the present invention and infecting other cells with the produced virus particle in the culture.

Screening for Anti-Viral Drugs and the Determination of Drug Resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Alternatively, the number of antigen-expressing cells is determined. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present invention may prove useful for different research topics.

The systems developed in this invention are ideal candidates for specific testing of therapeutics in general and therapeutics targeting viral entry, assembly and release.

Genomes with the sequences of the present invention are valuable for testing of neutralizing antibodies and other drugs acting on entry level, such as fusion inhibitors.

In one embodiment the present invention relates to a method for identifying neutralizing antibodies.

In another one embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

In one embodiment the present invention related to a method for screening new HCV genotype 2b inhibitors or neutralizing antibodies, comprising a) culturing at least one selected from the group consisting of a cell according to the present invention, a hepatitis C virus infected cell according to the present invention and a hepatitis C virus particle obtainable by the present invention together with a hepatitis C virus permissive cell, and b) subjecting said virus or virus infected cell culture to a blood sample or derivatives thereof from a HCV genotype 2b infected patient c) detecting the amount of replicating RNA and/or the virus particles.

Inhibitors targeting the HCV non-structural proteins NS3/4A, NS5A and NS5B are currently being developed. The first directly-acting antiviral compounds targeting the NS3/4A protease were licensed in 2011 (Telaprevir and Boceprevir). Clinicial phase studies show promising results for inhibitors of NS5A and the NS5B polymerase. The present invention offers novel culture systems where additional HCV isolates can be tested to generate efficient cross-reactive inhibitors.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

Thus, one embodiment of the present invention relates to a method for screening an anti-hepatitis C virus substance, comprising a) culturing at least one selected from the group consisting of a cell according to the present invention, a hepatitis C virus infected cell according to the present invention and a hepatitis C virus particle obtainable by the present invention together with a hepatitis C virus permissive cell, b) subjecting said virus or virus infected cell culture to the anti-hepatitis C virus substance, and c) detecting the replicating RNA and/or the virus particles in the resulting culture.

Another embodiment of the present invention relates to a method for screening an anti-hepatitis C virus substance, comprising a) culturing at least one selected from the group consisting of a cell according to the present invention and the hepatitis C virus particle according to the present invention together with a hepatitis C virus permissive cell, and
b) detecting the replicating RNA or the virus particles in the resulting culture.

Yet another embodiment of the present invention relates to a hepatitis C vaccine comprising a hepatitis C virus particle of the present invention or a part thereof.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

Another embodiment of the present invention relates to an antibody against the hepatitis C virus particle of the present invention.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modelling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 nM to 25 µM, more preferably from about 0.0001 nM to 10 µM, and even more preferably from about 0.0001 nM to 1 µM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology shows a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew Tupaiabelangerichinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The cell culture system developed of the present invention will be a valuable tool to address different research topics.

It will allow the isolate, subtype and genotype specific study of functions of all HCV genome regions and proteins using reverse genetics.

Accordingly the developed cell culture systems allow individual patient targeting. This means that when a new potential therapeutic candidate is discovered it is possible to test this particular candidate or combination of candidates on novel HCV isolates grown in culture.

Knowing which specific genotype the candidate is functioning towards, it allows an individual treatment of each patient dependent on which specific genotype the patient is infected with. Furthermore these cell culture systems allow the development of antibodies and vaccines targeting individual patients.

The replication level of a virus can be determined, in other embodiments, using techniques known in the art, and in other embodiments, as exemplified herein. For example, the genome level can be determined using RT-PCR, and northern blot. To determine the level of a viral protein, one can use techniques including ELISA, immunoprecipitation, immunofluorescence, EIA, RIA, and Western blotting analysis.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture.

In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

Furthermore the invention also provides test kits, for screening for new HCV inhibitors, neutralizing and cross neutralizing antibodies, comprising HCV virus components.

A further aspect of the present invention relates to a method for obtaining an isolated nucleic acid molecule encoding a human hepatitis C virus with adaptive mutations, comprising identification of one or more adaptive mutations as described in the above method, incorporation of said one or more adaptive mutations into a nucleic acid molecule encoding a full length human hepatitis C virus, and isolating the nucleic acid molecule encoding a human hepatitis C virus with adaptive mutations.

One embodiment of the present invention relates to an isolated nucleic acid molecule obtained from the above method.

Another embodiment of the present invention relates to an isolated nucleic acid molecule according to the present invention, wherein the human hepatitis C virus is of genotype 2b.

EXAMPLES

Example 1

Highly Efficient Infectious Cell Culture of Three HCV Genotype 2b Strains and Sensitivity to Lead Protease, NS5A, and Polymerase Inhibitors List of Abbreviations HCV, hepatitis C virus; DAA, direct acting antivirals; ORF, open reading frame; UTR, untranslated region; nt, nucleotide; aa, amino-acid; FFU/mL, focus forming units per milliliter; IU/mL, international units per milliliter; NI, nucleoside/nucleotide inhibitor; NNI, non-nucleoside inhibitor; PI, protease inhibitor.

Abstract

Hepatitis C virus (HCV) is a genetically diverse virus with multiple genotypes exhibiting remarkable differences, particularly in drug susceptibility. Drug and vaccine development will benefit from high-titer HCV cultures mimicking the complete viral life cycle, but such systems only exist for genotypes 1a and 2a.

The present inventors have developed efficient culture systems for the epidemiologically important genotype 2b. Full-length molecular clones of patient-strains DH8 and DH10 were adapted to efficient growth in Huh7.5 cells by using F1468L/A1676S/D3001G (LSG) mutations.

The previously developed J8cc prototype 2b recombinant was further adapted. DH8 and J8 achieved infectivity titers >4.5 Log 10 focus-forming units/mL. A defined set of DH8 mutations had cross-isolate adapting potential. A chimeric genome with the DH10 polyprotein coding sequence inserted into a vector with J8 untranslated regions was viable. Importantly, we succeeded in generating DH8, J8, and DH10 viruses with authentic sequences in the regions targeted by lead direct acting antivirals. NS5B inhibitors Sofosbuvir, Mericitabine, and BI207127 had activity against 1a (strain TN), 2a (strains JFH1 and J6), and the 2b strains, whereas VX-222 and Filibuvir only inhibited 1a.

Genotype 2b strains were least sensitive to seven lead protease inhibitors, including MK-5172 with high overall potency. NS5A inhibitor Daclatasvir was exceptionally potent, but efficacy was affected by the HCV strain. Conclusion: Highly efficient HCV full-length 2b culture systems can be established by using consensus clones with defined mutations.

Lead protease and NS5A inhibitors, as well as polymerase inhibitors Sofosbuvir, Mericitabine, and BI207127, show cross-activity against full-length 1a, 2a, and 2b viruses, but important sensitivity differences exist at the isolate level. Infectious cultures for different HCV strains will advance studies on viral biology and pathogenesis, and promote individualized patient treatment.

About 150 million people are infected with hepatitis C virus (HCV) worldwide, and over 350 thousand are estimated to die from associated chronic liver disease each year. The economic and social burden of hepatitis C is enormous, and efficient therapies and vaccines are needed. Infectious culture systems are important for HCV studies, contributing to drug and vaccine development. However, only few HCV strains can be studied due to the lack of efficient culture systems.

HCV is an enveloped, positive strand RNA virus from the family Flaviviridae. Its genome contains ~9600 nucleotides (nts) with a single open reading frame (ORF) flanked by 5' and 3' untranslated regions (UTRs). The polyprotein of ~3000 amino acids (aa) is processed into structural (Core, E1, and E2) and nonstructural (p7, NS2, NS3, NS4A, NS4B, NS5A, and NS5B) proteins with complex roles in the viral life-cycle. HCV presents significant genetic diversity with 6 epidemiologically important genotypes and numerous subtypes.

Viruses recovered from infected individuals are referred to as isolates or strains, and they circulate as quasispecies. Genotypes 1, 2, and 3 are the most prevalent and globally distributed. Genotype 2 is highly prevalent in West Africa and Asian countries like China and Japan. In the U.S, genotype 2 is the second in prevalence, with subtype 2b accounting for 10% of all infections. Genotypes 1 and 2 respond differently to standard Interferon/Ribavirin therapy, with genotype 2 infected patients achieving higher clearance rates. However, limited information is available about sensitivity of genotype 2 viruses to directly acting antivirals (DAAs), both in vivo and in vitro.

DAAs are expected to improve HCV clearance rates in patients with chronic hepatitis C. The sub-genomic replicon systems have been of major importance for discovery, development, and pre-clinical testing of these compounds, however, replicons do not recapitulate the complete viral life cycle and are not suitable for testing the effect of drugs beyond viral replication. Therefore it is essential to develop infectious culture systems for different HCV strains from the major genotypes and subtypes that reproduce all viral functions. Nevertheless, development of such systems has been a major challenge and they are only available for a few adapted genotype 1 and 2 isolates. Among these, only chimeric J6/JFH1(2a), JFH1(2a), J6(2a), and TN(1a) could release high-titer infectious virus particles in cell culture.

In this study the present inventors developed efficient full-length cell culture systems for three genotype 2b isolates. After long-term culture, viruses reached high infectivity titers by acquiring specific cell culture adaptive mutations that were then used to generate highly efficient molecular recombinants. These 2b systems permitted analysis of sensitivity to frontline HCV DAAs, in comparison to previously developed 1a and 2a full-length viruses. We found differential sensitivity to NS3/NS4A protease, NS5A, and NS5B inhibitors, both at the genotype and isolate level.

Importantly, we also identified frontline drugs that are efficient against all viruses, thus possibly overcoming HCV genetic diversity.

Materials and Methods

Viral Sequence Analysis and Reverse Genetics.

The consensus ORF sequence of two genotype 2b isolates, DH8 and DH10, was determined in sera of chronically infected patients from Denmark; the core-NS2 sequence was previously described. Full-length recombinants were assembled by chemical synthesis (Genscript) or standard molecular cloning; for DH10, the ORF was cloned into a vector with J8 UTRs. Nt changes for reverse genetics studies were introduced by standard cloning procedures. The complete HCV sequence of final plasmid preparations (HiSpeed Plasmid Maxi Kit, Qiagen) was sequence confirmed (Macrogen).

For determination of ORF sequences of cell culture derived viruses, the present inventors performed direct sequencing of overlapping amplicons (FIG. 5). Nt and aa positions are numbered according to the corresponding 2b genomes.

Transfection and passage of recombinant full-length HCV in Huh7.5 cells. Transfections with RNA transcripts were performed as reported. For viral passage, cell free supernatants were incubated with 4×105 Huh7.5 cells overnight. Cultures were split every 2-3 days and progression of infection was monitored by immunostaining on cells seeded in slides and co-stained with primary antibodies anti-core C7-50 (Enzo Life Sciences) and anti-NS5A 9E108, at dilution 1/25010. Infectivity titers expressed as Log 10 Focus Forming Units (FFU)/mL were determined as described. To improve staining, we used a mixture of anti-core C7- and anti-NS5A 9E10 at dilutions 1/450 and 1/1000, respectively. HCV RNA titers (IU/mL) on passage supernatants with peak infectivity titers were determined as previously described.

Antiviral Treatments in Huh7.5 Cells.

HCV infected cultures were treated with NS3 Protease, NS5A, and NS5B polymerase inhibitors (purchased from Acme Bioscience) in a high throughput assay. Immunostaining of fixed 96-well plates was performed using anti-core C7- and anti-NS5A 9E10 at dilutions 1/450 and 1/1000, respectively.

Concentration-response curves and EC50 values were calculated. The non-cytotoxic dose ranges for all drugs were determined with a cytotoxicity assay (CellTiter 96 AQueous One Solution Cell Proliferation Assay, Promega).

Generation of HCV Full-Length Clones of Genotype 2b

The complete ORF sequence of HCV from isolates DH8 and DH10 was determined from serum samples of two patients infected with genotype 2b, from Denmark. The sequence of the region encompassing Core to NS2 of DH8 and DH10 had been previously described. The rest of the ORF was deduced from TA-cloned PCR products spanning from NS2 to the variable region of the 3' UTR, with an overlap of 925 nucleotides with the previously determined Core-NS2 sequence.

In more detail, for determination of viral consensus sequences, viral RNA was extracted from 200 microliters (µL) of serum using the High Pure Viral RNA Kit (Roche Applied Science) and subjected to cDNA synthesis using Superscript III system (Invitrogen) with a genome specific reverse primer annealing to the 3'UTR variable region of HCV (5'-GCAAACCCTAGCTACACTCCATAG-3'). Three µL of cDNA were used in a PCR (Advantage 2 polymerase, Clontech) with primers annealing to NS2 and the variable region of the 3'UTR (forward: 5'-TGGTGGCTGTCCTA-CATGCTG-3' and reverse: 5'-GCAAACCCTAGCTA-CACTCCATAG-3') generating an amplicon covering the HCV genome from nucleotides 2892 to 9385, according to H77 reference sequence (AF009606). These amplicons were TA cloned (TOPO TA cloning kit, Invitrogen) and the sequence of multiple clones was analyzed (Macrogen, Sequencher, ClustalX, MEGA). A consensus sequence for the targeted region was determined and combined with the Core-NS2 sequence to generate a complete HCV ORF sequence for both isolates.

For the isolate DH8, five clones were analyzed, and three populations were observed based on pairwise genetic distance analysis. Two of them contained only one clone and the third population included 3 clones that were the genetically most related. Therefore, the consensus was based on this third population. For the DH10 isolate, the ORF was based on the sequences of six clones. According to pairwise genetic distance analysis, the clones were divided into three populations. The first population contained a single clone, the second population comprised two clones and the remaining three clones were grouped in a third population. The consensus was based in populations one and three; the second population was excluded due to its higher genetic distance in respect to the other two.

For DH8, we determined the 5'UTR sequence and partial 3'UTR. Briefly, 5'RACE of the 5'UTR was performed as previously described and after TA cloning of amplicons, a consensus sequence was made from 3 clones. The first nucleotide of the 5'UTR for DH8 was Guanine (G). A partial 3'UTR sequence encompassing the variable region, poly U/UC and 16 nucleotides of the X tail was determined by nested PCR as previously described. The 3'UTR consensus sequence was determined from 14 clones. The variable region of the 3'UTR was identical in all clones and also with previous published variable region sequences of genotype 2b isolates (AB030907 and AB559564). The poly(U/UC) tract had the same structure in all clones UUCCUnCUUCU6AU5CCUUCUUUCUU where "n" varied among clones (range 26-34). We decided to elaborate a consensus polyU/C that respected the overall structure but that contained a longer Un; specifically 59 U residues at this position, in order to reach the final length of the 3'UTR sequences of JFH-1 (AB047639) and J8CF (JQ745651). With nested PCR protocol, we could only obtain the first 16 nucleotides of the 3'X tail; since they were identical to the 2b isolate JPUT (AB030907), we decided to use the remaining 82 nts of the 3'X tail sequence from this isolate generating DH8CF.

By using the backbone plasmid DH8/JFH1 (DH8 Core-NS2 JFH1 recombinant) the present inventors chemically synthesized the rest of the ORF and 5' and 3'UTR sequences (Genscript) and assembled the fragments using AfeI, SfiI, BamHI and XbaI restriction sites, thus generating a full-length HCV molecular clone of a new genotype 2b isolate, DH8CF.

The HCV full-length clone for DH10 was generated after combining the complete ORF with UTRs from J8CF (JQ745651). To assemble a full-length HCV clone for DH10, the backbone plasmid DH10/JFH1 (DH10 Core-NS2, JFH1 recombinant) was used. The remaining DH10 ORF sequence and UTR sequences of J8CF were chemically synthesized (Genscript) and the full-length HCV molecular clone was assembled with SpeI, BamHI, MreI and XbaI restriction sites. The generated DH10 full-length clone contained the adaptive mutations F1468L, A1676S, and D3001G and therefore was named DH10_LSG.

ORF Sequence Analysis of Cell Cultured Viruses

Viral RNA was extracted from 200 µL of cell free culture supernatant using the High Pure Viral RNA Kit (Roche Applied Science) and subjected to cDNA synthesis using Superscript III system (Invitrogen) with a genome specific reverse primer annealing to the 3'UTR variable region of HCV (FIG. 5). Three µL of cDNA were used in a PCR (Advantage 2 polymerase, Clontech) with primers annealing to the 5'UTR and the variable region of the 3'UTR (FIG. 5). For the 2nd round PCR, 2.5 µL of 1st round PCR was subjected to 11 overlapping PCRs encompassing the entire ORF with specific genotype 2b primers (FIG. 5). Amplicons were sequenced (Macrogen), assembled, and analyzed (Sequencher).

Results

Development of a Highly Efficient Full-Length HCV Cell Culture System for Genotype 2b, Strain DH8.

Based on the consensus sequence of patient strain DH8, we generated a novel full-length clone (DH8CF); the ORF consisted of 9099 nts, encoding 3033 aa. The DH8CF ORF differed by 8.4% and 5.3% at the nt and aa level, from the prototype 2b full-length clone J8CF (JQ745651). RNA transcripts of DH8CF were transfected into Huh7.5 cells, in three independent experiments. No HCV positive cells were detected during 53, 12, and 10 days, respectively. Thus, wild-type DH8 was non-viable in Huh7.5 cells.

Figure 6:
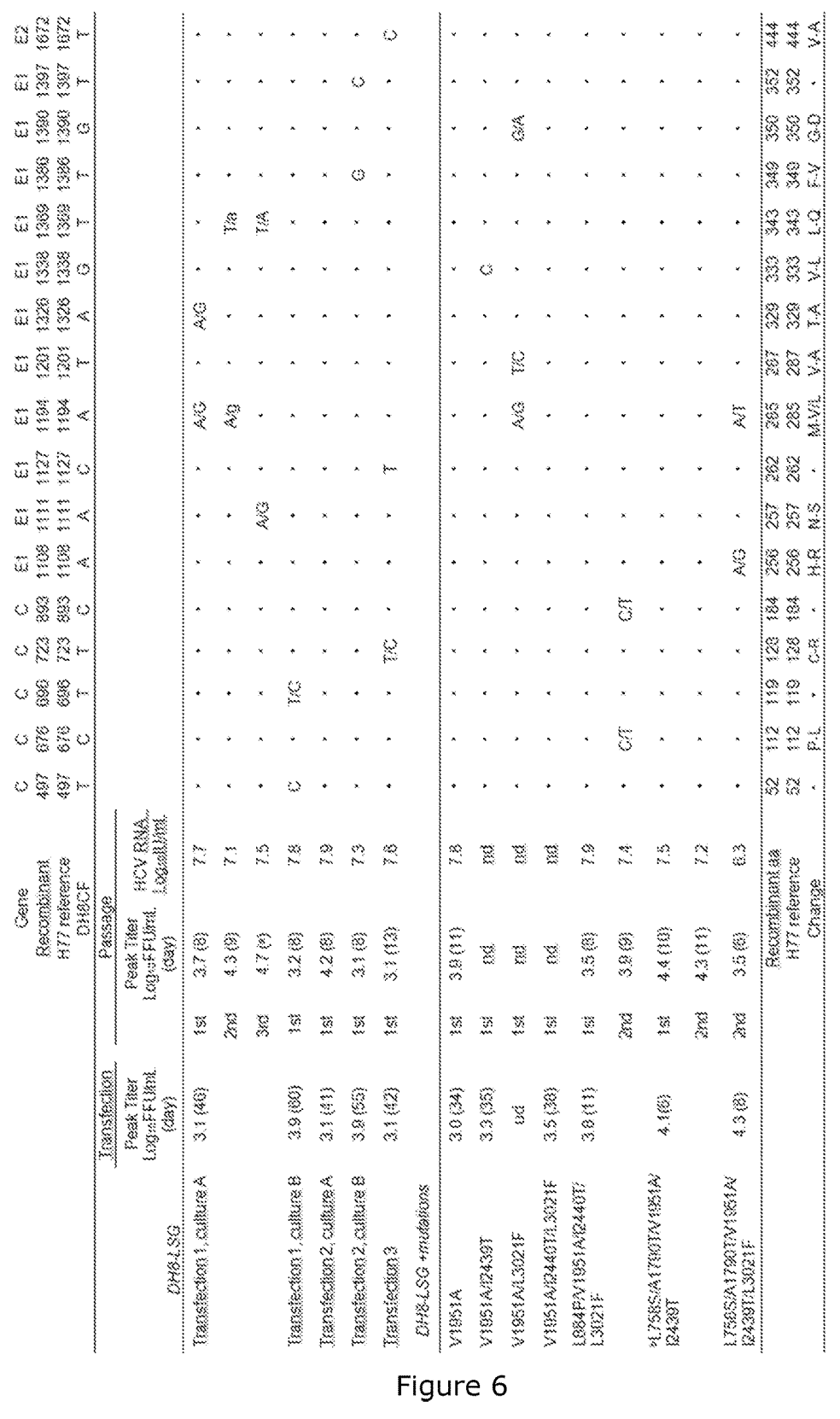
Figure 6:
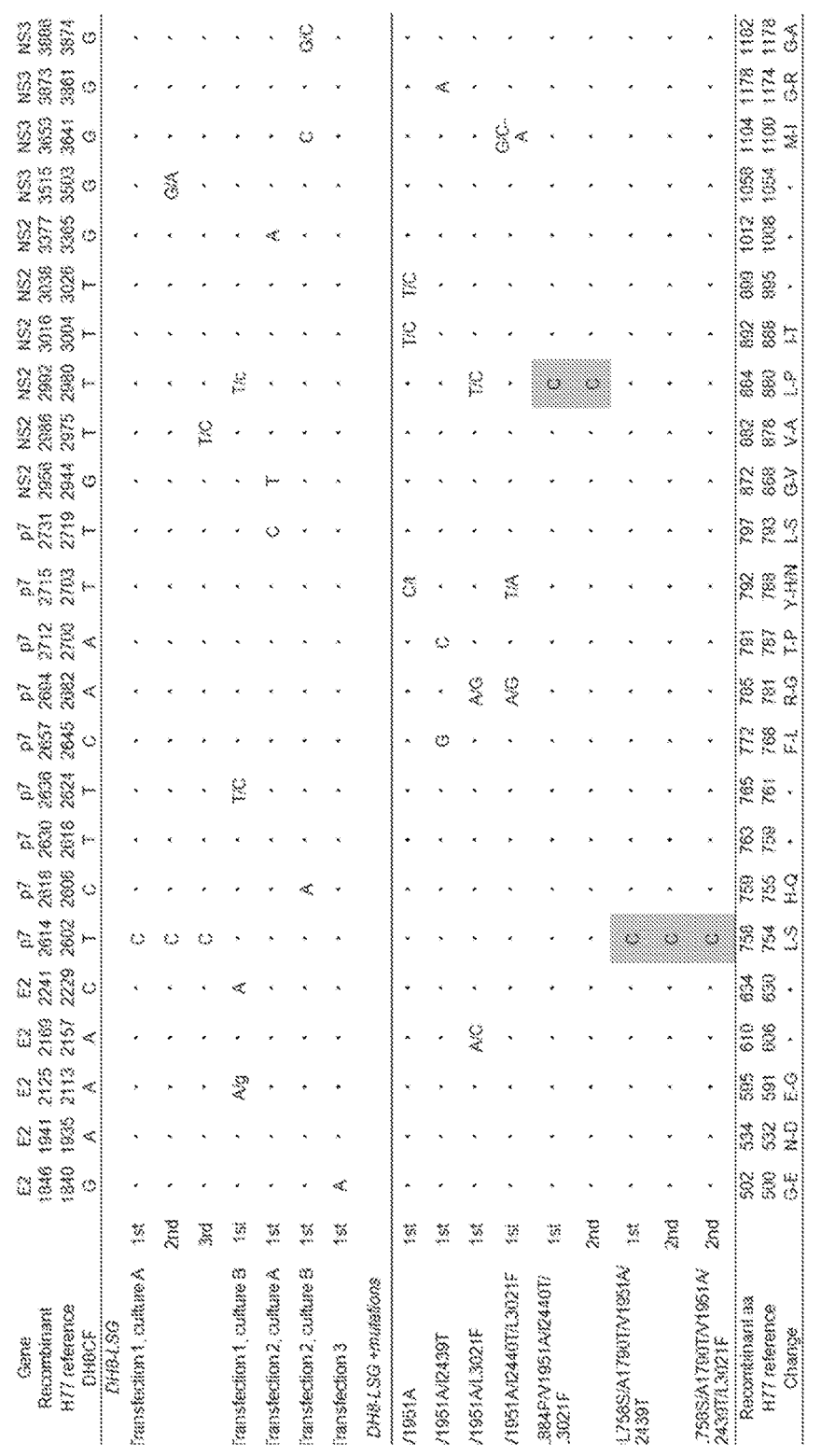
Figure 6:
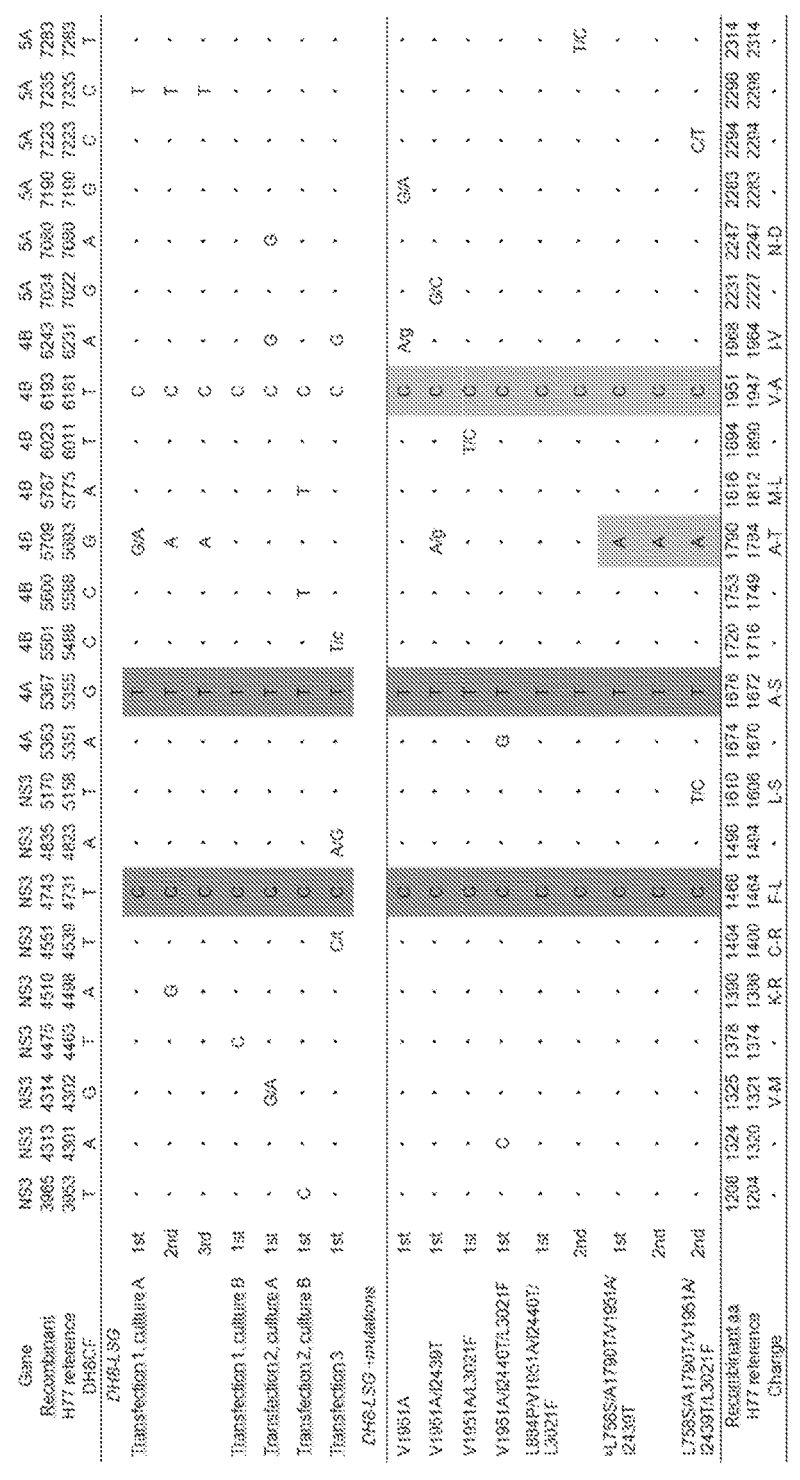
Figure 6:
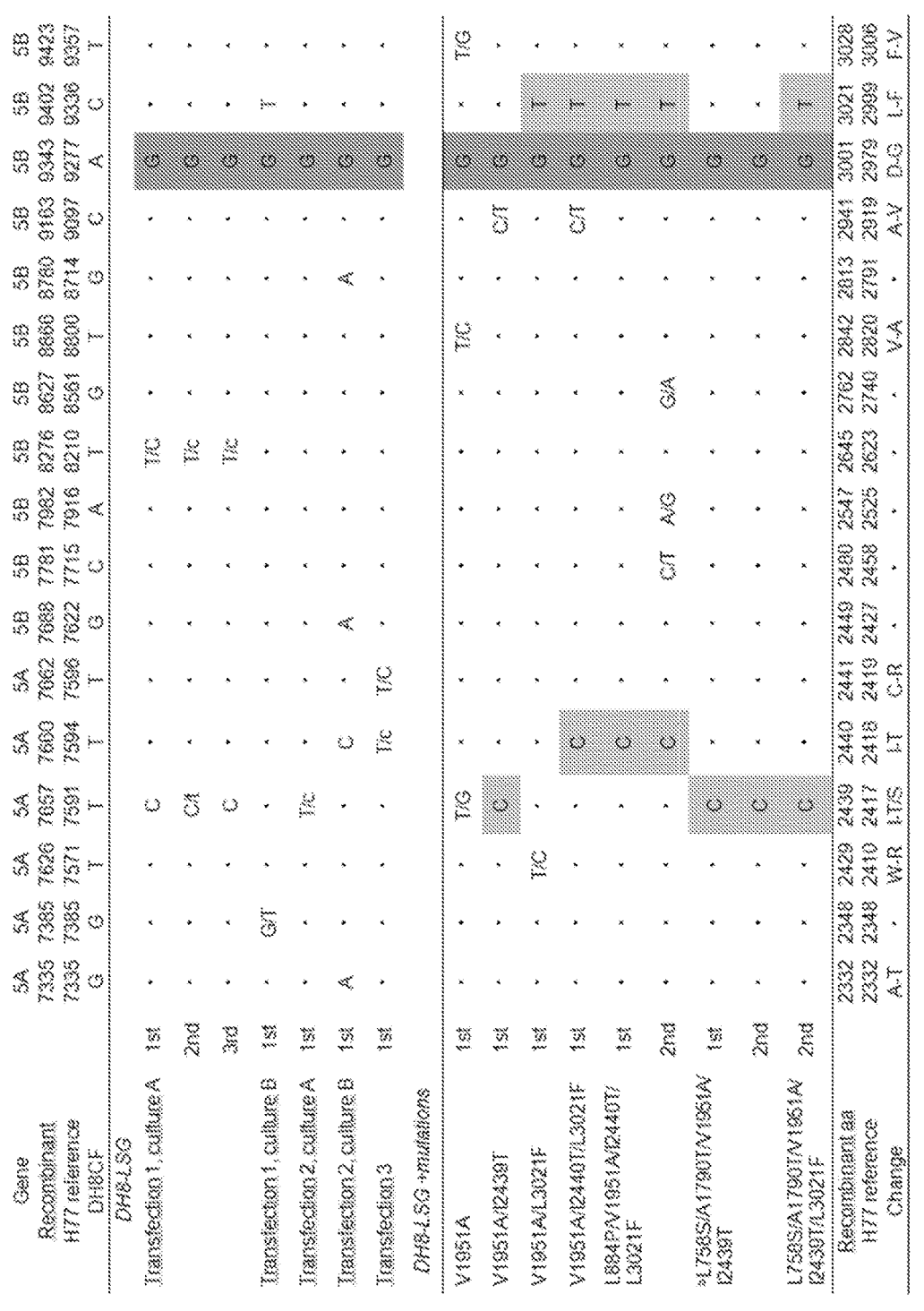

The present inventors recently described mutations F1468L (NS3 helicase), A1676S (NS4A), and D3001G (NS5B) in genotype 2a, designated LSG, that were instrumental for culture adaptation of full-length clones J6CF, J8CF, and TN. The present inventors performed three independent transfections of Huh7.5 cells with DH8CF containing LSG, designated DH8_LSG; HCV positive cells were observed from day 1. At day 9, two transfection-cultures were split into two replicates (A and B) for a total of 5 cultures followed long-term (FIGS. 6 and 8).

Spread of infection (defined as ≥80% HCV-antigen positive cells) was observed at days 36-53, with HCV infectivity titers of 3.1-3.9 Log 10 FFU/mL. In 1st viral passage to naïve Huh7.5 cells, viruses spread at days 5-8 reaching 3.1-4.2 Log 10 FFU/mL. The ORF sequences of DH8_LSG recovered from all five 1st passages were determined (FIGS. 6 and 8). Coding changes were present in multiple genes, but V1951A (NS4B) was a common aa change. Also, four of five cultures had I to T change at either aa position 2439 or 2440 in NS5A.

To generate an efficient DH8 recombinant, we tested the effect of V1951A (NS4B), which emerged in all transfections, in DH8_LSG. However, the virus did not spread until day 27, with titers of 3.0 Log 10 FFU/mL (FIG. 6). After passage, the virus had acquired multiple changes, including I2439I/S. Since changes of I2439 were observed during DH8_LSG passages, we next tested DH8_LSG/V1951A/I2439T. After transfection, the virus spread at day 33, with titers of 3.3 Log 10 FFU/mL, and showed additional coding changes (FIG. 6). Thus, V1951A alone or the combination V1951A/I2439T was not sufficient for full adaptation of DH8_LSG.

Since the DH8_LSG transfection 1B virus had only the dominant change L3021F (NS5B), in addition to V1951A, we tested DH8_LSG/V1951A/L3021F. This recombinant had delayed spread (day 27) with low titers, and recovered viruses had acquired several changes including quasispecies L884L/P (NS2) and W2429W/R (NS5A) (FIG. 6). We thus added I2440T (NS5A) with or without L884P to DH8_LSG/V1951A/L3021F. Spread of DH8_LSG/V1951A/I2440T/L3021F and DH8_LSG/L884P/V1951A/I2440T/L3021F occurred at days 27 (3.5 Log 10 FFU/mL) and 6 (3.8 Log 10 FFU/mL, FIG. 1A) post-transfection, respectively. DH8_LSG/L884P/V1951A/I2440T/L3021F reached titers of 3.9 Log 10 FFU/mL in 2nd passage. The recovered virus had nt changes but none resulted in dominant aa substitutions (FIG. 6). Thus, we had developed an efficient full-length infectious DH8 recombinant.

In an alternative approach we engineered the 4 dominant coding changes from the 3rd passage of transfection 1 culture A, with infectivity titers of 4.7 Log 10 FFU/mL (FIGS. 6 and 8). The resulting recombinant DH8_LSG/L758S/A1790T/V1951A/I2439T spread at day 6 after transfection, reaching 4.1 Log 10 FFU/mL (FIGS. 1A and B); it had peak titers of 4.4 and 4.3 Log 10 FFU/mL after 1st and 2nd passage, respectively. The ORF sequence of the 2nd passage virus showed no additional mutations, suggesting that the virus was genetically stable. Since NS5B mutations had an important role in adaptation of previously developed full-length cell culture systems, we explored the benefit of adding L3021F; after transfection, DH8_LSG/L758S/A1790T/V1951A/I2439T/L3021F spread at day 6 with titers of 4.3 Log 10 FFU/mL (FIG. 1A). After 2nd passage, the recovered virus had 3 coding changes as quasispecies (FIG. 6). Thus, the addition of L3021F did apparently not improve viability.

Taken together, the reverse genetics experiments demonstrated that L758S, A1790T, V1951A and I2439T mutations most efficiently adapted DH8_LSG, resulting in high HCV infectivity titers. The present inventors thus named this recombinant DH8cc.

Development of a high titer culture system for the prototype 2b strain, J8. Since the present inventors had generated a highly efficient DH8 culture system using mutations identified from serial passage of DH8_LSG, we set out to improve the efficiency of our published genotype 2b system J8cc, by serial passages. J8cc contained LSG/F772C/W864R/A1208T/I1968V/E2263V/H2922R, and reached 3.2 Log 10 FFU/mL after transfection 10. Here, the present inventors found that infectivity titers increased to >4.6 Log 10 FFU/mL in 4th and 5th passage in Huh7.5 cells, and 7 additional coding changes were identified (FIG. 9); one of these changes, I2440T, had also appeared in DH8_LSG (FIG. 8). We then generated J8cc/M292L/L612M/G1154A/N1217Y/Q1763R/I2440T, which spread at day 3 post-transfection and reached infectivity titers of 4.7 Log 10 FFU/mL (FIG. 1B); the recovered passaged virus had no nt changes (FIG. 9). This efficient J8 recombinant was designated J8cc-HT, for "J8 cell culture, high titer".

Development of a Chimeric Genotype 2b Culture System Expressing the Polyprotein of Strain DH10 Using J8 5' and 3' UTR Sequences.

Genetic divergence of HCV isolates is concentrated in the ORF, which encodes the proteins that participates in the viral life cycle and are targeted by the most advanced DAAs. In contrast, the untranslated regions are the most conserved genomic elements of HCV, required for replication and translation. Determination of 3'UTR sequences from HCV isolates is a technical challenge, often requiring high titer serum samples or liver tissue. Therefore, we explored the possibility of generating a viable chimeric genome by inserting the ORF of a 2b patient isolate (strain DH10) into a vector containing the 5' and 3' UTRs of the prototype 2b (strain J8). The length of the DH10 ORF is 9099 nt, encoding 3033 aa. At the nt level, the DH10 ORF differs from J8 and DH8 by 8.8% and 8.5%, respectively, and at the aa level the difference is 5.9% and 5.5%. To test viability of this chimeric genome in vitro, we inserted the LSG mutations (recombinant designated DH10_LSG).

Figure 7:
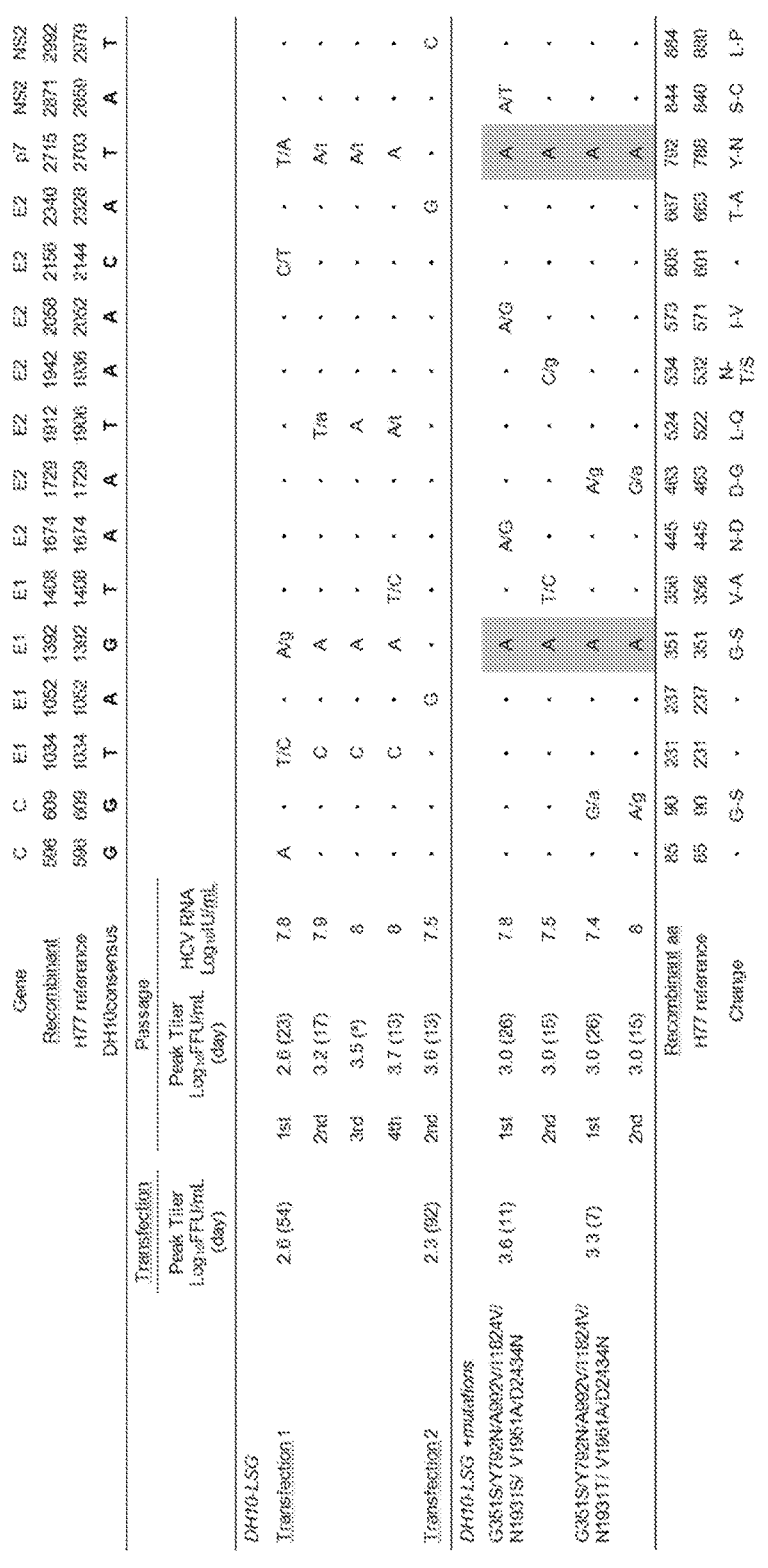
Figure 7:
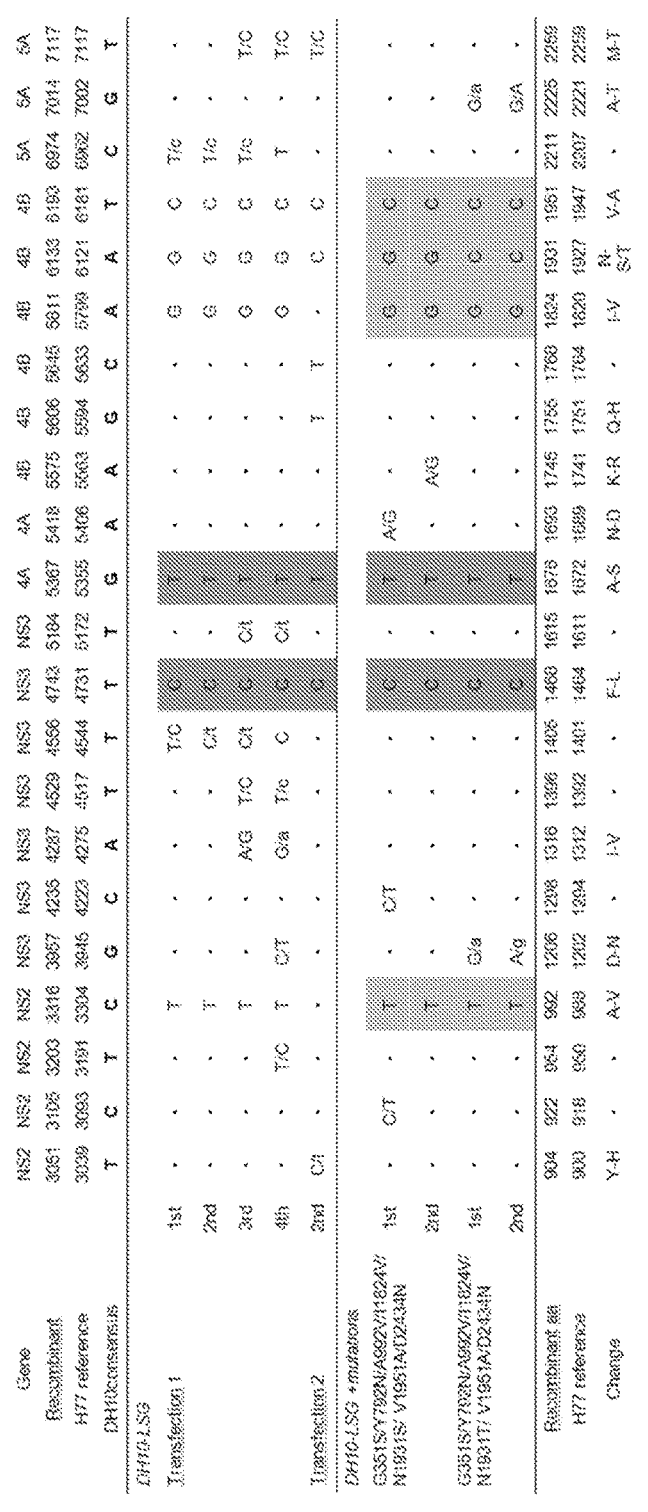

Two independent transfections of DH10_LSG were performed (FIG. 10 and FIG. 7). In transfection 1, positive cells were observed at day 10 and the virus spread at day 47, reaching 2.6 Log 10 FFU/mL. However, in transfection 2, positive cells were not observed consistently until day 64, and spread occurred at day 83, reaching 2.3 Log 10 FFU/mL. We performed serial passages of transfection 1 virus, and reached infectivity titers of 3.7 Log 10 FFU/mL in 4th passage. The ORF sequence presented various coding changes, including NS4B mutations V1951A, (observed also in DH8_LSG) and N1931S (observed in J6 and TN full-length viruses). Second passage viruses from transfection 2 had titers of 3.6 Log 10 FFU/mL and interestingly, changes V1951A and N1931T (S in transfection 1) were also present.

To generate an efficient DH10_LSG recombinant, we initially tested the adaptive potential of V1951A (NS4B). After transfection, DH10_LSG/V1951A spread at day 49, confirming that V1951A was not sufficient for adaptation. We then combined 7 aa changes observed in 1st passage of DH10_LSG, generating two recombinants, DH10_LSG/G351S/Y792N/A992V/I1824V/N1931X/V1951A/D2434N (X corresponds to T or S, respectively). After transfection, both viruses behaved similarly, spreading at day 5 with titers of 3.6 and 3.3 Log 10 FFU/mL, respectively (FIG. 1B, FIGS. 6 and 10). The ORF sequence of the passaged virus with N1931S showed only 1 dominant coding change, N534T (E2) (FIG. 10). In contrast, the N1931T virus had several dominant coding changes (FIG. 6). Overall, it was possible to generate a 2b culture system by using the ORF from a patient isolate inserted into a vector with J8 5' and 3' UTRs.

HCV genetic divergence influences the sensitivity to lead direct acting antivirals. Our developed full-length culture systems permit the study of frontline HCV DAAs in the context of the complete HCV life cycle. Thus, we determined the efficacy of DAAs targeting different viral proteins against genotype 1a (strain TN), 2a (strain J6 and recombinant J6core-NS2/JFH18, referred to as JFH1, since it has the JFH1 protease, NS5A and NS5B), and 2b (strains DH8, J8, and DH10). For 2b viruses we used 3rd passage DH8_LSG, 5th passage J8cc, and 3rd passage DH10_LSG (FIGS. 6-10).

Analysis of NS5B Inhibitors.

The present inventors analyzed the efficacy of the most advanced NS5B nucleoside/tide inhibitors (NIs) and non-nucleoside inhibitors (NNIs), currently in phase 2 or 3 clinical trials (FIG. 2A-C and FIG. 11). Polymerase inhibitors had not previously been tested on genotype 2b viruses, and in addition the NNIs had not been tested on genotype 1a viruses.

Sofosbuvir (nucleotide analog) and Mericitabine (nucleoside analog) both inhibited 1a, 2a, and 2b viruses in a dose-dependent manner (FIG. 2A). However, Sofosbuvir had lower EC50 values indicating higher potency of the nucleotide analog (FIG. 11). For both drugs the most sensitive virus was J6(2a); the TN(1a), JFH1(2a) and the 2b viruses had similar EC50 values.

In contrast to NI, NNI apparently lack pan-genotypic activity. In this study we tested two thumb II inhibitors, VX-222 and Filibuvir, and a thumb I inhibitor, BI207127. VX-222 and Filibuvir inhibited TN(1a) in a dose dependent manner (FIG. 2B); VX-222 was the most potent inhibitor (FIG. 11). However, these two NNI drugs had no or very limited inhibition of the 2a and 2b virus strains at non-cytotoxic drug concentrations (FIG. 2B). In contrast, thumb I inhibitor BI207127 was able to inhibit all viruses in a dose dependent manner (FIG. 2C), being as potent against most genotype 2 strains as Sofosbuvir (FIG. 11). TN(1a) appeared to be the most sensitive virus to this drug and moreover, BI207127 was the polymerase inhibitor that most efficiently suppressed infectivity of the 1a virus (FIG. 11).

Analysis of NS5A Inhibitor.

We assessed the activity of lead NS5A inhibitor Daclatasvir, which has not been previously tested on genotype 2b viruses. Overall, this drug inhibited all viruses and showed high potency (FIG. 2D). Daclatasvir is the inhibitor that shows the lowest EC50 values of all antivirals tested in this study (FIG. 11), however, it is also the drug that shows the higher differences in activity among strains of the same genotype and subtype. Viruses could be divided into two groups; those inhibited at sub-nanomolar drug concentration: JFH1(2a), DH8(2b), and TN(1a), and those inhibited at nanomolar concentration: J6(2a), J8(2b), and DH10(2b).

Analysis of NS3/4a Protease Inhibitors (PI).

The PIs selected in this study have not been previously tested against genotype 2b viruses, and in addition the data on the MK-5172 is also the first reported activity against 1a cell culture viruses. The tested PIs inhibited all viruses in a dose dependent manner (FIG. 3A-C). For the two licensed PIs, Boceprevir and Telaprevir, J8(2b) and TN(1a) were most sensitive (FIG. 11). TN(1a) was most sensitive to other PIs in phase 3, except for Simeprevir, where J8(2b) had a lower EC50 (FIG. 11). Phase 2 MK-5172 showed higher potency than any other PIs, with TN(1a) and JFH1(2a) being the most sensitive viruses (FIG. 11). Overall, licensed and phase 3 NS3/4A inhibitors had differential efficacy against 1a, 2a, and 2b full-length viruses, with some marked differences between isolates of genotype 2b. The phase 2 next-generation drug MK-5172 showed remarkably higher potency than other Pis tested, but it also presented differential efficacy against various HCV strains from the same genotype/subtype.

Development of an efficient J8 full-length cell culture virus with authentic protease sequence reveals that adaptive protease mutations influenced sensitivity to PIs. Due to the different pattern of susceptibility to PI drugs observed for J8(2b) in comparison to DH8(2b) and DH10(2b), we hypothesized that adaptive mutations present in the protease domain of NS3 in the J8cc 5th passage virus (FIG. 9) might have been responsible for the general increase in sensitivity of this virus; DH8 and DH10 viruses did not have protease mutations. Therefore we set out to generate an efficient J8 virus that was not dependent on adaptive protease mutations.

Since combination of LSG with mutations in p7 (L758S), NS4B (A1790T and V1951A) and in NS5A (either I2439T or I2440T, that had also emerged in J8cc passages) adapted DH8, and the resulting viruses did not have any protease mutations, we tested their cross-isolate adaptation potential in J8. We generated the recombinant J8_LSG/L758S/A1790T/V1951A/I2440T, which spread at day 5 after transfection, reaching titers of 3.8 Log 10 FFU/mL (FIG. 1B). The 2nd passage virus ORF sequence had only two changes, both in the NS3 helicase domain (FIG. 9). Thus, we had generated an efficient J8 virus with authentic NS3 protease (designated J8_LSG/STAT).

The present inventors performed new PI treatment assays using J8_LSG/STAT (2nd passage) and the original J8 (with protease adaptive mutations), for direct comparisons (FIG. 4). For all drugs tested, J8_LSG/STAT showed decreased susceptibility when compared to the original J8 with protease adaptive mutations, and the EC50 values for J8_LSG/STAT were similar to those for DH8 and DH10 (FIG. 4; FIG.

9). These results indicate a role of adaptive protease mutations G1154A and A1208T in the phenotype of increased sensitivity of J8.

Discussion

Full-length HCV culture systems that represent all viral genotypes and important subtypes will benefit drug and vaccine development for this important human pathogen. However, so far only adapted recombinant JFH1(2a), J6(2a), and TN(1a) strains yielded high titer cultures. In the present study, we developed efficient full-length cell culture systems for genotype 2b strains DH8, J8, and DH10, of which DH8 and J8 yielded high infectivity titers. Recombinants were adapted to growth in Huh7.5 cells and a defined set of mutations could adapt two strains proving cross isolate effect. Efficient cell culture of DH10 was achieved by determining only the patient derived ORF sequence, which was inserted into a cassette containing the 5' and 3'UTR from J8. These findings might facilitate the development of HCV culture systems for other genotype 2b isolates, as well as for other genotypes and subtypes.

The present inventors tested, for the first time, lead HCV inhibitors against full-length genotype 2b viruses. Our results reveal a differential activity of these drugs towards full-length genotypes 1a, 2a, and 2b viruses. Genotype 2b is less sensitive to most protease inhibitors and the efficacy of Daclatasvir against genotypes 2a and 2b is largely influenced by HCV variability at the isolate level. We have demonstrated that not only NIs (Sofosbuvir and Mericitabine) are active against non-genotype 1 viruses, but also the NNI BI201127 possess activity against full-length 1a, 2a, and 2b viruses, suggesting unique pan-genotypic properties among NNIs.

Development of infectious full-length cell culture systems for HCV has been a major challenge, since molecular clones of HCV generated from patient sequences do not spontaneously replicate and spread in vitro. Approaches that used sub-genomic replicon derived mutations to adapt full-length clones have only led to culture systems with relatively low infectivity, possibly because replicon mutations introduce constraints in viral production. The present inventors recently identified three mutations in the NS3 helicase, NS4A, and NS5B, named LSG, that promoted adaptation of HCV genotype 1 and 2 full-length clones, and used them to adapt novel genotype 2b isolates in the present study. Similarly to J8, LSG permitted in vitro growth of DH8 and DH10. Besides LSG, additional mutations were required for production of viruses with high infectivity titers. These mutations represent unique amino acids that are rarely present in natural patient derived sequences. A1951 and V1968, in NS4B, are found in less than 1% of genotype 2b sequences (Los Alamos HCV Database) and T2439 or T2440 are not present in any of the 73 deposited NS5A 2b sequences. In addition, we had previously demonstrated that changes at amino acids 1931 (NS4B), 1968 (NS4B) and 2439 (NS5A) constitute key adaptive mutations in cell culture systems.

The present inventors also demonstrated that it is possible to develop functional chimeric genomes by inserting the ORF of a 2b isolate into a cassette vector with 5'/3'UTR of another 2b isolate, for which the UTR's were known to be functional in vitro. This finding is of major relevance for the culture of clinical isolates, since the sequence of the UTRs is technically difficult to obtain. Similar chimeric genomes have been proven functional in vivo.

The full-length cell culture systems permit us to explore the evolutionary potential of HCV. Viruses can adapt to cell culture by acquiring different combinations of mutations and maintaining wild type sequences in specific genes or domains. We generated genotype 2b viruses that did not have any changes in the NS3 protease, NS5A domain I, and NS5B finger, palm, and thumb domains (except c-terminal portion), making them optimal tools for the study of most DAAs. Contrarily, replicon based systems often accumulate mutations in the protease domain of NS36, potentially affecting the natural isolate sensitivity towards PIs. The importance of using viruses without cell-culture adaptive mutations in the NS3 protease domain was demonstrated for the J8 isolate, where viruses with mutations G1154A and A1208T had increased drug sensitivity when compared to J8 viruses without these changes. Similarly, we succeeded in developing cell culture adapted viruses for DH8, which did not contain mutations in p7, and which could be of importance for functional or drug studies targeting this important viral protein.

The present inventors tested sensitivity of full-length viruses to selected front line DAAs targeting NS3/4A protease, NS5A, and NS5B polymerase. Currently there are very limited data on the activity of PIs in genotype 2 patients; small studies have suggested a benefit of Telaprevir and Boceprevir when added to therapy with Interferon/Ribavirin. In our in vitro systems, most PIs had higher activity against TN(1a) than against genotype 2 isolates. Among genotype 2, isolates from subtype 2b were generally less sensitive to tested PIs, in comparison with 2a isolates. These findings stresses the importance of subtype determination in the clinical setting, which may be of more relevance in the era of DAA-based therapy. Our data on PI MK-5172, highlighting its exceptional higher antiviral potency when compared to other PIs, represent the first reported testing of this drug in HCV full-length cell culture systems of various genotypes. Similarly to MK-5172, NS5A inhibitor Daclatasvir was shown to be a highly potent HCV inhibitor, but its activity was most influenced by HCV genetic divergence at the isolate level for genotype 2b, as previously indicated for genotypes 1a and 2a. Importantly, for all our viruses, NS5A domain I, the target region of Daclatasvir, represented authentic patient-derived sequences without cell culture adaptive mutations.

Thus, natural sequence variation was responsible for these extensive differences. NS5B inhibitors currently in phase 2 and 3 clinical trials are among the most promising anti-HCV drugs. However, they have not been extensively studied in cell culture viruses for different genotypes and subtypes, due to the lack of culture systems with genotype specific polymerases. In the present work, we report the effect of front line polymerase inhibitors on full-length viruses of genotypes 1a, 2a, and 2b. As expected, NIs Mericitabine and Sofosbuvir were active not only against 1a, but also against 2a and 2b, which is in agreement with their apparent pan-genotypic activity in patients infected with genotypes 1, 2, and 3, in combination with Interferon/Ribavirin.

The present inventors investigated the activity of front line NNIs currently in phase 2, Filibuvir, VX-222 and BI207127. Filibuvir has been reported to significantly reduce HCV titers in clinical studies, when used in monotherapy, in genotype 1 infected patients. Our data supports the efficacy of Filibuvir and VX-against genotype 1 but reveals limited or no activity against genotype 2 viruses. Contrarily, the NNI BI207127 was active against all viruses. Efficacy against genotype 2 was similar to that of Sofosbuvir, while efficacy against TN(1a) was higher for BI207127 than for Sofosbuvir. This might be explained by the fact that NNIs target the different pocket (or allosteric) sites of the RNA polymerase, which present higher genetic variability among HCV genotypes. In addition, they could be specific for genotype 1, since they have been mostly developed using Con1 replicons. Therefore, significant differences in antiviral activity against genotype 1 and non-1 viruses are expected. Among the different allosteric sites that are targeted by current advanced thumb-NNIs, our results with BI207127 supports that thumb pocket I is the preferable target of future NNIs with potential pan-genotypic activity.

In conclusion, we have established efficient cell culture systems for three HCV genotype 2b isolates. Approaches applied in viral adaptation should have relevance for advancing culture development for other 2b isolates, and perhaps other genotype strains. These systems represent authentic patient derived sequences in all the corresponding targets of the most relevant DAAs, making them optimal models for the study of antivirals. These full-length systems will, for the first time, permit the study of combination treatment with drugs targeting all structural and non-structural proteins in genotype 2b. They will allow future studies promoting escape to current DAAs, in the context of the whole genetic background of HCV. Finally, since the viruses generated mimics all the steps of the HCV life cycle they will permit genotype specific functional studies of all viral proteins, thus promoting drug and vaccine development.

The invention claimed is:

1. An isolated nucleic acid molecule, which encodes a human hepatitis C virus, wherein the hepatitis C virus is derived from genotype 2b and comprises the mutations F1468L in NS3, A1676S in NS4A, and D3001G in NS5B, and wherein the isolated nucleic acid molecule further comprises adaptive mutations:

(i) L758S, A1790T, V1951A, and I2439T; or (ii) L884P, V1951A, I2440T, and L3021F.

2. The isolated nucleic acid molecule according to claim 1, which is strain J8cc-HT having the nucleic acid sequence set forth in SEQ ID NO:14.

3. The isolated nucleic acid molecule according to claim 1, which is strain J8_LSG/STAT having the nucleic acid sequence set forth in SEQ ID NO:15.

4. The isolated nucleic acid molecule according to claim 1 that has an open reading frame (ORF) nucleic acid sequence with 90% sequence identity to SEQ ID NO:56.

5. The isolated nucleic acid molecule according to claim 1, which is strain DH10_LSG having the nucleic acid sequence set forth in SEQ ID NO:10 or strain DH10cc having the nucleic acid sequence set forth in SEQ ID NO:13.

6. The isolated nucleic acid molecule according to claim 1, which is strain DH8cc having the nucleic acid sequence as set forth in SEQ ID NO:8 or strain DH8_LSG_PATF having the nucleic acid sequence as set forth in SEQ ID NO:7.

7. The isolated nucleic acid molecule according to claim 1, wherein the strain is DH8cc having the nucleic acid sequence as set forth in SEQ ID NO:8.

8. A method for producing a cell, which replicates human hepatitis C virus and produces a virus particle comprising introducing the nucleic acid molecule of claim 1 into a cell.

9. A method of screening for an anti-hepatitis C virus substance, comprising: a) culturing a cell comprising the nucleic acid molecule of claim 1 with a hepatitis C virus permissive cell, b) contacting the cell with a candidate anti-hepatitis C substance, and c) measuring the level of replicating RNA or virus particles in the resulting culture and comparing the level to that of a control.

* * * * *

SEQUENCE LISTING

<160> NUMBER OF SEQ ID NOS: 56

<210> SEQ ID NO 1
<211> LENGTH: 9663
<212> TYPE: DNA
<213> ORGANISM: Hepatitis C virus

<400> SEQUENCE: 1

```
gcccgcccc  taatggggc  gacactccgc  catgaatcac  tcccctgtga  ggaactactg      60
tcttcacgca  gaaagcgtct  agccatggcg  ttagtatgag  tgtcgtacag  cctccaggcc    120 ccccctccc   gggagagcca  tagtggtctg  cggaaccggt  gagtacaccg  gaattaccgg    180
aaagactggg  tcctttcttg  gataaaccca  ctctatgtcc  ggtcatttgg  gcgtgcccc     240 gcaagactgc  tagcctagta  gcgttgggtt  gcgaacggcc  ttgtggtact  gcctgatagg    300
gtgcttgcga  gtgccccggg  aggtctcgta  gaccgtgcat  catgagcaca  aatcctaaac    360
ctcaaagaaa  aaccaaaaga  aacacaaacc  gtcgcccaca  ggacgtcaag  ttcccgggtg    420
gcggtcagat  cgttggcgga  gtttacttgc  tgccgcgcag  gggccccagg  ttgggtgtgc    480
gcgcaacaag  gaagacttcc  gagcggtccc  agccgcgtgg  gagacgccag  cccatcccaa    540
aagatcggcg  ctccaccggc  aagtcctggg  gaaagccagg  atatccttgg  cctctgtatg    600
gaaacgaggg  ctgcggctgg  gcaggttggc  tcctgtcccc  tcgcgggtct  cgtcctactt    660
ggggccccac  tgacccccgg  catagatcac  gcaatttagg  taaagtcatc  gataccatta    720
cgtgtggttt  tgccgacctc  atggggtaca  tccccgtcgt  tggcgccccg  gtcggaggcg    780
tcgccagagc  cctggcacac  ggtgttaggg  tcctggagga  cgggataaat  tatgcaacag    840
ggaatctgcc  tggttgctct  ttttctatct  tcttactcgc  ccttctgtcg  tgcatcacag    900
tgccagtgtc  tgcggtggaa  gtcaggaaca  ttagctctgg  ctactacgcc  actaatgatt    960
gctcgaacaa  cagcatcacc  tggcagctca  ctaacgcagt  tctccatctt  cccggatgcg   1020
tcccatgtga  gaacgacaat  ggcaccctgc  gctgctggat  acaagtaaca  cctaatgtgg   1080
ctgtgaaaca  ccgcggcgcg  ctcactcaca  acctgcgaac  gcatgtcgac  gtggttgtga   1140
tggcagccac  gatctgctcg  gccttgtatg  tgggagacgt  gtgtggggcc  gtgatgatcg   1200
tatctcaggc  atttatactg  tcgccagagc  gccacaactt  tacccaggag  tgcaattgtt   1260
ccatctacca  aggtcatatc  accggccacc  gcatggcatg  ggacatgatg  ttaaactggt   1320
caccaactct  taccatggtc  ctcgcctatg  ctgctcgtgt  tcctgagcta  gtccttgaag   1380
ttgtcttcgg  cggccattgg  ggtgtggtgt  ttggcttggc  ctatttctcc  atgcagggag   1440
catgggccaa  agttatggcc  atcctcctcc  ttgtcgcagg  agtggacgca  cacacctatt   1500
ccaccggtgc  ccgagcgggt  caagcagcct  cgggcttaac  ttccctttt   tccgttggtt   1560 ctaggcagag  gctcagtcta  attcacacca  atggcagttg  gcacataaac  cggactgccc   1620
```

```
tcaattgcaa tgacagcttg catacgggtt tcatcgcttc ccttctttac gtcaacaatt    1680
tcaacagctc tggctgcccc gagcgcatgt cttcctgccg tgcgctggat gatttccgca    1740
tcgggtgggg aaccttggag tacgaaacca atgtcaccaa cgacgaggac atgaggccgt    1800
actgctggca ttatcctccg aagccttgcg gtatcgttcc ggctgggacg gtttgcgggc    1860
cggtctactg cttcactccc agccctgttg ttgtgggtac cactgacaag cagggcgtgc    1920
ccacctataa ctgggggaa atgagaccg atgtcttcct gctgaatagc acgagacccc    1980
cgcaaggggc ttggttcggc tgcacttgga tgaacgggac tgggttcact aagacatgcg    2040
gtgcaccacc ttgccgcatt aggagggact acaacgaaac cctcgatctg ttgtgcccca    2100
cagactgttt taggaagcac ccagaaacca cctatcttag gtgcggatca gggccttggt    2160
tgaccccag atgcctggtg gattaccctt atagattgtg gcattatccg tgcactgtga    2220
atttcaccat ctttaaggtg cggatgtatg tgggggagt ggagcatcgg ttgtccgcag    2280
catgtaactt cacgcgcggg gaccgctgca atttagaaga tagggatagg ggtcagcaga    2340
gtccgctgct gcactccacc actgagtggg cggtgttacc atgctctttc tccgacctac    2400
cggcactatc tactggttta ttgcacctcc atcaaaacat cgtggacgtg cagtacctct    2460
atggactttc tccggctatc acaagataca tcgtgaagtg ggagtgggtg gttctcctct    2520
tcttgttgtt ggcagatgcc agggtctgtg catgcctttg gatgctcatc atactgggcc    2580
aagccgaggc ggcgcttgag aagcttatca tcttgcactc tgctagcgct gctagtgcca    2640
atgggccgct gtggttcttc atcttcttca tagcggcctg gtacttaaag ggcagggtgg    2700
tccccatggc cacgtactct gttcttggct tgtggtcctt tttcctccta gtcctggcct    2760
taccacagca ggcttatgct ctggacgccg ttgaacaagg ggaactgggg ctggttttgt    2820
taggggtcat atcaatcttc actcttaccc cagcatacaa gactctcctg agccgttcag    2880
tatggtggct gtcctacatg ctggtcttgg ccgaggccca gattcagcaa tgggttcccc    2940
ccctggaagc ccgagggggc cgtgacggga tcatctgggt agctgtcatt ctacgcccat    3000
gccttgtgtt tgagatcacg aaatggctgt tggcagttct ggggcctgcc tacctcctta    3060
gagcgtccct gctacgggta ccgtactttg tgagggccca cgcccgctac cgactgtgtg    3120
ccctggtgag acacctcgca ggagctaggt acatccagat gctgttgatc accataggca    3180
ggtggactgg tacttacatc tatgaccacc tctcccctt atcaacttgg gcagcccagg    3240
gtttgcggga cctagcggtc gccgtggagc ctgtggtgtt tagcccaatg gagaagaagg    3300
tcattgtgtg gggggctgag acagtggcgt gtggggatat cctgcatggc ctcccggtgt    3360
ccgcgaggct aggtagggaa attctgctcg gccccgccga tggctacacc tcgaaggggt    3420
ggaagctcct ggctcctatc actgcttata tcagcagac ccgtggtctc ctgggtgcca    3480
tagtggtcag tctgacgggc cgcgacaaaa atgagcaggc tgggcaggtc caggttctgt    3540
cctccgtcac acaatctttc ttggggacat ctatttcggg ggtcctctgg acagtatacc    3600
atggggctgg taataagacc ttggctggcc ccagaggacc agtcactcag atgtactcca    3660
gcgcagaggg ggacctcgtg ggatggccta gcccccccgg gactaagtct ttagacccctt    3720
gtacctgtgg ggccgtggac ctctacctgg tcacccgaaa cgctgatgtc attccggtcc    3780
ggaggagaga tgaccggcgg ggcgcactac tctcgccaag gcctctctcg accctcaaag    3840
ggtcatccgg tggacccgtg ctctgctccc ggggacatgc cgtgggcttg ttcagggcgg    3900
ccgtgtgcac caggggtgtg gccaagtcca ttgacttcat ccctgttgaa tctctcgatg    3960
```

```
tcgctgcacg atcgcccagt ttctctgaca acagcactcc accagctgtg cctcagtctt    4020
accaagtggg ctacttacac gcgccaacag gcagcgggaa gagcaccaag gtccctgccg    4080
catacgccag tcaggggtat aaagtacttg tactgaatcc ctctgtcgcg ccacactcg     4140
gctttggggc ctacatgtcc aaggcccacg gaatcaaccc taacatcagg accggggtac   4200
ggactgtgac caccggggac ccaataactt actccactta tggcaagttc ctcgctgatg   4260
gaggctgctc agctgcgcc tatgacatca tcatatgcga cgaatgccat tcagtggacg    4320
ccactaccat ccttggcatt ggaacagtcc tcgaccaggc cgagaccgca ggcgccaggc   4380
tagtagtctt ggctacagcc acgcctcctg gtacagtgac aactcccat agcaacatag    4440
aggaggtggc tcttggtcat gaaggcgaga tccctttta cggcaaggct attcctctag    4500
cttatatcaa gggaggcagg cacctgatct tctgccactc aaagaagaag tgcgatgagc   4560
tcgcagcagc ccttcggggc atgggtgtca atgccgttgc ttactacagg ggtctcgacg   4620
tctccgtcat accacttcaa ggagacgtgg tggtagtcgc caccgatgcc ctaatgactg    4680
gatttaccgg tgactttgat tctgtcatcg actgcaacgt tgcagtcact cagattgttg    4740
acttcagcct agacccgacc tttactatca ccactcaaac tgtccctcag gacgccgtct   4800
cccgtagtca acgtagaggg agaactgggc gaggacggtt gggcatttac aggtatgttt   4860
cgtcaggtga aaggccgtct gggatgttcg acagcgtagt gctctgcgag tgctatgatg   4920
ccgggggcagc ctggtacgaa ctcacgcctg ctgaaactac agtgagactc cgggcctatt  4980
tgaacacgcc cggtctgccc gtgtgtcagg accacctgga attttgggag gcggtcttca   5040
caggtctcac acacattgat gcccacttcc tctcccagac gaaacaagga ggagacaact   5100
ttgcgtatct aacggcctat caggccacgg tatgcgctag ggcgagggcg cccccctcctt   5160
cctgggactt gatgtggaag tgtctaacta ggctcaagcc tacactgaat ggccctaccc   5220
cccttctata ccgcttgggt gccgtgacca acgaggtcac cctgactcac cccgtgacga    5280
aatatatcgc cacgtgtatg caagctgacc ttgagatcat gacaagtaca tgggttctag   5340
cgggggggggt gctagccgcc gtagcagctt actgcctggc gaccggctgt gtttccatca    5400
ttggccgcct acacctgaat gatcgagtgg ttgtggcccc tgataaggaa atcttatatg    5460
aggcctttga tgagatggaa gagtgcgcct ccaaagccgc cctcattgag gaagggcagc    5520
ggatggcgga gatgctcaag accaagatac aaggcctcct acaacaggcc acaagacaag   5580
cccaagacat acagccagcc atacagtcat cgtggcccaa gcttgaacaa ttttgggcca   5640
agcacatgtg gaacttcatc agtggcatac agtacctggc gggactctcc acgctaccag   5700
ggaatcccgc ggtggcgtca atgatggctt ttagcgccgc attgactagc ccactgccca   5760
ccagcaccac catcctcttg aacatcatgg ggggatggtt ggcctctcag atcgccccc    5820
ctgccggggc cactggcttt gttgtcagtg gtctggtagg ggcggccgtc ggaagtatag    5880
gcctgggtaa gatactggtg gatgttttgg ccgggtatgg tgcaggcatt tcaggggccc    5940
tcgtagcttt caagatcatg agcggcgaga agcctacggt agaagatgtt gtgaatctcc   6000
tgcctgctat cctgtctcct ggtgctttag tagtgggagt catctgtgca gcaatttttgc   6060
gccgccacat cggccaggga gaggggcgg tccagtggat gaacagactc atcgccttcg    6120
cctccagagg aaaccatgtt gcccctaccc actacgtggc agagtctgac gcctcgcagc   6180
gcgtgacgca agtgctgagt tcactcacaa ttaccagctt actcaggaga ctacatgcct   6240
ggatcactga agattgccca gtcccgtgct cgggtcttg gctccgggac atctgggatt   6300
gggtctgttc cattctcaca gactttaaga actggctgtc ttcaaaactg ctccccaagc   6360
```

```
tgcccggcct tcccttcatc tcttgccaaa agggatacag gggcgtatgg gctggcacgg    6420
gagtcatgac cactcggtgc ccgtgcggag ctaccatctc gggccatgtc cgcatgggta    6480
ccatgaaaat aacaggccca aagacctgct tgaacatgtg gcagggtcc ttccccatca     6540 attgttacac agaagggcct tgcgtgccaa aacccctcc taactacaag accgcaattt     6600
ggagggttgc agcgtcggag tacgttgaaa tcacgcaaca cggctcattc tcgtacgtaa    6660
cggggttaac taatgacaac cttaaggtcc cctgccaagt accagctcca gaattttct    6720 cttgggtgga cggggtgcag atacaccggt tcgcccccac tccaggtccc ttctttcggg    6780
atgaggtaac gttcaccgta ggccttaatt cctttgtggt cggctctcag ctcccctgcg    6840
accctgagcc ggacaccgag gtattggcct ccatgttgac agacccgtcc cacattacag    6900
cggaggcggc agctaggcga ttggccaggg ggtctccccc ctcacaggct agctcttcgg    6960
cgagccagct ctccgccccg tccttgaagg ccacctgtac cacccataag gtggcatatg    7020
attgtgacat ggtggacgcc aacctgttca tgggaggcga tgtgacccgg attgagtcca    7080
actccaaggt ggtcattctt gactccctcg attccatgac tgaggtagag gacgaccgtg    7140
agccttctat cccatcagag tacctgatca ggaggagaaa gttccaccg gcactacctc     7200 cctgggcccg tccagactac aaccctcctg tggtcgagac atggaagagg ccggactatg    7260
aaccacccac tgtcctaggc tgtgccctac cccccacacc tcaggcgcca gtgcctccac    7320
cccggaggcg ccgcgccaaa gtcctgaccc aggacaatgt ggaggggtt ctcaaggaga     7380 tggcggacaa agttcttagc cctctccgag attgtaatga ctccggtcac tccactggag    7440
cggataccgg ggcagacagc gtccagcagc ccctgacga gactgccgct tcagaggcgg     7500
gatcactgtc ctccatgcct ccccttgagg gagagccggg ggaccctgac ctggagtttg    7560
aaccagctgg atccgctccc ccttcagagg gggagtgtga ggtcattgat tcggactcta    7620
agtcgtggtc tacagtctct gatcaggagg attccattat ctgctgctcc atgtcatact    7680
cctggacggg agccctcata acaccatgtg ggcccgaaga ggagaagttg ccaatcaacc    7740
ctctgagtaa ctcgcttatg cggttccata caaggtgta ctcgacaacc tcgaggagcg     7800
cctctcagag agcaaaaaag gtgacctttg acagggtgca ggtgctggac aaacactacg    7860
actcagtctt gcaggacgtt aagcgggccg cctctaaggt tagtgcgagg ctcctctcaa    7920
tagaggaagc ctgcgcgctg accccgcctc actccgccaa atcgcggtat ggatttgggg    7980
caaaagaggt gcgcagctta tccaggaggg ccgtcaacca catccagtcc gtgtgggagg    8040
accttctgga agaccaacat actccaattg agacaactat catggccaag aacgaggtgt    8100
tctgcgttga tcccgctaaa ggcgggaaaa agtcagctcg cctcattgta taccctgacc    8160 ttgggggtcag agtgtgcgaa aaaatggccc tctatgacat tgcacaaaag cttcccaagg    8220
caataatggg tccatcctat gggttccaat actctcccgc agagcgggtc gattttctcc    8280
tcaaagcttg gggaagcaag aaggacccaa tggggttctc gtatgacacc cgctgcttcg    8340
actcaaccgt cacggagaga gatatacgaa cagaagaatc catatatcag gcttgttccc    8400
tgcctcaaga ggccagagtt gccatacact cacttactga gagactctac gtaggagggc    8460
ccatgctaaa cagcaagggc caatcctgcg gttacaggcg ttgccgcgcg agcggcgttt    8520
tcaccaccag catggggaat accatgacat gctacatcaa agcccttgcg gcgtgccaag    8580
ccgcagggat cgtggacccc gttatgctgg tgtgtggaga cgacctggtc gtcatctcag    8640
agagtcaagg taacgatgag gacgagcgaa acctgagagc tttcacggag gctatgacca    8700
```

-continued

```
ggtattcagc ccctcctggt gaccttccca gaccggaata tgacttggag cttataacat    8760
cctgctcctc aaacgtatcg gtagcgctgg accctcgggg tcgccgccgg tactacctaa    8820
ccagagaccc taccactcca atctcccgag ccgcttggga aacagtaaga cactcccctg    8880
tcaattcttg gctgggcaac atcatccaat acgccccac aatctgggtc cggatggtca     8940
taatgaccca tttcttctcc atactattgg cccaggacac tctgaaccaa aatctcaact    9000
ttgagatgta tggggcagta tattcggtca atccattaga cctaccggcc ataattgaaa    9060
ggctacacgg gcttgacgcc ttttcactgc acacatactc tccccacgaa ctctcacggg    9120
tggcagcgac tctcagaaaa cttggagcgc ctccccttag agcgtggaag agtcgggcac    9180
gtgctgtgag ggcctcactc atcgcccagg agggaaggc agccatttgt ggccgctacc     9240
tcttcaactg ggcggtgaag acaaagctca aactcactcc attgcccgag gcgagccgcc    9300
tggatttatc cggggtggttc accgtgggcg ccggcggggg cgacatcttt cacagcgtgt   9360
cgcatgcccg accccgccta ttactccttt gcctactcct acttagcgta ggggtaggca    9420
tcttttact ccccgctcgg tagagcggca aaccctagct acactccata gctagttcct     9480
ttttttttt tttttttttt tttttttttt tttttttttt tttttttttt ttttttttct    9540
tctttttat ttttccttct ttcttggtgg ctccatctta gccctagtca cggctagctg     9600
tgaaaggtcc gtgagccgca tgactgcaga gagtgccgta actggtctct ctgcagatca    9660
tgt                                                                   9663

<210> SEQ ID NO 2
<211> LENGTH: 9663
<212> TYPE: DNA
<213> ORGANISM: Hepatitis C virus

<400> SEQUENCE: 2
gcccgccccc taatgggggc gacactccgc catgaatcac tcccctgtga ggaactactg     60
tcttcacgca gaaagcgtct agccatggcg ttagtatgag tgtcgtacag cctccaggcc    120
ccccctccc gggagagcca tagtggtctg cggaaccggt gagtacaccg gaattaccgg     180
aaagactggg tcctttcttg gataaaccca ctctatgtcc ggtcatttgg gcgtgccccc    240
gcaagactgc tagcctagta gcgttgggtt gcgaacggcc ttgtggtact gcctgatagg    300
gtgcttgcga gtgccccggg aggtctcgta gaccgtgcat catgagcaca atcctaaac     360
ctcaaagaaa accaaaaga aacacaaacc gtcgcccaca ggacgtcaag ttcccgggtg    420
gcggtcagat cgttggcgga gtttacttgc tgccgcgcag gggccccagg ttgggtgtgc    480
gcgcaacaag gaagacttcc gagcggtccc agccgcgtgg gagacgccag cccatcccaa    540
aagatcggcg ctccaccggc aagtcctggg gaaagccagg atatccttgg cctctgtatg    600
gaaacgaggg ctgcggctgg gcaggttggc tcctgtcccc tcgcgggtct cgtcctactt    660
ggggcccac tgaccccggg catagatcac gcaattaggg taaagtcatc gataccatta    720
cgtgtggttt tgccgacctc atgggtacat ccccgtcgt tggcgccccg gtcggaggcg    780
tcgccagagc cctggcacac ggtgttaggg tcctgaggga cgggataaat tatgcaacag    840
ggaatctgcc tggttgctct ttttctatct tcttactcgc ccttctgtcg tgcatcacag    900
tgccagtgtc tgcggtggaa gtcaggaaca ttagctctgg ctactacgcc actaatgatt    960
gctcgaacaa cagcatcacc tggcagctca ctaacgcagt tctccatctt cccggatgcg    1020
tcccatgtga gaacgacaat ggcacccctgc gctgctggta caagtaaca cctaatgtgg    1080
ctgtgaaaca ccgcggcgcg ctcactcaca acctgcgaac gcatgtcgac gtggttgtga    1140
```

```
tggcagccac gatctgctcg gccttgtatg tgggagacgt gtgtgggcc gtgatgatcg   1200 tatctcaggc atttatactg tcgccagagc gccacaactt tacccaggag tgcaattgtt   1260
ccatctacca aggtcatatc accggccacc gcatggcatg ggacatgatg ttaaactggt   1320
caccaactct taccatggtc ctcgcctatg ctgctcgtgt tcctgagcta gtccttgaag   1380
ttgtcttcgg cggccattgg ggtgtggtgt ttggcttggc ctatttctcc atgcagggag   1440
catgggccaa agttatggcc atcctcctcc ttgtcgcagg agtggacgca cacacctatt   1500
ccaccggtgc ccgagcgggt caagcagcct cgggcttaac ttccctttt tccgttggtt   1560 ctaggcagag gctcagtcta attcacacca atggcagttg gcataaaac cggactgccc   1620 tcaattgcaa tgacagcttg catacggggtt tcatcgcttc ccttctttac gtcaacaatt   1680
tcaacagctc tggctgcccc gagcgcatgt cttcctgccg tgcgctggat gatttccgca   1740
tcgggtgggg aaccttggag tacgaaacca atgtcaccaa cgacgaggac atgaggccgt   1800
actgctggca ttatcctccg aagccttgcg gtatcgttcc ggctgggacg gtttgcgggc   1860
cggtctactg cttcactccc agccctgttg ttgtgggtac cactgacaag cagggcgtgc   1920
ccacctataa ctgggggaa aatgagaccg atgtcttcct gctgaatagc acgagacccc   1980 cgcaagggc ttggttcggc tgcacttgga tgaacggac tgggttcact aagacatgcg   2040
gtgcaccacc ttgccgcatt aggagggact acaacggaac cctcgatctg ttgtgcccca   2100
cagactgttt taggaagcac ccagaaacca cctatcttag gtgcggatca gggccttggt   2160 tgaccccag atgcctggtg gattacccctt atagattgtg gcattatccg tgcactgtga   2220
atttccacat ctttaaggtg cggatgtatg tggggggagt ggagcatcgg ttgtccgcag   2280
catgtaactt cacgcgcggg gaccgctgca atttagaaga tagggatagg ggtcagcaga   2340
gtccgctgct gcactccacc actgagtggg cggtgttacc atgctctttc tccgacctac   2400
cggcactatc tactggttta ttgcacctcc atcaaaacat cgtggacgtg cagtacctct   2460
atggactttc tccggctatc acaagataca tcgtgaagtg ggagtgggtg gttctcctct   2520
tcttgttgtt ggcagatgcc agggtctgtg catgcctttg gatgctcatc atactgggcc   2580
aagccgaggc ggcgcttgag aagcttatca tcttgcactc tgctagcgct gctagtgcca   2640
atgggccgct gtggttcttc atcttcttca tagcggcctg gtacttaaag ggcagggtgg   2700
tccccatggc cacgtactct gttcttggct tgtggtcctt tttcctccta gtcctggcct   2760
taccacagca ggcttatgct ctggacgccg ttgaacaagg ggaactgggg ctggtttgt   2820 tagggtcat atcaatcttc actcttaccc cagcatacaa gactctcctg agccgttcag   2880
tatggtggct gtcctacatg ctggtcttgg ccgaggccca gattcagcaa tgggttcccc   2940
ccctggaagc ccgagggggc cgtgacggga tcatctgggt agctgtcatt ctacgcccat   3000
gccttgtgtt tgagatcacg aaatggctgt tggcagttct ggggcctgcc tacctcctta   3060
gagcgtccct gctacgggta ccgtactttg tgagggccca cgccctgcta cgactgtgtg   3120
ccctggtgag acacctcgca ggagctaggt acatccagat gctgttgatc accataggca   3180
ggtggactgg tacttacatc tatgaccacc tctcccctt atcaacttgg gcagcccagg   3240
gtttgcggga cctagcggtc gccgtggagc ctgtggtgtt tagcccaatg gagaagaagg   3300
tcattgtgtg gggggctgag acagtggcgt gtggggatat cctgcatggc ctcccggtgt   3360
ccgcgaggct aggtagggaa attctgctcg gccccgccga tggctacacc tcgaagggg   3420 ggaagctcct ggctcctatc actgcttata ctcagcagac ccgtggtctc ctgggtgcca   3480
```

```
tagtggtcag tctgacgggc cgcgacaaaa atgagcaggc tgggcaggtc caggttctgt    3540
cctccgtcac acaatctttc ttggggacat ctatttcggg ggtcctctgg acagtatacc    3600
atggggctgg taataagacc ttggctggcc ccagaggacc agtcactcag atgtactcca    3660
gcgcagaggg ggacctcgtg ggatggccta gccccccccgg gactaagtct ttagacccctt   3720
gtacctgtgg ggccgtggac ctctacctgg tcacccgaaa cgctgatgtc attccggtcc    3780
ggaggagaga tgaccggcgg ggcgcactac tctcgccaag gcctctctcg accctcaaag    3840
ggtcatccgg tggacccgtg ctctgctccc ggggacatgc cgtgggcttg ttcagggcgg    3900
ccgtgtgcac caggggtgtg gccaagtcca ttgacttcat ccctgttgaa tctctcgatg    3960
tcgctgcacg atcgcccagt ttctctgaca acagcactcc accagctgtg cctcagtctt    4020
accaagtggg ctacttacac gcgccaacag gcagcgggaa gagcaccaag gtccctgccg    4080
catacgccag tcagggg tat aaagtacttg tactgaatcc ctctgtcgcg ccacactcg    4140
gctttgggc ctacatgtcc aaggcccacg gaatcaaccc taacatcagg accgggg tac    4200
ggactgtgac caccggggac ccaataactt actccactta tggcaagttc ctcgctgatg    4260
gaggctgctc agctggcgcc tatgacatca tcatatgcga cgaatgccat tcagtggacg    4320
ccactaccat ccttggcatt ggaacagtcc tcgaccaggc cgagaccgca ggcgccaggc    4380
tagtagtctt ggctacagcc acgcctcctg gtacagtgac aactccccat agcaacatag    4440
aggaggtggc tcttggtcat gaaggcgaga tcccttttta cggcaaggct attcctctag    4500
cttatatcaa gggaggcagg cacctgatct tctgccactc aaagaagaag tgcgatgagc    4560
tcgcagcagc ccttcggggc atgggtgtca atgccgttgc ttactacagg ggtctcgacg    4620
tctccgtcat accacttcaa ggagacgtgg tggtagtcgc caccgatgcc ctaatgactg    4680
gatttaccgg tgactttgat tctgtcatcg actgcaacgt tgcagtcact cagattgttg    4740
acctcagcct agacccgacc tttactatca ccactcaaac tgtccctcag gacgccgtct    4800
cccgtagtca acgtagaggg agaactgggc gaggacggtt gggcatttac aggtatgttt    4860
cgtcaggtga aaggccgtct gggatgttcg acagcgtagt gctctgcgag tgctatgatg    4920
ccgggggcagc ctggtacgaa ctcacgcctg ctgaaactac agtgagactc cgggcctatt    4980
tgaacacgcc cggtctgccc gtgtgtcagg accacctgga atttttgggag gcggtcttca    5040
caggtctcac acacattgat gcccacttcc tctcccagac gaaacaagga ggagacaact    5100
ttgcgtatct aacggcctat caggccacgg tatgcgctag ggcgagggcg cccccctcctt   5160
cctgggactt gatgtggaag tgtctaacta ggctcaagcc tacactgaat ggccctaccc    5220
cccttctata ccgcttgggt gccgtgacca acgaggtcac cctgactcac cccgtgacga    5280
aatatatcgc cacgtgtatg caagctgacc ttgagatcat gacaagtaca tgggttctag    5340
cggggggggt gctagccgcc gtagcatctt actgcctggc gaccggctgt gtttccatca    5400
ttggccgcct acacctgaat gatcgagtgg ttgtggcccc tgataaggaa atcttatatg    5460
aggcctttga tgagatggaa gagtgcgcct ccaaagccgc cctcattgag gaagggcagc    5520
ggatggcgga gatgctcaag accaagatac aaggcctcct acaacaggcc acaagacaag    5580
cccaagacat acagccagcc atacagtcat cgtggcccaa gcttgaacaa ttttggggcca    5640
agcacatgtg gaacttcatc agtggcatac agtacctggc gggactctcc acgctaccag    5700
ggaatcccgg ggtggcgtca atgatggctt ttagcgccgc attgactagc ccactgccca    5760
ccagcaccac catcctcttg aacatcatgg ggggatggtt ggcctctcag atcgccccc    5820
ctgccggggc cactggcttt gttgtcagtg gtctggtagg ggcggccgtc ggaagtatag    5880
```

```
gcctgggtaa gatactggtg gatgttttgg ccgggtatgg tgcaggcatt tcaggggccc    5940
tcgtagcttt caagatcatg agcggcgaga agcctacggt agaagatgtt gtgaatctcc    6000
tgcctgctat cctgtctcct ggtgctttag tagtgggagt catctgtgca gcaattttgc    6060
gccgccacat cggccaggga gaggggcgg tccagtggat gaacagactc atcgccttcg     6120
cctccagagg aaaccatgtt gcccctaccc actacgtggc agagtctgac gcctcgcagc    6180
gcgtgacgca agtgctgagt tcactcacaa ttaccagctt actcaggaga ctacatgcct    6240
ggatcactga agattgccca gtcccgtgct cggggtcttg gctccgggac atctgggatt    6300
gggtctgttc cattctcaca gactttaaga actggctgtc ttcaaaactg ctccccaagc    6360
tgcccggcct tcccttcatc tcttgccaaa agggatacag gggcgtatgg gctggcacgg    6420
gagtcatgac cactcggtgc ccgtgcgag ctaccatctc gggccatgtc cgcatgggta     6480
ccatgaaaat aacaggccca aagacctgct tgaacatgtg gcagggtcc ttccccatca     6540
attgttacac agaagggcct tgcgtgccaa aaccccctcc taactacaag accgcaattt    6600
ggagggttgc agcgtcggag tacgttgaaa tcacgcaaca cggctcattc tcgtacgtaa    6660
cggggttaac taatgacaac cttaaggtcc cctgccaagt accagctcca gaattttct     6720
cttgggtgga cggggtgcag atacaccggt tcgcccccac tccaggtccc ttctttcggg    6780
atgaggtaac gttcaccgta ggccttaatt cctttgtggt cggctctcag ctcccctgcg    6840
accctgagcc ggacaccgag gtattggcct ccatgttgac agaccegtcc cacattacag    6900
cggaggcggc agctaggcga ttggccaggg ggtctccccc ctcacaggct agctcttcgg    6960
cgagccagct ctccgccccg tccttgaagg ccacctgtac cacccataag gtggcatatg    7020
attgtgacat ggtggacgcc aacctgttca tgggaggcga tgtgacccgg attgagtcca    7080
actccaaggt ggtcattctt gactccctcg attccatgac tgaggtagag gacgaccgtg    7140
agccttctat cccatcagag tacctgatca ggaggagaaa gttccaccg gcactacctc     7200
cctgggcccg tccagactac aaccctcctg tggtcgagac atggaagagg ccggactatg    7260
aaccacccac tgtcctaggc tgtgccctac cccccacacc tcaggcgcca gtgcctccac    7320
cccggaggcg ccgcgccaaa gtcctgaccc aggacaatgt ggagggggtt ctcaaggaga    7380
tggcggacaa agttcttagc cctctccgag attgtaatga ctccggtcac tccactggag    7440
cggataccgg ggcagacagc gtccagcagc cccctgacga dactgccgct tcagaggcgg    7500
gatcactgtc ctccatgcct ccccttgagg gagagccggg ggaccctgac ctggagtttg    7560
aaccagctgg atccgctccc ccttcagagg gggagtgtga ggtcattgat tcggactcta    7620
agtcgtggtc tacagtctct gatcaggagg attccattat ctgctgctcc atgtcatact    7680
cctggacggg agccctcata acaccatgtg ggcccgaaga ggagaagttg ccaatcaacc    7740
ctctgagtaa ctcgcttatg cggttccata caaggtgta ctcgacaacc tcgaggagcg     7800
cctctcagag agcaaaaaag gtgacctttg acagggtgca ggtgctggac aaacactacg    7860
actcagtctt gcaggacgtt aagcgggccg cctctaaggt tagtgcgagg ctcctctcaa    7920
tagaggaagc ctgcgcgctg accccgcctc actccgccaa atcgcggtat ggatttgggg    7980
caaaagaggt gcgcagctta tccagagggg ccgtcaacca catccagtcc gtgtgggagg    8040
accttctgga agaccaacat actccaattg agacaactat catggccaag aacgaggtgt    8100
tctgcgttga tccgctaaa ggcggaaaa agtcagctcg cctcattgta taccctgacc     8160
ttgggggtcag agtgtgcgaa aaaatggccc tctatgacat tgcacaaaag cttcccaagg    8220
```

```
caataatggg tccatcctat gggttccaat actctcccgc agagcgggtc gattttctcc    8280
tcaaagcttg gggaagcaag aaggacccaa tggggttctc gtatgacacc cgctgcttcg    8340
actcaaccgt cacggagaga gatatacgaa cagaagaatc catatatcag gcttgttccc    8400
tgcctcaaga ggccagagtt gccatacact cacttactga gagactctac gtaggagggc    8460
ccatgctaaa cagcaagggc caatcctgcg gttacaggcg ttgccgcgcg agcggcgttt    8520
tcaccaccag catggggaat accatgacat gctacatcaa agcccttgcg gcgtgccaag    8580
ccgcagggat cgtggacccc gttatgctgg tgtgtggaga cgacctggtc gtcatctcag    8640
agagtcaagg taacgatgag gacgagcgaa acctgagagc tttcacggag gctatgacca    8700
ggtattcagc ccctcctggt gaccttccca gaccggaata tgacttggag cttataacat    8760
cctgctcctc aaacgtatcg gtagcgctgg accctcgggg tcgccgccgg tactacctaa    8820
ccagagaccc taccactcca atctcccgag ccgcttggga aacagtaaga cactcccctg    8880
tcaattcttg gctgggcaac atcatccaat acgcccccac aatctgggtc cggatggtca    8940
taatgaccca tttcttctcc atactattgg cccaggacac tctgaaccaa aatctcaact    9000
ttgagatgta tggggcagta tattcggtca atccattaga cctaccggcc ataattgaaa    9060
ggctacacgg gcttgacgcc ttttcactgc acacatactc tccccacgaa ctctcacggg    9120
tggcagcgac tctcagaaaa cttggagcgc ctcccttag agcgtggaag agtcgggcac    9180
gtgctgtgag ggcctcactc atcgcccagg agggaaggc agccatttgt ggccgctacc    9240
tcttcaactg gcggtgaag acaaagctca aactcactcc attgcccgag gcgagccgcc    9300
tggatttatc cggtggttc accgtgggcg ccggcggggg cggcatcttt cacagcgtgt    9360
cgcatgcccg accccgccta ttactccttt gcctactcct acttagcgta ggggtaggca    9420
tcttttact ccccgctcgg tagagcggca aaccctagct acactccata gctagttcct    9480
ttttttttt tttttttttt tttttttttt tttttttttt tttttttttt tttttttct    9540
tcttttttat ttttccttct ttcttggtgg ctccatctta gccctagtca cggctagctg    9600
tgaaaggtcc gtgagccgca tgactgcaga gagtgccgta actggtctct ctgcagatca    9660
tgt                                                                  9663

<210> SEQ ID NO 3
<211> LENGTH: 9663
<212> TYPE: DNA
<213> ORGANISM: Hepatitis C virus

<400> SEQUENCE: 3
gcccgccccc taatgggggc gacactccgc catgaatcac tcccctgtga ggaactactg      60
tcttcacgca gaaagcgtct agccatggcg ttagtatgag tgtcgtacag cctccaggcc     120
ccccctccc gggagagcca tagtggtctg cggaaccggt gagtacaccg gaattaccgg     180
aaagactggg tccttttcttg gataaaccca ctctatgtcc ggtcatttgg gcgtgccccc     240
gcaagactgc tagcctagta gcgttgggtt gcgaacggcc ttgtggtact gcctgatagg     300
gtgcttgcga gtgccccggg aggtctcgta gaccgtgcat catgagcaca atcctaaac     360
ctcaaagaaa aaccaaaaga acacaaaacc gtcgcccaca ggacgtcaag ttcccgggtg     420
gcggtcagat cgttggcgga gtttacttgc tgccgcgcag gggcccagg ttgggtgtgc     480
gcgcaacaag gaagacttcc gagcggtccc agccgcgtgg gagacgccag cccatcccaa     540
aagatcggcg ctccaccggc aagtcctggg gaaagccagg atatccttgg cctctgtatg     600
gaaacgaggg ctgcggctgg gcaggttggc tcctgtcccc tcgcgggtct cgtcctactt     660
```

```
ggggcccac tgaccccgg catagatcac gcaatttagg taaagtcatc gataccatta    720
cgtgtggttt tgccgacctc atggggtaca tccccgtcgt tggcgcccg gtcggaggcg    780
tcgccagagc cctggcacac ggtgttaggg tcctggagga cgggataaat tatgcaacag   840
ggaatctgcc tggttgctct ttttctatct tcttactcgc ccttctgtcg tgcatcacag   900
tgccagtgtc tgcggtggaa gtcaggaaca ttagctctgg ctactacgcc actaatgatt   960
gctcgaacaa cagcatcacc tggcagctca ctaacgcagt tctccatctt cccggatgcg  1020
tcccatgtga aacgacaat ggcaccctgc gctgctggat acaagtaaca cctaatgtgg   1080
ctgtgaaaca ccgcggcgcg ctcactcaca acctgcgaac gcatgtcgac gtggttgtga   1140
tggcagccac gatctgctcg gccttgtatg tgggagacgt gtgtggggcc gtgatgatcg   1200
tatctcaggc atttatactg tcgccagagc gccacaactt tacccaggag tgcaattgtt   1260
ccatctacca aggtcatatc accggccacc gcatggcatg ggacatgatg ttaaactggt   1320
caccaactct taccatggtc ctcgcctatg ctgctcgtgt tcctgagcta gtccttgaag   1380
ttgtcttcgg cggccattgg ggtgtggtgt ttggcttggc ctatttctcc atgcagggag   1440
catgggccaa agttatggcc atcctcctcc ttgtcgcagg agtggacgca cacacctatt   1500
ccaccggtgc ccgagcgggt caagcagcct cgggcttaac ttccctttttt tccgttggtt   1560
ctaggcagag gctcagtcta attcacacca atggcagttg gcacataaac cggactgccc   1620
tcaattgcaa tgacagcttg catacgggtt tcatcgcttc ccttctttac gtcaacaatt   1680
tcaacagctc tggctgcccc gagcgcatgt cttcctgccg tgcgctggat gatttccgca   1740
tcgggtgggg aaccttggag tacgaaacca atgtcaccaa cgacgaggac atgaggccgt   1800
actgctggca ttatcctccg aagccttgcg gtatcgttcc ggctgggacg gtttgcgggc   1860
cggtctactg cttcactccc agccctgttg ttgtgggtac cactgacaag cagggcgtgc   1920
ccacctataa ctggggggaa aatgagaccg atgtcttcct gctgaatagc acgagacccc   1980
cgcaagggc ttggttcggc tgcacttgga tgaacgggac tgggttcact aagacatgcg   2040
gtgcaccacc ttgccgcatt aggagggact acaacgaaac cctcgatctg ttgtgcccca   2100
cagactgttt taggaagcac ccagaaacca cctatcttag gtgcggatca gggccttggt   2160
tgaccccag atgcctggtg gattaccctt atagattgtg gcattatccg tgcactgtga   2220
atttcaccat ctttaaggtg cggatgtatg tgggggagt ggagcatcgg ttgtccgcag   2280
catgtaactt cacgcgcggg gaccgctgca atttagaaga tagggatagg ggtcagcaga   2340
gtccgctgct gcactccacc actgagtggg cggtgttacc atgctctttc tccgacctac   2400
cggcactatc tactggttta ttgcacctcc atcaaaacat cgtggacgtg cagtacctct   2460
atggactttc tccggctatc acaagataca tcgtgaagtg ggagtgggtg gttctcctct   2520
tcttgttgtt ggcagatgcc agggtctgtg catgcctttg gatgctcatc atactgggcc   2580
aagccgaggc ggcgcttgag aagcttatca tcttgcactc tgctagcgct gctagtgcca   2640
atgggccgct gtggttcttc atcttcttca tagcggcctg gtacttaaag ggcagggtgg   2700
tccccatggc cacgtactct gttcttggct tgtggtcctt tttcctccta gtcctggcct   2760
taccacagca ggcttatgct ctggacgccg ttgaacaagg ggaactgggg ctggttttgt   2820
taggggtcat atcaatcttc actcttaccc cagcatacaa gactctcctg agccgttcag   2880
tatggtggct gtcctacatg ctggtcttgg ccgaggccca gattcagcaa tgggttcccc   2940
ccctggaagc ccgagggggc cgtgacggga tcatctgggt agctgtcatt ctacgcccat   3000
```

-continued

```
gccttgtgtt tgagatcacg aaatggctgt tggcagttct ggggcctgcc tacctcctta   3060
gagcgtccct gctacgggta ccgtactttg tgagggccca cgccctgcta cgactgtgtg   3120
ccctggtgag acacctcgca ggagctaggt acatccagat gctgttgatc accataggca   3180
ggtggactgg tacttacatc tatgaccacc tctccccttt atcaacttgg gcagcccagg   3240
gtttgcggga cctagcggtc gccgtggagc ctgtggtgtt tagcccaatg gagaagaagg   3300
tcattgtgtg gggggctgag acagtggcgt gtggggatat cctgcatggc ctcccggtgt   3360
ccgcgaggct aggtagggaa attctgctcg gccccgccga tggctacacc tcgaaggggt   3420
ggaagctcct ggctcctatc actgcttata ctcagcagac ccgtggtctc ctgggtgcca   3480
tagtggtcag tctgacgggc cgcgacaaaa atgagcaggc tgggcaggtc caggttctgt   3540
cctccgtcac acaatctttc ttggggacat ctatttcggg ggtcctctgg acagtatacc   3600
atggggctgg taataagacc ttggctggcc ccagaggacc agtcactcag atgtactcca   3660
gcgcagaggg ggacctcgtg ggatggccta gcccccccgg gactaagtct ttagacccct   3720
gtacctgtgg ggccgtggac ctctacctgg tcacccgaaa cgctgatgtc attccggtcc   3780
ggaggagaga tgaccggcgg ggcgcactac tctcgccaag gcctctctcg accctcaaag   3840
ggtcatccgg tggacccgtg ctctgctccc ggggacatgc cgtgggcttg ttcagggcgg   3900
ccgtgtgcac caggggtgtg gccaagtcca ttgacttcat ccctgttgaa tctctcgatg   3960
tcgctgcacg atcgcccagt ttctctgaca acagcactcc accagctgtg cctcagtctt   4020
accaagtggg ctacttacac gcgccaacag gcagcgggaa gagcaccaag gtccctgccg   4080
catacgccag tcagggtat aaagtacttg tactgaatcc ctctgtcgcg ccacactcg    4140
gctttggggc ctacatgtcc aaggcccacg gaatcaaccc taacatcagg accggggtac   4200
ggactgtgac caccggggac ccaataactt actccactta tggcaagttc ctcgctgatg   4260
gaggctgctc agctggcgcc tatgacatca tcatatgcga cgaatgccat tcagtggacg   4320
ccactaccat ccttggcatt ggaacagtcc tcgaccaggc cgagaccgca ggcgccaggc   4380
tagtagtctt ggctacagcc acgcctcctg gtacagtgac aactccccat agcaacatag   4440
aggaggtggc tcttggtcat gaaggcgaga tccctttta cggcaaggct attcctctag   4500
cttatatcaa gggaggcagg cacctgatct tctgccactc aaagaagaag tgcgatgagc   4560
tcgcagcagc ccttcgggc atgggtgtca atgccgttgc ttactacagg ggtctcgacg   4620
tctccgtcat accacttcaa ggagacgtgg tggtagtcgc caccgatgcc ctaatgactg   4680
gatttaccgg tgactttgat tctgtcatcg actgcaacgt tgcagtcact cagattgttg   4740
acctcagcct agacccgacc tttactatca ccactcaaac tgtccctcag gacgccgtct   4800
cccgtagtca acgtagaggg agaactgggc gaggacggtt gggcatttac aggtatgttt   4860
cgtcaggtga aaggccgtct gggatgttcg acagcgtagt gctctgcgag tgctatgatg   4920
ccggggcagc ctggtacgaa ctcacgcctg ctgaaactac agtgagactc cgggcctatt   4980
tgaacacgcc cggtctgccc gtgtgtcagg accacctgga attttgggag gcggtcttca   5040
caggtctcac acacattgat gcccacttcc tctcccagac gaaacaagga ggagacaact   5100
ttgcgtatct aacggcctat caggccacgg tatgcgctag ggcgagggcg cccctcctt    5160
cctgggactt gatgtggaag tgtctaacta ggctcaagcc tacactgaat ggccctaccc   5220
cccttctata ccgcttgggt gccgtgacca acgaggtcac cctgactcac cccgtgacga   5280
aatatatcgc cacgtgtatg caagctgacc ttgatcat dacaagtaca tgggttctag    5340
cggggggggt gctagccgcc gtagcatctt actgcctggc gaccggctgt gtttccatca   5400
```

```
ttggccgcct acacctgaat gatcgagtgg ttgtggcccc tgataaggaa atcttatatg    5460
aggcctttga tgagatggaa gagtgcgcct ccaaagccgc cctcattgag gaagggcagc    5520
ggatggcgga gatgctcaag accaagatac aaggcctcct acaacaggcc acaagacaag    5580
cccaagacat acagccagcc atacagtcat cgtggcccaa gcttgaacaa ttttgggcca    5640
agcacatgtg gaacttcatc agtggcatac agtacctggc gggactctcc acgctaccag    5700
ggaatcccgc ggtggcgtca atgatggctt ttagcgccgc attgactagc ccactgccca    5760
ccagcaccac catcctcttg aacatcatgg ggggatggtt ggcctctcag atcgcccccc    5820
ctgccggggc cactggcttt gttgtcagtg gtctggtagg ggcggccgtc ggaagtatag    5880
gcctgggtaa gatactggtg gatgttttgg ccgggtatgg tgcaggcatt tcaggggccc    5940
tcgtagcttt caagatcatg agcggcgaga agcctacggt agaagatgtt gtgaatctcc    6000
tgcctgctat cctgtctcct ggtgctttag tagtgggagt catctgtgca gcaattttgc    6060
gccgccacat cggccaggga gaggggcgg tccagtggat gaacagactc atcgccttcg    6120
cctccagagg aaaccatgtt gcccctaccc actacgtggc agagtctgac gcctcgcagc    6180
gcgtgacgca agcgctgagt tcactcacaa ttaccagctt actcaggaga ctacatgcct    6240
ggatcactga agattgccca gtcccgtgct cggggtcttg gctccgggac atctgggatt    6300
gggtctgttc cattctcaca gactttaaga actggctgtc ttcaaaactg ctccccaagc    6360
tgcccggcct tcccttcatc tcttgccaaa agggatacag gggcgtatgg gctggcacgg    6420
gagtcatgac cactcggtgc ccgtgcgag ctaccatctc gggccatgtc cgcatgggta    6480
ccatgaaaat aacaggccca agacctgct tgaacatgtg gcaggggtcc ttccccatca    6540
attgttacac agaagggcct tgcgtgccaa accccctcc taactacaag accgcaattt    6600
ggagggttgc agcgtcggag tacgttgaaa tcacgcaaca cggctcattc tcgtacgtaa    6660
cggggttaac taatgacaac cttaaggtcc cctgccaagt accagctcca gaattttct    6720 cttgggtgga cggggtgcag atacaccggt tcgcccccac tccaggtccc ttctttcggg    6780
atgaggtaac gttcaccgta ggccttaatt cctttgtggt cggctctcag ctcccctgcg    6840
accctgagcc ggacaccgag gtattggcct ccatgttgac agaccccgtcc cacattacag    6900 cggaggcggc agctaggcga ttggccaggg ggtctccccc ctcacaggct agctcttcgg    6960
cgagccagct ctccgccccg tccttgaagg ccacctgtac cacccataag gtggcatatg    7020
attgtgacat ggtggacgcc aacctgttca tgggaggcga tgtgacccgg attgagtcca    7080
actccaaggt ggtcattctt gactccctcg attccatgac tgaggtagag gacgaccgtg    7140
agccttctat cccatcagag tacctgatca ggaggagaaa gttcccaccg gcactacctc    7200
cctgggcccg tccagactac aaccctcctg tggtcgagac atggaagagg ccggactatg    7260
aaccacccac tgtcctaggc tgtgccctac cccccacacc tcaggcgcca gtgcctccac    7320
cccggaggcg ccgcgccaaa gtcctgaccc aggacaatgt ggagggggtt ctcaaggaga    7380
tggcggacaa agttcttagc cctctccgag attgtaatga ctccggtcac tccactggag    7440
cggatcccgg ggcagacagc gtccagcagc cccctgacga gactgccgct tcagaggcgg    7500
gatcactgtc ctccatgcct ccccttgagg gagagccggg ggaccctgac ctggagtttg    7560
aaccagctgg atccgctccc ccttcagagg gggagtgtga ggtcattgat tcggactcta    7620
agtcgtggtc tacagtctct gatcaggagg attccattat ctgctgctcc atgtcatact    7680
cctggacggg agccctcata acaccatgtg ggcccgaaga ggagaagttg ccaatcaacc    7740
```

| | |
|---|---:|
| ctctgagtaa ctcgcttatg cggttccata acaaggtgta ctcgacaacc tcgaggagcg | 7800 |
| cctctcagag agcaaaaaag gtgacctttg acagggtgca ggtgctggac aaacactacg | 7860 |
| actcagtctt gcaggacgtt aagcgggccg cctctaaggt tagtgcgagg ctcctctcaa | 7920 |
| tagaggaagc ctgcgcgctg accccgcctc actccgccaa atcgcggtat ggatttgggg | 7980 |
| caaaagaggt gcgcagctta tccaggaggg ccgtcaacca catccagtcc gtgtgggagg | 8040 |
| accttctgga agaccaacat actccaattg agacaactat catggccaag aacgaggtgt | 8100 |
| tctgcgttga tcccgctaaa gcgggaaaaa agtcagctcg cctcattgta taccctgacc | 8160 |
| tgggggtcag agtgtgcgaa aaaatggccc tctatgacat tgcacaaaag cttcccaagg | 8220 |
| caataatggg tccatcctat gggttccaat actctcccgc agagcgggtc gattttctcc | 8280 |
| tcaaagcttg gggaagcaag aaggacccaa tggggttctc gtatgacacc cgctgcttcg | 8340 |
| actcaaccgt cacggagaga gatatacgaa cagaagaatc catatatcag gcttgttccc | 8400 |
| tgcctcaaga ggccagagtt gccatacact cacttactga gagactctac gtaggagggc | 8460 |
| ccatgctaaa cagcaagggc caatcctgcg gttacaggcg ttgccgcgcg agcggcgttt | 8520 |
| tcaccaccag catggggaat accatgacat gctacatcaa agcccttgcg gcgtgccaag | 8580 |
| ccgcagggat cgtggacccc gttatgctgg tgtgtggaga cgacctggtc gtcatctcag | 8640 |
| agagtcaagg taacgatgag gacgagcgaa acctgagagc tttcacggag gctatgacca | 8700 |
| ggtattcagc ccctcctggt gaccttccca gaccggaata tgacttggag cttataacat | 8760 |
| cctgctcctc aaacgtatcg gtagcgctgg accctcgggg tcgccgccgg tactacctaa | 8820 |
| ccagagaccc taccactcca atctcccgag ccgcttggga aacagtaaga cactcccctg | 8880 |
| tcaattcttg gctgggcaac atcatccaat acgcccccac aatctgggtc cggatggtca | 8940 |
| taatgaccca tttcttctcc atactattgg cccaggacac tctgaaccaa atctcaactt | 9000 |
| tgagatgta tggggcagta tattcggtca atccattaga cctaccggcc ataattgaaa | 9060 |
| ggctacacgg gcttgacgcc ttttcactgc acacatactc tccccacgaa ctctcacggg | 9120 |
| tggcagcgac tctcagaaaa cttggagcgc ctccccttag agcgtggaag agtcgggcac | 9180 |
| gtgctgtgag ggcctcactc atcgcccagg agggaaggc agccatttgt ggccgctacc | 9240 |
| tcttcaactg gcgggtgaag acaaagctca aactcactcc attgcccgag gcgagccgcc | 9300 |
| tggatttatc cggtggttc accgtgggcg ccggcggggg cggcatcttt cacagcgtgt | 9360 |
| cgcatgcccg accccgccta ttactccttt gcctactcct acttagcgta ggggtaggca | 9420 |
| tcttttact ccccgctcgg tagagcggca aaccctagct acactccata gctagttcct | 9480 |
| ttttttttt ttttttttt tttttttt tttttttt tttttttt ttttttct | 9540 |
| tctttttat ttttccttct ttcttggtgg ctccatctta gccctagtca cggctagctg | 9600 |
| tgaaaggtcc gtgagccgca tgactgcaga gagtgccgta actggtctct ctgcagatca | 9660 |
| tgt | 9663 |

<210> SEQ ID NO 4
<211> LENGTH: 9663
<212> TYPE: DNA
<213> ORGANISM: Hepatitis C virus

<400> SEQUENCE: 4

| | |
|---|---:|
| gcccgccccc taatgggggc gacactccgc catgaatcac tcccctgtga ggaactactg | 60 |
| tcttcacgca gaaagcgtct agccatggcg ttagtatgag tgtcgtacag cctccaggcc | 120 |
| cccccctccc gggagagcca tagtggtctg cggaaccggt gagtacaccg gaattaccgg | 180 |

```
aaagactggg tcctttcttg gataaaccca ctctatgtcc ggtcatttgg gcgtgccccc    240
gcaagactgc tagcctagta gcgttgggtt gcgaacggcc ttgtggtact gcctgatagg    300
gtgcttgcga gtgccccggg aggtctcgta gaccgtgcat catgagcaca aatcctaaac    360
ctcaaagaaa aaccaaaaga aacacaaacc gtcgcccaca ggacgtcaag ttcccgggtg    420
gcggtcagat cgttggcgga gtttacttgc tgccgcgcag gggccccagg ttgggtgtgc    480
gcgcaacaag gaagacttcc gagcggtccc agccgcgtgg gagacgccag cccatcccaa    540
aagatcggcg ctccaccggc aagtcctggg gaaagccagg atatccttgg cctctgtatg    600
gaaacgaggg ctgcggctgg gcaggttggc tcctgtcccc tcgcgggtct cgtcctactt    660
ggggccccac tgaccccggg catagatcac gcaatttagg taaagtcatc gataccatta    720
cgtgtggttt gccgacctc atggggtaca tccccgtcgt tggcgccccg gtcggaggcg    780
tcgccagagc cctggcacac ggtgttaggg tcctggagga cgggataaat tatgcaacag    840
ggaatctgcc tggttgctct ttttctatct tcttactcgc ccttctgtcg tgcatcacag    900
tgccagtgtc tgcggtggaa gtcaggaaca ttagctctgg ctactacgcc actaatgatt    960
gctcgaacaa cagcatcacc tggcagctca ctaacgcagt tctccatctt cccggatgcg   1020
tcccatgtga gaacgacaat ggcaccctgc gctgctggat acaagtaaca cctaatgtgg   1080
ctgtgaaaca ccgcggcgcg ctcactcaca acctgcgaac gcatgtcgac gtggttgtga   1140
tggcagccac gatctgctcg gccttgtatg tgggagacgt gtgtggggcc gtgatgatcg   1200
tatctcaggc atttatactg tcgccagagc gccacaactt tacccaggag tgcaattgtt   1260
ccatctacca aggtcatatc accggccacc gcatggcatg ggacatgatg ttaaactggt   1320
caccaactct taccatggtc ctcgcctatg ctgctcgtgt tcctgagcta gtccttgaag   1380
ttgtcttcgg cggccattgg ggtgtggtgt ttggcttggc ctatttctcc atgcagggag   1440
catgggccaa agttatggcc atcctcctcc ttgtcgcagg agtggacgca cacacctatt   1500
ccaccggtgc ccgagcgggt caagcagcct cgggcttaac ttcccttttt tccgttggtt   1560
ctaggcagag gctcagtcta attcacacca atggcagttg gcacataaac cggactgccc   1620
tcaattgcaa tgacagcttg catacggggtt tcatcgcttc ccttctttac gtcaacaatt   1680
tcaacagctc tggctgcccc gagcgcatgt cttcctgccg tgcgctggat gatttccgca   1740
tcgggtgggg aaccttggag tacgaaacca atgtcaccaa cgacgaggac atgaggccgt   1800
actgctggca ttatcctccg aagccttgcg gtatcgttcc ggctgggacg gtttgcgggc   1860
cggtctactg cttcactccc agccctgttg ttgtgggtac cactgacaag cagggcgtgc   1920
ccacctataa ctggggggaa aatgagaccg atgtcttcct gctgaatagc acgagacccc   1980
cgcaaggggc ttggttcggc tgcacttgga tgaacgggac tgggttcact aagacatgcg   2040
gtgcaccacc ttgccgcatt aggagggact acaacggaac cctcgatctg ttgtgcccca   2100
cagactgttt taggaagcac ccagaaacca cctatcttag gtgcggatca gggcttggt   2160 tgacccccag atgcctggtg gattacccctt atagattgtg gcattatccg tgcactgtga   2220 atttccaccat ctttaaggtg cggatgtatg tgggggagt ggagcatcgg ttgtccgcag   2280
catgtaactt cacgcgcggg gaccgctgca atttagaaga tagggatagg ggtcagcaga   2340
gtccgctgct gcactccacc actgagtggg cggtgttacc atgctctttc tccgacctac   2400
cggcactatc tactggtttta ttgcacctcc atcaaaacat cgtggacgtg cagtacctct   2460
atggactttc tccggctatc acaagataca tcgtgaagtg ggagtgggtg gttctcctct   2520
```

```
tcttgttgtt ggcagatgcc agggtctgtg catgcctttg gatgctcatc atactgggcc   2580
aagccgaggc ggcgcttgag aagcttatca tcttgcactc tgctagcgct gctagtgcca   2640
atgggccgct gtggttcttc atcttcttca tagcggcctg gtacttaaag gcagggtgg    2700 tccccatggc cacgtactct gttcttggct tgtggtcctt tttcctccta gtcctggcct   2760
taccacagca ggcttatgct ctggacgccg ttgaacaagg ggaactgggg ctggttttgt   2820 tagggtcat atcaatcttc actcttaccc cagcatacaa gactctcctg agccgttcag    2880
tatggtggct gtcctacatg ctggtcttgg ccgaggccca gattcagcaa tgggttcccc   2940
ccctggaagc ccgaggggc cgtgacggga tcatctgggt agctgtcatt ctacgcccat    3000
gccttgtgtt tgagatcacg aaatggctgt tggcagttct ggggcctgcc tacctcctta   3060
gagcgtccct gctacgggta ccgtactttg tgagggccca cgccctgcta cgactgtgtg   3120
ccctggtgag acacctcgca ggagctaggt acatccagat gctgttgatc accataggca   3180
ggtggactgg tacttacatc tatgaccacc tctccccttt atcaacttgg gcagcccagg   3240
gtttgcggga cctagcggtc gccgtggagc ctgtggtgtt tagcccaatg gagaagaagg   3300
tcattgtgtg gggggctgag acagtggcgt gtggggatat cctgcatggc ctcccggtgt   3360
ccgcgaggct aggtagggaa attctgctcg gccccgccga tggctacacc tcgaaggggt   3420
ggaagctcct ggctcctatc actgcttata ctcagcagac ccgtggtctc ctgggtgcca   3480
tagtggtcag tctgacgggc gcgacaaaa tgagcaggc tgggcaggtc caggttctgt     3540
cctccgtcac acaatctttc ttggggacat ctatttcggg ggtcctctgg acagtatacc   3600
atggggctgg taataagacc ttggctggcc ccagaggacc agtcactcag atgtactcca   3660
gcgcagaggg ggacctcgtg ggatggccta gccccccgg gactaagtct ttagacccctt   3720 gtacctgtgg ggccgtggac ctctacctgg tcacccgaaa cgctgatgtc attccggtcc   3780
ggaggagaga tgaccggcgg ggcgcactac tctcgccaag gcctctctcg accctcaaag   3840
ggtcatccgg tggacccgtg ctctgctccc ggggacatgc cgtgggcttg ttcagggcgg   3900
ccgtgtgcac caggggtgtg gccaagtcca ttgacttcat ccctgttgaa tctctcgatg   3960
tcgctgcacg atcgcccagt ttctctgaca acagcactcc accagctgtg cctcagtctt   4020
accaagtggg ctacttacac gcgccaacag gcagcgggaa gagcaccaag gtccctgccg   4080
catacgccag tcaggggtat aaagtacttg tactgaatcc ctctgtcgcg gccacactcg   4140 gctttgggc ctacatgtcc aaggcccacg gaatcaaccc taacatcagg accggggtac    4200
ggactgtgac caccggggac ccaataactt actccactta tggcaagttc ctcgctgatg   4260
gaggctgctc agctggcgcc tatgacatca tcatatgcga cgaatgccat tcagtggacg   4320
ccactaccat ccttggcatt ggaacagtcc tcgaccaggc cgagaccgca ggcgccaggc   4380
tagtagtctt ggctacagcc acgcctcctg gtacagtgac aactcccat agcaacatag    4440 aggaggtggc tcttggtcat gaaggcgaga tccctttta cggcaaggct attcctctag   4500
cttatatcaa gggaggcagg cacctgatct tctgccactc aaagaagaag tgcgatgagc   4560
tcgcagcagc ccttcggggc atgggtgtca atgccgttgc ttactacagg ggtctcgacg   4620
tctccgtcat accacttcaa ggagacgtgg tggtagtcgc caccgatgcc ctaatgactg   4680
gatttaccgg tgactttgat tctgtcatcg actgcaacgt tgcagtcact cagattgttg   4740
acctcagcct agacccgacc tttactatca ccactcaaac tgtccctcag gacgccgtct   4800
cccgtagtca acgtagaggg agaactgggc gaggacggtt gggcatttac aggtatgttt   4860
cgtcaggtga aaggccgtct gggatgttcg acagcgtagt gctctgcgag tgctatgatg   4920
```

```
ccggggcagc ctggtacgaa ctcacgcctg ctgaaactac agtgagactc cgggcctatt   4980
tgaacacgcc cggtctgccc gtgtgtcagg accacctgga attttgggag gcggtcttca   5040
caggtctcac acacattgat gcccacttcc tctcccagac gaaacaagga ggagacaact   5100
ttgcgtatct aacggcctat caggccacgg tatgcgctag ggcgagggcg ccccctcctt   5160
cctgggactt gatgtggaag tgtctaacta ggctcaagcc tacactgaat ggccctaccc   5220
cccttctata ccgcttgggt gccgtgacca acgaggtcac cctgactcac cccgtgacga   5280
aatatatcgc cacgtgtatg caagctgacc ttgagatcat gacaagtaca tgggttctag   5340
cgggggggt gctagccgcc gtagcatctt actgcctggc gaccggctgt gtttccatca   5400
ttggccgcct acacctgaat gatcgagtgg ttgtggcccc tgataaggaa atcttatatg   5460
aggcctttga tgagatggaa gagtgcgcct ccaaagccgc cctcattgag gaagggcagc   5520
ggatggcgga gatgctcaag accaagatac aaggcctcct acaacaggcc acaagacaag   5580
cccaagacat acagccagcc atacagtcat cgtggcccaa gcttgaacaa ttttgggcca   5640
agcacatgtg gaacttcatc agtggcatac agtacctggc gggactctcc acgctaccag   5700
ggaatcccgc ggtggcgtca atgatggctt ttagcgccgc attgactagc ccactgccca   5760
ccagcaccac catcctcttg aacatcatgg ggggatggtt ggcctctcag atcgccccc   5820
ctgccgggc cactggcttt gttgtcagtg gtctggtagg ggcggccgtc ggaagtatag   5880
gcctgggtaa gatactggtg gatgttttgg ccgggtatgg tgcaggcatt tcaggggccc   5940
tcgtagcttt caagatcatg agcggcgaga agcctacggt agaagatgtt gtgaatctcc   6000
tgcctgctat cctgtctcct ggtgctttag tagtgggagt catctgtgca gcaattttgc   6060
gccgccacat cggccaggga gaggggcgg tccagtggat gaacagactc atcgccttcg   6120
cctccagagg aaaccatgtt gcccctaccc actacgtggc agagtctgac gcctcgcagc   6180
gcgtgacgca agcgctgagt tcactcacaa ttaccagctt actcaggaga ctacatgcct   6240
ggatcactga agattgccca gtcccgtgct cggggtcttg gctccgggac atctgggatt   6300
gggtctgttc cattctcaca gactttaaga actggctgtc ttcaaaactg ctccccaagc   6360
tgcccggcct tcccttcatc tcttgccaaa agggatacag gggcgtatgg gctggcacgg   6420
gagtcatgac cactcggtgc ccgtgcggag ctaccatctc gggccatgtc cgcatgggta   6480
ccatgaaaat aacaggccca aagacctgct tgaacatgtg gcaggggtcc ttccccatca   6540
attgttacac agaagggcct tgcgtgccaa accccctcc taactacaag accgcaattt   6600
ggaggggttgc agcgtcggag tacgttgaaa tcacgcaaca cggctcattc tcgtacgtaa   6660
cggggttaac taatgacaac cttaaggtcc cctgccaagt accagctcca gaattttcct   6720
cttgggtgga cggggtgcag atacaccggt tcgcccccac tccaggtccc ttctttcggg   6780
atgaggtaac gttcaccgta ggccttaatt cctttgtggt cggctctcag ctcccctgcg   6840
accctgagcc ggacaccgag gtattggcct ccatgttgac agaccccgtcc cacattacag   6900
cggaggcggc agctaggcga ttggccaggg ggtctcccc ctcacaggct agctcttcgg   6960
cgagccagct ctccgcccg tccttgaagg ccacctgtac cacccataag gtggcatatg   7020
attgtgacat ggtggacgcc aacctgttca tgggaggcga tgtgacccgg attgagtcca   7080
actccaaggt ggtcattctt gactccctcg attccatgac tgaggtagag gacgaccgtg   7140
agccttctat cccatcagag tacctgatca ggaggagaaa gttccaccg gcactacctc   7200
cctgggcccg tccagactac aaccctcctg tggtcgagac atggaagagg ccggactatg   7260
```

```
aaccacccac tgtcctaggc tgtgccctac cccccacacc tcaggcgcca gtgcctccac      7320
cccggaggcg ccgcgccaaa gtcctgaccc aggacaatgt ggaggggtt ctcaaggaga       7380 tggcggacaa agttcttagc cctctccgag attgtaatga ctccggtcac tccactggag     7440
cggataccgg ggcagacagc gtccagcagc cccctgacga gactgccgct tcagaggcgg     7500
gatcactgtc ctccatgcct ccccttgagg gagagccggg ggaccctgac ctggagtttg     7560
aaccagctgg atccgctccc ccttcagagg gggagtgtga ggtcattgat tcggactcta    7620
agtcgtggtc tacagtctct gatcaggagg attccactat ctgctgctcc atgtcatact    7680
cctggacggg agccctcata acaccatgtg ggcccgaaga ggagaagttg ccaatcaacc    7740
ctctgagtaa ctcgcttatg cggttccata acaaggtgta ctcgacaacc tcgaggagcg    7800
cctctcagag agcaaaaaag gtgacctttg acagggtgca ggtgctggac aaacactacg    7860
actcagtctt gcaggacgtt aagcgggccg cctctaaggt tagtgcgagg ctcctctcaa    7920
tagaggaagc ctgcgcgctg accccgcctc actccgccaa atcgcggtat ggatttgggg    7980
caaaagaggt gcgcagctta tccaggaggg ccgtcaacca catccagtcc gtgtgggagg    8040
accttctgga agaccaacat actccaattg agacaactat catggccaag aacgaggtgt    8100
tctgcgttga tcccgctaaa ggcgggaaaa agtcagctcg cctcattgta taccctgacc    8160
ttggggtcag agtgtgcgaa aaaatggccc tctatgacat tgcacaaaag cttcccaagg    8220
caataatggg tccatcctat gggttccaat actctcccgc agagcgggtc gattttctcc    8280
tcaaagcttg gggaagcaag aaggacccaa tggggttctc gtatgacacc cgctgcttcg    8340
actcaaccgt cacggagaga gatatacgaa cagaagaatc catatatcag gcttgttccc    8400
tgcctcaaga ggccagagtt gccatacact cacttactga gagactctac gtaggagggc    8460
ccatgctaaa cagcaagggc caatcctgcg gttacaggcg ttgccgcgcg agcggcgttt    8520
tcaccaccag catggggaat accatgacat gctacatcaa agcccttgcg gcgtgccaag    8580
ccgcagggat cgtggacccc gttatgctgg tgtgtggaga cgacctggtc gtcatctcag    8640
agagtcaagg taacgatgag gacgagcgaa acctgagagc tttcacggag gctatgacca    8700
ggtattcagc ccctcctggt gaccttccca gaccggaata tgacttggag cttataacat    8760
cctgctcctc aaacgtatcg gtagcgctgg acctcggggg tcgccgccgg tactacctaa    8820
ccagagaccc taccactcca atctcccgag ccgcttggga aacagtaaga cactcccctg    8880
tcaattcttg gctgggcaac atcatccaat acgcccccac aatctgggtc cggatggtca    8940
taatgaccca tttcttctcc atactattgg cccaggacac tctgaaccaa aatctcaact    9000
ttgagatgta tggggcagta tattcggtca atccattaga cctaccggcc ataattgaaa    9060
ggctacacgg gcttgacgcc ttttcactgc acacatactc tccccacgaa ctctcacggg    9120
tggcagcgac tctcagaaaa cttggagcgc ctccccttag agcgtggaag agtcgggcac    9180
gtgctgtgag ggcctcactc atcgcccagg gagggaaggc agccatttgt ggccgctacc    9240
tcttcaactg ggcggtgaag acaaagctca aactcactcc attgcccgag gcgagccgcc    9300
tggatttatc cggtggttc accgtgggcg ccggcggggg cggcatcttt cacagcgtgt     9360
cgcatgcccg accccgccta ttactccttt gcctactcct acttagcgta ggggtaggca    9420 tcttttact ccccgctcgg tagagcggca aaccctagct acactccata gctagttcct      9480
tttttttttt tttttttttt tttttttttt tttttttttt tttttttttt ttttttttct    9540
tcttttttat ttttccttct ttcttggtgg ctccatctta gccctagtca cggctagctg    9600
tgaaaggtcc gtgagccgca tgactgcaga gagtgccgta actggtctct ctgcagatca    9660
``` tgt                                                                 9663

<210> SEQ ID NO 5
<211> LENGTH: 9663
<212> TYPE: DNA
<213> ORGANISM: Hepatitis C virus

<400> SEQUENCE: 5

| | | | | | |
|---|---|---|---|---|---|
| gcccgccccc | taatgggggc | gacactccgc | catgaatcac | tcccctgtga | ggaactactg | 60 |
| tcttcacgca | gaaagcgtct | agccatggcg | ttagtatgag | tgtcgtacag | cctccaggcc | 120 |
| cccccctccc | gggagagcca | tagtggtctg | cggaaccggt | gagtacaccg | gaattaccgg | 180 |
| aaagactggg | tcctttcttg | gataaaccca | ctctatgtcc | ggtcatttgg | gcgtgccccc | 240 |
| gcaagactgc | tagcctagta | gcgttgggtt | gcgaacggcc | ttgtggtact | gcctgatagg | 300 |
| gtgcttgcga | gtgccccggg | aggtctcgta | gaccgtgcat | catgagcaca | aatcctaaac | 360 |
| ctcaaagaaa | aaccaaaaga | aacacaaacc | gtcgcccaca | ggacgtcaag | ttcccgggtg | 420 |
| gcggtcagat | cgttggcgga | gtttacttgc | tgccgcgcag | gggccccagg | ttgggtgtgc | 480 |
| gcgcaacaag | gaagacttcc | gagcggtccc | agcgcgtgg | gagacgccag | cccatcccaa | 540 |
| aagatcggcg | ctccaccggc | aagtcctggg | gaaagccagg | atatccttgg | cctctgtatg | 600 |
| gaaacgaggg | ctgcggctgg | gcaggttggc | tcctgtcccc | tcgcgggtct | cgtcctactt | 660 |
| ggggccccac | tgaccccggg | catagatcac | gcaatttagg | taaagtcatc | gataccatta | 720 |
| cgtgtggttt | tgccgacctc | atggggtaca | tccccgtcgt | tggcgccccg | gtcggaggcg | 780 |
| tcgccagagc | cctggcacac | ggtgttaggg | tcctggagga | cgggataaat | tatgcaacag | 840 |
| ggaatctgcc | tggttgctct | ttttctatct | tcttactcgc | ccttctgtcg | tgcatcacag | 900 |
| tgccagtgtc | tgcggtggaa | gtcaggaaca | ttagctctgg | ctactacgcc | actaatgatt | 960 |
| gctcgaacaa | cagcatcacc | tggcagctca | ctaacgcagt | tctccatctt | cccggatgcg | 1020 |
| tcccatgtga | gaacgacaat | ggcaccctgc | gctgctggat | acaagtaaca | cctaatgtgg | 1080 |
| ctgtgaaaca | ccgcggcgcg | ctcactcaca | acctgcgaac | gcatgtcgac | gtggttgtga | 1140 |
| tggcagccac | gatctgctcg | gccttgtatg | tgggagacgt | gtgtggggcc | gtgatgatcg | 1200 |
| tatctcaggc | atttatactg | tcgccagagc | gccacaactt | tacccaggag | tgcaattgtt | 1260 |
| ccatctacca | aggtcatatc | accggccacc | gcatggcatg | ggacatgatg | ttaaactggt | 1320 |
| caccaactct | taccatggtc | ctcgcctatg | ctgctcgtgt | tcctgagcta | gtccttgaag | 1380 |
| ttgtcttcgg | cggccattgg | ggtgtggtgt | ttggcttggc | ctatttctcc | atgcaggagg | 1440 |
| catgggccaa | agttatggcc | atcctcctcc | ttgtcgcagg | agtggacgca | cacacctatt | 1500 |
| ccaccggtgc | ccgagcgggt | caagcagcct | cgggcttaac | ttccctttttt | tccgttggtt | 1560 |
| ctaggcagag | gctcagtcta | attcacacca | atggcagttg | gcacataaac | cggactgccc | 1620 |
| tcaattgcaa | tgacagcttg | catacggggtt | tcatcgcttc | ccttctttac | gtcaacaatt | 1680 |
| tcaacagctc | tggctgcccc | gagcgcatgt | cttcctgccg | tgcgctggat | gatttccgca | 1740 |
| tcgggtgggg | aaccttggag | tacgaaacca | atgtcaccaa | cgacgaggac | atgaggccgt | 1800 |
| actgctggca | ttatcctccg | aagccttgcg | gtatcgttcc | ggctgggacg | gtttgcgggc | 1860 |
| cggtctactg | cttcactccc | agccctgttg | ttgtgggtac | cactgacaag | cagggcgtgc | 1920 |
| ccacctataa | ctgggggaa | aatgagaccg | atgtcttcct | gctgaatagc | acagacccc | 1980 |
| cgcaagggc | ttggttcggc | tgcacttgga | tgaacgggac | tgggttcact | aagacatgcg | 2040 |

```
gtgcaccacc ttgccgcatt aggagggact acaacggaac cctcgatctg ttgtgcccca    2100
cagactgttt taggaagcac ccagaaacca cctatcttag gtgcggatca gggccttggt    2160 tgaccccag  atgcctggtg gattaccctt atagattgtg gcattatccg tgcactgtga    2220
atttcaccat ctttaaggtg cggatgtatg tgggggagt  ggagcatcgg ttgtccgcag    2280
catgtaactt cacgcgcggg gaccgctgca atttagaaga tagggatagg ggtcagcaga    2340
gtccgctgct gcactccacc actgagtggg cggtgttacc atgctctttc tccgacctac    2400
cggcactatc tactggttta ttgcacctcc atcaaaacat cgtggacgtg cagtacctct    2460
atggactttc tccggctatc acaagataca tcgtgaagtg ggagtgggtg gttctcctct    2520
tcttgttgtt ggcagatgcc agggtctgtg catgcctttg gatgctcatc atactgggcc    2580
aagccgaggc ggcgcttgag aagcttatca tcttgcactc tgctagcgct gctagtgcca    2640
atgggccgct gtggttcttc atcttcttca tagcggcctg gtacttaaag ggcagggtgg    2700
tccccatggc cacgtactct gttcttggct tgtggtcctt tttcctccta gtcctggcct    2760
taccacagca ggcttatgct ctggacgccg ttgaacaagg ggaactgggg ctggttttgt    2820 tagggggtcat atcaatcttc actcttaccc cagcatacaa gactctcctg agccgttcag    2880
tatggtggct gtcctacatg ctggtcttgg ccgaggccca gattcagcaa tgggttcccc    2940
ccctggaagc ccgaggggc  cgtgacggga tcatctgggt agctgtcatt ctacgcccat    3000
gccttgtgtt tgagatcacg aaatggctgt tggcagttct ggggcctgcc tacctcctta    3060
gagcgtccct gctacgggta ccgtactttg tgagggccca cgccctgcta cgactgtgtg    3120
ccctggtgag acacctcgca ggagctaggt acatccagat gctgttgatc accataggca    3180
ggtggactgg tacttacatc tatgaccacc tctccccttt atcaacttgg gcagcccagg    3240
gtttgcggga cctagcggtc gccgtggagc ctgtggtgtt tagcccaatg gagaagaagg    3300
tcattgtgtg gggggctgag acagtggcgt gtggggatat cctgcatggc ctccggtgt    3360 ccgcgaggct aggtagggaa attctgctcg gccccgccga tggctacacc tcgaaggggt    3420
ggaagctcct ggctcctatc actgcttata ctcagcagac ccgtggtctc ctgggtgcca    3480
tagtggtcag tctgacgggc cgcgacaaaa atgagcaggc tgggcaggtc caggttctgt    3540
cctccgtcac acaatctttc ttggggacat ctatttcggg ggtcctctgg acagtatacc    3600
atggggctgg taataagacc ttggctggcc ccagaggacc agtcactcag atgtactcca    3660
gcgcagaggg ggacctcgtg ggatggccta gcccccccgg gactaagtct ttagacccttt   3720 gtacctgtgg ggccgtggac ctctacctgg tcacccgaaa cgctgatgtc attccggtcc    3780
ggaggagaga tgaccggcgg ggcgcactac tctcgccaag gcctctctcg accctcaaag    3840
ggtcatccgg tggacccgtg ctctgctccc ggggacatgc cgtgggcttg ttcagggcgg    3900
ccgtgtgcac caggggtgtg gccaagtcca ttgacttcat ccctgttgaa tctctcgatg    3960
tcgctgcacg atcgcccagt ttctctgaca acagcactcc accagctgtg cctcagtctt    4020
accaagtggg ctacttacac gcgccaacag gcagcgggaa gagcaccaag gtccctgccg    4080
catacgccag tcaggggtat aaagtacttg tactgaatcc ctctgtcgcg gccacactcg    4140 gctttgggc  ctacatgtcc aaggcccacg gaatcaaccc taacatcagg accggggtac    4200
ggactgtgac caccggggac ccaataactt actccactta tggcaagttc ctcgctgatg    4260
gaggctgctc agctggcgcc tatgacatca tcatatgcga cgaatgccat tcagtggacg    4320
ccactaccat ccttggcatt ggaacagtcc tcgaccaggc cgagaccgca ggcgccaggc    4380
tagtagtctt ggctacagcc acgcctcctg gtacagtgac aactcccat  agcaacatag    4440
```

```
aggaggtggc tcttggtcat gaaggcgaga tccctttta cggcaaggct attcctctag    4500
cttatatcaa gggaggcagg cacctgatct tctgccactc aaagaagaag tgcgatgagc    4560
tcgcagcagc ccttcgggc atgggtgtca atgccgttgc ttactacagg ggtctcgacg     4620
tctccgtcat accacttcaa ggagacgtgg tggtagtcgc caccgatgcc ctaatgactg    4680
gatttaccgg tgactttgat tctgtcatcg actgcaacgt tgcagtcact cagattgttg    4740
acctcagcct agaccccgacc tttactatca ccactcaaac tgtccctcag gacgccgtct   4800
cccgtagtca acgtagaggg agaactgggc gaggacggtt gggcatttac aggtatgttt    4860
cgtcaggtga aaggccgtct gggatgttcg acagcgtagt gctctgcgag tgctatgatg    4920
ccggggcagc ctggtacgaa ctcacgcctg ctgaaactac agtgagactc cgggcctatt    4980
tgaacacgcc cggtctgccc gtgtgtcagg accacctgga atttgggag gcggtcttca     5040
caggtctcac acacattgat gcccacttcc tctcccagac gaaacaagga ggagacaact    5100
ttgcgtatct aacggcctat caggccacgg tatgcgctag ggcgagggcg ccccctcctt    5160
cctgggactt gatgtggaag tgtctaacta ggctcaagcc tacactgaat ggccctaccc    5220
cccttctata ccgcttgggt gccgtgacca acgaggtcac cctgactcac cccgtgacga    5280
aatatatcgc cacgtgtatg caagctgacc ttgagatcat gacaagtaca tgggttctag    5340
cgggggggt gctagccgcc gtagcatctt actgcctggc gaccggctgt gtttccatca     5400
ttggccgcct acacctgaat gatcgagtgg ttgtggcccc tgataaggaa atcttatatg    5460
aggcctttga tgagatggaa gagtgcgcct ccaaagccgc cctcattgag gaagggcagc    5520
ggatggcgga gatgctcaag accaagatac aaggcctcct acaacaggcc acaagacaag    5580
cccaagacat acagccagcc atacagtcat cgtggcccaa gcttgaacaa ttttgggcca    5640
agcacatgtg gaacttcatc agtggcatac agtacctggc gggactctcc acgctaccag    5700
ggaatcccgc ggtggcgtca atgatggctt ttagcgccgc attgactagc ccactgccca    5760
ccagcaccac catcctcttg aacatcatgg ggggatggtt ggcctctcag atcgcccccc    5820
ctgccggggc cactggcttt gttgtcagtg gtctggtagg ggcggccgtc ggaagtatag    5880
gcctgggtaa gatactggtg gatgttttgg ccgggtatgg tgcaggcatt tcaggggccc    5940
tcgtagcttt caagatcatg agcggcgaga agcctacggt agaagatgtt gtgaatctcc    6000
tgcctgctat cctgtctcct ggtgctttag tagtgggagt catctgtgca gcaatttgtc    6060
gccgccacat cggccaggga gaggggcgg tccagtggat gaacagactc atcgccttcg     6120
cctccagagg aaaccatgtt gcccctaccc actacgtggc agagtctgac gcctcgcagc    6180
gcgtgacgca agcgctgagt tcactcacaa ttaccagctt actcaggaga ctacatgcct    6240
ggatcactga agattgccca gtcccgtgct cggggtcttg gctccgggac atctgggatt    6300
gggtctgttc cattctcaca gactttaaga actggctgtc ttcaaaactg ctccccaagc    6360
tgccccggcct tcccttcatc tcttgccaaa agggatacag gggcgtatgg gctggcacgg    6420
gagtcatgac cactcggtgc ccgtgcggag ctaccatctc gggccatgtc cgcatgggta    6480
ccatgaaaat aacaggccca aagacctgct tgaacatgtg gcagggtcc ttccccatca     6540
attgttacac agaagggcct tgcgtgccaa accccctcc taactacaag accgcaattt     6600
ggagggttgc agcgtcggag tacgttgaaa tcacgcaaca cggctcattc tcgtacgtaa    6660
cggggttaac taatgacaac cttaaggtcc cctgccaagt accagctcca gaattttct     6720
cttgggtgga cgggggtgcag atacaccggt tcgcccccac tccaggtccc ttctttcggg   6780
```

| | |
|---|---|
| atgaggtaac gttcaccgta ggccttaatt cctttgtggt cggctctcag ctcccctgcg | 6840 |
| accctgagcc ggacaccgag gtattggcct ccatgttgac agacccgtcc cacattacag | 6900 |
| cggaggcggc agctaggcga ttggccaggg ggtctccccc ctcacaggct agctcttcgg | 6960 |
| cgagccagct ctccgccccg tccttgaagg ccacctgtac cacccataag gtggcatatg | 7020 |
| attgtgacat ggtggacgcc aacctgttca tgggaggcga tgtgacccgg attgagtcca | 7080 |
| actccaaggt ggtcattctt gactccctcg attccatgac tgaggtagag gacgaccgtg | 7140 |
| agccttctat cccatcagag tacctgatca ggaggagaaa gttcccaccg gcactacctc | 7200 |
| cctgggcccg tccagactac aaccctcctg tggtcgagac atggaagagg ccggactatg | 7260 |
| aaccacccac tgtcctaggc tgtgccctac cccccacacc tcaggcgcca gtgcctccac | 7320 |
| cccggaggcg ccgcgccaaa gtcctgaccc aggacaatgt ggagggggtt ctcaaggaga | 7380 |
| tggcggacaa agttcttagc cctctccgag attgtaatga ctccggtcac tccactggag | 7440 |
| cggataccgg ggcagacagc gtccagcagc cccctgacga gactgccgct tcagaggcgg | 7500 |
| gatcactgtc ctccatgcct cccttgagg gagagccggg ggaccctgac ctggagtttg | 7560 |
| aaccagctgg atccgctccc ccttcagagg gggagtgtga ggtcattgat tcggactcta | 7620 |
| agtcgtggtc tacagtctct gatcaggagg attccattat ctgctgctcc atgtcatact | 7680 |
| cctggacggg agccctcata acaccatgtg ggcccgaaga ggagaagttg ccaatcaacc | 7740 |
| ctctgagtaa ctcgcttatg cggttccata acaaggtgta ctcgcacaacc tcgaggagcg | 7800 |
| cctctcagag agcaaaaaag gtgacctttg acagggtgca ggtgctggac aaacactacg | 7860 |
| actcagtctt gcaggacgtt aagcgggccg cctctaaggt tagtgcgagg ctcctctcaa | 7920 |
| tagaggaagc ctgcgcgctg accccgcctc actccgccaa atcgcggtat ggatttgggg | 7980 |
| caaaagaggt gcgcagctta tccaggaggg ccgtcaacca catccagtcc gtgtgggagg | 8040 |
| accttctgga agaccaacat actccaattg agacaactat catggccaag aacgaggtgt | 8100 |
| tctgcgttga tccgctaaa ggcgggaaaa agtcagctcg cctcattgta tacccctgacc | 8160 |
| ttggggtcag agtgtgcgaa aaaatggccc tctatgacat tgcacaaaag cttcccaagg | 8220 |
| caataatggg tccatcctat gggttccaat actctcccgc agagcgggtc gattttctcc | 8280 |
| tcaaagcttg gggaagcaag aaggacccaa tggggttctc gtatgacacc cgctgcttcg | 8340 |
| actcaaccgt cacggagaga gatatacgaa cagaagaatc catatatcag gcttgttccc | 8400 |
| tgcctcaaga ggccagagtt gccatacact cacttactga gagactctac gtaggagggc | 8460 |
| ccatgctaaa cagcaagggc caatcctgcg gttacaggcg ttccgcgcg agcggcgttt | 8520 |
| tcaccaccag catggggaat accatgacat gctacatcaa agcccttgcg gcgtgccaag | 8580 |
| ccgcagggat cgtggacccc gttatgctgg tgtgtggaga cgacctggtc gtcatctcag | 8640 |
| agagtcaagg taacgatgag gacgagcgaa acctgagagc tttcacggag gctatgacca | 8700 |
| ggtattcagc ccctcctggt gaccttccca gaccggaata tgacttggag cttataacat | 8760 |
| cctgctcctc aaacgtatcg gtagcgctgg accctcgggg tcgccgccgg tactacctaa | 8820 |
| ccagagaccc taccactcca atctcccgag ccgcttggga aacagtaaga cactcccctg | 8880 |
| tcaattcttg gctgggcaac atcatccaat acgccccac aatctgggtc cggatggtca | 8940 |
| taatgaccca tttcttctcc atactattgg cccaggacac tctgaaccaa aatctcaact | 9000 |
| ttgagatgta tggggcagta tattcggtca atcattagga cctaccggcc ataattgaaa | 9060 |
| ggctacacgg gcttgacgcc ttttcactgc acacatactc tccccacgaa ctctcacggg | 9120 |
| tggcagcgac tctcagaaaa cttggagcgc ctccccttag agcgtggaag agtcgggcac | 9180 |

```
gtgctgtgag ggcctcactc atcgcccagg gagggaaggc agccatttgt ggccgctacc    9240
tcttcaactg ggcggtgaag acaaagctca aactcactcc attgcccgag gcgagccgcc    9300
tggatttatc cgggtggttc accgtgggcg ccggcggggg cggcatcttt cacagcgtgt    9360
cgcatgcccg accccgccta ttactccttt gcctactcct atttagcgta ggggtaggca    9420 tcttttttact ccccgctcgg tagagcggca aaccctagct acactccata gctagttcct    9480
tttttttttt tttttttttt tttttttttt tttttttttt tttttttttt ttttttttct    9540
tcttttttat ttttccttct ttcttggtgg ctccatctta gccctagtca cggctagctg    9600
tgaaaggtcc gtgagccgca tgactgcaga gagtgccgta actggtctct ctgcagatca    9660
tgt                                                                  9663
```

<210> SEQ ID NO 6
<211> LENGTH: 9663
<212> TYPE: DNA
<213> ORGANISM: Hepatitis C virus

<400> SEQUENCE: 6

```
gcccgccccc taatgggggc gacactccgc catgaatcac tcccctgtga ggaactactg      60
tcttcacgca gaaagcgtct agccatggcg ttagtatgag tgtcgtacag cctccaggcc     120 ccccccctccc gggagagcca tagtggtctg cggaaccggt gagtacaccg gaattaccgg     180
aaagactggg tcctttcttg gataaaccca ctctatgtcc ggtcatttgg gcgtgccccc     240
gcaagactgc tagcctagta gcgttgggtt cgaacggcc ttgtggtact gcctgatagg     300
gtgcttgcga gtgccccggg aggtctcgta gaccgtgcat catgagcaca aatcctaaac     360
ctcaaagaaa aaccaaaaga aacacaaacc gtcgcccaca ggacgtcaag ttcccgggtg     420
gcggtcagat cgttggcgga gtttacttgc tgccgcgcag gggccccagg ttgggtgtgc     480
gcgcaacaag gaagacttcc gagcggtccc agccgcgtgg gagacgccag cccatcccaa     540
aagatcggcg ctccaccggc aagtcctggg gaaagccagg atatccttgg cctctgtatg     600
gaaacgaggg ctgcggctgg gcaggttggc tcctgtcccc tcgcgggtct cgtcctactt     660
ggggccccac tgaccccggg catagatcac gcaatttagg taaagtcatc gataccatta     720
cgtgtggttt tgccgacctc atggggtaca tcccgtcgt tggcgccccg gtcggaggcg     780
tcgccagagc cctggcacac ggtgttaggg tcctggagga cggataaaat tatgcaacag     840
ggaatctgcc tggttgctct ttttctatct tcttactcgc ccttctgtcg tgcatcacag     900
tgccagtgtc tgcggtggaa gtcaggaaca ttagctctgg ctactacgcc actaatgatt     960
gctcgaacaa cagcatcacc tggcagctca ctaacgcagt tctccatctt cccggatgcg    1020 tccccatgtga aacgacaat ggcacccctgc gctgctggat acaagtaaca cctaatgtgg    1080
ctgtgaaaca ccgcggcgcg ctcactcaca acctgcgaac gcatgtcgac gtggttgtga    1140
tggcagccac gatctgctcg gccttgtatg tgggagacgt gtgtggggcc gtgatgatcg    1200
tatctcaggc atttatactg tcgccagagc gccacaactt tacccaggag tgcaattgtt    1260
ccatctacca aggtcatatc accggccacc gcatggcatg ggacatgatg ttaaactggt    1320
caccaactct taccatggtc ctcgcctatg ctgctcgtgt tcctgagcta gtccttgaag    1380
ttgtcttcgg cggccattgg ggtgtggtgt ttggcttggc ctatttctcc atgcagggag    1440
catgggccaa agttatggcc atcctcctcc ttgtcgcagg agtggacgca cacacctatt    1500
ccaccggtgc ccgagcgggt caagcagcct cgggcttaac ttccctttttt tccgttggtt    1560
```

```
ctaggcagag gctcagtcta attcacacca atggcagttg gcacataaac cggactgccc    1620
tcaattgcaa tgacagcttg catacgggtt tcatcgcttc ccttctttac gtcaacaatt    1680
tcaacagctc tggctgcccc gagcgcatgt cttcctgccg tgcgctggat gatttccgca    1740
tcgggtgggg aaccttggag tacgaaacca atgtcaccaa cgacgaggac atgaggccgt    1800
actgctggca ttatcctccg aagccttgcg gtatcgttcc ggctgggacg gtttgcgggc    1860
cggtctactg cttcactccc agccctgttg ttgtgggtac cactgacaag cagggcgtgc    1920
ccacctataa ctgggggaa atgagaccg atgtcttcct gctgaatagc acgagacccc    1980
cgcaaggggc ttggttcggc tgcacttgga tgaacgggac tgggttcact aagacatgcg    2040
gtgcaccacc ttgccgcatt aggagggact acaacggaac cctcgatctg ttgtgcccca    2100
cagactgttt taggaagcac ccagaaacca cctatcttag gtgcggatca gggccttggt    2160 tgaccccag atgcctggtg gattaccctt atagattgtg gcattatccg tgcactgtga    2220
atttcaccat ctttaaggtg cggatgtatg tgggggagt ggagcatcgg ttgtccgcag    2280
catgtaactt cacgcgcggg gaccgctgca atttagaaga tagggatagg ggtcagcaga    2340
gtccgctgct gcactccacc actgagtggg cggtgttacc atgctctttc tccgacctac    2400
cggcactatc tactggttta ttgcacctcc atcaaaacat cgtggacgtg cagtacctct    2460
atggactttc tccggctatc acaagataca tcgtgaagtg ggagtgggtg gttctcctct    2520
tcttgttgtt ggcagatgcc agggtctgtg catgcctttg gatgctcatc atactgggcc    2580
aagccgaggc ggcgcttgag aagcttatca tcttgcactc tgctagcgct gctagtgcca    2640
atgggccgct gtggttcttc atcttcttca tagcggcctg gtacttaaag ggcagggtgg    2700
tccccatggc cacgtactct gttcttggct tgtggtcctt tttcctccta gtcctggcct    2760
taccacagca ggcttatgct ctggacgccg ttgaacaagg ggaactgggg ctggttttgt    2820
taggggtcat atcaatcttc actcttaccc cagcatacaa gactctcctg agccgttcag    2880 tatggtggc gtcctacatg ctggtcttgg ccgaggccca gattcagcaa tgggttcccc    2940
ccctggaagc ccgagggggc cgtgacggga tcatctgggt agctgtcatt ctacgcccat    3000
gccttgtgtt tgagatcacg aaatggctgt tggcagttct ggggcctgcc tacctcctta    3060
gagcgtccct gctacgggta ccgtactttg tgagggccca cgccctgcta cgactgtgtg    3120
ccctggtgag acacctcgca ggagctaggt acatccagat gctgttgatc accataggca    3180
ggtggactgg tacttacatc tatgaccacc tctcccctt atcaacttgg gcagcccagg    3240
gtttgcggga cctagcggtc gccgtggagc ctgtggtgtt tagcccaatg gagaagaagg    3300
tcattgtgtg gggggctgag acagtggcgt gtggggatat cctgcatggc ctcccggtgt    3360
ccgcgaggct aggtagggaa attctgctcg gccccgccga tggctacacc tcgaaggggt    3420
ggaagctcct ggctcctatc actgcttata ctcagcagac ccgtggtctc ctgggtgcca    3480
tagtggtcag tctgacgggc cgcgacaaaa atgagcaggc tggcaggtc caggttctgt    3540 cctccgtcac acaatctttc ttggggacat ctatttcggg ggtcctctgg acagtatacc    3600
atggggctgg taataagacc ttggctggcc ccagaggacc agtcactcag atgtactcca    3660
gcgcagaggg ggacctcgtg ggatggccta gcccccccgg gactaagtct ttagaccctt    3720
gtacctgtgg ggccgtggac ctctacctgg tcacccgaaa cgctgatgtc attccggtcc    3780
ggaggagaga tgaccggcgg ggcgcactac tctcgccaag gcctctctcg accctcaaag    3840
ggtcatccgc tggaccccgtg ctctgctccc ggggacatgc cgtgggcttg ttcagggcgg    3900
ccgtgtgcac caggggtgtg gccaagtcca ttgacttcat ccctgttgaa tctctcgatg    3960
```

```
tcgctgcacg atcgcccagt ttctctgaca acagcactcc accagctgtg cctcagtctt    4020
accaagtggg ctacttacac gcgccaacag gcagcgggaa gagcaccaag gtccctgccg    4080
catacgccag tcaggggtat aaagtacttg tactgaatcc ctctgtcgcg gccacactcg    4140
gctttggggc ctacatgtcc aaggcccacg gaatcaaccc taacatcagg accggggtac    4200
ggactgtgac caccggggac ccaataactt actccactta tggcaagttc ctcgctgatg    4260
gaggctgctc agctggcgcc tatgacatca tcatatgcga cgaatgccat tcagtggacg    4320
ccactaccat ccttggcatt ggaacagtcc tcgaccaggc cgagaccgca ggcgccaggc    4380
tagtagtctt ggctacagcc acgcctcctg gtacagtgac aactccccat agcaacatag    4440
aggaggtggc tcttggtcat gaaggcgaga tccctttttta cggcaaggct attcctctag    4500
cttatatcaa gggaggcagg cacctgatct tctgccactc aaagaagaag tgcgatgagc    4560
tcgcagcagc ccttcggggc atgggtgtca atgccgttgc ttactacagg ggtctcgacg    4620
tctccgtcat accacttcaa ggagacgtgg tggtagtcgc caccgatgcc ctaatgactg    4680
gatttaccgg tgactttgat tctgtcatcg actgcaacgt tgcagtcact cagattgttg    4740
acctcagcct agacccgacc tttactatca ccactcaaac tgtccctcag gacgccgtct    4800
cccgtagtca acgtagaggg agaactgggc gaggacggtt gggcatttac aggtatgttt    4860
cgtcaggtga aaggccgtct gggatgttcg acagcgtagt gctctgcgag tgctatgatg    4920
ccggggcagc ctggtacgaa ctcacgcctg ctgaaactac agtgagactc cgggcctatt    4980
tgaacacgcc cggtctgccc gtgtgtcagg accacctgga attttgggag gcggtcttca    5040
caggtctcac acacattgat gcccacttcc tctcccagac gaaacaagga ggagacaact    5100
ttgcgtatct aacggcctat caggccacgg tatgcgctag ggcgagggcg cccccctcctt    5160 cctgggactt gatgtggaag tgtctaacta ggctcaagcc tacactgaat ggccctaccc    5220
cccttctata ccgcttgggt gccgtgacca acgaggtcac cctgactcac cccgtgacga    5280
aatatatcgc cacgtgtatg caagctgacc ttgagatcat gacaagtaca tgggttctag    5340
cggggggggt gctagccgcc gtagcatctt actgcctggc gaccggctgt gtttccatca    5400
ttggccgcct acacctgaat gatcgagtgg ttgtggcccc tgataaggaa atcttatatg    5460
aggcctttga tgagatggaa gagtgcgcct ccaaagccgc cctcattgag gaagggcagc    5520
ggatggcgga gatgctcaag accaagatac aaggcctcct acaacaggcc acaagacaag    5580
cccaagacat acagccagcc atacagtcat cgtggcccaa gcttgaacaa ttttgggcca    5640
agcacatgtg gaacttcatc agtggcatac agtacctggc gggactctcc acgctaccag    5700
ggaatcccgc ggtggcgtca atgatggctt ttagcgccgc attgactagc ccactgccca    5760
ccagcaccac catcctcttg aacatcatgg ggggatggtt ggcctctcag atcgcccccc    5820
ctgccggggc cactggcttt gttgtcagtg gtctggtagg ggcggccgtc ggaagtatag    5880
gcctgggtaa gatactggtg gatgttttgg ccgggtatgg tgcaggcatt tcaggggccc    5940
tcgtagcttt caagatcatg agcggcgaga agcctacggt agaagatgtt gtgaatctcc    6000
tgcctgctat cctgtctcct ggtgctttag tagtgggagt catctgtgca gcaattttgc    6060
gccgccacat cggccaggga gaggggcgg tccagtggat gaacagactc atcgccttcg    6120
cctccagagg aaaccatgtt gcccctaccc actacgtggc agagtctgac gcctcgcagc    6180
gcgtgacgca agcgctgagt tcactcacaa ttaccagctt actcaggaga ctacatgcct    6240
ggatcactga agattgccca gtcccgtgct cggggtcttg gctccgggac atctgggatt    6300
```

```
gggtctgttc cattctcaca gactttaaga actggctgtc ttcaaaactg ctccccaagc    6360
tgcccggcct tcccttcatc tcttgccaaa agggatacag gggcgtatgg gctggcacgg    6420
gagtcatgac cactcggtgc ccgtgcggag ctaccatctc gggccatgtc cgcatgggta    6480
ccatgaaaat aacaggccca aagacctgct tgaacatgtg gcagggtcc ttccccatca     6540
attgttacac agaagggcct tgcgtgccaa acccctcc taactacaag accgcaattt      6600
ggagggttgc agcgtcggag tacgttgaaa tcacgcaaca cggctcattc tcgtacgtaa    6660
cggggttaac taatgacaac cttaaggtcc cctgccaagt accagctcca gaattttct     6720
cttgggtgga cggggtgcag atacaccggt tcgcccccac tccaggtccc ttctttcggg    6780
atgaggtaac gttcaccgta ggccttaatt cctttgtggt cggctctcag ctccctgcg     6840
accctgagcc ggacaccgag gtattggcct ccatgttgac agacccgtcc cacattacag    6900
cggaggcggc agctaggcga ttggccaggg ggtctccccc ctcacaggct agctcttcgg    6960
cgagccagct ctccgccccg tccttgaagg ccacctgtac cacccataag gtggcatatg    7020
attgtgacat ggtggacgcc aacctgttca tgggaggcga tgtgacccgg attgagtcca    7080
actccaaggt ggtcattctt gactccctcg attccatgac tgaggtagag gacgaccgtg    7140
agccttctat cccatcagag tacctgatca ggaggagaaa gttcccaccg gcactacctc    7200
cctgggcccg tccagactac aaccctcctg tggtcgagac atggaagagg ccggactatg    7260
aaccaccac tgtcctaggc tgtgccctac cccccacacc tcaggcgcca gtgcctccac     7320
cccggaggcg ccgcgccaaa gtcctgaccc aggacaatgt ggaggggggtt ctcaaggaga   7380
tggcggacaa agttcttagc cctctccgag attgtaatga ctccggtcac tccactggag    7440
cggataccgg ggcagacagc gtccagcagc ccctgacga gactgccgct tcagaggcgg     7500
gatcactgtc ctccatgcct ccccttgagg gagagccggg ggaccctgac ctggagtttg    7560
aaccagctgg atccgctccc ccttcagagg gggagtgtga ggtcattgat tcggactcta    7620
agtcgtggtc tacagtctct gatcaggagg attccattac ctgctgctcc atgtcatact    7680
cctggacggg agccctcata acaccatgtg ggcccgaaga ggagaagttg ccaatcaacc    7740
ctctgagtaa ctcgcttatg cggttccata acaaggtgta ctcgacaacc tcgaggagcg    7800
cctctcagag agcaaaaaag gtgaccttg acagggtgca ggtgctggac aaacactacg      7860
actcagtctt gcaggacgtt aagcgggccg cctctaaggt tagtgcgagg ctcctctcaa     7920
tagaggaagc ctgcgcgctg accccgcctc actccgccaa atcgcggtat ggatttgggg    7980
caaaagaggt gcgcagctta tccaggaggg ccgtcaacca catccagtcc gtgtgggagg    8040
accttctgga agaccaacat actccaattg agacaactat catggccaag aacgaggtgt    8100
tctgcgttga tccgctaaa ggcgggaaaa agtcagctcg cctcattgta taccctgacc     8160
ttgggggtcag agtgtgcgaa aaaatggccc tctatgacat tgcacaaaag cttcccaagg   8220
caataatggg tccatcctat gggttccaat actctcccgc agagcgggtc gattttctcc    8280
tcaaagcttg gggaagcaag aaggacccaa tggggttctc gtatgacacc cgctgcttcg    8340
actcaaccgt cacggagaga gatatacgaa cagaagaatc catatatcag gcttgttccc    8400
tgcctcaaga ggccagagtt gccatacact cacttactga gagactctac gtaggagggc    8460
ccatgctaaa cagcaagggc caatcctgcg gttacaggcg ttgccgcgcg agcggcgttt    8520
tcaccaccag catggggaat accatgacat gctacatcaa agcccttgcg gcgtgccaag    8580
ccgcagggat cgtggacccc gttatgctgg tgtgtggaga cgacctggtc gtcatctcag    8640
agagtcaagg taacgatgag gacgagcgaa acctgagagc tttcacggag gctatgacca    8700
```

```
ggtattcagc ccctcctggt gaccttccca gaccggaata tgacttggag cttataacat    8760
cctgctcctc aaacgtatcg gtagcgctgg accctcgggg tcgccgccgg tactacctaa    8820
ccagagaccc taccactcca atctcccgag ccgcttggga aacagtaaga cactcccctg    8880
tcaattcttg gctgggcaac atcatccaat acgcccccac aatctgggtc cggatggtca    8940
taatgaccca tttcttctcc atactattgg cccaggacac tctgaaccaa aatctcaact    9000
ttgagatgta tgggggcagta tattcggtca atccattaga cctaccggcc ataattgaaa    9060
ggctacacgg gcttgacgcc ttttcactgc acacatactc tccccacgaa ctctcacggg    9120
tggcagcgac tctcagaaaa cttggagcgc ctcccttag agcgtggaag agtcgggcac    9180
gtgctgtgag ggcctcactc atcgcccagg gagggaaggc agccatttgt ggccgctacc    9240
tcttcaactg gcggtgaag acaaagctca aactcactcc attgcccgag cgagccgcc    9300 tggatttatc cgggtggttc accgtgggcg ccggcggggg cggcatcttt cacagcgtgt    9360
cgcatgcccg accccgccta ttactccttt gcctactcct atttagcgta ggggtaggca    9420 tcttttact ccccgctcgg tagagcggca aaccctagct acactccata gctagttcct    9480
tttttttttt tttttttttt tttttttttt tttttttttt tttttttttt tttttttct    9540 tctttttat ttttccttct ttcttggtgg ctccatctta gccctagtca cggctagctg    9600
tgaaaggtcc gtgagccgca tgactgcaga gagtgccgta actggtctct ctgcagatca    9660
tgt                                                                  9663

<210> SEQ ID NO 7
<211> LENGTH: 9663
<212> TYPE: DNA
<213> ORGANISM: Hepatitis C virus

<400> SEQUENCE: 7
gcccgccccc taatgggggc gacactccgc catgaatcac tcccctgtga ggaactactg      60
tcttcacgca gaaagcgtct agccatggcg ttagtatgag tgtcgtacag cctccaggcc     120
cccccctccc gggagagcca tagtggtctg cggaaccggt gagtacaccg gaattaccgg     180
aaagactggg tcctttcttg gataaaccca ctctatgtcc ggtcatttgg gcgtgccccc     240
gcaagactgc tagcctagta gcgttgggtt gcgaacggcc ttgtggtact gcctgatagg     300
gtgcttgcga gtgccccggg aggtctcgta ccgtgcat catgagcaca aatcctaaac     360
ctcaaagaaa aaccaaaaga aacacaaacc gtcgcccaca ggacgtcaag ttcccgggtg     420
gcggtcagat cgttggcgga gtttacttgc tgccgcgcag gggccccagg ttgggtgtgc     480
gcgcaacaag gaagacttcc gagcggtccc agccgcgtgg gagacgccag cccatcccaa     540
aagatcggcg ctccaccggc aagtcctggg gaaagccagg atatccttgg cctctgtatg     600
gaaacgaggg ctgcggctgg gcaggttggc tcctgtcccc tcgcgggtct cgtcctactt     660
ggggccccac tgaccccggg catagatcac gcaatttagg taaagtcatc gataccatta     720
cgtgtggttt tgccgacctc atggggtaca tccccgtcgt tggcgccccg tcggaggcg     780 tcgccagagc cctggcacac ggtgttaggg tcctggagga cgggataaat tatgcaacag     840
ggaatctgcc tggttgctct ttttctatct tcttactcgc ccttctgtcg tgcatcacag     900
tgccagtgtc tgcggtggaa gtcaggaaca ttagctctgg ctactacgcc actaatgatt     960
gctcgaacaa cagcatcacc tggcagctca ctaacgcagt tctccatctt cccgatgcg    1020 tcccatgtga gaacgacaat ggcacccctg gctgctggat acaagtaaca cctaatgtgg    1080
```

-continued

```
ctgtgaaaca ccgcggcgcg ctcactcaca acctgcgaac gcatgtcgac gtggttgtga      1140
tggcagccac gatctgctcg gccttgtatg tgggagacgt gtgtgggggcc gtgatgatcg     1200 tatctcaggc atttatactg tcgccagagc gccacaactt tacccaggag tgcaattgtt      1260
ccatctacca aggtcatatc accggccacc gcatggcatg ggacatgatg ttaaactggt      1320
caccaactct taccatggtc ctcgcctatg ctgctcgtgt tcctgagcta gtccttgaag      1380
ttgtcttcgg cggccattgg ggtgtggtgt ttggcttggc ctatttctcc atgcagggag      1440
catgggccaa agttatggcc atcctcctcc ttgtcgcagg agtggacgca cacacctatt      1500
ccaccggtgc ccgagcgggt caagcagcct cgggcttaac ttccctttt tccgttggtt       1560 ctaggcagag gctcagtcta attcacacca atggcagttg gcacataaac cggactgccc      1620
tcaattgcaa tgacagcttg catacgggtt tcatcgcttc ccttctttac gtcaacaatt      1680
tcaacagctc tggctgcccc gagcgcatgt cttcctgccg tgcgctggat gatttccgca      1740
tcgggtgggg aaccttggag tacgaaacca atgtcaccaa cgacgaggac atgaggccgt      1800
actgctggca ttatcctccg aagccttgcg gtatcgttcc ggctgggacg gtttgcgggc      1860
cggtctactg cttcactccc agccctgttg ttgtgggtac cactgacaag cagggcgtgc      1920
ccacctataa ctgggggggaa aatgagaccg atgtcttcct gctgaatagc acgagacccc     1980
cgcaaggggc ttggttcggc tgcacttgga tgaacgggac tgggttcact aagacatgcg      2040
gtgcaccacc ttgccgcatt aggagggact acaacgaaac cctcgatctg ttgtgcccca     2100
cagactgttt taggaagcac ccagaaacca cctatcttag gtgcggatca gggccttggt      2160 tgaccccccag atgcctggtg gattacccctt atagattgtg gcattatccg tgcactgtga    2220
atttcaccat cttttaaggtg cggatgtatg tggggggagt ggagcatcgg ttgtccgcag     2280
catgtaactt cacgcgcggg gaccgctgca atttagaaga tagggatagg ggtcagcaga     2340
gtccgctgct gcactccacc actgagtggg cggtgttacc atgctctttc tccgacctac      2400
cggcactatc tactggtttta ttgcacctcc atcaaaacat cgtggacgtg cagtacctct     2460
atggactttc tccggctatc acaagataca tcgtgaagtg ggagtgggtg gttctcctct      2520
tcttgttgtt ggcagatgcc agggtctgtg catgcctttg gatgctcatc atactgggcc      2580
aagccgaggc ggcgcttgag aagcttatca tcttgcactc tgctagcgct gctagtgcca     2640
atgggccgct gtggttcttc atcttcttca tagcggcctg gtacttaaag ggcagggtgg      2700
tccccatggc cacgtactct gttcttggct tgtggtcctt tttcctccta gtcctggcct      2760
taccacagca ggcttatgct ctggacgccg ttgaacaagg ggaactgggg ctggttttgt      2820
taggggtcat atcaatcttc actcttaccc cagcatacaa gactctcctg agccgttcag      2880
tatggtggct gtcctacatg ctggtcttgg ccgaggccca gattcagcaa tgggttcccc      2940
ccctggaagc ccgagggggc cgtgacggga tcatctgggt agctgtcatt ccacgcccat      3000
gccttgtgtt tgagatcacg aaatggctgt tggcagttct ggggcctgcc tacctcctta     3060
gagcgtccct gctacgggta ccgtactttg tgagggccca cgcccctgcta cgactgtgtg    3120 ccctggtgag acacctcgca ggagctaggt acatccagat gctgttgatc accataggca      3180
ggtggactgg tacttacatc tatgaccacc tctcccctttt atcaacttgg gcagcccagg     3240
gtttgcggga cctagcggtc gccgtggagc ctgtggtgtt tagcccaatg gagaagaagg      3300
tcattgtgtg ggggggctgag acagtggcgt gtgggggatat cctgcatggc ctcccggtgt    3360
ccgcgaggct aggtagggaa attctgctcg gccccgccga tggctacacc tcgagggggt     3420
ggaagctcct ggctcctatc actgcttata ctcagcagac ccgtggtctc ctgggtgcca     3480
```

```
tagtggtcag tctgacgggc cgcgacaaaa atgagcaggc tgggcaggtc caggttctgt      3540
cctccgtcac acaatctttc ttggggacat ctatttcggg ggtcctctgg acagtatacc      3600
atggggctgg taataagacc ttggctggcc ccagaggacc agtcactcag atgtactcca      3660
gcgcagaggg ggacctcgtg ggatggccta gccccccccgg gactaagtct ttagacccctt     3720 gtacctgtgg ggccgtggac ctctacctgg tcacccgaaa cgctgatgtc attccggtcc      3780
ggaggagaga tgaccggcgg ggcgcactac tctcgccaag gcctctctcg accctcaaag      3840
ggtcatccgg tggacccgtg ctctgctccc ggggacatgc cgtgggcttg ttcagggcgg      3900
ccgtgtgcac caggggtgtg gccaagtcca ttgacttcat ccctgttgaa tctctcgatg      3960
tcgctgcacg atcgcccagt ttctctgaca acagcactcc accagctgtg cctcagtctt      4020
accaagtggg ctacttacac gcgccaacag gcagcgggaa gagcaccaag gtccctgccg      4080
catacgccag tcaggggtat aaagtacttg tactgaatcc ctctgtcgcg gccacactcg      4140
gctttggggc ctacatgtcc aaggcccacg gaatcaaccc taacatcagg accggggtac      4200
ggactgtgac caccggggac ccaataactt actccactta tggcaagttc ctcgctgatg      4260
gaggctgctc agctggcgcc tatgacatca tcatatgcga cgaatgccat tcagtggacg      4320
ccactaccat ccttggcatt ggaacagtcc tcgaccaggc cgagaccgca ggcgccaggc      4380
tagtagtctt ggctacagcc acgcctcctg gtacagtgac aactccccat agcaacatag      4440
aggaggtggc tcttggtcat gaaggcgaga tcccttttta cggcaaggct attcctctag      4500
cttatatcaa gggaggcagg cacctgatct tctgccactc aaagaagaag tgcgatgagc      4560
tcgcagcagc ccttcggggc atgggtgtca atgccgttgc ttactacagg ggtctcgacg      4620
tctccgtcat accacttcaa ggagacgtgg tggtagtcgc caccgatgcc ctaatgactg      4680
gatttaccgg tgactttgat tctgtcatcg actgcaacgt tgcagtcact cagattgttg      4740
acctcagcct agacccgacc tttactatca ccactcaaac tgtccctcag gacgccgtct      4800
cccgtagtca acgtagaggg agaactgggc gaggacggtt gggcatttac aggtatgttt      4860
cgtcaggtga aaggccgtct gggatgttcg acagcgtagt gctctgcgag tgctatgatg      4920
ccggggcagc ctggtacgaa ctcacgcctg ctgaaactac agtgagactc cgggcctatt      4980
tgaacacgcc cggtctgccc gtgtgtcagg accacctgga attttgggag gcggtcttca      5040
caggtctcac acacattgat gcccacttcc tctcccagac gaaacaagga ggagacaact      5100
ttgcgtatct aacggcctat caggccacgg tatgcgctag ggcgagggcg cccccctcctt     5160 cctgggactt gatgtggaag tgtctaacta ggctcaagcc tacactgaat ggccctaccc      5220
cccttctata ccgcttgggt gccgtgacca acgaggtcac cctgactcac cccgtgacga      5280
aatatatcgc cacgtgtatg caagctgacc ttgagatcat gacaagtaca tgggttctag      5340 cgggggggt gctagccgcc gtagcatctt actgcctggc gaccggctgt gtttccatca      5400
ttggccgcct acacctgaat gatcgagtgg ttgtggcccc tgataaggaa atcttatatg      5460
aggcctttga tgagatggaa gagtgcgcct ccaaagccgc cctcattgag gaagggcagc      5520
ggatggcgga gatgctcaag accaagatac aaggcctcct acaacaggcc acaagacaag      5580
cccaagacat acagccagcc atacagtcat cgtggcccaa gcttgaacaa ttttgggcca      5640
agcacatgtg gaacttcatc agtggcatac agtacctggc gggactctcc acgctaccag      5700
ggaatcccgc ggtggcgtca atgatggctt tagcgccgc attgactagc ccactgccca      5760
ccagcaccac catcctcttg aacatcatgg ggggatggtt ggcctctcag atcgcccccc      5820
```

```
ctgccggggc cactggcttt gttgtcagtg gtctggtagg ggcggccgtc ggaagtatag    5880
gcctgggtaa gatactggtg gatgttttgg ccgggtatgg tgcaggcatt tcagggggccc   5940
tcgtagcttt caagatcatg agcggcgaga agcctacggt agaagatgtt gtgaatctcc    6000
tgcctgctat cctgtctcct ggtgcttag tagtgggagt catctgtgca gcaattttgc     6060
gccgccacat cggccaggga gaggggcgg tccagtggat gaacagactc atcgccttcg     6120
cctccagagg aaaccatgtt gccctaccc actacgtggc agagtctgac gcctcgcagc     6180
gcgtgacgca agcgctgagt tcactcacaa ttaccagctt actcaggaga ctacatgcct    6240
ggatcactga agattgccca gtcccgtgct cggggtcttg gctccgggac atctgggatt    6300
gggtctgttc cattctcaca gactttaaga actggctgtc ttcaaaactg ctccccaagc    6360
tgcccggcct tcccttcatc tcttgccaaa agggatacag gggcgtatgg gctggcacgg    6420
gagtcatgac cactcggtgc ccgtgcggag ctaccatctc gggccatgtc cgcatgggta    6480
ccatgaaaat aacaggccca aagacctgct tgaacatgtg gcaggggtcc ttccccatca    6540
attgttacac agaagggcct tgcgtgccaa accccctcc taactacaag accgcaattt     6600
ggagggttgc agcgtcggag tacgttgaaa tcacgcaaca cggctcattc tcgtacgtaa    6660
cggggttaac taatgacaac cttaaggtcc cctgccaagt accagctcca gaatttttct    6720
cttgggtgga cggggtgcag atacaccggt tcgccccac tccaggtccc ttctttcggg     6780
atgaggtaac gttcaccgta ggccttaatt cctttgtggt cggctctcag ctccctgcg    6840
accctgagcc ggacaccgag gtattggcct ccatgttgac agaccccgtcc cacattacag   6900
cggaggcggc agctaggcga ttggccaggg ggtctcccc ctcacaggct agctcttcgg     6960
cgagccagct ctccgccccg tccttgaagg ccacctgtac cacccataag gtggcatatg    7020
attgtgacat ggtggacgcc aacctgttca tgggaggcga tgtgacccgg attgagtcca    7080
actccaaggt ggtcattctt gactccctcg attccatgac tgaggtagag gacgaccgtg    7140
agccttctat cccatcagag tacctgatca ggaggagaaa gttcccaccg gcactacctc    7200
cctgggcccg tccagactac aaccctcctg tggtcgagac atggaagagg ccggactatg    7260
aaccaccac tgtcctaggc tgtgccctac ccccacacc tcaggcgcca gtgcctccac     7320
cccggaggcg ccgcgccaaa gtcctgaccc aggacaatgt ggagggggtt ctcaaggaga    7380
tggcggacaa agttcttagc cctctccgag attgtaatga ctccggtcac tccactggag    7440
cggataccgg ggcagacagc gtccagcagc ccctgacga gactgccgct tcagaggcgg     7500
gatcactgtc ctccatgcct ccccttgagg gagagccggg ggaccctgac ctggagtttg    7560
aaccagctgg atccgctccc ccttcagagg gggagtgtga ggtcattgat tcggactcta    7620
agtcgtggtc tacagtctct gatcaggagg attccattac ctgctgctcc atgtcatact    7680
cctggacggg agccctcata acaccatgtg ggcccgaaga ggagaagttg ccaatcaacc    7740
ctctgagtaa ctcgcttatg cggttccata caaggtgta ctcgacaacc tcgaggagcg     7800
cctctcagag agcaaaaaag gtgacctttg acagggtgca ggtgctggac aaacactacg    7860
actcagtctt gcaggacgtt aagcgggccg cctctaaggt tagtgcgagg ctcctctcaa    7920
tagaggaagc ctgcgcgctg accccgcctc actccgccaa atcgcggtat ggatttgggg    7980
caaaagaggt gcgcagctta tccaggaggg ccgtcaacca catccagtcc gtgtgggagg    8040
accttctgga agaccaacat actccaattg agacaactat catggccaag aacgaggtgt    8100
tctgcgttga tccgctaaa ggcgggaaaa agtcagctcg cctcattgta taccctgacc     8160
ttgggggtcag agtgtgcgaa aaaatggccc tctatgacat tgcacaaaag cttcccaagg   8220
```

```
caataatggg tccatcctat gggttccaat actctcccgc agagcgggtc gattttctcc    8280
tcaaagcttg gggaagcaag aaggacccaa tggggttctc gtatgacacc cgctgcttcg    8340
actcaaccgt cacggagaga gatatacgaa cagaagaatc catatatcag gcttgttccc    8400
tgcctcaaga ggccagagtt gccatacact cacttactga gagactctac gtaggagggc    8460
ccatgctaaa cagcaagggc caatcctgcg gttacaggcg ttgccgcgcg agcggcgttt    8520
tcaccaccag catggggaat accatgacat gctacatcaa agcccttgcg gcgtgccaag    8580
ccgcagggat cgtggacccc gttatgctgg tgtgtggaga cgacctggtc gtcatctcag    8640
agagtcaagg taacgatgag gacgagcgaa acctgagagc tttcacggag gctatgacca    8700
ggtattcagc ccctcctggt gaccttccca gaccggaata tgacttggag cttataacat    8760
cctgctcctc aaacgtatcg gtagcgctgg accctcgggg tcgccgccgg tactacctaa    8820
ccagagaccc taccactcca atctcccgag ccgcttggga aacagtaaga cactcccctg    8880
tcaattcttg gctgggcaac atcatccaat acgccccccac aatctgggtc cggatggtca    8940
taatgaccca tttcttctcc atactattgg cccaggacac tctgaaccaa aatctcaact    9000
ttgagatgta tggggcagta tattcggtca atccattaga cctaccggcc ataattgaaa    9060
ggctacacgg gcttgacgcc ttttcactgc acacatactc tccccacgaa ctctcacggg    9120
tggcagcgac tctcagaaaa cttggagcgc ctccccttag agcgtggaag agtcgggcac    9180
gtgctgtgag ggcctcactc atcgcccagg gagggaaggc agccatttgt ggccgctacc    9240
tcttcaactg gcgggtgaag acaaagctca aactcactcc attgcccgag gcgagccgcc    9300
tggatttatc cggtggttc accgtgggcg ccggcggggg cggcatcttt cacagcgtgt    9360
cgcatgcccg accccgccta ttactccttt gcctactcct atttagcgta ggggtaggca    9420
tctttttact ccccgctcgg tagagcggca aaccctagct cacactccata gctagttcct    9480 ttttttttt tttttttttt tttttttttt tttttttttt tttttttttt ttttttttct    9540 tctttttat ttttccttct ttcttggtgg ctccatctta gccctagtca cggctagctg    9600
tgaaaggtcc gtgagccgca tgactgcaga gagtgccgta actggtctct ctgcagatca    9660
tgt                                                                 9663
```

<210> SEQ ID NO 8
<211> LENGTH: 9663
<212> TYPE: DNA
<213> ORGANISM: Hepatitis C virus

<400> SEQUENCE: 8

```
gcccgccccc taatgggggc gacactccgc catgaatcac tcccctgtga ggaactactg      60
tcttcacgca gaaagcgtct agccatggcg ttagtatgag tgtcgtacag cctccaggcc     120 ccccctccc gggagagcca tagtggtctg cggaaccggt gagtacaccg gaattaccgg     180
aaagactggg tcctttcttg gataaaccca ctctatgtcc ggtcatttgg gcgtgccccc     240
gcaagactgc tagcctagta gcgttgggtt gcgaacggcc ttgtggtact gcctgatagg     300
gtgcttgcga gtgccccggg aggtctcgta gaccgtgcat catgagcaca atcctaaac     360 ctcaaagaaa aaccaaaaga aacacaaacc gtcgcccaca ggacgtcaag ttcccgggtg     420
gcggtcagat cgttggcgga gtttacttgc tgccgcgcag gggcccagg ttgggtgtgc     480 gcgcaacaag gaagacttcc gagcggtccc agcgcgtgg gagacgccag cccatcccaa     540
aagatcggcg ctccaccggc aagtcctggg gaaagccagg atatccttgg cctctgtatg     600
```

```
gaaacgaggg ctgcggctgg gcaggttggc tcctgtcccc tcgcgggtct cgtcctactt    660
ggggccccac tgaccccgg catagatcac gcaatttagg taaagtcatc gataccatta     720
cgtgtggttt tgccgacctc atggggtaca tccccgtcgt tggcgccccg gtcggaggcg    780
tcgccagagc cctggcacac ggtgttaggg tcctggagga cgggataaat tatgcaacag    840
ggaatctgcc tggttgctct ttttctatct tcttactcgc ccttctgtcg tgcatcacag    900
tgccagtgtc tgcggtggaa gtcaggaaca ttagctctgg ctactacgcc actaatgatt    960
gctcgaacaa cagcatcacc tggcagctca ctaacgcagt tctccatctt cccggatgcg   1020
tcccatgtga aacgacaat ggcaccctgc gctgctggat acaagtaaca cctaatgtgg    1080
ctgtgaaaca ccgcggcgcg ctcactcaca acctgcgaac gcatgtcgac gtggttgtga   1140
tggcagccac gatctgctcg gccttgtatg tgggagacgt gtgtggggcc gtgatgatcg   1200
tatctcaggc atttatactg tcgccagagc gccacaactt tacccaggag tgcaattgtt   1260
ccatctacca aggtcatatc accggccacc gcatggcatg ggacatgatg ttaaactggt   1320
caccaactct taccatggtc ctcgcctatg ctgctcgtgt tcctgagcta gtccttgaag   1380
ttgtcttcgg cggccattgg ggtgtggtgt ttggcttggc ctatttctcc atgcagggag   1440
catgggccaa agttatggcc atcctcctcc ttgtcgcagg agtggacgca cacacctatt   1500
ccaccggtgc ccgagcgggt caagcagcct cgggcttaac ttccctttttt tccgttggtt   1560 ctaggcagag gctcagtcta attcacacca atggcagttg gcacataaac cggactgccc   1620
tcaattgcaa tgacagcttg catacggggtt tcatcgcttc ccttctttac gtcaacaatt   1680
tcaacagctc tggctgcccc gagcgcatgt cttcctgccg tgcgctggat gatttccgca   1740
tcgggtgggg aaccttggag tacgaaacca atgtcaccaa cgacgaggac atgaggccgt   1800
actgctggca ttatcctccg aagccttgcg gtatcgttcc ggctgggacg gtttgcgggc   1860
cggtctactg cttcactccc agccctgttg ttgtgggtac cactgacaag cagggcgtgc   1920
ccacctataa ctgggggga aatgagaccg atgtcttcct gctgaatagc acgagacccc   1980 cgcaagggggc ttggttcggc tgcacttgga tgaacgggac tgggttcact aagacatgcg   2040
gtgcaccacc ttgccgcatt aggagggact acaacgaac cctcgatctg ttgtgcccca   2100
cagactgttt taggaagcac ccagaaacca cctatcttag gtgcggatca gggccttggt   2160 tgaccccag atgcctggtg gattacccctt atagattgtg gcattatccg tgcactgtga   2220
atttcaccat cttaaggtg cggatgtatg tggggggagt ggagcatcgg ttgtccgcag    2280
catgtaactt cacgcgcggg gaccgctgca atttagaaga tagggatagg ggtcagcaga   2340
gtccgctgct gcactccacc actgagtggg cggtgttacc atgctctttc tccgacctac   2400
cggcactatc tactggtta ttgcacctcc atcaaaacat cgtggacgtg cagtacctct    2460
atggactttc tccggctatc acaagataca tcgtgaagtg ggagtgggtg gttctcctct   2520
tcttgttgtt ggcagatgcc agggtctgtg catgcctttg gatgctcatc atactgggcc   2580
aagccgaggc ggcgcttgag aagcttatca tctcgcactc tgctagcgct gctagtgcca   2640
atgggccgct gtggttcttc atcttcttca tagcggcctg gtacttaaag ggcagggtgg   2700
tccccatggc cacgtactct gttcttggct tgtggtcctt tttcctccta gtcctggcct   2760
taccacagca ggcttatgct ctggacgccg ttgaacaagg ggaactgggg ctggttttgt   2820
taggggtcat atcaatcttc actcttaccc cagcatacaa gactctcctg agccgttcag   2880
tatggtggct gtcctacatg ctggtcttgg ccgaggccca gattcagcaa tgggttcccc   2940
ccctggaagc ccgaggggc cgtgacggga tcatctgggt agctgtcatt ctacgcccat   3000
```

```
gccttgtgtt tgagatcacg aaatggctgt tggcagttct ggggcctgcc tacctcctta   3060
gagcgtccct gctacgggta ccgtactttg tgagggccca cgccctgcta cgactgtgtg   3120
ccctggtgag acacctcgca ggagctaggt acatccagat gctgttgatc accataggca   3180
ggtggactgg tacttacatc tatgaccacc tctccccttt atcaacttgg gcagcccagg   3240
gtttgcggga cctagcggtc gccgtggagc ctgtggtgtt tagcccaatg gagaagaagg   3300
tcattgtgtg gggggctgag acagtggcgt gtggggatat cctgcatggc ctcccggtgt   3360
ccgcgaggct aggtagggaa attctgctcg gccccgccga tggctacacc tcgaaggggt   3420
ggaagctcct ggctcctatc actgcttata ctcagcagac ccgtggtctc ctgggtgcca   3480
tagtggtcag tctgacgggc cgcgacaaaa atgagcaggc tgggcaggtc caggttctgt   3540
cctccgtcac acaatctttc ttggggacat ctatttcggg ggtcctctgg acagtatacc   3600
atggggctgg taataagacc ttggctggcc ccagaggacc agtcactcag atgtactcca   3660
gcgcagaggg ggacctcgtg ggatggccta gccccccccgg gactaagtct ttagacccct   3720
gtacctgtgg ggccgtggac ctctacctgg tcacccgaaa cgctgatgtc attccggtcc   3780
ggaggagaga tgaccggcgg ggcgcactac tctcgccaag gcctctctcg accctcaaag   3840
ggtcatccgg tggacccgtg ctctgctccc ggggacatgc cgtgggcttg ttcagggcgg   3900
ccgtgtgcac caggggtgtg gccaagtcca ttgacttcat ccctgttgaa tctctcgatg   3960
tcgctgcacg atcgcccagt ttctctgaca acagcactcc accagctgtg cctcagtctt   4020
accaagtggg ctacttacac gcgccaacag gcagcgggaa gagcaccaag gtccctgccg   4080
catacgccag tcagggggtat aaagtacttg tactgaatcc ctctgtcgcg ccacactcg   4140 gctttggggc ctacatgtcc aaggcccacg gaatcaaccc taacatcagg accgggtac   4200 ggactgtgac caccggggac ccaataactt actccactta tggcaagttc ctcgctgatg   4260
gaggctgctc agctgcgcc tatgacatca tcatatgcga cgaatgccat tcagtggacg   4320
ccactaccat ccttggcatt ggaacagtcc tcgaccaggc cgagaccgca ggcgccaggc   4380
tagtagtctt ggctacagcc acgcctcctg gtacagtgac aactcccat agcaacatag   4440 aggaggtggc tcttggtcat gaaggcgaga tcccttttta cggcaaggct attcctctag   4500
cttatatcaa gggaggcagg cacctgatct tctgccactc aaagaagaag tgcgatgagc   4560
tcgcagcagc ccttcggggc atgggtgtca atgccgttgc ttactacagg ggtctcgacg   4620
tctccgtcat accacttcaa ggagacgtgg tggtagtcgc caccgatgcc ctaatgactg   4680
gatttaccgg tgactttgat tctgtcatcg actgcaacgt tgcagtcact cagattgttg   4740
acctcagcct agacccgacc tttactatca ccactcaaac tgtccctcag gacgccgtct   4800
cccgtagtca acgtagaggg agaactgggc gaggacggtt gggcatttac aggtatgttt   4860
cgtcaggtga aaggccgtct gggatgttcg acagcgtagt gctctgcgag tgctatgatg   4920
ccggggcagc ctggtacgaa ctcacgcctg ctgaaactac agtgagactc cgggcctatt   4980
tgaacacgcc cggtctgccc gtgtgtcagg accacctgga attttgggag gcggtcttca   5040
caggtctcac acacattgat gcccacttcc tctcccagac gaaacaagga ggagacaact   5100
ttgcgtatct aacggcctat caggccacgg tatgcgctag ggcgagggcg ccccctcctt   5160
cctgggactt gatgtggaag tgtctaacta ggctcaagcc tacactgaat ggccctaccc   5220
cccttctata ccgcttgggt gccgtgacca acgaggtcac cctgactcac cccgtgacga   5280
aatatatcgc cacgtgtatg caagctgacc ttgagatcat gacaagtaca tgggttctag   5340
```

```
cgggggggggt gctagccgcc gtagcatctt actgcctggc gaccggctgt gtttccatca    5400
ttggccgcct acacctgaat gatcgagtgg ttgtggcccc tgataaggaa atcttatatg    5460
aggcctttga tgagatggaa gagtgcgcct ccaaagccgc cctcattgag aagggcagc     5520 ggatggcgga gatgctcaag accaagatac aaggcctcct acaacaggcc acaagacaag    5580
cccaagacat acagccagcc atacagtcat cgtggcccaa gcttgaacaa ttttgggcca    5640
agcacatgtg gaacttcatc agtggcatac agtacctggc gggactctcc acgctaccag    5700
ggaatcccac ggtggcgtca atgatggctt ttagcgccgc attgactagc ccactgccca    5760
ccagcaccac catcctcttg aacatcatgg ggggatggtt ggcctctcag atcgcccccc    5820
ctgccggggc cactggcttt gttgtcagtg gtctggtagg ggcggccgtc ggaagtatag    5880
gcctgggtaa gatactggtg gatgttttgg ccgggtatgg tgcaggcatt tcaggggccc    5940
tcgtagcttt caagatcatg agcggcgaga agcctacggt agaagatgtt gtgaatctcc    6000
tgcctgctat cctgtctcct ggtgctttag tagtgggagt catctgtgca gcaattttgc    6060
gccgccacat cggccaggga gaggggcgg tccagtggat gaacagactc atcgccttcg     6120
cctccagagg aaaccatgtt gcccctaccc actacgtggc agagtctgac gcctcgcagc    6180
gcgtgacgca agcgctgagt tcactcacaa ttaccagctt actcaggaga ctacatgcct    6240
ggatcactga agattcccca gtcccgtgct cggggtcttg gctccgggac atctgggatt    6300
gggtctgttc cattctcaca gactttaaga actggctgtc ttcaaaactg ctccccaagc    6360
tgcccggcct tcccttcatc tcttgccaaa agggatacag gggcgtatgg gctggcacgg    6420
gagtcatgac cactcggtgc ccgtgcgag ctaccatctc gggccatgtc cgcatgggta     6480
ccatgaaaat aacaggccca aagacctgct tgaacatgtg gcagggtcc ttccccatca     6540 attgttacac agaagggcct tgcgtgccaa aaccccctcc taactacaag accgcaattt    6600
ggagggttgc agcgtcggag tacgttgaaa tcacgcaaca cggctcattc tcgtacgtaa    6660
cggggttaac taatgacaac cttaaggtcc cctgccaagt accagctcca gaattttct     6720 cttgggtgga cggggtgcag atacaccggt tcgcccccac tccaggtccc ttctttcggg    6780
atgaggtaac gttcaccgta ggccttaatt cctttgtggt cggctctcag ctcccctgcg    6840 acccctgagcc ggacaccgag gtattggcct ccatgttgac agaccccgtcc cacattacag   6900 cggaggcgga agctaggcga ttggccaggg ggtctccccc ctcacaggct agctcttcgg    6960
cgagccagct ctccgccccg tccttgaagg ccacctgtac cacccataag gtggcatatg    7020
attgtgacat ggtggacgcc aacctgttca tgggaggcga tgtgacccgg attgagtcca    7080
actccaaggt ggtcattctt gactccctcg attccatgac tgaggtagag gacgaccgtg    7140
agccttctat cccatcagag tacctgatca ggaggagaaa gttccaccccg gcactacctc    7200 cctgggcccg tccagactac aaccctcctg tggtcgagac atggaagagg ccggactatg    7260
aaccacccac tgtcctaggc tgtgcccta ccccacacacc tcaggcgcca gtgcctccac     7320
cccggaggcg ccgcgccaaa gtcctgaccc aggacaatgt ggagggggtt ctcaaggaga    7380
tggcggacaa agttcttagc cctctccgag attgtaatga ctccggtcac tccactggag    7440
cggataccgg ggcagacagc gtccagcagc cccctgacga gactgccgct tcagaggcgg    7500
gatcactgtc ctccatgcct cccttgagg gagagccggg ggaccctgac ctggagtttg     7560
aaccagctgg atccgctccc ccttcagagg gggagtgtga ggtcattgat tcggactcta    7620
agtcgtggtc tacagtctct gatcaggagg attccactat ctgctgctcc atgtcatact    7680
cctggacggg agccctcata acaccatgtg ggcccgaaga ggagaagttg ccaatcaacc    7740
```

```
ctctgagtaa ctcgcttatg cggttccata acaaggtgta ctcgacaacc tcgaggagcg    7800
cctctcagag agcaaaaaag gtgacctttg acagggtgca ggtgctggac aaacactacg    7860
actcagtctt gcaggacgtt aagcgggccg cctctaaggt tagtgcgagg ctcctctcaa    7920
tagaggaagc ctgcgcgctg accccgcctc actccgccaa atcgcggtat ggatttgggg    7980
caaaagaggt gcgcagctta tccaggaggg ccgtcaacca catccagtcc gtgtgggagg    8040
accttctgga agaccaacat actccaattg agacaactat catggccaag aacgaggtgt    8100
tctgcgttga tcccgctaaa ggcgggaaaa agtcagctcg cctcattgta taccctgacc    8160
ttggggtcag agtgtgcgaa aaaatggccc tctatgacat tgcacaaaag cttcccaagg    8220
caataatggg tccatcctat gggttccaat actctcccgc agagcgggtc gattttctcc    8280
tcaaagcttg gggaagcaag aaggacccaa tggggttctc gtatgacacc cgctgcttcg    8340
actcaaccgt cacggagaga gatatacgaa cagaagaatc catatatcag gcttgttccc    8400
tgcctcaaga ggccagagtt gccatacact cacttactga gagactctac gtaggagggc    8460
ccatgctaaa cagcaagggc caatcctgcg gttacaggcg ttgccgcgcg agcggcgttt    8520
tcaccaccag catggggaat accatgacat gctacatcaa agcccttgcg gcgtgccaag    8580
ccgcagggat cgtggacccc gttatgctgg tgtgtggaga cgacctggtc gtcatctcag    8640
agagtcaagg taacgatgag gacgagcgaa acctgagagc tttcacggag gctatgacca    8700
ggtattcagc ccctcctggt gaccttccca gaccggaata tgacttggag cttataacat    8760
cctgctcctc aaacgtatcg gtagcgctgg accctcgggg tcgccgccgg tactacctaa    8820
ccagagaccc taccactcca atctcccgag ccgcttggga aacagtaaga cactcccctg    8880
tcaattcttg gctgggcaac atcatccaat acgcccccac aatctgggtc cggatggtca    8940
taatgaccca tttcttctcc atactattgg cccaggacac tctgaaccaa aatctcaact    9000
ttgagatgta tggggcagta tattcggtca atccattaga cctaccggcc ataattgaaa    9060
ggctacacgg gcttgacgcc ttttcactgc acacatactc tccccacgaa ctctcacggg    9120
tggcagcgac tctcagaaaa cttggagcgc ctccccttag agcgtggaag agtcgggcac    9180
gtgctgtgag ggcctcactc atcgcccagg gagggaaggc agccatttgt ggccgctacc    9240
tcttcaactg gcgcgtgaag acaaagctca aactcactcc attgcccgag gcgagccgcc    9300
tggatttatc cggtggttc accgtggcg ccggcgggg cggcatcttt cacagcgtgt    9360
cgcatgcccg acccgcccta ttactccttt gcctactcct acttagcgta ggggtaggca    9420 tcttttact ccccgctcgg tagagcggca aaccctagct acactccata gctagttcct    9480
tttttttttt tttttttttt tttttttttt tttttttttt tttttttttt tttttttct    9540 tcttttttat ttttccttct ttcttggtgg ctccatctta gccctagtca cggctagctg    9600
tgaaaggtcc gtgagccgca tgactgcaga gagtgccgta actggtctct ctgcagatca    9660
tgt                                                                 9663
```

<210> SEQ ID NO 9
<211> LENGTH: 9663
<212> TYPE: DNA
<213> ORGANISM: Hepatitis C virus

<400> SEQUENCE: 9

```
gcccgccccc taatgggggc gacactccgc catgaatcac tcccctgtga ggaactactg      60
tcttcacgca gaaagcgtct agccatggcg ttagtatgag tgtcgtacag cctccaggcc     120
```

```
cccccctccc gggagagcca tagtggtctg cggaaccggt gagtacaccg gaattaccgg    180
aaagactggg tcctttcttg gataaaccca ctctatgtcc ggtcatttgg gcgtgccccc    240
gcaagactgc tagcctagta gcgttgggtt gcgaacggcc ttgtggtact gcctgatagg    300
gtgcttgcga gtgccccggg aggtctcgta gaccgtgcat catgagcaca aatcctaaac    360
ctcaaagaaa aaccaaaaga aacacaaacc gtcgcccaca ggacgtcaag ttcccgggtg    420
gcggtcagat cgttggcgga gtttacttgc tgccgcgcag gggccccagg ttgggtgtgc    480
gcgcaacaag gaagacttcc gagcggtccc agccgcgtgg gagacgccag cccatcccaa    540
aagatcggcg ctccaccggc aagtcctggg gaaagccagg atatccttgg cctctgtatg    600
gaaacgaggg ctgcggctgg gcaggttggc tcctgtcccc tcgcgggtct cgtcctactt    660
ggggccccac tgaccccggg catagatcac gcaatttagg taaagtcatc gataccatta    720
cgtgtggttt tgccgacctc atggggtaca tccccgtcgt tggcgccccg gtcggaggcg    780
tcgccagagc cctggcacac ggtgttaggg tcctggagga cgggataaat tatgcaacag    840
ggaatctgcc tggttgctct ttttctatct tcttactcgc ccttctgtcg tgcatcacag    900
tgccagtgtc tgcggtggaa gtcaggaaca ttagctctgg ctactacgcc actaatgatt    960
gctcgaacaa cagcatcacc tggcagctca ctaacgcagt tctccatctt cccggatgcg   1020
tcccatgtga gaacgacaat ggcaccctgc gctgctggat acaagtaaca cctaatgtgg   1080
ctgtgaaaca ccgcggcgcg ctcactcaca acctgcgaac gcatgtcgac gtggttgtga   1140
tggcagccac gatctgctcg gccttgtatg tgggagacgt gtgtgggcc gtgatgatcg   1200 tatctcaggc atttatactg tcgccagagc gccacaactt tacccaggag tgcaattgtt   1260
ccatctacca aggtcatatc accggccacc gcatggcatg ggacatgatg ttaaactggt   1320
caccaactct taccatggtc ctcgcctatg ctgctcgtgt tcctgagcta gtccttgaag   1380
ttgtcttcgg cggccattgg ggtgtggtgt ttggcttggc ctatttctcc atgcagggag   1440
catgggccaa agttatggcc atcctcctcc ttgtcgcagg agtggacgca cacacctatt   1500
ccaccggtgc ccgagcgggt caagcagcct cgggcttaac ttcccttttt tccgttggtt   1560
ctaggcagag gctcagtcta attcacacca atggcagttg gcacataaac cggactgccc   1620
tcaattgcaa tgacagcttg catacgggtt tcatcgcttc ccttctttac gtcaacaatt   1680
tcaacagctc tggctgcccc gagcgcatgt cttcctgccg tgcgctggat gatttccgca   1740
tcgggtgggg aaccttggag tacgaaacca atgtcaccaa cgacgaggac atgaggccgt   1800
actgctggca ttatcctccg aagccttgcg gtatcgttcc ggctgggacg gtttgcgggc   1860
cggtctactg cttcactccc agccctgttg ttgtgggtac cactgacaag cagggcgtgc   1920
ccacctataa ctgggggaa aatgagaccg atgtcttcct gctgaatagc acgagacccc   1980 cgcaagggc ttggttcggc tgcacttgga tgaacgggac tgggttcact aagacatgcg   2040
gtgcaccacc ttgccgcatt aggagggact acaacgaaac cctcgatctg ttgtgcccca   2100
cagactgttt taggaagcac ccagaaacca cctatcttag gtgcggatca gggcttggt   2160 tgacccccag atgcctggtg gattaccctt atagattgtg gcattatccg tgcactgtga   2220
atttcaccat ctttaaggtg cggatgtatg tggggggagt ggagcatcgg ttgtccgcag   2280
catgtaactt cacgcgcggg gaccgctgca atttagaaga tagggatagg ggtcagcaga   2340
gtccgctgct gcactccacc actgagtggg cggtgttacc atgctctttc tccgacctac   2400
cggcactatc tactggtttta ttgcacctcc atcaaaacat cgtggacgtg cagtacctct   2460
atggactttc tccggctatc acaagataca tcgtgaagtg ggagtgggtg gttctcctct   2520
```

```
tcttgttgtt ggcagatgcc agggtctgtg catgcctttg gatgctcatc atactgggcc    2580
aagccgaggc ggcgcttgag aagcttatca tctcgcactc tgctagcgct gctagtgcca    2640
atgggccgct gtggttcttc atcttcttca tagcggcctg gtacttaaag ggcagggtgg    2700
tccccatggc cacgtactct gttcttggct tgtggtcctt tttcctccta gtcctggcct    2760
taccacagca ggcttatgct ctggacgccg ttgaacaagg ggaactgggg ctggttttgt    2820 tagggtcat atcaatcttc actcttaccc cagcatacaa gactctcctg agccgttcag    2880
tatggtggct gtcctacatg ctggtcttgg ccgaggccca gattcagcaa tgggttcccc    2940
ccctggaagc ccgaggggc cgtgacggga tcatctgggt agctgtcatt ctacgcccat     3000
gccttgtgtt tgagatcacg aaatggctgt tggcagttct ggggcctgcc tacctcctta    3060
gagcgtccct gctacgggta ccgtactttg tgagggccca cgccctgcta cgactgtgtg    3120
ccctggtgag acacctcgca ggagctaggt acatccagat gctgttgatc accataggca    3180
ggtggactgg tacttacatc tatgaccacc tctcccctt atcaacttgg gcagcccagg     3240
gtttgcggga cctagcggtc gccgtggagc ctgtggtgtt tagcccaatg gagaagaagg    3300
tcattgtgtg gggggctgag acagtggcgt gtggggatat cctgcatggc ctcccggtgt    3360
ccgcgaggct aggtagggaa attctgctcg gccccgccga tggctacacc tcgaaggggt    3420
ggaagctcct ggctcctatc actgcttata ctcagcagac ccgtggtctc ctgggtgcca    3480
tagtggtcag tctgacgggc gcgacaaaa atgagcaggc tgggcaggtc caggttctgt     3540
cctccgtcac acaatctttc ttggggacat ctatttcggg ggtcctctgg acagtatacc    3600
atggggctgg taataagacc ttggctggcc ccagaggacc agtcactcag atgtactcca    3660
gcgcagaggg ggacctcgtg ggatggccta gccccccgg gactaagtct ttagacccct     3720
gtacctgtgg ggccgtggac ctctacctgg tcacccgaaa cgctgatgtc attccggtcc    3780
ggaggagaga tgaccggcgg ggcgcactac tctcgccaag gcctctctcg accctcaaag    3840
ggtcatccgg tggacccgtg ctctgctccc ggggacatgc cgtgggcttg ttcagggcgg    3900
ccgtgtgcac caggggtgtg gccaagtcca ttgacttcat ccctgttgaa tctctcgatg    3960
tcgctgcacg atcgcccagt ttctctgaca acagcactcc accagctgtg cctcagtctt    4020
accaagtggg ctacttacac gcgccaacag gcagcgggaa gagcaccaag gtccctgccg    4080
catacgccca tcagggtat aaagtacttg tactgaatcc ctctgtcgcg ccacactcg     4140 gctttggggc ctacatgtcc aaggcccacg gaatcaaccc taacatcagg accggggtac    4200
ggactgtgac caccggggac ccaataactt actccactta tggcaagttc ctcgctgatg    4260
gaggctgctc agctggcgcc tatgacatca tcatatgcga cgaatgccat tcagtggacg    4320
ccactaccat ccttggcatt ggaacagtcc tcgaccaggc cgagaccgca ggcgccaggc    4380
tagtagtctt ggctacagcc acgcctcctg gtacagtgac aactccccat agcaacatag    4440
aggaggtggc tcttggtcat gaaggcgaga tccctttta cggcaaggct attcctctag    4500
cttatatcaa gggaggcagg cacctgatct tctgccactc aaagaagaag tgcgatgagc    4560
tcgcagcagc ccttcgggc atgggtgtca atgccgttgc ttactacagg ggtctcgacg    4620
tctccgtcat accacttcaa ggagacgtgg tggtagtcgc caccgatgcc ctaatgactg    4680
gatttaccgg tgactttgat tctgtcatcg actgcaacgt tgcagtcact cagattgttg    4740
acctcagcct agacccgacc tttactatca ccactcaaac tgtccctcag gacgccgtct    4800
cccgtagtca acgtagaggg agaactgggc gaggacggtt gggcatttac aggtatgttt    4860
```

```
cgtcaggtga aaggccgtct gggatgttcg acagcgtagt gctctgcgag tgctatgatg   4920
ccggggcagc ctggtacgaa ctcacgcctg ctgaaactac agtgagactc cgggcctatt   4980
tgaacacgcc cggtctgccc gtgtgtcagg accacctgga attttgggag cggtcttca    5040
caggtctcac acacattgat gcccacttcc tctcccagac gaaacaagga ggagacaact   5100
ttgcgtatct aacggcctat caggccacgg tatgcgctag ggcgagggcg cccccctcctt  5160
cctgggactt gatgtggaag tgtctaacta ggctcaagcc tacactgaat ggccctaccc   5220
cccttctata ccgcttgggt gccgtgacca acgaggtcac cctgactcac cccgtgacga   5280
aatatatcgc cacgtgtatg caagctgacc ttgagatcat gacaagtaca tgggttctag   5340
cgggggggt gctagccgcc gtagcatctt actgcctggc gaccggctgt gtttccatca    5400
ttggccgcct acacctgaat gatcgagtgg ttgtggcccc tgataaggaa atcttatatg   5460
aggcctttga tgagatggaa gagtgcgcct ccaaagccgc cctcattgag gaagggcagc   5520
ggatggcgga gatgctcaag accaagatac aaggcctcct acaacaggcc acaagacaag   5580
cccaagacat acagccagcc atacagtcat cgtggcccaa gcttgaacaa ttttgggcca   5640
agcacatgtg gaacttcatc agtggcatac agtacctggc gggactctcc acgctaccag   5700
ggaatcccac ggtggcgtca atgatggctt ttagcgccgc attgactagc ccactgccca   5760
ccagcaccac catcctcttg aacatcatgg ggggatggtt ggcctctcag atcgccccc    5820
ctgccggggc cactggctt ttgtcagtg gtctggtagg ggcggccgtc ggaagtatag      5880
gcctgggtaa gatactggtg gatgttttgg ccgggtatgg tgcaggcatt tcaggggccc   5940
tcgtagcttt caagatcatg agcggcgaga agcctacggt agaagatgtt gtgaatctcc   6000
tgcctgctat cctgtctcct ggtgctttag tagtgggagt catctgtgca gcaattttgc   6060
gccgccacat cggccaggga gaggggggcgg tccagtggat gaacagactc atcgccttcg   6120
cctccagagg aaaccatgtt gcccctaccc actacgtggc agagtctgac gcctcgcagc   6180
gcgtgacgca agcgctgagt tcactcacaa ttaccagctt actcaggaga ctacatgcct   6240
ggatcactga agattgccca gtcccgtgct cggggtcttg gctccgggac atctgggatt   6300
gggtctgttc cattctcaca gactttaaga actggctgtc ttcaaaactg ctccccaagc   6360
tgccccggcct tcccttcatc tcttgccaaa agggatacag gggcgtatgg gctggcacgg   6420
gagtcatgac cactcggtgc ccgtgcggag ctaccatctc gggccatgtc cgcatgggta   6480
ccatgaaaat aacaggccca aagacctgct tgaacatgtg gcagggtcc ttccccatca    6540
attgttacac agaagggcct tgcgtgccaa aacccctcc taactacaag accgcaattt    6600
ggagggttgc agcgtcggag tacgttgaaa tcacgcaaca cggctcattc tcgtacgtaa   6660
cggggttaac taatgacaac cttaaggtcc cctgccaagt accagctcca gaattttct    6720
cttgggtgga cggggtgcag atacaccggt tcgcccccac tccaggtccc ttctttcggg   6780
atgaggtaac gttcaccgta ggccttaatt cctttgtggt cggctctcag ctcccctgcg   6840
accctgagcc ggacaccgag gtattggcct ccatgttgac agaccgtcc cacattacag    6900
cggaggcggc agctaggcga ttggccaggg ggtctccccc ctcacaggct agctcttcgg   6960
cgagccagct ctccgcccg tccttgaagg ccacctgtac cacccataag gtggcatatg     7020
attgtgacat ggtggacgcc aacctgttca tgggaggcga tgtgacccgg attgagtcca   7080
actccaaggt ggtcattctt gactccctcg attccatgac tgaggtagag gacgaccgtg   7140
agccttctat cccatcagag tacctgatca ggaggagaaa gttccaccg gcactacctc    7200
cctgggcccg tccagactac aaccctcctg tggtcgagac atggaagagg ccggactatg   7260
```

```
aaccacccac tgtcctaggc tgtgccctac cccccacacc tcaggcgcca gtgcctccac    7320
cccggaggcg ccgcgccaaa gtcctgaccc aggacaatgt ggaggggtt ctcaaggaga     7380
tggcggacaa agttcttagc cctctccgag attgtaatga ctccggtcac tccactggag    7440
cggataccgg ggcagacagc gtccagcagc ccctgacga gactgccgct tcagaggcgg     7500
gatcactgtc ctccatgcct cccttgagg gagagccggg ggaccctgac ctggagtttg     7560
aaccagctga atccgctccc ccttcagagg gggagtgtga ggtcattgat tcggactcta    7620
agtcgtggtc tacagtctct gatcaggagg attccactat ctgctgctcc atgtcatact    7680
cctgacggga agccctcata acaccatgtg ggcccgaaga ggagaagttg ccaatcaacc    7740
ctctgagtaa ctcgcttatg cggttccata acaaggtgta ctcgacaacc tcgaggagcg    7800
cctctcagag agcaaaaaag gtgacctttg acagggtgca ggtgctggac aaacactacg    7860
actcagtctt gcaggacgtt aagcgggccg cctctaaggt tagtgcgagg ctcctctcaa    7920
tagaggaagc ctgcgcgctg accccgcctc actccgccaa atcgcggtat ggatttgggg    7980
caaaagaggt gcgcagctta tccaggaggg ccgtcaacca catccagtcc gtgtgggagg    8040
accttctgga agaccaacat actccaattg agacaactat catggccaag aacgaggtgt    8100
tctgcgttga tcccgctaaa ggcgggaaaa agtcagctcg cctcattgta taccctgacc    8160
ttggggtcag agtgtgcgaa aaaatggccc tctatgacat tgcacaaaag cttcccaagg    8220
caataatggg tccatcctat gggttccaat actctcccgc agagcgggtc gattttctcc    8280
tcaaagcttg gggaagcaag aaggacccaa tggggttctc gtatgacacc cgctgcttcg    8340
actcaaccgt cacggagaga gatatacgaa cagaagaatc catatatcag gcttgttccc    8400
tgcctcaaga ggccagagtt gccatacact cacttactga gagactctac gtaggagggc    8460
ccatgctaaa cagcaagggc caatcctgcg gttacaggcg ttgccgcgcg agcggcgttt    8520
tcaccaccag catggggaat accatgacat gctacatcaa agcccttgcg gcgtgccaag    8580
ccgcagggat cgtggacccc gttatgctgg tgtgtggaga cgacctggtc gtcatctcag    8640
agagtcaagg taacgatgag gacgagcgaa acctgagagc tttcacggag gctatgacca    8700
ggtattcagc ccctcctggt gaccttccca gaccggaata tgacttggag cttataacat    8760
cctgctcctc aaacgtatcg gtagcgctgg accctcgggg tcgccgccgg tactacctaa    8820
ccagagaccc taccactcca atctcccgag ccgcttggga aacagtaaga cactcccctg    8880
tcaattcttg gctgggcaac atcatccaat acgcccccac aatctgggtc cggatggtca    8940
taatgaccca tttcttctcc atactattgg cccaggacac tctgaaccaa aatctcaact    9000
ttgagatgta tgggcagta tattcggtca atccattaga cctaccggcc ataattgaaa     9060
ggctacacgg gcttgacgcc ttttcactgc acacatactc tccccacgaa ctctcacggg    9120
tggcagcgac tctcagaaaa cttggagcgc ctccccttag agcgtggaag agtcgggcac    9180
gtgctgtgag ggcctcactc atcgcccagg gagggaaggc agccatttgt ggccgctacc    9240
tcttcaactg ggcggtgaag acaaagctca aactcactcc attgcccgag gcgagccgcc    9300
tggatttatc cggtggttc accgtgggcg ccggcgggg cggcatcttt cacagcgtgt     9360
cgcatgcccg accccgccta ttactccttt gcctactcct atttagcgta ggggtaggca    9420
tcttttact ccccgctcgg tagagcggca aaccctagct acactccata gctagttcct     9480
ttttttttt tttttttttt tttttttttt tttttttttt tttttttttt ttttttttct    9540
tcttttttat ttttccttct ttcttggtgg ctccatctta gccctagtca cggctagctg    9600
```

```
tgaaaggtcc gtgagccgca tgactgcaga gagtgccgta actggtctct ctgcagatca    9660
tgt                                                                  9663

<210> SEQ ID NO 10
<211> LENGTH: 9659
<212> TYPE: DNA
<213> ORGANISM: Hepatitis C virus

<400> SEQUENCE: 10
gcccgccccc tgatgggggc gacactccgc catgaatcac tcccctgtga ggaactactg      60
tcttcacgca gaaagcgtct agccatggcg ttagtatgag tgtcgtacag cctccaggcc     120 ccccccctccc gggagagcca tagtggtctg cggaaccggt gagtacaccg gaattaccgg    180
aaagactggg tcctttcttg gataaaccca ctctatgtcc ggtcatttgg gcgcgccccc     240
gcaagactgc tagccgagta gcgttgggtt gcgaaaggcc ttgtggtact gcctgatagg     300
gtgcttgcga gtgccccggg aggtctcgta gaccgtgcat catgagcaca atcccaaac      360 ctcaaagaaa aaccaaaaga aacacaaacc gccgcccaca ggacgtcaag ttcccgggtg    420
gcggccagat cgttggcgga gtttatttgt tgccgcgcag gggccccagg ttgggtgtgc    480
gcgcgacaag gaagacttcc gagcgatccc agccgcgtgg gagacgccag cccatcccga    540
aagatcggcg ctccaccggc aagtcctggg gaaagccagg atatccttgg ccctgtatg     600 gaaacgaggg ctgcggctgg gcaggttggc tcctgtcccc ccgcgggtcc cgtcctactt    660
ggggccccac tgacccccgg catagatcac gtaatttggg cagagtcatc gacaccatta    720
cgtgtggttt tgccgacctc atggggtaca tccccgtcgt tggcgccccg gtcggaggcg    780
tcgccagagc tctggcacac ggtgttaggg ttctggagga cgggataaat tatgcaacag    840
ggaatctgcc tggttgctct ttttctatct tcttacttgc tctcctgtcg tgcttcacag    900
tgccagtgtc cgcggtggaa gtcaggaaca ttagttctag ttactatgcc accaatgatt    960
gctcaaacag cagcatcacc tggcaacttg ccgacgcagt cctccacctt cctggatgcg   1020
tcccatgtga aaataacaat ggcaccccgc gatgctggat acaagtgaca cctaatgtag   1080
ctgtgaaata ccgcggcgca ctcactcaca gcctacgaac acatatcgat gtgatcgtaa   1140
tggcagccac ggtctgctcg gccttgtacg tgggagacgt atgcggggcc gtgatgatcg   1200
tgtcgcaggc tttcatagtg tcgccacagt tccacaactt tacccaagag tgcaactgtt   1260
ccatctatca aggtcacatc accggccacc gcatggcatg ggacatgatg ctaaactggt   1320
caccaactct caccatgatt cttgcctatg ccactcgtgt tcctgagcta gctcttgaga   1380
ttgtcttcgg cggccattgg ggtgtggtgt tcggcttggc ttatttctcc ttgcagggag   1440
cgtgggccaa agtcgttgcc atcctccttc ttgtagcagg agtggatgca cacactcagc   1500
tcaccggcac aaacgtgggt cggaccaccg caggctttgc tagtttgttt gctcctggcg   1560
cccggcagga aatcagtctg atcaacacca tggcagctg gcacgtaaac cggacagccc   1620
tcaattgcaa cgacagcttg aatacggggtt tccttacagc cctgttttat cgcaacaagt   1680
tcaacagctc tggctgcccc gagcgcttgt cttcctgccg tgagctggac gatttccgca   1740
tcgggtgggg gaccgtggaa tacgagaccg ttgtcaccaa cgatgaggac atgaggccgt   1800
actgctggca ctaccctccg aagccttgcg gtattgtctc ggctaagaca gtgtgcgggc   1860
cagtctactg tttttactcct agccctgttg tcgtgggtac cactgacaga ctgggcgcgc   1920
ccacctacaa ttgggggata aacgagactg atgtcttcct gctgaatagc acaaggcccc   1980
cgcaaggagc ttggttcggc tgcacttgga tgaatgggac tgggttcact aagacatgcg   2040
```

```
gcgcaccacc ttgccgcatt aggagagacc acaacagcac cctcgatcta ttgtgtccaa    2100
cagactgttt cagaaagcac ccagacacta cctatcttaa gtgcggagca gggccctggt    2160
tgacccccaa atgcctgata gattaccctt acagattgtg gcattatccg tgcactgtaa    2220
attttaccat cttcaaggtg cggatgtatg ttggggggt agagcaccgc ttggacgcgg     2280
cgtgcaactt cacgcgtggg gaccgctgca gactggaaga tagggacagg ggtcagcaga    2340
ctccactgct gcattccacc actgagtggg cgatactgcc atgcactttc tccgacttac    2400
cggcgctgtc tactggtcta ttgcacctcc accaaaacac tgtggacgtg cagtacctct    2460
atggacttac tccggctatc acaagataca tcgtgaagtg ggagtgggtg gtcctccttt    2520
tcttgttgtt ggcggacgct agggtctgtg catgcctttg gatgctcatc atactgggcc    2580
aggccgaggc agcgcttgag aagcttatca tcttgcactc cgctagcgct gctagtgcca    2640
atgggccgct atggttcttc atcttcttta tagcggcctg gtacttaaag ggcagggtgg    2700
tccccgcggc cacatactct gttctcggct tgtggtcctt tctcctccta gtcctggcct    2760
tgccacaaca ggcttatgcc ctggacgcca ctgagcaagg agaactgggg ctagttatgt    2820
tagtagtttt atccatcttt actcttaccc cagcatacaa gacccttctg agccgctcgg    2880
tgtggtggct gtcctacatg ctggtcttgg ccgaagctca ggttcagcaa tgggtgcccc    2940
ccctggaagc ccgaggggg cgtgacggga tcatatgggc agctgtcatt ctacacccac     3000
gccttgtgtt tgagatcacg aagtggttac tggcaatcct ggggcctgcc tacttcctta    3060
aagcgtctct gctacgggtt ccatactttg tgagggctca cgccctgcta cgaatgtgta    3120
ccctggtgag acaccttgcg ggagctaagt acatccagat gctgttgatc accataggca    3180
ggtggaccgg cacttacatc tatgaccacc tctcccctt gtcaacttgg gcagcccagg     3240
gtttacggga cctggcagtc gccgtggagc ctgtggtgtt tagcccaatg gagaagaagg    3300
tcatcgtgtg gggggctgag acagcggcat gtgggacat cctgcatggc ctcccggttt     3360
ccgcgaggct aggtagggaa gtgctgctcg gtcccgccga tggctacacc tccaagggg     3420 ggaagctctt ggctcccatc actgcttata cccagcagac tcgtggtctc ctgggtagca    3480
tcgtggtctg tttgacaggc cgcgacaaaa atgagcaggc tgggcacgtc caggttctgt    3540
cctccgtcac acaatctttc ttggggacat ctatctcggg ggtcctctgg acggtatatc    3600
acggagctgg caacaagacc ttagctggcc ccaaaggacc aatcactcaa atgtacacca    3660
gcgcagaagg ggacctcgtg ggatggccta gccccccgg gactaagtct ttagacccct     3720
gcacttgcgg ggctgtggac ctctacctgg tcacccgaaa cgctgatgtc attccagtcc    3780
ggaggaaaga cgaccggcgg ggtgcactgc tctcgccaag gcccctctca actctcaagg    3840
gatcatccgg tggaccgtg ctctgcccca gggggcacgc tgtgggcttg ttcagggcgg     3900
ccttgtgcgc caggggtgta gccaaatcca tcgacttcat ccctgttgaa tctcttgata    3960
tcgtcgcacg gtcacccagt ttttctgaca acagcacgcc accagccgtg cctcagacct    4020
accaggtggg ctacttgcac gcaccgacgg gcagcgggaa gagcaccaag gtccccgccg    4080
cttatgccag tcagggtat aaagtacttg tactaaatcc ctctgttgcg gccacactcg     4140 gttttgggc ctacatgtcc aaagcccacg ggatcaaccc caacatcaga accggagtac     4200
ggactgtgac caccggggac cctatcacct actccactta tggcaagttt ctcgcagatg    4260
gaggctgctc ggctggtgcc tatgacatca tcatatgcga cgaatgccat gcagtggatg    4320
ccactaccat ccttggcatt ggaacagtcc tcgaccaggc tgagaccgca ggtgccagac    4380
```

```
tagtggtctt ggccacggcc acacctcctg gtacagtgac aactcctcac agtaatatag    4440
aggaggtggc tctcggtcac gaaggcgaga tcccttttta cggcaaggct atccccctag    4500
ctttcatcaa gggggcaga cacctgattt tttgccactc aaagaagaag tgcgatgagg     4560
tcgcggcggc ccttcggagc gtgggtgtca atgccgttgc ttactacagg ggtctcgacg    4620
tctccgttat accaacccaa ggggacgtgg tggtcgtcgc caccgatgcc ctaatgaccg    4680
ggtacaccgg tgactttgat tctgttatcg actgcaatgt tgcggtcact cagattgttg    4740
accttagcct agacccaacc tttaccatca ccactcaaac cgtccctcag gacgctgtct    4800
cccgtagtca acgcagaggg agaactggga ggggacgact gggcatttac aggtatgtct    4860
catcaggtga aaggccgtct gggatgttcg acagcgtagt actctgcgag tgctatgatg    4920
ccggggcagc ctggtatgaa ctcacgcctg ctgagactac agtgagactc cgggcttatt    4980
tcaacacgcc cggtctgccc gtgtgtcaag accacttgga gttctgggag gcggtcttca    5040
caggtctcac acacatcgat gcccacttcc tctcccagac gaagcaagga ggagataatt    5100
ttgcgtatct aacggcctac caggccacag tatgcgctag ggcaaaggcc cctcctcctt    5160
cgtgggacgt gatgtggaag tgtttgacta ggcttaaacc cacactgact ggtcctaccc    5220
ccctcctgta ccgcttgggt gccgtcacca atgaaatcac cctgacgcac cccgtgacga    5280
agtatatcgc cacgtgcatg caagctgatc ttgagatcat gacaagcaca tgggttctgg    5340
caggaggggt gctagctgcc gtggcatctt actgcctggc aactggctgc atttccatca    5400
ttggccgcct acacctgaat gatcgggtag ttgtggcccc tgacaaggaa attctgtatg    5460
aggcctttga tgagatggaa gagtgcgcct ccaaagctgc cctcattgag gaagggcacc    5520
ggatggcaga gatgctgaag tctaagatac aaggcctctt acaacaggcc acaaaacagg    5580
cccaagacat acagccagcc atacagtcat catggcccaa gcttgaacaa ttctgggcca    5640
aacacatgtg gaacttcatc agtggcatac agtacctggc gggactctcc accctaccgg    5700
gaaatcccgc agtggcatca atgatggctt tcagcgctgc attgactagc ccgctgccca    5760
ccagcaccac catcctcttg aacatcatgg gggatggct ggcctctcag atagcccccc     5820
ccgccggagc cactggcttt gttgtcagtg gtcagtggg ggcggccgtc ggaagcatag      5880
gcctgggtaa gatattggtg gacgtcttgg ccgggtatgg cgcaggcatt tcgggggccc    5940
tcgtagcttt taagatcatg agcggcgaga agccctcggt agaagatgtt gtgaatctcc    6000
tgcctgctat cctatctcct ggcgctttgg tagtgggggt catctgtgcg gcaatcttgc    6060
gccgccacgt tggccaggga gaggggcgg tccagtggat gaacagactg atcgcctttg      6120
cctccagagg aaaccatgtt gcccctaccc actacgtggc agagtctgac gcttcgcagc    6180
gcgtgacgca agtgttgagt tcactcacaa ttaccagctt acttaggaga ctacatgcct    6240
ggatcactga agattgccca gtcccatgct cggggtcttg gctccgggac atttgggatt    6300
gggtttgttc catcctcaca gactttaaga actggctgtc ttcaaaactg ctccccaaac    6360
tgcccggcct tccctttatt tcttgtcaaa agggatacaa gggtgtatgg gctggtacgg    6420
ggatcatgac cactcggtgt tcatgcggag caaacatctc gggccatgtc cgcatgggta    6480
ccatgaaaat aacaggcccg aagacctgct tgaacttatg gcagggggacc ttccccatca    6540
attgttacac agaagggccc tgcgtgccaa agccccctcc taattacaaa actgcaattt    6600
ggagggtggc agcgtcggag tacgttgaga tcacgcagca tggttctttc tcgtacgtaa    6660
cggggttaac cagtgacaac cttaaggtcc cttgccaggt accagcccca gaattttttct   6720
catgggtgga cggggtgcag atacaccgat tcgcccccac tccaggtccc ttctttcggg    6780
```

```
atgaggtaac gttttctgtg ggcctcaatt ccttcgtggt cggctctcag ctcccttgtg   6840
accctgagcc ggacacggag gtgttagcct ccatgttgac agaccegtcc cacattacag   6900 cggaggcggc agctaggcga ttggccaggg gatccccccc ttcacaggcc agctcttcag   6960
cgagccagct ctccgccccg tccttgaagg ctacctgtac cacccataag atggcatatg   7020
actgtgacat ggtggatgct aaccttttca tgggaggtga tgtgacccgg atcgagtcca   7080
actcgaaggt gattgttctc gactccctcg attccatgac tgaggcagag gacgatcgtg   7140
agccttccat accatcagag tacttgatca ggaggaaaaa gttcccaccg gcactacctc   7200
cctgggctcg tccagactac aaccctcctg tgatcgagac atggaagagg ccgggctatg   7260
aaccacccac tgtcctaggt tgtgcccttc cccccacacc tcaagcgcca gtgccccac   7320 ctcggaggcg ccgcgccaaa gtcctgactc aggacaatgt ggagggggtt ctcaaggaga   7380
tggcggacaa agtgcttagc cctctccaag attacaacga ctccggtcac tccactggag   7440
tgggtaccgg gggagacagc gtccaggagc cctctgacga gactgccgct tcggaagtgg   7500
gatcactgtc ctccatgcct ccccttgagg gagagccggg ggaccctgac ttggagtttg   7560
agccagctag atccgctccc ccttccgagg gagagtgcga ggtcgttgat tcggactcca   7620
agtcgtggtc cacagtctct gatcaagagg attctatcgt ctgctgctct atgtcatact   7680
cctggacagg ggccctcata acaccatgtg ggcccgagga ggagaagttg ccaatcaacc   7740
ctctgagcaa ttcgctcatg cggttccata acaaggtgta ctccacaacc tcgaggagtg   7800
ccgctctgag ggcaaagaag gtaacttttg acagagtgca gatactggac acatattatg   7860
attcagtctt gcaggacgtc aagcgggccg cctctaaggt tagtgctagg ctcctctcag   7920
tagaggaagc ctgcgcgctg accccgcccc actccgccag atcgcgatac ggatttgggg   7980
caaaagaggt gcgcagcttg tccaggaggg ccgttaacca catccagtcc gtgtgggagg   8040
acctcctgga agaccaaaat actccaattg agacaaccat catggccaaa aatgaggtgt   8100
tctgtgtcga tccagccaag ggcgggaaga aggcagctcg cctcattgta taccccgacc   8160
ttggggtcag ggtgtgcgaa agatggccc tctatgacat tgcacaaaag cttcccaagg   8220
caataatggg gccgtcctat gggttccaat actctcctgc agaacgggtc gatttteete   8280 tcaaagcttg gggaagtaag aaggacccaa tggggttctc gtatgacacc cgctgctttg   8340
actcaaccgt cacggagagg gacataagaa cagaagaatc catatatcag gcttgttccc   8400
tgcctcaaga ggccagaact gtcatacact cgctcactga gagactttac gtaggagggc   8460
ccatgctaaa cagcaaaggt caatcctgcg gttacaggcg ttgtcgcgca agcggcgtgt   8520
tcactaccag catggggaat accatgacat gctacatcaa agcccttgca gcgtgcaaag   8580
ctgcagggat cgtggaccct gttatgctgg tgtgtggaga cgacctggtt gtcatctcag   8640
agagccaagg taacgaggag gacgagcgaa acctgagagc cttcacggag gccatgacca   8700
ggtattcagc ccctcccgt gaccttccca gaccagaata tgacctagag cttataacat   8760
cctgctcctc aaacgtgtcg gtagcgctgg accctcgggg tcgccgccgg tactacctaa   8820
ccagagaccc tatcactcca atctcccgag ccgcttggga aacagtaaga cactcccccg   8880
tcaattcttg gctgggcaac atcattcaat atgcccctac aatctgggtc cggatggtca   8940
taatgaccca cttctttgcc atactattgg cccaggacac tctgaaccaa aatctcaact   9000
ttgagatgta tggggcagta tattcggtca atccattaga cctaccagcc ataattgaga   9060
ggctacatgg gcttgatgct ttttcactgc acacatactc tccccaccgaa ctcacacggg   9120
```

-continued

| | |
|---|---|
| tggcagcagc tctcagaaaa cttggagcgc ctcccctcag agcgtggaag agccgggcac | 9180 |
| gtgctgtgag agcctcactc ctcgcccagg gagggagggc ggccatttgt ggccgctacc | 9240 |
| tcttcaactg ggcggtgaaa acaaagctca aactcactcc attgcccgag gcgagccgcc | 9300 |
| tggatttgtc caggtggttc accgtgggcg ccggcggggg cggcatcttt cacagcgtgt | 9360 |
| cgcatgcccg accccgccta ttactccttt gcctactcct acttagcgta ggggtaggca | 9420 |
| tcttttact ccccgctcgg tagagcggca aaccctagct acactccata gctagtttcc | 9480 |
| gtttttttt tttgttttt tttttttttt tttttttttt tttttttttt tttcttttcc | 9540 |
| tttttttttt ttctctttct tggtggctcc atcttagccc tagtcacggc tagctgtgaa | 9600 |
| aggtccgtga gccgcatgac tgcagagagt gccgtaactg gtctctctgc agatcatgt | 9659 |

<210> SEQ ID NO 11
<211> LENGTH: 9659
<212> TYPE: DNA
<213> ORGANISM: Hepatitis C virus

<400> SEQUENCE: 11

| | |
|---|---|
| gcccgccccc tgatggggc gacactccgc catgaatcac tccctgtga ggaactactg | 60 |
| tcttcacgca gaaagcgtct agccatggcg ttagtatgag tgtcgtacag cctccaggcc | 120 |
| ccccctccc gggagagcca tagtggtctg cggaaccggt gagtacaccg gaattaccgg | 180 |
| aaagactggg tcctttcttg gataaaccca ctctatgtcc ggtcatttgg gcacgccccc | 240 |
| gcaagactgc tagccgagta gcgttgggtt gcgaaaggcc ttgtggtact gcctgatagg | 300 |
| gtgcttgcga gtccccgggg aggtctcgta gaccgtgcat catgagcaca aatcccaaac | 360 |
| ctcaaagaaa aaccaaaaga aacacaaacc gccgcccaca ggacgtcaag ttcccgggtg | 420 |
| gcggccagat cgttggcgga gtttatttgt tgccgcgcag gggccccagg ttgggtgtgc | 480 |
| gcgcgacaag gaagacttcc gagcgatccc agccgcgtgg gagacgccag cccatcccga | 540 |
| aagatcggcg ctcaccggc aagtcctggg gaaagccagg atatccttgg cccctgtatg | 600 |
| gaaacgaggg ctgcggctgg gcaggttggc tcctgtcccc ccgcgggtcc cgtcctactt | 660 |
| ggggcccac tgaccccggg catagatcac gtaatttggg cagagtcatc gacaccatta | 720 |
| cgtgtggttt tgccgacctc atggggtaca tcccgtcgt tggcgccccg gtcggaggcg | 780 |
| tcgccagagc tctggcacac ggtgttaggg ttctggagga cgggataaat tatgcaacag | 840 |
| ggaatctgcc tggttgctct ttttctatct tcttacttgc tctcctgtcg tgcttcacag | 900 |
| tgccagtgtc cgcggtggaa gtcaggaaca ttagttctag ttactatgcc accaatgatt | 960 |
| gctcaaacag cagcatcacc tggcaacttg ccgacgcagt cctccacctt cctggatgcg | 1020 |
| tcccatgtga aaataacaat ggcacccgc gatgctggat acaagtgaca cctaatgtag | 1080 |
| ctgtgaaata ccgcggcgca ctcactcaca gcctacgaac acatatcgat gtgatcgtaa | 1140 |
| tggcagccac ggtctgctcg gccttgtacg tgggagacgt atgcggggcc gtgatgatcg | 1200 |
| tgtcgcaggc tttcatagtg tcgccacagt tccacaactt tacccaagag tgcaactgtt | 1260 |
| ccatctatca aggtcacatc accggccacc gcatggcatg gacatgatg ctaaactggt | 1320 |
| caccaactct caccatgatt cttgcctatg ccactcgtgt tcctgagcta gctcttgaga | 1380 |
| ttgtcttcgg cggccattgg ggtgtggtgt tcggcttggc ttatttctcc ttgcagggag | 1440 |
| cgtgggccaa agtcgttgcc atcctccttc ttgtagcagg agtggatgca cacactcagc | 1500 |
| tcaccggcac aaacgtgggt cggaccaccg caggctttgc tagtttgttt gctcctggcg | 1560 |
| cccggcagga aatcagtctg atcaacacca atggcagctg gcacgtaaac cggacagccc | 1620 |

```
tcaattgcaa cgacagcttg aatacgggtt tccttacagc cctgttttat cgcaacaagt   1680
tcaacagctc tggctgcccc gagcgcttgt cttcctgccg tgagctggac gatttccgca   1740
tcgggtgggg gaccgtggaa tacgagaccg ttgtcaccaa cgatgaggac atgaggccgt   1800
actgctggca ctaccctccg aagccttgcg gtattgtctc ggctaagaca gtgtgcgggc   1860
cagtctactg ttttactcct agccctgttg tcgtgggtac cactgacaga ctgggcgcgc   1920
ccacctacaa ttgggggata aacgagactg atgtcttcct gctgaatagc acaaggcccc   1980
cgcaaggagc ttggttcggc tgcacttgga tgaatgggac tgggttcact aagacatgcg   2040
gcgcaccacc ttgccgcatt aggagagacc acaacagcac cctcgatcta ttgtgtccaa   2100
cagactgttt cagaaagcac ccagacacta cctatcttaa gtgcggagca gggccctggt   2160
tgacccccaa atgcctgata gattacccct acagattgtg gcattatccg tgcactgtaa   2220
attttaccat cttcaaggtg cggatgtatg ttgggggggt agagcaccgc ttggacgcgg   2280
cgtgcaactt cacgcgtggg gaccgctgca gactggaaga tagggacagg ggtcagcaga   2340
ctccactgct gcattccacc actgagtggg cgatactgcc atgcactttc tccgacttac   2400
cggcgctgtc tactggtcta ttgcacctcc accaaaacac tgtggacgtg cagtacctct   2460
atggacttac tccggctatc acaagataca tcgtgaagtg ggagtgggtg gtcctccttt   2520
tcttgttgtt ggcggacgct agggtctgtg catgcctttg gatgctcatc atactgggcc   2580
aggccgaggc agcgcttgag aagcttatca tcttgcactc cgctagcgct gctagtgcca   2640
atgggccgct atggttcttc atcttcttta tagcggcctg gtacttaaag ggcagggtgg   2700
tccccgcggc cacatactct gttctcggct tgtggtcctt tctcctccta gtcctggcct   2760
tgccacaaca ggcttatgcc ctggacgcca ctgagcaagg agaactgggg ctagttatgt   2820
tagtagtttt atccatcttt actcttaccc cagcatacaa gacccttctg agccgctcgg   2880
tgtggtggct gtcctacatg ctggtcttgg ccgaagctca ggttcagcaa tgggtgcccc   2940
ccctggaagc ccgagggggg cgtgacggga tcatatgggc agctgtcatt ctacacccac   3000
gccttgtgtt tgagatcacg aagtggttac tggcaatcct ggggcctgcc tacttcctta   3060
aagcgtctct gctacgggtt ccatactttg tgagggctca cgcccgcta cgaatgtgta   3120
ccctggtgag acaccttgcg ggagctaagt acatccagat gctgttgatc accataggca   3180
ggtggaccgg cacttacatc tatgaccacc tctccccttt gtcaacttgg gcagcccagg   3240
gtttacggga cctggcagtc gccgtggagc ctgtggtgtt tagcccaatg gagaagaagg   3300
tcatcgtgtg gggggctgag acagcggcat gtggggacat cctgcatggc ctcccggttt   3360
ccgcgaggct aggtagggaa gtgctgctcg gtcccgccga tggctacacc tccaagggt   3420
ggaagctctt ggctcccatc actgcttata cccagcagac tcgtggtctc ctgggtagca   3480
tcgtggtctg tttgacaggc cgcgacaaaa atgagcaggc tgggcacgtc caggttctgt   3540
cctccgtcac acaatctttc ttggggacat ctatctcggg ggtcctctgg acggtatatc   3600
acggagctgg caacaagacc ttagctggcc ccaaaggacc aatcactcaa atgtacacca   3660
gcgcagaagg ggacctcgtg ggatggccta gcccccccgg gactaagtct ttagacccct   3720
gcacttgcgg ggctgtggac ctctacctgg tcacccgaaa cgctgatgtc attccagtcc   3780
ggaggaaaga cgaccggcgg ggtgcactgc tctcgccaag gcccctctca actctcaagg   3840
gatcatccgg tggacccgtg ctctgcccca ggggcacgc tgtgggcttg ttcagggcgg   3900
ccttgtgcgc caggggtgta gccaaatcca tcgacttcat ccctgttgaa tctcttgata   3960
```

```
tcgtcgcacg gtcacccagt ttttctgaca acagcacgcc accagccgtg cctcagacct    4020
accaggtggg ctacttgcac gcaccgacgg gcagcgggaa gagcaccaag gtccccgccg    4080
cttatgccag tcaggggtat aaagtacttg tactaaatcc ctctgttgcg ccacactcg     4140
gttttggggc ctacatgtcc aaagcccacg ggatcaaccc caacatcaga accggagtac    4200
ggactgtgac caccggggac cctatcacct actccactta tggcaagttt ctcgcagatg    4260
gaggctgctc ggctggtgcc tatgacatca tcatatgcga cgaatgccat gcagtggatg    4320
ccactaccat ccttggcatt ggaacagtcc tcgaccaggc tgagaccgca ggtgccagac    4380
tagtggtctt ggccacggcc acacctcctg gtacagtgac aactcctcac agtaatatag    4440
aggaggtggc tctcggtcac gaaggcgaga tcccttttta cggcaaggct atcccctag    4500
ctttcatcaa gggggcaga cacctgattt tttgccactc aaagaagaag tgcgatgagg    4560
tcgcggcggc ccttcggagc gtgggtgtca atgccgttgc ttactacagg ggtctcgacg    4620
tctccgttat accaacccaa ggggacgtgg tggtcgtcgc caccgatgcc ctaatgaccg    4680
ggtacaccgg tgactttgat tctgttatcg actgcaatgt tgcggtcact cagattgttg    4740
accttagcct agacccaacc tttaccatca ccactcaaac cgtccctcag gacgctgtct    4800
cccgtagtca acgcagaggg agaactggga ggggacgact gggcatttac aggtatgtct    4860
catcaggtga aaggccgtct gggatgttcg acagcgtagt actctgcgag tgctatgatg    4920
ccggggcagc ctggtatgaa ctcacgcctg ctgagactac agtgagactc cgggcttatt    4980
tcaacacgcc cggtctgccc gtgtgtcaag accacttgga gttctgggag gcggtcttca    5040
caggtctcac acacatcgat gcccacttcc tctcccagac gaagcaagga ggagataatt    5100
ttgcgtatct aacggcctac caggccacag tatgcgctag ggcaaaggcc cctcctcctt    5160
cgtgggacgt gatgtggaag tgtttgacta ggcttaaacc cacactgact ggtcctaccc    5220
ccctcctgta ccgcttgggt gccgtcacca atgaaatcac cctgacgcac cccgtgacga    5280
agtatatcgc cacgtgcatg caagctgatc ttgagatcat gacaagcaca tgggttctgg    5340
caggagggt gctagctgcc gtggcatctt actgcctggc aactggctgc atttccatca    5400
ttggccgcct acacctgaat gatcgggtag ttgtggcccc tgacaaggaa attctgtatg    5460
aggcctttga tgagatggaa gagtgcgcct ccaaagctgc cctcattgag gaagggcacc    5520
ggatggcaga gatgctgaag tctaagatac aaggcctctt acaacaggcc acaaaacagg    5580
cccaagacat acagccagcc atacagtcat catggcccaa gcttgaacaa ttctgggcca    5640
aacacatgtg gaacttcatc agtggcatac agtacctggc gggactctcc accctaccgg    5700
gaaatcccgc agtggcatca atgatggctt tcagcgctgc attgactagc ccgctgccca    5760
ccagcaccac catcctcttg aacatcatgg ggggatggct ggcctctcag atagcccccc    5820
ccgccggagc cactggcttt gttgtcagtg gtctagtggg ggcggccgtc ggaagcatag    5880
gcctgggtaa gatattggtg gacgtcttgg ccgggtatgg cgcaggcatt tcggggccc    5940
tcgtagcttt taagatcatg agcggcgaga agccctcggt gaagatgtt gtgaatctcc     6000
tgcctgctat cctatctcct ggcgcttttg tagtgggggt catctgtgcg gcaatcttgc    6060
gccgccacgt tggccaggga gaggggcgg tccagtggat gaacagactg atcgcctttg    6120
cctccagagg aaaccatgtt gcccctaccc actacgtggc agagtctgac gcttcgcagc    6180
gcgtgacgca agcgttgagt tcactcacaa ttaccagctt acttaggaga ctacatgcct    6240
ggatcactga agattgccca gtcccatgct cggggtcttg gctccgggac atttgggatt    6300
gggtttgttc catcctcaca gactttaaga actggctgtc ttcaaaactg ctccccaaac    6360
```

```
tgcccggcct tccctttatt tcttgtcaaa agggatacaa gggtgtatgg gctggtacgg    6420
ggatcatgac cactcggtgt tcatgcggag caaacatctc gggccatgtc cgcatgggta    6480
ccatgaaaat aacaggcccg aagacctgct tgaacttatg gcaggggacc ttccccatca    6540
attgttacac agaagggccc tgcgtgccaa agcccctcc taattacaaa actgcaattt     6600
ggagggtggc agcgtcggag tacgttgaga tcacgcagca tggttctttc tcgtacgtaa    6660
cggggttaac cagtgacaac cttaaggtcc cttgccaggt accagcccca gaattttct     6720 catgggtgga cggggtgcag atacaccgat tcgcccccac tccaggtccc ttctttcggg    6780
atgaggtaac gttttctgtg ggcctcaatt ccttcgtggt cggctctcag ctcccttgtg    6840
accctgagcc ggacacggag gtgttagcct ccatgttgac agacccgtcc cacattacag    6900
cggaggcggc agctaggcga ttggccaggg gatccccccc ttcacaggcc agctcttcag    6960
cgagccagct ctccgccccg tccttgaagg ctacctgtac cacccataag atggcatatg    7020
actgtgacat ggtggatgct aaccttttca tgggaggtga tgtgacccgg atcgagtcca    7080
actcgaaggt gattgttctc gactccctcg attccatgac tgaggcagag gacgatcgtg    7140
agccttccat accatcagag tacttgatca ggaggaaaaa gttcccaccg gcactacctc    7200
cctgggctcg tccagactac aaccctcctg tgatcgagac atggaagagg ccgggctatg    7260
aaccaccacc tgtcctaggt tgtgcccttc cccccacacc tcaagcgcca gtgccccac     7320 ctcggaggcg ccgcgccaaa gtcctgactc aggacaatgt ggaggggtt ctcaaggaga     7380 tggcggacaa agtgcttagc cctctccaag attacaacga ctccggtcac tccactggag    7440
tgggtaccgg gggagacagc gtccaggagc cctctgacga gactgccgct tcggaagtgg    7500
gatcactgtc ctccatgcct cccttgagg gagagccggg ggaccctgac ttggagtttg     7560
agccagctag atccgctccc ccttccgagg gagagtgcga ggtcgttgat tcggactcca    7620
agtcgtggtc cacagtctct gatcaagagg attctatcgt ctgctgctct atgtcatact    7680
cctggacagg ggccctcata acaccatgtg ggcccgagga ggagaagttg ccaatcaacc    7740
ctctgagcaa ttcgctcatg cggttccata acaaggtgta ctccacaacc tcgaggagtg    7800
ccgctctgag ggcaaagaag gtaacttttg acagagtgca gatactggac acatattatg    7860
attcagtctt gcaggacgtc aagcgggccg cctctaaggt tagtgctagg ctcctctcag    7920
tagaggaagc ctgcgcgctg accccgcccc actccgccag atcgcgatac ggatttgggg    7980
caaaagaggt gcgcagcttg tccaggaggg ccgttaacca catccagtcc gtgtgggagg    8040
acctcctgga agaccaaaat actccaattg agacaaccat catggccaaa atgaggtgt     8100 tctgtgtcga tccagccaag ggcgggaaga aggcagctcg cctcattgta tacccgacc     8160 ttggggtcag ggtgtgcgaa aagatggccc tctatgacat tgcacaaaag cttcccaagg    8220
caataatggg gccgtcctat gggttccaat actctcctgc agaacgggtc gattttctcc    8280
tcaaagcttg gggaagtaag aaggacccaa tggggttctc gtatgacacc cgctgctttg    8340
actcaaccgt cacggagagg gacataagaa cagaagaatc catatatcag gcttgttccc    8400
tgcctcaaga ggccagaact gtcatacact cgctcactga gagctttac gtaggagggc     8460 ccatgctaaa cagcaaggt caatcctgcg gttacaggcg ttgtcgcgca agcggcgtgt     8520
tcactaccag catggggaat accatgacat gctacatcaa agcccttgca gcgtgcaaag    8580
ctgcagggat cgtggaccct gttatgctgg tgtgtggaga cgacctggtt gtcatctcag    8640
agagccaagg taacgaggag gacgagcgaa acctgagagc cttcacggag gccatgacca    8700
```

| | |
|---|---|
| ggtattcagc ccctcccggt gaccttccca gaccagaata tgacctagag cttataacat | 8760 |
| cctgctcctc aaacgtgtcg gtagcgctgg accctcgggg tcgccgccgg tactacctaa | 8820 |
| ccagagaccc tatcactcca atctcccgag ccgcttggga aacagtaaga cactcccccg | 8880 |
| tcaattcttg gctgggcaac atcattcaat atgcccctac aatctgggtc cggatggtca | 8940 |
| taatgaccca cttctttgcc atactattgg cccaggacac tctgaaccaa aatctcaact | 9000 |
| ttgagatgta tgggcagta tattcggtca atccattaga cctaccagcc ataattgaga | 9060 |
| ggctacatgg gcttgatgct ttttcactgc acacatactc tcccaccgaa ctcacacggg | 9120 |
| tggcagcagc tctcagaaaa cttggagcgc ctcccctcag agcgtggaag agccgggcac | 9180 |
| gtgctgtgag agcctcactc ctcgcccagg gagggagggc ggccatttgt ggccgctacc | 9240 |
| tcttcaactg ggcggtgaaa acaaagctca aactcactcc attgcccgag gcgagccgcc | 9300 |
| tggatttgtc caggtggttc accgtgggcg ccggcggggg cggcatcttt cacagcgtgt | 9360 |
| cgcatgcccg accccgccta ttactccttt gcctactcct acttagcgta ggggtaggca | 9420 |
| tcttttact ccccgctcgg tagagcggca aaccctagct acactccata gctagtttcc | 9480 |
| gtttttttt tttttgtttt tttttttttt tttttttttt tttttttttt tttcttttcc | 9540 |
| tttttttttt ttctctttct tggtggctcc atcttagccc tagtcacggc tagctgtgaa | 9600 |
| aggtccgtga gccgcatgac tgcagagagt gccgtaactg gtctctctgc agatcatgt | 9659 |

<210> SEQ ID NO 12
<211> LENGTH: 9659
<212> TYPE: DNA
<213> ORGANISM: Hepatitis C virus

<400> SEQUENCE: 12

| | |
|---|---|
| gcccgccccc tgatgggggc gacactccgc catgaatcac tcccctgtga ggaactactg | 60 |
| tcttcacgca gaaagcgtct agccatggcg ttagtatgag tgtcgtacag cctccaggcc | 120 |
| ccccctccc gggagagcca tagtggtctg cggaaccggt gagtacaccg gaattaccgg | 180 |
| aaagactggg tccttctg gataaaccca ctctatgtcc ggtcatttgg gcacgccccc | 240 |
| gcaagactgc tagccgagta gcgttgggtt gcgaaaggcc ttgtggtact gcctgatagg | 300 |
| gtgcttgcga gtgccccggg aggtctcgta gaccgtgcat catgagcaca aatcccaaac | 360 |
| ctcaaagaaa aaccaaaaga aacacaaacc gccgcccaca ggacgtcaag ttcccgggtg | 420 |
| gcggccagat cgttggcgga gtttatttgt tgccgcgcag gggccccagg ttgggtgtgc | 480 |
| gcgcgacaag gaagacttcc gagcgatccc agcgcgtgg gagacgccag cccatcccga | 540 |
| aagatcggcg ctccaccggc aagtcctggg gaaagccagg atatccttgg cccctgtatg | 600 |
| gaaacgaggg ctgcggctgg gcaggttggc tcctgtcccc ccgcgggtcc cgtcctactt | 660 |
| ggggccccac tgaccccgg catagatcac gtaatttggg cagagtcatc gacaccatta | 720 |
| cgtgtggttt tgccgacctc atgggtaca tcccgtcgt tggcgcccg tcggaggcg | 780 |
| tcgccagagc tctggcacac ggtgttaggg ttctggagga cgggataaat tatgcaacag | 840 |
| ggaatctgcc tggttgctct ttttctatct tcttacttgc tctcctgtcg tgcttcacag | 900 |
| tgccagtgtc cgcggtggaa gtcaggaaca ttagttctag ttactatgcc accaatgatt | 960 |
| gctcaaacag cagcatcacc tggcaacttg ccgacgcagt cctccacctt cctggatgcg | 1020 |
| tcccatgtga aataacaat ggcaccccgc gatgctggat acaagtgaca cctaatgtag | 1080 |
| ctgtgaaata ccgcggcgca ctcactcaca gcctacgaac acatatcgat gtgatcgtaa | 1140 |
| tggcagccac ggtctgctcg gccttgtacg tgggagacgt atgcgggggcc gtgatgatcg | 1200 |

```
tgtcgcaggc tttcatagtg tcgccacagt tccacaactt tacccaagag tgcaactgtt    1260
ccatctatca aggtcacatc accggccacc gcatggcatg ggacatgatg ctaaactggt    1320
caccaactct caccatgatt cttgcctatg ccactcgtgt tcctgagcta gctcttgaga    1380
ttgtcttcgg cagccattgg ggtgtggtgt tcggcttggc ttatttctcc ttgcagggag    1440
cgtgggccaa agtcgttgcc atcctccttc ttgtagcagg agtggatgca cacactcagc    1500
tcaccggcac aaacgtgggt cggaccaccg caggctttgc tagtttgttt gctcctggcg    1560
cccggcagga aatcagtctg atcaacacca atggcagctg gcacgtaaac cggacagccc    1620
tcaattgcaa cgacagcttg aatacgggtt tccttacagc cctgttttat cgcaacaagt    1680
tcaacagctc tggctgcccc gagcgcttgt cttcctgccg tgagctggac gatttccgca    1740
tcgggtgggg gaccgtggaa tacgagaccg ttgtcaccaa cgatgaggac atgaggccgt    1800
actgctggca ctaccctccg aagccttgcg gtattgtctc ggctaagaca gtgtgcgggc    1860
cagtctactg ttttactcct agccctgttg tcgtgggtac cactgacaga ctgggcgcgc    1920
ccacctacaa ttgggggata acgagactg atgtcttcct gctgaatagc acaaggcccc    1980
cgcaaggagc ttggttcggc tgcacttgga tgaatgggac tgggttcact aagacatgcg    2040
gcgcaccacc ttgccgcatt aggagagacc acaacagcac cctcgatcta ttgtgtccaa    2100
cagactgttt cagaaagcac ccagacacta cctatcttaa gtgcggagca gggcctggt    2160
tgacccccaa atgcctgata gattacccctt acagattgtg gcattatccg tgcactgtaa    2220
attttaccat cttcaaggtg cggatgtatg ttgggggggt agagcaccgc ttggacgcgg    2280
cgtgcaactt cacgcgtggg gaccgctgca gactggaaga tagggacagg ggtcagcaga    2340
ctccactgct gcattccacc actgagtggg cgatactgcc atgcactttc tccgacttac    2400
cggcgctgtc tactggtcta ttgcacctcc accaaaacac tgtggacgtg cagtacctct    2460
atggacttac tccggctatc acaagataca tcgtgaagtg ggagtgggtg gtcctccttt    2520
tcttgttgtt ggcggacgct agggtctgtg catgcctttg gatgctcatc atactgggcc    2580
aggccgaggc agcgcttgag aagcttatca tcttgcactc cgctagcgct gctagtgcca    2640
atgggccgct atggttcttc atcttcttta tagcggcctg gtacttaaag ggcagggtgg    2700
tccccgcggc cacaaactct gttctcggct tgtggtcctt tctcctccta gtcctggcct    2760
tgccacaaca ggcttatgcc ctggacgcca ctgagcaagg agaactgggg ctagttatgt    2820
tagtagtttt atccatcttt actcttaccc cagcatacaa gaccccttctg agccgctcgg    2880
tgtggtggct gtcctacatg ctggtcttgg ccgaagctca ggttcagcaa tgggtgcccc    2940
ccctggaagc ccgagggggg cgtgacggga tcatatgggc agctgtcatt ctacacccac    3000
gccttgtgtt tgagatcacg aagtggttac tggcaatcct ggggcctgcc tacttcctta    3060
aagcgtctct gctacgggtt ccatactttg tgagggctca cgccctgcta cgaatgtgta    3120
ccctggtgag acaccttgcg ggagctaagt acatccagat gctgttgatc accataggca    3180
ggtggaccgg cacttacatc tatgaccacc tctcccctt gtcaacttgg gcagcccagg    3240
gtttacggga cctggcagtc gccgtggagc ctgtggtgtt tagcccaatg gagaagaagg    3300
tcatcgtgtg gggggttgag acagcggcat gtggggacat cctgcatggc ctcccggttt    3360
ccgcgaggct aggtagggaa gtgctgctcg gtcccgccga tggctacacc tccaagggt    3420
ggaagctctt ggctcccatc actgcttata cccagcagac tcgtggtctc ctgggtagca    3480
tcgtggtctg tttgacaggc cgcgacaaaa atgagcaggc tgggcacgtc caggttctgt    3540
```

```
cctccgtcac acaatctttc ttggggacat ctatctcggg ggtcctctgg acggtatatc    3600
acggagctgg caacaagacc ttagctggcc ccaaaggacc aatcactcaa atgtacacca    3660
gcgcagaagg ggacctcgtg ggatggccta gccccccggg gactaagtct ttagacccct    3720
gcacttgcgg ggctgtggac ctctacctgg tcacccgaaa cgctgatgtc attccagtcc    3780
ggaggaaaga cgaccggcgg ggtgcactgc tctcgccaag gcccctctca actctcaagg    3840
gatcatccgg tggacccgtg ctctgcccca gggggcacgc tgtgggcttg ttcagggcgg    3900
ccttgtgcgc caggggtgta gccaaatcca tcgacttcat ccctgttgaa tctcttgata    3960
tcgtcgcacg gtcacccagt ttttctgaca acagcacgcc accagccgtg cctcagacct    4020
accaggtggg ctacttgcac gcaccgacgg gcagcgggaa gagcaccaag gtccccgccg    4080
cttatgccag tcagggtat aaagtacttg tactaaatcc ctctgttgcg gccacactcg    4140
gttttggggc ctacatgtcc aaagcccacg ggatcaaccc caacatcaga accggagtac    4200
ggactgtgac caccggggac cctatcacct actccactta tggcaagttt ctcgcagatg    4260
gaggctgctc ggctggtgcc tatgacatca tcatatgcga cgaatgccat gcagtggatg    4320
ccactaccat ccttggcatt ggaacagtcc tcgaccaggc tgagaccgca ggtgccagac    4380
tagtggtctt ggccacggcc acacctcctg gtacagtgac aactcctcac agtaatatag    4440
aggaggtggc tctcggtcac gaaggcgaga tccctttta cggcaaggct atccccctag    4500
ctttcatcaa ggggggcaga cacctgattt tttgccactc aaagaagaag tgcgatgagg    4560
tcgcggcggc ccttcggagc gtgggtgtca atgccgttgc ttactacagg ggtctcgacg    4620
tctccgttat accaacccaa ggggacgtgg tggtcgtcgc caccgatgcc ctaatgaccg    4680
ggtacaccgg tgactttgat tctgttatcg actgcaatgt tgcggtcact cagattgttg    4740
accttagcct agaccaacc tttaccatca ccactcaaac cgtccctcag gacgctgtct    4800
cccgtagtca acgcagaggg agaactggga ggggacgact gggcatttac aggtatgtct    4860
catcaggtga aaggccgtct gggatgttcg acagcgtagt actctgcgag tgctatgatg    4920
ccggggcagc ctggtatgaa ctcacgcctg ctgagactac agtgagactc cgggcttatt    4980
tcaacacgcc cggtctgccc gtgtgtcaag accacttgga gttctgggag gcggtcttca    5040
caggtctcac acacatcgat gcccacttcc tctcccagac gaagcaagga ggagataatt    5100
ttgcgtatct aacggcctac caggccacag tatgcgctag ggcaaaggcc cctcctcctt    5160
cgtgggacgt gatgtggaag tgtttgacta ggcttaaacc cacactgact ggtcctaccc    5220
ccctcctgta ccgcttgggt gccgtcacca atgaaatcac cctgacgcac cccgtgacga    5280
agtatatcgc cacgtgcatg caagctgatc ttgagatcat gacaagcaca tgggttctgg    5340
caggaggggt gctagctgcc gtggcatctt actgcctggc aactggctgc atttccatca    5400
ttggccgcct acacctgaat gatcgggtag ttgtggcccc tgacaaggaa attctgtatg    5460
aggcctttga tgagatggaa gagtgcgcct ccaaagctgc cctcattgag gaagggcacc    5520
ggatggcaga gatgctgaag tctaagatac aaggcctctt acaacaggcc acaaaacagg    5580
cccaagacat acagccagcc atacagtcat catggcccaa gcttgaacaa ttctgggcca    5640
aacacatgtg gaacttcatc agtggcatac agtacctggc gggactctcc accctaccgg    5700
gaaatcccgc agtggcatca atgatggctt tcagcgctgc attgactagc ccgctgccca    5760
ccagcaccac catcctcttg aacatcatgg ggggatggct ggcctctcag gtagccccca    5820
ccgccggagc cactggcttt gttgtcagtg gtctagtggg ggcggccgtc ggaagcatag    5880
gcctgggtaa gatattggtg gacgtcttgg ccgggtatgg cgcaggcatt tcgggggccc    5940
```

```
tcgtagcttt taagatcatg agcggcgaga agccctcggt agaagatgtt gtgaatctcc    6000
tgcctgctat cctatctcct ggcgctttgg tagtgggggt catctgtgcg gcaatcttgc    6060
gccgccacgt tggccaggga gaggggggcgg tccagtggat gaacagactg atcgcctttg   6120
cctccagagg aagccatgtt gcccctaccc actacgtggc agagtctgac gcttcgcagc    6180
gcgtgacgca agcgttgagt tcactcacaa ttaccagctt acttaggaga ctacatgcct    6240
ggatcactga agattgccca gtcccatgct cggggtcttg gctccgggac atttgggatt    6300
gggtttgttc catcctcaca gactttaaga actggctgtc ttcaaaactg ctccccaaac    6360
tgcccggcct tcccttttatt tcttgtcaaa agggatacaa gggtgtatgg gctggtacgg   6420
ggatcatgac cactcggtgt tcatgcggag caaacatctc gggccatgtc cgcatgggta    6480
ccatgaaaat aacaggcccg aagacctgct tgaacttatg cagggggacc ttccccatca    6540
attgttacac agaagggccc tgcgtgccaa agcccctcc taattacaaa actgcaattt     6600
ggagggtggc agcgtcggag tacgttgaga tcacgcagca tggttctttc tcgtacgtaa    6660
cggggttaac cagtgacaac cttaaggtcc cttgccaggt accagcccca gaatttttct    6720 catggggtgga cggggtgcag atacaccgat tcgcccccac tccaggtccc ttctttcggg   6780
atgaggtaac gttttctgtg ggcctcaatt ccttcgtggt cggctctcag ctcccttgtg    6840
accctgagcc ggacacggag gtgttagcct ccatgttgac agaccgtcc cacattacag     6900 cggaggcggc agctaggcga ttggccaggg gatccccccc ttcacaggcc agctcttcag    6960
cgagccagct ctccgccccg tccttgaagg ctacctgtac cacccataag atggcatatg    7020
actgtgacat ggtggatgct aacctttca tgggaggtga tgtgacccgg atcgagtcca     7080
actcgaaggt gattgttctc gactccctcg attccatgac tgaggcagag gacgatcgtg    7140
agccttccat accatcagag tacttgatca ggaggaaaaa gttcccaccg gcactacctc    7200
cctgggctcg tccagactac aaccctcctg tgatcgagac atggaagagg ccgggctatg    7260
aaccacccac tgtcctaggt tgtgcccttc ccccacacc tcaagcgcca gtgccccac     7320 ctcggaggcg ccgcgccaaa gtcctgactc aggacaatgt ggagggggtt ctcaaggaga    7380
tggcggacaa agtgcttagc cctctccaag attacaacga ctccggtcac tccactggag    7440
tgggtaccgg gggagacagc gtccaggagc cctctgacga gactgccgct tcggaagtgg    7500
gatcactgtc ctccatgcct cccccttgagg gagagccggg ggaccctgac ttggagtttg   7560
agccagctag atccgctccc ccttccgagg gagagtgcga ggtcgttgat tcggactcca    7620
agtcgtggtc cacagtctct aatcaagagg attctatcgt ctgctgctct atgtcatact    7680
cctggacagg ggccctcata acaccatgtg ggcccgagga ggagaagttg ccaatcaacc    7740
ctctgagcaa ttcgctcatg cggttccata acaaggtgta ctccacaacc tcgaggagtg    7800
ccgctctgag ggcaaagaag gtaacttttg acagagtgca gatactggac acatattatg    7860
attcagtctt gcaggacgtc aagcgggccg cctctaaggt tagtgctagg ctcctctcag    7920
tagaggaagc ctgcgcgctg accccgcccc actccgccag atcgcgatac ggatttgggg    7980
caaaagaggt gcgcagcttg tccaggaggg ccgttaacca catccagtcc gtgtgggagg    8040
acctcctgga agaccaaaat actccaattg agacaaccat catggccaaa aatgaggtgt    8100
tctgtgtcga tccagccaag ggcgggaaga aggcagctcg cctcattgta taccccgacc    8160
ttggggtcag ggtgtgcgaa aagatggccc tctatgacat tgcacaaaag cttcccaagg    8220
caataatggg gccgtcctat gggttccaat actctcctgc agaacgggtc gattttctcc    8280
```

```
tcaaagcttg gggaagtaag aaggacccaa tggggttctc gtatgacacc cgctgctttg    8340
actcaaccgt cacggagagg gacataagaa cagaagaatc catatatcag gcttgttccc    8400
tgcctcaaga ggccagaact gtcatacact cgctcactga gagactttac gtaggagggc    8460
ccatgctaaa cagcaaaggt caatcctgcg gttacaggcg ttgtcgcgca agcggcgtgt    8520
tcactaccag catggggaat accatgacat gctacatcaa agcccttgca gcgtgcaaag    8580
ctgcagggat cgtggaccct gttatgctgg tgtgtggaga cgacctggtt gtcatctcag    8640
agagccaagg taacgaggag gacgagcgaa acctgagagc cttcacggag gccatgacca    8700
ggtattcagc ccctcccggt gaccttccca gaccagaata tgacctagag cttataacat    8760
cctgctcctc aaacgtgtcg gtagcgctgg accctcgggg tcgccgccgg tactacctaa    8820
ccagagaccc tatcactcca atctcccgag ccgcttggga aacagtaaga cactcccccg    8880
tcaattcttg gctgggcaac atcattcaat atgcccctac aatctgggtc cggatggtca    8940
taatgaccca cttctttgcc atactattgg cccaggacac tctgaaccaa aatctcaact    9000
ttgagatgta tgggcagta tattcggtca atccattaga cctaccagcc ataattgaga    9060
ggctacatgg gcttgatgct ttttcactgc acacatactc tcccaccgaa ctcacacggg    9120
tggcagcagc tctcagaaaa cttggagcgc ctcccctcag agcgtggaag agccgggcac    9180
gtgctgtgag agcctcactc ctcgcccagg agggagggc ggccatttgt ggccgctacc    9240
tcttcaactg gcggtgaaa acaaagctca aactcactcc attgcccgag gcgagccgcc    9300
tggatttgtc caggtggttc accgtgggcg ccggcggggg cggcatcttt cacagcgtgt    9360
cgcatgcccg accccgccta ttactccttt gcctactcct acttagcgta ggggtaggca    9420
tctttttact ccccgctcgg tagagcggca aacccctagct acactccata gctagttttcc    9480 gttttttttt ttttgttttt ttttttttttt ttttttttt tttcttttcc    9540 tttttttttt ttctctttct tggtggctcc atcttagccc tagtcacggc tagctgtgaa    9600
aggtccgtga gccgcatgac tgcagagagt gccgtaactg gtctctctgc agatcatgt     9659
```

<210> SEQ ID NO 13
<211> LENGTH: 9659
<212> TYPE: DNA
<213> ORGANISM: Hepatitis C virus

<400> SEQUENCE: 13

```
gcccgccccc tgatgggggc gacactccgc catgaatcac tcccctgtga ggaactactg     60
tcttcacgca gaaagcgtct agccatggcg ttagtatgag tgtcgtacag cctccaggcc    120 ccccctccc gggagagcca tagtggtctg cggaaccggt gagtacaccg gaattaccgg    180
aaagactggg tcctttcttg gataaaccca ctctatgtcc ggtcatttgg gcacgccccc    240
gcaagactgc tagccgagta gcgttgggtt gcgaaaggcc ttgtggtact gcctgatagg    300
gtgcttgcga gtgccccggg aggtctcgta gaccgtgcat catgagcaca atcccaaac    360 ctcaaagaaa accaaaaga aacacaaacc gccgcccaca ggacgtcaag ttcccgggtg    420
gcggccagat cgttggcgga gtttatttgt tgccgcgcag gggccccagg ttgggtgtgc    480
gcgcgacaag gaagacttcc gagcgatccc agcgcgtgg gagacgccag ccatcccga    540 aagatcggcg ctccaccggc aagtcctggg gaaagccagg atatccttgg ccctgtatg    600 gaaacgaggg ctgcggctgg gcaggttggc tcctgtcccc ccgcgggtcc cgtcctactt    660 gggccccac tgaccccggg catagatcac gtaatttggg cagagtcatc gacaccatta    720
cgtgtggttt tgccgacctc atggggtaca tccccgtcgt tggcgcccg gtcggaggcg    780
```

```
tcgccagagc tctggcacac ggtgttaggg ttctggagga cgggataaat tatgcaacag    840
ggaatctgcc tggttgctct ttttctatct tcttacttgc tctcctgtcg tgcttcacag    900
tgccagtgtc cgcggtggaa gtcaggaaca ttagttctag ttactatgcc accaatgatt    960
gctcaaacag cagcatcacc tggcaacttg ccgacgcagt cctccacctt cctggatgcg   1020
tcccatgtga aaataacaat ggcaccccgc gatgctggat acaagtgaca cctaatgtag   1080
ctgtgaaata ccgcggcgca ctcactcaca gcctacgaac acatatcgat gtgatcgtaa   1140
tggcagccac ggtctgctcg gccttgtacg tgggagacgt atgcggggcc gtgatgatcg   1200
tgtcgcaggc tttcatagtg tcgccacagt tccacaactt tacccaagag tgcaactgtt   1260
ccatctatca aggtcacatc accggccacc gcatggcatg ggacatgatg ctaaactggt   1320
caccaactct caccatgatt cttgcctatg ccactcgtgt tcctgagcta gctcttgaga   1380
ttgtcttcgg cagccattgg ggtgtggtgt tcggcttggc ttatttctcc ttgcagggag   1440
cgtgggccaa agtcgttgcc atcctccttc ttgtagcagg agtggatgca cacactcagc   1500
tcaccggcac aaacgtgggt cggaccaccg caggctttgc tagtttgttt gctcctggcg   1560
cccggcagga aatcagtctg atcaacacca atggcagctg gcacgtaaac cggacagccc   1620
tcaattgcaa cgacagcttg aatacgggtt tccttacagc cctgttttat cgcaacaagt   1680
tcaacagctc tggctgcccc gagcgcttgt cttcctgccg tgagctggac gatttccgca   1740
tcgggtgggg gaccgtggaa tacgagaccg ttgtcaccaa cgatgaggac atgaggccgt   1800
actgctggca ctaccctccg aagccttgcg gtattgtctc ggctaagaca gtgtgcgggc   1860
cagtctactg ttttactcct agccctgttg tcgtgggtac cactgacaga ctgggcgcgc   1920
ccacctacaa ttgggggata aacgagactg atgtcttcct gctgaatagc acaaggcccc   1980
cgcaaggagc ttggttcggc tgcacttgga tgaatgggac tgggttcact aagacatgcg   2040
gcgcaccacc ttgccgcatt aggagagacc acaacagcac cctcgatcta ttgtgtccaa   2100
cagactgttt cagaaagcac ccagacacta cctatcttaa gtgcggagca gggccctggt   2160 tgaccccccaa atgcctgata gattacccctt acagattgtg gcattatccg tgcactgtaa   2220
attttaccat cttcaaggtg cggatgtatg ttggggggt agagcaccgc ttggacgcgg   2280
cgtgcaactt cacgcgtggg gaccgctgca gactggaaga tagggacagg ggtcagcaga   2340
ctccactgct gcattccacc actgagtggg cgatactgcc atgcactttc tccgacttac   2400
cggcgctgtc tactggtcta ttgcacctcc accaaaacac tgtggacgtg cagtacctct   2460
atggacttac tccggctatc acaagataca tcgtgaagtg ggagtgggtg gtcctccttt   2520
tcttgttgtt ggcggacgct agggtctgtg catgcctttg gatgctcatc atactgggcc   2580
aggccgaggc agcgcttgag aagcttatca tcttgcactc cgctagcgct gctagtgcca   2640
atgggccgct atggttcttc atcttcttta tagcggcctg gtacttaaag gcagggtgg   2700 tccccgcggc cacaaactct gttctcggct tgtggtcctt tctcctccta gtcctggcct   2760
tgccacaaca ggcttatgcc ctggacgcca ctgagcaagg agaactgggg ctagttatgt   2820
tagtagtttt atccatcttt actcttaccc cagcatacaa gacccttctg agccgctcgg   2880
tgtggtggct gtcctacatg ctggtcttgg ccgaagctca ggttcagcaa tgggtgcccc   2940
ccctggaagc ccgaggggg cgtgacggga tcatatgggc agctgtcatt ctacacccac   3000
gccttgtgtt tgagatcacg aagtggttac tggcaatcct ggggcctgcc tacttcctta   3060
aagcgtctct gctacgggtt ccatactttg tgagggctca cgccctgcta cgaatgtgta   3120
```

```
ccctggtgag acaccttgcg ggagctaagt acatccagat gctgttgatc accataggca    3180
ggtggaccgg cacttacatc tatgaccacc tctccccttt gtcaacttgg gcagcccagg    3240
gtttacggga cctggcagtc gccgtggagc ctgtggtgtt tagcccaatg gagaagaagg    3300
tcatcgtgtg gggggttgag acagcggcat gtggggacat cctgcatggc ctcccggttt    3360
ccgcgaggct aggtagggaa gtgctgctcg gtcccgccga tggctacacc tccaaggggt    3420
ggaagctctt ggctcccatc actgcttata cccagcagac tcgtggtctc ctgggtagca    3480
tcgtggtctg tttgacaggc cgcgacaaaa atgagcaggc tgggcacgtc caggttctgt    3540
cctccgtcac acaatctttc ttggggacat ctatctcggg ggtcctctgg acggtatatc    3600
acggagctgg caacaagacc ttagctggcc ccaaaggacc aatcactcaa atgtacacca    3660
gcgcagaagg ggacctcgtg ggatggccta gccccccccgg gactaagtct ttagacccct    3720
gcacttgcgg ggctgtggac ctctacctgg tcacccgaaa cgctgatgtc attccagtcc    3780
ggaggaaaga cgaccggcgg ggtgcactgc tctcgccaag gccctctca actctcaagg    3840
gatcatccgg tggaccgtg ctctgcccca ggggcacgc tgtgggcttg ttcagggcgg    3900
ccttgtgcgc caggggtgta gccaaatcca tcgacttcat ccctgttgaa tctcttgata    3960
tcgtcgcacg gtcacccagt ttttctgaca acagcacgcc accagccgtg cctcagacct    4020
accaggtggg ctacttgcac gcaccgacgg gcagcgggaa gagcaccaag gtccccgccg    4080
cttatgccag tcagggtat aaagtacttg tactaaatcc ctctgttgcg gccacactcg    4140
gttttggggc ctacatgtcc aaagcccacg ggatcaaccc caacatcaga accggagtac    4200
ggactgtgac caccggggac cctatccacct actccactta tggcaagttt ctcgcagatg    4260
gaggctgctc ggctggtgcc tatgacatca tcatatgcga cgaatgccat gcagtggatg    4320
ccactaccat ccttggcatt ggaacagtcc tcgaccaggc tgagaccgca ggtgccagac    4380
tagtggtctt ggccacggcc acacctcctg gtacagtgac aactcctcac agtaatatag    4440
aggaggtggc tctcggtcac gaaggcgaga tccctttttta cggcaaggct atccccctag    4500
cttttcatcaa ggggggcaga cacctgattt tttgccactc aaagaagaag tgcgatgagg    4560
tcgcggcggc ccttcggagc gtgggtgtca atgccgttgc ttactacagg ggtctcgacg    4620
tctccgttat accaacccaa ggggacgtgg tggtcgtcgc caccgatgcc ctaatgaccg    4680
ggtacaccgg tgactttgat tctgttatcg actgcaatgt tgcggtcact cagattgttg    4740
accttagcct agacccaacc tttaccatca ccactcaaac cgtccctcag gacgctgtct    4800
cccgtagtca acgcagaggg agaactggga ggggacgact gggcatttac aggtatgtct    4860
catcaggtga aaggccgtct gggatgttcg acagcgtagt actctgcgag tgctatgatg    4920
ccggggcagc ctggtatgaa ctcacgcctg ctgagactac agtgagactc cgggcttatt    4980
tcaacacgcc cggtctgccc gtgtgtcaag accacttgga gttctgggag gcggtcttca    5040
caggtctcac acacatcgat gcccacttcc tctcccagac gaagcaagga ggagataatt    5100
ttgcgtatct aacggcctac caggccacag tatgcgctag ggcaaaggcc cctcctcctt    5160
cgtgggacgt gatgtggaag tgtttgacta ggcttaaacc cacactgact ggtcctaccc    5220
ccctcctgta ccgcttgggt gccgtcacca atgaaatcac cctgacgcac cccgtgacga    5280
agtatatcgc cacgtgcatg caagctgatc ttgagatcat gacaagcaca tgggttctgg    5340
caggagggt gctagctgcc gtggcatctt actgcctggc aactggctgc atttccatca    5400
ttggccgcct acacctgaat gatcgggtag ttgtggcccc tgacaaggaa attctgtatg    5460
aggcctttga tgagatggaa gagtgcgcct ccaaagctgc cctcattgag gaagggcacc    5520
```

```
ggatggcaga gatgctgaag tctaagatac aaggcctctt acaacaggcc acaaaacagg    5580
cccaagacat acagccagcc atacagtcat catgggcccaa gcttgaacaa ttctgggcca    5640
aacacatgtg gaacttcatc agtggcatac agtacctggc gggactctcc accctaccgg    5700
gaaatcccgc agtggcatca atgatggctt tcagcgctgc attgactagc ccgctgccca    5760
ccagcaccac catcctcttg aacatcatgg ggggatggct ggcctctcag gtagcccccc    5820
ccgccggagc cactggcttt gttgtcagtg gtcagtgggg ggcggccgtc ggaagcatag    5880
gcctgggtaa gatattggtg gacgtcttgg ccgggtatgg cgcaggcatt tcgggggccc    5940
tcgtagcttt taagatcatg agcggcgaga agccctcggt agaagatgtt gtgaatctcc    6000
tgcctgctat cctatctcct ggcgctttgg tagtggggt catctgtgcg gcaatcttgc    6060
gccgccacgt tggccaggga gaggggggcgg tccagtggat gaacagactg atcgcctttg    6120
cctccagagg aacccatgtt gcccctaccc actacgtggc agagtctgac gcttcgcagc    6180
gcgtgacgca agcgttgagt tcactcacaa ttaccagctt acttaggaga ctacatgcct    6240
ggatcactga agattgccca gtcccatgct cggggtcttg gctccgggac atttgggatt    6300
gggtttgttc catcctcaca gactttaaga actggctgtc ttcaaaactg ctccccaaac    6360
tgcccggcct tccctttatt tcttgtcaaa agggatacaa gggtgtatgg gctggtacgg    6420
ggatcatgac cactcggtgt tcatgcgag caaacatctc gggccatgtc cgcatgggta    6480
ccatgaaaat aacaggcccg aagacctgct tgaacttatg gcaggggacc ttccccatca    6540
attgttacac agaagggccc tgcgtgccaa agccccctcc taattacaaa actgcaattt    6600
ggagggtggc agcgtcggag tacgttgaga tcacgcagca tggttctttc tcgtacgtaa    6660
cggggttaac cagtgacaac cttaaggtcc cttgccaggt accagcccca gaattttct    6720
catggtgga cggggtgcag atacaccgat tcgcccccac tccaggtccc ttctttcggg    6780
atgaggtaac gttttctgtg ggcctcaatt ccttcgtggt cggctctcag ctcccttgtg    6840
accctgagcc ggacacggag gtgttagcct ccatgttgac agacccgtcc cacattacag    6900
cggaggcggc agctaggcga ttggccaggg gatcccccc ttcacaggcc agctcttcag    6960
cgagccagct ctccgccccg tccttgaagg ctacctgtac cacccataag atggcatatg    7020
actgtgacat ggtggatgct aaccttttca tgggaggtga tgtgacccgg atcgagtcca    7080
actcgaaggt gattgttctc gactcccctcg attccatgac tgaggcagag gacgatcgtg    7140
agccttccat accatcagag tacttgatca ggaggaaaaa gttcccaccg gcactacctc    7200
cctgggctcg tccagactac aaccctcctg tgatcgagac atggaagagg ccgggctatg    7260
aaccacccac tgtcctaggt tgtgcccttc cccccacacc tcaagcgcca gtgccccac    7320
ctcggaggcg ccgcgccaaa gtcctgactc aggacaatgt ggaggggtt ctcaaggaga    7380
tggcggacaa agtgcttagc cctctccaag attacaacga ctccggtcac tccactggag    7440
tgggtaccgg gggagacagc gtccaggagc cctctgacga gactgccgct tcggaagtgg    7500
gatcactgtc ctccatgcct cccccttgagg gagagccggg ggaccctgac ttggagtttg    7560
agccagctag atccgctccc ccttccgagg gagagtgcga ggtcgttgat tcggactcca    7620
agtcgtggtc cacagtctct aatcaagagg attctatcgt ctgctgctct atgtcatact    7680
cctggacagg ggccctcata acaccatgtg ggcccgagga ggagaagttg ccaatcaacc    7740
ctctgagcaa ttcgctcatg cggttccata caaggtgta ctccacaacc tcgaggagtg    7800
ccgctctgag ggcaaagaag gtaactttg acagagtgca gatactggac acatattatg    7860
```

| | |
|---|---|
| attcagtctt gcaggacgtc aagcgggccg cctctaaggt tagtgctagg ctcctctcag | 7920 |
| tagaggaagc ctgcgcgctg accccgcccc actccgccag atcgcgatac ggatttgggg | 7980 |
| caaaagaggt gcgcagcttg tccaggaggg ccgttaacca catccagtcc gtgtgggagg | 8040 |
| acctcctgga agaccaaaat actccaattg agacaaccat catggccaaa aatgaggtgt | 8100 |
| tctgtgtcga tccagccaag ggcgggaaga aggcagctcg cctcattgta tacccgacc | 8160 |
| ttgggggtcag ggtgtgcgaa agatggccc tctatgacat tgcacaaaag cttcccaagg | 8220 |
| caataatggg gccgtcctat gggttccaat actctcctgc agaacgggtc gattttctcc | 8280 |
| tcaaagcttg gggaagtaag aaggacccaa tggggttctc gtatgacacc cgctgctttg | 8340 |
| actcaaccgt cacggagagg gacataagaa cagaagaatc catatatcag gcttgttccc | 8400 |
| tgcctcaaga ggccagaact gtcatacact cgctcactga gactttac gtaggagggc | 8460 |
| ccatgctaaa cagcaaaggt caatcctgcg gttacaggcg ttgtcgcgca agcggcgtgt | 8520 |
| tcactaccag catggggaat accatgacat gctacatcaa gcccttgca gcgtgcaaag | 8580 |
| ctgcagggat cgtggaccct gttatgctgg tgtgtggaga cgacctggtt gtcatctcag | 8640 |
| agagccaagg taacgaggag gacgagcgaa acctgagagc cttcacggag gccatgacca | 8700 |
| ggtattcagc ccctcccggt gaccttccca gaccagaata tgacctagag cttataacat | 8760 |
| cctgctcctc aaacgtgtcg gtagcgctgg accctcgggg tcgccgccgg tactacctaa | 8820 |
| ccagagaccc tatcactcca atctcccgag ccgcttggga aacagtaaga cactcccccg | 8880 |
| tcaattcttg gctgggcaac atcattcaat atgcccctac aatctgggtc cggatggtca | 8940 |
| taatgaccca cttctttgcc atactattgg cccaggacac tctgaaccaa aatctcaact | 9000 |
| ttgagatgta tgggcagta tattcggtca atccattaga cctaccagcc ataattgaga | 9060 |
| ggctacatgg gcttgatgct ttttcactgc acacatactc tcccaccgaa ctcacacggg | 9120 |
| tggcagcagc tctcagaaaa cttggagcgc ctcccctcag agcgtggaag agccgggcac | 9180 |
| gtgctgtgag agcctcactc ctcgcccagg gagggagggc ggccatttgt ggccgctacc | 9240 |
| tcttcaactg ggcggtgaaa acaaagctca aactcactcc attgcccgag gcgagccgcc | 9300 |
| tggatttgtc caggtggttc accgtgggcg ccggcggggg cggcatcttt cacagcgtgt | 9360 |
| cgcatgcccg accccgccta ttactccttt gcctactcct acttagcgta ggggtaggca | 9420 |
| tcttttact ccccgctcgg tagagcggca aaccctagct acactccata gctagtttcc | 9480 |
| gttttttctt tttgtttt tttttttttt tttttttttt tttttttttt tttctttcc | 9540 |
| tttttttttt ttctctttct tggtggctcc atcttagccc tagtcacggc tagctgtgaa | 9600 |
| aggtccgtga gccgcatgac tgcagagagt gccgtaactg gtctctctgc agatcatgt | 9659 |

<210> SEQ ID NO 14
<211> LENGTH: 9659
<212> TYPE: DNA
<213> ORGANISM: Hepatitis C virus

<400> SEQUENCE: 14

| | |
|---|---|
| gcccgccccc tgatggggc gacactccgc catgaatcac tcccctgtga ggaactactg | 60 |
| tcttcacgca gaaagcgtct agccatggcg ttagtatgag tgtcgtacag cctccaggcc | 120 |
| cccccctccc gggagagcca tagtggtctg cggaaccggt gagtacaccg gaattaccgg | 180 |
| aaagactggg tccttcttg gataaaccca ctctatgtcc ggtcatttgg gcacgccccc | 240 |
| gcaagactgc tagccgagta gcgttgggtt gcgaaaggcc ttgtggtact gcctgatagg | 300 |
| gtgcttgcga gtgccccggg aggtctcgta gaccgtgcat catgagcaca aatcctaaac | 360 |

-continued

```
ctcaaagaaa aaccaaaaga aacacaaacc gccgcccaca ggacgttaag ttcccgggtg    420
gcggtcagat cgttggcgga gtttacttgc tgccgcgcag gggccccagg ttgggtgtgc    480
gcgcgacaag gaagacttct gagcgatccc agccgcgtgg acgacgccag cccatcccga    540
aagatcggcg ctccaccggc aagtcctggg gaaagccagg atatccttgg ccctgtacg     600 gaaacgaggg ttgcggctgg gcgggttggc tcctgtcccc ccgcgggtct cgtcctactt    660
ggggccccac cgaccccggg catagatcac gcaatttggg cagagtcatc gataccatta    720
cgtgtggttt tgccgacctc atggggtaca tccctgtcgt tggcgccccg gttggaggcg    780
tcgccagagc tctggcacac ggtgttaggg tcctggagga cgggataaat tacgcaacag    840
ggaatttacc cggttgctct ttttctatct ttttgcttgc tcttctgtca tgcgtcacag    900
tgccagtgtc tgcagtggaa gtcaggaaca ttagttctag ctactacgcc actaatgatt    960
gctcaaacaa cagcatcacc tggcagctca ctgacgcagt tctccatctt cctggatgcg   1020
tcccatgtga gaatgataat ggcaccttgc attgctggat acaagtaaca cccaacgtgg   1080
ctgtgaaaca ccgcggtgcg ctcactcgta gcctgcgaac acacgtcgac atgatcgtaa   1140
tggcagctac ggcctgctcg gccttgtatg tgggagatgt gtgcggggcc gtgatgattc   1200
tatcgcaggc tttcctggta tcaccacaac gccacaactt cacccaagag tgcaactgtt   1260
ccatctacca aggtcacatc accggccatc gcatggcatg ggacatgatg ctgaactggt   1320
ctccaactct tgccatgatc ctcgcctacg ccgctcgtgt tcccgagatg gtcctcgaaa   1380
ttattttcgg cggccattgg ggtgtggtgt ttggcttggc ctacttctcc atgcaaggag   1440
cgtgggccaa agtcattgcc atcctccttc ttgttgcggg agtggatgca accacctatt   1500
ccagcggcca ggaagcgggt cgtaccgtct tggggttcac taacctcttt acttctggtg   1560
ccaagcagaa cctctattta atcaacacca atggcagctg gcacataaac cggactgccc   1620
tcaattgcaa tgacagctta cagacggggtt tcatggcttc cctgttttac acccacaggt   1680
tcaacagctc tggctgcccc gagcgcttgt cttcctgccg cgggctggac gattttcgca   1740
tcggctgggg aaccttggaa tacgaaaccc acgtcaccaa cgatgaggac atgaggccgt   1800
actgctggca ttaccctccg aggccttgcg gcatcgtccc ggctagaacg gtttgcggac   1860
cggtctattg tttcacccct agccctgttg tcgtgggcac cactgacaag cagggcgtac   1920
ccacctacac ctgggggggaa aacgagaccg atgtcttcct gctgaatagc acaagacccc   1980
cgcgaggagc ttggttcggc tgcacttgga tgaacgggac tgggttcact aagacatgcg   2040
gtgcaccacc ttgccgcatt aggaaagact acaacagcac tatcgattta ttgtgccca    2100 cagactgttt taggaagcac cccgatgcta cctatcttaa gtgtggagca gggccttggt   2160
taactcccag gtgcatggta gactaccctt atagactgtg gcattatccg tgcactgtaa   2220
acttcaccat ctttaaggcg cggatgtatg taggaggggt ggagcatcga ttctccgcag   2280
catgcaactt cacgcgcgga gatcgctgca gactggaaga tagggatagg ggtcagcaga   2340
gtccactgct gcattccact actgagtggg cggtgctccc atgctccttc tctgacctac   2400
cagcactatc cactggccta ttgcacctcc accaaaacat cgtggacgtg cagtacccttt   2460 acggactttc tccggctctg acaagataca tcgtgaagtg ggagtggggtg atcctccttt   2520 tcttgttgtt ggcagacgcc aggatctgtg catgcctttg gatgctcatc atactgggcc   2580
aagccgaagc ggcgcttgag aagctcatca tcttgcactc cgctagtgct gctagtgcca   2640
atggtccgct gtggtgtttc atcttctttta cagcggcctg gtacttaaag ggcagggtgg   2700
```

-continued

```
tccccgtggc cacgtactct gttctcggct tatggtcctt cctcctccta gtcctggcct      2760
taccacagca ggcttatgcc ttggacgctg ctgaacaagg ggaactgggg ctggccatat      2820
tagtaattat atccatcttt actcttaccc cagcatacaa gatcctcctg agccgttcag      2880
tgtggtggct gtcctacatg ctggtcttgg ccgaggccca gattcagcaa cgggttcccc      2940
ccctggaggt ccgaggggg cgtgacggaa tcatctgggt ggctgtcatt ctacacccac       3000
gccttgtgtt tgaggtcacg aaatggttgt tagcaatcct ggggcctgcc tacctcctta      3060
aagcgtctct gctacggata ccgtactttg tgagggccca cgctttgcta cgagtgtgta      3120
ccctggtgaa acacctcgcg ggggctaggt acatccagat gctgttgatc accataggca      3180
gatggaccgg cacttacatc tacgaccacc tctcccattt atcaacttgg gcggcccagg      3240
gtttgcggga cctggcaatc gccgtggagc ctgtggtgtt cagcccaatg agaagaagg       3300 tcattgtgtg gggggctgag acagtggcgt gtggagacat cctgcatggc ctcccggtct      3360
ccgcgaggct aggtagggag gttctgctcg gccctgccga cggctacacc tccaaggggt      3420
ggaagctcct agctcccatt actgcttaca ctcagcaaac tcgtggtctc ctgggtgcta      3480
tcgtggtcag cctaacgggc cgcgacaaaa atgagcaggc tgggcaggtc caggttctgt      3540
cctccgtcac acaaactttc ttggggacat ccatttcggg cgtcctctgg acagtatatc      3600
acggggctgg taataagacc ttggccggcc ccaagggacc agtcactcag atgtacacca      3660
gcgcagaagg ggacctcgtg ggatggccta gtccccccgg gactaagtca ttggaccct       3720 gtacctgcgg ggccgtagac ctctacctgg tcacccgaaa cgctgatgtc attccggtcc      3780
ggaggaaaga tgaccgacgg gctgcattac tctcgccaag gccctctca accctcaaag       3840 gatcatccgg agggcccgtg ctctgctcaa ggggacacgc cgtgggcttg ttcagagcgg      3900
ccgtgtgtgc caggggtgta gccaaatcta ttgacttcat ccccgtcgaa tcactcgatg      3960
tcaccacacg gacgcccagt ttctctgact acagtacgcc gccagctgtg cccagtctt      4020 accaggtggg ttacttgcac gcaccaacag gcagcgaaa gagcaccaag gtccctgccg      4080
cgtatgccag tcaggggtat aaagtactcg tactaaatcc ctctgtcgcg ccacacttg       4140 gttttgggc ctacatgtcc aaagcccacg ggatcaaccc taatatcaga actggagtgc       4200
ggaccgttac caccggggac tctatcactt actccactta tggcaagttt atcgcagatg      4260
gaggctgtgc agccggtgcc tatgacatca tcatatgcga cgaatgccat tcagtggacg      4320
ctactaccat ccttggcatt ggaacagtcc ttgaccaagc tgagaccgca ggcgtcaggc      4380
tagtggtttt ggccacagcc acgcctcccg gtacggtgac aactcccccac agtaacatag      4440 aggaggtggc ccttggtcac gagggcgaga tcccttttta tggcaaagcc attcccctag      4500
ctttcatcaa gggggcaga cacttgatct tttgccattc aaagaagaag tgcgacgagc      4560
tcgcagcggc cctccggggc atgggtgtca atgccgttgc atactatagg ggtctcgacg      4620
tctccgttat accaactcaa ggagacgtgg tggttgtcgc cactgatgcc ctaatgactg      4680
ggtacaccgg cgactttgac tctgtcatcg actgtaatgt tgcagtctct cagattgttg      4740
acctcagcct agaccaacc ttcaccatca ccactcaaat cgtccctcag gacgctgtct       4800
cccgtagtca acgtagaggg agaactggga ggggcgatt gggcgtttac aggtatgttt      4860
cgtcaggcga aaggccgtct gggatgttcg acagcgtagt gctctgcgag tgctatgatg      4920
ccggggcagc ctggtacgag cttacacctg ctgagactac ggtgagactc cgggcttatt      4980
tcaacacgcc cggtttgccc gtatgtcaag accacctgga gttctgggaa gcggtctta       5040 caggtctcac acacattgac gcccacttcc tctcccagac gaagcaagga ggagaaaact      5100
```

```
ttgcgtatct aacggcctac caggccacag tatgcgccag ggcaaaggcc cctcctcctt    5160
cgtgggacgt gatgtggaag tgtctaacta ggctcaaacc tacactgact ggtcccaccc    5220
ccctcctgta ccgcttgggt gccgtgacca atgaggtcac cttgacgcac cccgtgacga    5280
aatacatcgc cacgtgcatg caagctgacc tcgagatcat gacgagctca tgggtcctgg    5340
cgggggggt gctagccgcc gtggcatctt actgcctggc gactggctgc atttccatca    5400
ttggccgcct acacctgaat gatcgggtgg ttgtggcccc cgacaaggaa atcttatatg    5460
aggcctttga tgagatggaa gaatgcgcct ccaaagccgc cctcattgag aagggcagc    5520
ggatggcgga gatgctcaaa tctaagatac aaggcctcct acaacaggcc acaaggcaag    5580
ctcaagacat acagccagct atacagtcat catggcccaa gcttgaacga ttttgggcca    5640
aacacatgtg gaacttcatc agtggtatac agtacctagc aggactctcc accctaccgg    5700
gaaatcctgc agtagcatca atgatggctt ttagcgccgc gctgactagc ccactaccca    5760
ccagcaccac catcctcttg aacatcatgg aggatggtt ggcctctcag attgcccccc    5820
ctgccggagc cactggcttc gttgtcagtg gtctagtggg ggcggccgtc ggaagcatag    5880
gcctgggtaa gatactggtg gacgttttgg ccgggtacgg cgcaggcatt tcaggggccc    5940
tcgtagcttt taagatcatg agcggcgaga agcccacggt agaagacgtt gtgaatctcc    6000
tgcctgctat tctgtctcct ggtgcgttgg tagtgggagt catctgtgca gcaatcctgc    6060
gccgccacgt cggtcaggga gaggggcgg tccagtggat gaacagactg atcgccttcg    6120
cctccagggg aaaccacgtt gcccctaccc actacgtggt ggagtctgac gcttcacagc    6180
gtgtaacgca ggtgctgagt tcacttacaa ttaccagctt acttaggaga ctacatgcct    6240
gggtcactga agattgccca gtcccatgct cggggtcttg gctccaggac atttgggatt    6300
gggtttgttc catcctcaca gacttcaaaa actggctgtc ttcaaaatta ctccccaaga    6360
tgcccggcat tccctttatc tcttgccaga agggatacaa gggtgtatgg gctggtacgg    6420
gtgtcatgac tactcggtgc ccatgtggag caaacatctc gggccatgtc cgcatgggca    6480
ccatgaaaat aacaggcccg aagacttgct tgaacctgtg gcaggggact ttccccatta    6540
attgttacac agaagggcct tgcgtgccaa accccctcc taattacaag accgcaattt    6600
ggagggtggc agcgtcggag tacgttgagg tcacacagca tggctctttc tcgtatgtaa    6660
cagggttaac cagtgacaac cttaaggtcc cttgccaggt accagctcca gaattttct    6720
cttgggtgga cggggtgcaa atccaccgat tcgcccccgt tccaggtccc ttctttcggg    6780
atgaggtaac gttcaccgta ggccttaact ccttcgtggt cggctctcag ctcccttgcg    6840
atcctgagcc ggacaccgag gtactggcct ccatgttgac agacccgtcc cacatcaccg    6900
cggaggcgg agccaggcga ttggcaaggg gatctccccc ttcacaggct agctcctcag    6960
cgagccagct ctctgccccg tccttgaagg ctacctgtac cacccataag acagcatatg    7020
attgtgacat ggtggatgcc aacctttca tgggaggcga tgtgacccgg attgagtctg    7080
actctaaggt gatcgttctc gactccctcg attccatgac tgaggtagtg gatgatcgtg    7140
agccttctgt accatcagag tacctgatca agaggagaaa gttccaccg gcgctgcctc    7200
cttgggcccg tccagactac aatcctgttt tgatcgagac atggaagagg ccgggctatg    7260
aaccacccac tgtcctaggc tgtgccctcc cccacacacc tcaaacgcca gtgcctccac    7320
ctcggaggcg ccgcgccaaa gtcctgaccc aggacaatgt ggagggatc ctcagggaga    7380
tggctgacaa agtactcagc cctctccaag acaacaatga ctccggtcac tccactggag    7440
```

```
cggataccgg aggagacatc gtccagcaac cctctgacga gactgccgct tcagaagcgg      7500
ggtcactgtc ctccatgcct cccettgagg gagagccggg agaccctgac ctggagtttg      7560
aaccagtggg atccgctccc ccttctgagg gggagtgtga ggtcattgat tcggactcta      7620
agtcgtggtc cacagtctct gatcaagagg attctgttac ctgctgctct atgtcatact      7680
cctggacggg ggccctcata acaccatgtg ggcccgaaga ggagaagtta ccgatcaacc      7740
ctctgagtaa ttcgctcatg cggttccata ataaggtgta ctccacaacc tcgaggagtg      7800
cctctctgag ggcaaagaag gtgacttttg acagggtgca ggtgctggac gcacactatg      7860
actcagtctt gcaggacgtt aagcgggccg cctctaaggt tagtgcgagg ctcctcacgg      7920
tagaggaagc ctgcgcgctg accccgcccc actccgccaa atcgcgatac ggatttgggg      7980
caaaagaggt gcgcagctta tccaggaggg ccgttaacca catccggtcc gtgtgggagg      8040
acctcctgga agaccaacat accccaattg acacaactat catggctaaa aatgaggtgt      8100
tctgcattga tccaactaaa ggtgggaaaa agccagctcg cctcatcgta taccccgacc      8160
ttggggtcag ggtgtgcgaa aagatggccc tctatgacat cgcacaaaag cttcccaaag      8220
cgataatggg gccatcctat gggttccaat actctcccgc agaacgggtc gatttcctcc      8280
tcaaagcttg gggaagtaag aaggacccaa tggggttctc gtatgacacc cgctgctttg      8340
actcaaccgt cacggagagg gacataagaa cagaagaatc catatatcag gcttgttctc      8400
tgcctcaaga agccagaact gtcatacact cgctcactga gagactttac gtaggagggc      8460
ccatgacaaa cagcaagggg caatcctgcg gctacaggcg ttgccgcgca agcggtgttt      8520
tcaccaccag catggggaat accatgacat gttacatcaa agcccttgca gcgtgtaagg      8580
ctgcagggat cgtggaccct gttatgttgg tgtgtggaga cgacctggtc gtcatctcag      8640
agagccaagg taacgaggag gacgagcgaa acctgagagc tttcacggag gctatgacca      8700
ggtattccgc ccctcccggt gaccttccca ccggaata tgacttggag cttataacat      8760
cctgctcctc aaacgtatcg gtagcgctgg actctcgggg tcgccgccgg tacttcctaa      8820
ccagagaccc taccactcca atcacccgag ctgcttggga aacagtaaga cactcccctg      8880
tcaattcttg gctgggcaac atcatccagt acgcccccac aatctgggtc cggatggtca      8940
taatgactca cttcttctcc atactattgg cccaggacac tctgaaccaa aatctcaatt      9000
ttgagatgta cggggcagta tactcggtca atccattaga cctaccggcc ataattgaaa      9060
ggctacatgg gcttgaagcc ttttcactgc acacatactc tccccgcgaa ctctcacggg      9120
tggcagcaac tctcagaaaa cttggagcgc ctccccttag agcgtggaag agtcgggcgc      9180
gtgccgtgag agcttcactc atcgcccaag gagcgagggc ggccatttgt ggccgctacc      9240
tcttcaactg ggcggtgaaa acaaagctca aactcactcc attgcccgag gcgagccgcc      9300
tggatttatc cggtggttc accgtgggcg ccggcggggg cggcatttat acacagcgtgt      9360 cgcatgcccg accccgccta ttactccttt gcctactcct acttagcgta ggagtaggca      9420 tcttttact ccccgctcgg tagagcggca aaccctagct acactccata gctagtttcc      9480 gtttttttt tttgttttt ttttttttt ttttttttt ttttttttt tttcttttcc      9540 ttttttttt ttctctttct tggtggctcc atcttagccc tagtcacggc tagctgtgaa      9600
aggtccgtga gccgcatgac tgcagagagt gccgtaactg gtctctctgc agatcatgt      9659

<210> SEQ ID NO 15
<211> LENGTH: 9659
<212> TYPE: DNA
<213> ORGANISM: Hepatitis C virus
```

<400> SEQUENCE: 15

```
gcccgccccc tgatgggggc gacactccgc catgaatcac tccctgtga ggaactactg      60
tcttcacgca gaaagcgtct agccatggcg ttagtatgag tgtcgtacag cctccaggcc    120
ccccctccc gggagagcca tagtggtctg cggaaccggt gagtacaccg gaattaccgg    180
aaagactggg tcctttcttg gataaaccca ctctatgtcc ggtcatttgg gcacgccccc    240
gcaagactgc tagccgagta gcgttgggtt gcgaaaggcc ttgtggtact gcctgatagg    300
gtgcttgcga gtgccccggg aggtctcgta accgtgcat catgagcaca aatcctaaac    360
ctcaaagaaa aaccaaaaga aacacaaacc gccgcccaca ggacgttaag ttcccgggtg    420
gcggtcagat cgttggcgga gtttacttgc tgccgcgcag gggccccagg ttgggtgtgc    480
gcgcgacaag gaagacttct gagcgatccc agccgcgtgg acgacgccag cccatcccga    540
aagatcggcg ctccaccggc aagtcctggg gaaagccagg atatccttgg ccctgtacg    600
gaaacgaggt ttgcggctgg gcgggttggc tcctgtcccc ccgcgggtct cgtcctactt    660
ggggccccac cgacccccgg catagatcac gcaatttggg cagagtcatc gataccatta    720
cgtgtggttt tgccgacctc atggggtaca tccctgtcgt tggcgccccg gttggaggcg    780
tcgccagagc tctggcacac ggtgttaggg tcctggagga cgggataaat tacgcaacag    840
ggaatttacc cggttgctct ttttctatct ttttgcttgc tcttctgtca tgcgtcacag    900
tgccagtgtc tgcagtggaa gtcaggaaca ttagttctag ctactacgcc actaatgatt    960
gctcaaacaa cagcatcacc tggcagctca ctgacgcagt tctccatctt cctggatgcg   1020
tcccatgtga gaatgataat ggcaccttgc attgctggat acaagtaaca cccaacgtgg   1080
ctgtgaaaca ccgcggtgcg ctcactcgta gcctgcgaac acacgtcgac atgatcgtaa   1140
tggcagctac ggcctgctcg gccttgtatg tgggagatgt gtgcggggcc gtgatgattc   1200
tatcgcaggc tttcatggta tcaccacaac gccacaactt cacccaagag tgcaactgtt   1260
ccatctacca aggtcacatc accggccatc gcatggcatg ggacatgatg ctgaactggt   1320
ctccaactct tgccatgatc ctcgcctacg ccgctcgtgt tcccgagatg gtcctcgaaa   1380
ttattttcgg cggccattgg ggtgtggtgt ttggcttggc ctacttctcc atgcaaggag   1440
cgtgggccaa agtcattgcc atcctccttc ttgttgcggg agtggatgca accacctatt   1500
ccagcggcca ggaagcgggt cgtaccgtct gggggttcac taacctcttt acttctggtg   1560
ccaagcagaa cctctattta atcaacacca atggcagctg gcacataaac cggactgccc   1620
tcaattgcaa tgacagctta cagacgggtt tcatggcttc cctgttttac acccacaggt   1680
tcaacagctc tggctgcccc gagcgcttgt cttcctgccg cgggctggac gattttcgca   1740
tcggctgggg aaccttggaa tacgaaaccc acgtcaccaa cgatgaggac atgaggccgt   1800
actgctggca ttaccctccg aggccttgcg gcatcgtccc ggctagaacg gtttgcggac   1860
cggtctattg tttcaccct agccctgttg tcgtgggcac cactgacaag cagggcgtac   1920
ccacctacac ctgggggaa aacgagaccg atgtcttcct gctgaatagc acaagacccc   1980
cgcgaggagc ttggttcggc tgcacttgga tgaacgggac tgggttcact aagacatgcg   2040
gtgcaccacc ttgccgcatt aggaaagact acaacagcac tatcgattta ttgtgcccca   2100
cagactgttt taggaagcac cccgatgcta cctatcttaa gtgtggagca gggccttgt   2160
taactcccag gtgcctggta gactacccct atagactgtg gcattatccg tgcactgtaa   2220
acttcaccat ctttaaggcg cggatgtatg taggaggggt ggagcatcga ttctccgcag   2280
```

-continued

```
catgcaactt cacgcgcgga gatcgctgca gactggaaga tagggatagg ggtcagcaga    2340
gtccactgct gcattccact actgagtggg cggtgctccc atgctccttc tctgacctac    2400
cagcactatc cactggccta ttgcacctcc accaaaacat cgtggacgtg cagtaccttt    2460
acggactttc tccggctctg acaagataca tcgtgaagtg ggagtgggtg atcctccttt    2520
tcttgttgtt ggcagacgcc aggatctgtg catgcctttg gatgctcatc atactgggcc    2580
aagccgaagc ggcgcttgag aagctcatca tctcgcactc cgctagtgct gctagtgcca    2640
atggtccgct gtggttttc atcttcttta cagcggcctg gtacttaaag gcagggtgg     2700 tccccgtggc cacgtactct gttctcggct tatggtcctt cctcctccta gtcctggcct    2760
taccacagca ggcttatgcc ttggacgctg ctgaacaagg ggaactgggg ctggccatat    2820
tagtaattat atccatcttt actcttaccc cagcatacaa gatcctcctg agccgttcag    2880
tgtggtggct gtcctacatg ctggtcttgg ccgaggccca gattcagcaa tgggttcccc    2940
ccctggaggt ccgaggggg cgtgacggaa tcatctgggt ggctgtcatt ctacacccac     3000
gccttgtgtt tgaggtcacg aaatggttgt tagcaatcct ggggcctgcc tacctcctta    3060
aagcgtctct gctacggata ccgtactttg tgagggccca cgctttgcta cgagtgtgta    3120
ccctggtgaa acacctcgcg ggggctaggt acatccagat gctgttgatc accataggca    3180
gatggaccgg cacttacatc tacgaccacc tctcccettt atcaacttgg gcggcccagg    3240
gtttgcggga cctggcaatc gccgtggagc ctgtggtgtt cagcccaatg gagaagaagg    3300
tcattgtgtg gggggctgag acagtggcgt gtggagacat cctgcatggc ctccggtct    3360 ccgcgaggct aggtagggag gttctgctcg gccctgccga cggctacacc tccaaggggt    3420
ggaagctcct agctcccatt actgcttaca ctcagcaaac tcgtggtctc ctgggtgcta    3480
tcgtggtcag cctaacgggc cgcgacaaaa atgagcaggc tgggcaggtc caggttctgt    3540
cctccgtcac acaaactttc ttggggacat ccatttcggg cgtcctctgg acagtatatc    3600
acggggctgt taataagacc ttggccggcc ccaagggacc agtcactcag atgtacacca    3660
gcgcagaagg ggacctcgtg ggatggccta gtcccccegg gactaagtca ttggaccct     3720 gtacctgcgg ggccgtagac ctctacctgg tcacccgaaa cgctgatgtc attccggtcc    3780
ggaggaaaga tgaccgacgg ggtgcattac tctcgccaag gcccctctca accctcaaag    3840
gatcatccgg agggcccgtg ctctgctcaa ggggacacgc cgtgggcttg ttcagagcgg    3900
ccgtgtgtgc caggggtgta gccaaatcta ttgacttcat ccccgtcgaa tcactcgatg    3960
tcgccacacg gacgcccagt ttctctgaca acagtacgcc gccagctgtg ccccagtctt    4020
accaggtggg ttacttgcac gcaccaacag gcagcggaaa gagcaccaag gtccctgccg    4080
cgtatgccag tcaggggtat aaagtactcg tactaaatcc ctctgtcgcg ccacacttg     4140 gttttggggc ctacatgtcc aaagcccacg ggatcaaccc taatatcaga actggagtgc    4200
ggaccgttac caccgggggac tctatcactt actccactta tggcaagttt atcgcagatg    4260
gaggctgtgc agccggtgcc tatgacatca tcatatgcga cgaatgccat tcagtggacg    4320
ctactaccat ccttggcatt ggaacagtcc ttgaccaagc tgagaccgca ggcgtcaggc    4380
tagtggtttt ggccacagcc acgcctcccg gtacggtgac aactccccac agtaacatag    4440
aggaggtggc ccttggtcac gagggcgaga tcccttttta tggcaaagcc attcccctag    4500
ctttcatcaa gggggggcaga cacttgatct tttgccattc aaagaagaag tgcgacgagc    4560
tcgcagcggc cctccggggc atgggtgtca atgccgttgc atactatagg ggtctcgacg    4620
tctccgttat accaactcaa ggagacgtgg tggttgtcgc cactgatgcc ctaatgactg    4680
```

```
ggtacaccgg cgactttgac tctgtcatcg actgtaatgt tgcagtctct cagattgttg    4740
acctcagcct agacccaacc ttcaccatca ccactcaaat cgtccctcag gacgctgtct    4800
cccgtagtca acgtagaggg agaactggga gggggcgatt gggcgtttac aggtatgttt    4860
cgtcaggcga aaggccgtct gggatgttcg acagcgtagt gctctgcgag tgctatgatg    4920
ccggggcagc ctggtacgag cttacacctg ctgagactac ggtgagactc cgggcttatt    4980
tcaacacgcc cggtttgccc gtatgtcaag accacctgga gttctgggaa gcggtcttta    5040
caggtctcac acacattgac gcccacttcc tctcccagac gaagcaagga ggagaaaact    5100
ttgcgtatct aacggcctac caggccacag tatgcgccag gcaaaggcc cctcctcctt     5160 cgtgggacgt gatgtggaag tgtctaacta ggctcaaacc tacactgact ggtcccaccc    5220
ccctcctgta ccgcttgggt gccgtgacca atgaggtcac cttgacgcac cccgtgacga    5280
aatacatcgc cacgtgcatg caagctgacc tcgagatcat gacaagctca tgggtcctgg    5340
cggggggggt gctagccgcc gtggcatctt actgcctggc gactggctgc atttccatca    5400
ttggccgcct acacctgaat gatcgggtgg ttgtggcccc cgacaaggaa atcttatatg    5460
aggcctttga tgagatggaa gaatgcgcct ccaaagccgc cctcattgag gaagggcagc    5520
ggatggcgga gatgctcaaa tctaagatac aaggcctcct acaacaggcc acaaggcaag    5580
ctcaagacat acagccagct atacagtcat catgggccca gcttgaacaa ttttgggcca    5640
aacacatgtg gaacttcatc agtggtatac agtacctagc aggactctcc accctaccgg    5700
gaaatcctac agtagcatca atgatggctt ttagcgccgc gctgactagc ccactaccca    5760
ccagcaccac catcctcttg aacatcatgg gaggatggtt ggcctctcag attgccccc     5820 ctgccggagc cactggcttc gttgtcagtg gtctagtggg ggcggccgtc ggaagcatag    5880
gcctgggtaa gatactggtg gacgttttgg ccgggtacgg cgcaggcatt tcaggggccc    5940
tcgtagcttt taagatcatg agcggcgaga agcccacggt agaagacgtt gtgaatctcc    6000
tgcctgctat tctgtctcct ggtgcgttgg tagtgggagt catctgtgca gcaatcctgc    6060
gccgccacgt cggtcaggga gaggggcgg tccagtggat gaacagactg atcgccttcg     6120
cctccagggg aaaccacgtt gcccctaccc actacgtggt ggagtctgac gcttcacagc    6180
gtgtaacgca ggcgctgagt tcacttacaa ttaccagctt acttaggaga ctacatgcct    6240
ggatcactga agattgccca gtcccatgct cggggtcttg gctccaggac atttgggatt    6300
gggtttgttc catcctcaca gacttcaaaa actggctgtc ttcaaaatta ctccccaaga    6360
tgcccggcat tccctttatc tcttgccaga agggatacaa gggtgtatgg gctggtacgg    6420
gtgtcatgac tactcggtgc ccatgtggag caaacatctc gggccatgtc cgcatgggca    6480
ccatgaaaat aacaggcccg aagacttgct tgaacctgtg gcaggggact ttccccatta    6540
attgttacac agaagggcct tgcgtgccaa accccctcc taattacaag accgcaattt     6600
ggagggtggc agcgtcggag tacgttgagg tcacacagca tggctctttc tcgtatgtaa    6660
cagggttaac cagtgacaac cttaaggtcc cttgccaggt accagctcca gaattttttct    6720 cttgggtgga cggggtgcaa atccaccgat tcgcccccgt tccaggtccc ttctttcggg    6780
atgaggtaac gttcaccgta ggccttaact ccttcgtggt cggctctcag ctcccttgcg    6840
atcctgagcc ggacaccgag gtactggcct ccatgttgac agacccgtcc cacatcaccg    6900
cggaggcgga agcaggcgga ttggcaaggg gatctccccc ttcacaggct agctcctcag    6960
cgagccagct ctctgccccg tccttgaagg ctacctgtac cacccataag acagcatatg    7020
```

-continued

```
attgtgacat ggtggatgcc aacctttca tgggaggcga tgtgacccgg attgagtctg    7080
actctaaggt gatcgttctc gactccctcg attccatgac tgaggtagag gatgatcgtg    7140
agccttctgt accatcagag tacctgatca agaggagaaa gttcccaccg gcgctgcctc    7200
cttgggcccg tccagactac aatcctgttt tgatcgagac atggaagagg ccgggctatg    7260
aaccacccac tgtcctaggc tgtgccctcc ccccacacc tcaaacgcca gtgcctccac    7320
ctcggaggcg ccgcgccaaa gtcctgaccc aggacaatgt ggaggggatc ctcagggaga    7380
tggctgacaa agtactcagc cctctccaag acaacaatga ctccggtcac tccactggag    7440
cggataccgg aggagacatc gtccagcaac cctctgacga gactgccgct tcagaagcgg    7500
ggtcactgtc ctccatgcct cccttgagg gagagccggg agaccctgac ctggagtttg    7560
aaccagtggg atccgctccc ccttctgagg gggagtgtga ggtcattgat tcggactcta    7620
agtcgtggtc cacagtctct gatcaagagg attctgttac ctgctgctct atgtcatact    7680
cctggacggg ggccctcata acaccatgtg ggcccgaaga ggagaagtta ccgatcaacc    7740
ctctgagtaa ttcgctcatg cggttccata ataaggtgta ctccacaacc tcgaggagtg    7800
cctctctgag ggcaaagaag gtgacttttg acagggtgca ggtgctggac gcacactatg    7860
actcagtctt gcaggacgtt aagcgggccg cctctaaggt tagtgcgagg ctcctcacgg    7920
tagaggaagc ctgcgcgctg accccgcccc actccgccaa atcgcgatac ggatttgggg    7980
caaaagaggt gcgcagctta tccaggaggg ccgttaacca catccggtcc gtgtgggagg    8040
acctcctgga agaccaacat accccaattg acacaactat catggctaaa aatgaggtgt    8100
tctgcattga tccaactaaa ggtgggaaaa agccagctcg cctcatcgta taccccgacc    8160
ttggggtcag ggtgtgcgaa agatggccc tctatgacat cgcacaaaag cttcccaaag    8220
cgataatggg gccatcctat gggttccaat actctcccgc agaacgggtc gatttcctcc    8280
tcaaagcttg gggaagtaag aaggacccaa tggggttctc gtatgacacc cgctgctttg    8340
actcaaccgt cacggagagg gacataagaa cagaagaatc catatatcag gcttgttctc    8400
tgcctcaaga agccagaact gtcatacact cgctcactga gagactttac gtaggagggc    8460
ccatgacaaa cagcaaaggg caatcctgcg gctacaggcg ttccgcgca agcggtgttt    8520 tcaccaccag catggggaat accatgacat gttacatcaa agcccttgca gcgtgtaagg    8580
ctgcagggat cgtggaccct gttatgttgg tgtgtggaga cgacctggtc gtcatctcag    8640
agagccaagg taacgaggag acgagcgaaa acctgagagc tttcacggag gctatgacca    8700
ggtattccgc ccctccggt gaccttccca gaccggaata tgacttggag cttataacat    8760
cctgctcctc aaacgtatcg gtagcgctgg actctcgggg tcgccgccgg tacttcctaa    8820
ccagagaccc taccactcca atcacccgag ctgcttggga aacagtaaga cactcccctg    8880
tcaattcttg gctgggcaac atcatccagt acgcccccac aatctgggtc cggatggtca    8940
taatgactca cttcttctcc atactattgg cccaggacac tctgaaccaa aatctcaatt    9000
ttgagatgta cggggcagta tactcggtca atcattaga cctaccggcc ataattgaaa    9060
ggctacatgg gcttgaagcc ttttcactgc acacatactc tcccacgaa ctctcacggg    9120 tggcagcaac tctcagaaaa cttggagcgc ctccccttag agcgtggaag agtcgggcgc    9180
gtgccgtgag agcttcactc atcgcccaag gagcgagggc ggccatttgt ggccgctacc    9240
tcttcaactg ggcggtgaaa acaaagctca aactcactcc attgcccgag gcgagccgcc    9300
tggatttatc cggtggttc accgtgggcg ccggcgggg cggcatttat cacagcgtgt    9360
cgcatgcccg accccgccta ttactccttt gcctactcct acttagcgta ggagtaggca    9420
```

| | | | | |
|---|---|---|---|---|
| tcttttact | ccccgctcgg | tagagcggca | aaccctagct | acactccata gctagtttcc | 9480 |
| gtttttttt | tttgtttt | ttttttttt | ttttttttt | ttttttttt tttcttttcc | 9540 |
| ttttttttt | ttctctttct | tggtggctcc | atcttagccc | tagtcacggc tagctgtgaa | 9600 |
| aggtccgtga | gccgcatgac | tgcagagagt | gccgtaactg | gtctctctgc agatcatgt | 9659 |

<210> SEQ ID NO 16
<211> LENGTH: 3033
<212> TYPE: PRT
<213> ORGANISM: Hepatitis C virus

<400> SEQUENCE: 16

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Glu Val Arg Asn Ile Ser Ser Gly Tyr Tyr Ala Thr Asn Asp Cys Ser
        195                 200                 205

Asn Asn Ser Ile Thr Trp Gln Leu Thr Asn Ala Val Leu His Leu Pro
    210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Val Met Ala Ala Thr Ile Cys
            260                 265                 270

Ser Ala Leu Tyr Val Gly Asp Val Cys Gly Ala Val Met Ile Val Ser
        275                 280                 285

Gln Ala Phe Ile Leu Ser Pro Glu Arg His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Val Leu Ala Tyr
                325                 330                 335
```

```
Ala Ala Arg Val Pro Glu Leu Val Leu Glu Val Val Phe Gly Gly His
            340                 345                 350

Trp Gly Val Val Phe Gly Leu Ala Tyr Phe Ser Met Gln Gly Ala Trp
            355                 360                 365

Ala Lys Val Met Ala Ile Leu Leu Leu Val Ala Gly Val Asp Ala His
            370                 375                 380

Thr Tyr Ser Thr Gly Ala Arg Ala Gly Gln Ala Ala Ser Gly Leu Thr
385                 390                 395                 400

Ser Leu Phe Ser Val Gly Ser Arg Gln Arg Leu Ser Leu Ile His Thr
            405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Leu Tyr Val Asn Asn Phe Asn
            435                 440                 445

Ser Ser Gly Cys Pro Glu Arg Met Ser Ser Cys Arg Ala Leu Asp Asp
            450                 455                 460

Phe Arg Ile Gly Trp Gly Thr Leu Glu Tyr Glu Thr Asn Val Thr Asn
465                 470                 475                 480

Asp Glu Asp Met Arg Pro Tyr Cys Trp His Tyr Pro Pro Lys Pro Cys
            485                 490                 495

Gly Ile Val Pro Ala Gly Thr Val Cys Gly Pro Val Tyr Cys Phe Thr
            500                 505                 510

Pro Ser Pro Val Val Gly Thr Thr Asp Lys Gln Gly Val Pro Thr
            515                 520                 525

Tyr Asn Trp Gly Glu Asn Glu Thr Asp Val Phe Leu Leu Asn Ser Thr
            530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
            565                 570                 575

Tyr Asn Gly Thr Leu Asp Leu Leu Cys Pro Thr Asp Cys Phe Arg Lys
            580                 585                 590

His Pro Glu Thr Thr Tyr Leu Arg Cys Gly Ser Gly Pro Trp Leu Thr
            595                 600                 605

Pro Arg Cys Leu Val Asp Tyr Pro Tyr Arg Leu Trp His Tyr Pro Cys
610                 615                 620

Thr Val Asn Phe Thr Ile Phe Lys Val Arg Met Tyr Val Gly Gly Val
625                 630                 635                 640

Glu His Arg Leu Ser Ala Ala Cys Asn Phe Thr Arg Gly Asp Arg Cys
            645                 650                 655

Asn Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
            690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
            725                 730                 735

Ala Cys Leu Trp Met Leu Ile Ile Leu Gly Gln Ala Glu Ala Ala Leu
            740                 745                 750
```

-continued

```
Glu Lys Leu Ile Ile Leu His Ser Ala Ser Ala Ala Ser Ala Asn Gly
        755                 760                 765
Pro Leu Trp Phe Phe Ile Phe Phe Ile Ala Ala Trp Tyr Leu Lys Gly
    770                 775                 780
Arg Val Val Pro Met Ala Thr Tyr Ser Val Leu Gly Leu Trp Ser Phe
785                 790                 795                 800
Phe Leu Leu Val Leu Ala Leu Pro Gln Gln Ala Tyr Ala Leu Asp Ala
                805                 810                 815
Val Glu Gln Gly Glu Leu Gly Leu Val Leu Leu Gly Val Ile Ser Ile
            820                 825                 830
Phe Thr Leu Thr Pro Ala Tyr Lys Thr Leu Leu Ser Arg Ser Val Trp
        835                 840                 845
Trp Leu Ser Tyr Met Leu Val Leu Ala Glu Ala Gln Ile Gln Gln Trp
    850                 855                 860
Val Pro Pro Leu Glu Ala Arg Gly Gly Arg Asp Gly Ile Ile Trp Val
865                 870                 875                 880
Ala Val Ile Leu Arg Pro Cys Leu Val Phe Glu Ile Thr Lys Trp Leu
                885                 890                 895
Leu Ala Val Leu Gly Pro Ala Tyr Leu Leu Arg Ala Ser Leu Leu Arg
            900                 905                 910
Val Pro Tyr Phe Val Arg Ala His Ala Leu Leu Arg Leu Cys Ala Leu
        915                 920                 925
Val Arg His Leu Ala Gly Ala Arg Tyr Ile Gln Met Leu Leu Ile Thr
    930                 935                 940
Ile Gly Arg Trp Thr Gly Thr Tyr Ile Tyr Asp His Leu Ser Pro Leu
945                 950                 955                 960
Ser Thr Trp Ala Ala Gln Gly Leu Arg Asp Leu Ala Val Ala Val Glu
                965                 970                 975
Pro Val Val Phe Ser Pro Met Glu Lys Lys Val Ile Val Trp Gly Ala
            980                 985                 990
Glu Thr Val Ala Cys Gly Asp Ile Leu His Gly Leu Pro Val Ser Ala
        995                 1000                1005
Arg Leu Gly Arg Glu Ile Leu Leu Gly Pro Ala Asp Gly Tyr Thr
    1010                1015                1020
Ser Lys Gly Trp Lys Leu Leu Ala Pro Ile Thr Ala Tyr Thr Gln
    1025                1030                1035
Gln Thr Arg Gly Leu Leu Gly Ala Ile Val Val Ser Leu Thr Gly
    1040                1045                1050
Arg Asp Lys Asn Glu Gln Ala Gly Gln Val Gln Val Leu Ser Ser
    1055                1060                1065
Val Thr Gln Ser Phe Leu Gly Thr Ser Ile Ser Gly Val Leu Trp
    1070                1075                1080
Thr Val Tyr His Gly Ala Gly Asn Lys Thr Leu Ala Gly Pro Arg
    1085                1090                1095
Gly Pro Val Thr Gln Met Tyr Ser Ser Ala Glu Gly Asp Leu Val
    1100                1105                1110
Gly Trp Pro Ser Pro Pro Gly Thr Lys Ser Leu Asp Pro Cys Thr
    1115                1120                1125
Cys Gly Ala Val Asp Leu Tyr Leu Val Thr Arg Asn Ala Asp Val
    1130                1135                1140
Ile Pro Val Arg Arg Arg Asp Asp Arg Arg Gly Ala Leu Leu Ser
    1145                1150                1155
Pro Arg Pro Leu Ser Thr Leu Lys Gly Ser Ser Gly Gly Pro Val
```

```
            1160                1165                1170

Leu Cys Ser Arg Gly His Ala Val Gly Leu Phe Arg Ala Ala Val
    1175                1180                1185

Cys Thr Arg Gly Val Ala Lys Ser Ile Asp Phe Ile Pro Val Glu
    1190                1195                1200

Ser Leu Asp Val Ala Ala Arg Ser Pro Ser Phe Ser Asp Asn Ser
    1205                1210                1215

Thr Pro Pro Ala Val Pro Gln Ser Tyr Gln Val Gly Tyr Leu His
    1220                1225                1230

Ala Pro Thr Gly Ser Gly Lys Ser Thr Lys Val Pro Ala Ala Tyr
    1235                1240                1245

Ala Ser Gln Gly Tyr Lys Val Leu Val Leu Asn Pro Ser Val Ala
    1250                1255                1260

Ala Thr Leu Gly Phe Gly Ala Tyr Met Ser Lys Ala His Gly Ile
    1265                1270                1275

Asn Pro Asn Ile Arg Thr Gly Val Arg Thr Val Thr Thr Gly Asp
    1280                1285                1290

Pro Ile Thr Tyr Ser Thr Tyr Gly Lys Phe Leu Ala Asp Gly Gly
    1295                1300                1305

Cys Ser Ala Gly Ala Tyr Asp Ile Ile Ile Cys Asp Glu Cys His
    1310                1315                1320

Ser Val Asp Ala Thr Thr Ile Leu Gly Ile Gly Thr Val Leu Asp
    1325                1330                1335

Gln Ala Glu Thr Ala Gly Ala Arg Leu Val Val Leu Ala Thr Ala
    1340                1345                1350

Thr Pro Pro Gly Thr Val Thr Thr Pro His Ser Asn Ile Glu Glu
    1355                1360                1365

Val Ala Leu Gly His Glu Gly Glu Ile Pro Phe Tyr Gly Lys Ala
    1370                1375                1380

Ile Pro Leu Ala Tyr Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Val Asn Ala Val Ala Tyr Tyr Arg Gly Leu Asp Val Ser
    1415                1420                1425

Val Ile Pro Leu Gln Gly Asp Val Val Val Ala Thr Asp Ala
    1430                1435                1440

Leu Met Thr Gly Phe Thr Gly Asp Phe Asp Ser Val Ile Asp Cys
    1445                1450                1455

Asn Val Ala Val Thr Gln Ile Val Asp Phe Ser Leu Asp Pro Thr
    1460                1465                1470

Phe Thr Ile Thr Thr Gln Thr Val Pro Gln Asp Ala Val Ser Arg
    1475                1480                1485

Ser Gln Arg Arg Gly Arg Thr Gly Arg Gly Arg Leu Gly Ile Tyr
    1490                1495                1500

Arg Tyr Val Ser Ser Gly Glu Arg Pro Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ala Glu Thr Thr Val Arg Leu Arg Ala Tyr Leu Asn
    1535                1540                1545

Thr Pro Gly Leu Pro Val Cys Gln Asp His Leu Glu Phe Trp Glu
    1550                1555                1560
```

```
Ala Val Phe Thr Gly Leu Thr His Ile Asp Ala His Phe Leu Ser
1565                1570                1575

Gln Thr Lys Gln Gly Gly Asp Asn Phe Ala Tyr Leu Thr Ala Tyr
1580                1585                1590

Gln Ala Thr Val Cys Ala Arg Ala Arg Ala Pro Pro Pro Ser Trp
1595                1600                1605

Asp Leu Met Trp Lys Cys Leu Thr Arg Leu Lys Pro Thr Leu Asn
1610                1615                1620

Gly Pro Thr Pro Leu Leu Tyr Arg Leu Gly Ala Val Thr Asn Glu
1625                1630                1635

Val Thr Leu Thr His Pro Val Thr Lys Tyr Ile Ala Thr Cys Met
1640                1645                1650

Gln Ala Asp Leu Glu Ile Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Val Ser Ile Ile Gly Arg Leu His Leu Asn Asp Arg Val Val Val
1685                1690                1695

Ala Pro Asp Lys Glu Ile Leu Tyr Glu Ala Phe Asp Glu Met Glu
1700                1705                1710

Glu Cys Ala Ser Lys Ala Ala Leu Ile Glu Glu Gly Gln Arg Met
1715                1720                1725

Ala Glu Met Leu Lys Thr Lys Ile Gln Gly Leu Leu Gln Gln Ala
1730                1735                1740

Thr Arg Gln Ala Gln Asp Ile Gln Pro Ala Ile Gln Ser Ser Trp
1745                1750                1755

Pro Lys Leu Glu Gln Phe Trp Ala Lys His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Pro Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Ile Leu Val Asp Val Leu Ala Gly Tyr Gly Ala Gly Ile
1850                1855                1860

Ser Gly Ala Leu Val Ala Phe Lys Ile Met Ser Gly Glu Lys Pro
1865                1870                1875

Thr Val Glu Asp Val Val Asn Leu Leu Pro Ala Ile Leu Ser Pro
1880                1885                1890

Gly Ala Leu Val Val Gly Val Ile Cys Ala Ala Ile Leu Arg Arg
1895                1900                1905

His Ile Gly Gln Gly Glu Gly Ala Val Gln Trp Met Asn Arg Leu
1910                1915                1920

Ile Ala Phe Ala Ser Arg Gly Asn His Val Ala Pro Thr His Tyr
1925                1930                1935

Val Ala Glu Ser Asp Ala Ser Gln Arg Val Thr Gln Val Leu Ser
1940                1945                1950
```

Ser Leu Thr Ile Thr Ser Leu Leu Arg Arg Leu His Ala Trp Ile
1955         1960             1965

Thr Glu Asp Cys Pro Val Pro Cys Ser Gly Ser Trp Leu Arg Asp
1970         1975             1980

Ile Trp Asp Trp Val Cys Ser Ile Leu Thr Asp Phe Lys Asn Trp
1985         1990             1995

Leu Ser Ser Lys Leu Leu Pro Lys Leu Pro Gly Leu Pro Phe Ile
2000         2005             2010

Ser Cys Gln Lys Gly Tyr Arg Gly Val Trp Ala Gly Thr Gly Val
2015         2020             2025

Met Thr Thr Arg Cys Pro Cys Gly Ala Thr Ile Ser Gly His Val
2030         2035             2040

Arg Met Gly Thr Met Lys Ile Thr Gly Pro Lys Thr Cys Leu Asn
2045         2050             2055

Met Trp Gln Gly Ser Phe Pro Ile Asn Cys Tyr Thr Glu Gly Pro
2060         2065             2070

Cys Val Pro Lys Pro Pro Asn Tyr Lys Thr Ala Ile Trp Arg
2075         2080             2085

Val Ala Ala Ser Glu Tyr Val Glu Ile Thr Gln His Gly Ser Phe
2090         2095             2100

Ser Tyr Val Thr Gly Leu Thr Asn Asp Asn Leu Lys Val Pro Cys
2105         2110             2115

Gln Val Pro Ala Pro Glu Phe Phe Ser Trp Val Asp Gly Val Gln
2120         2125             2130

Ile His Arg Phe Ala Pro Thr Pro Gly Pro Phe Phe Arg Asp Glu
2135         2140             2145

Val Thr Phe Thr Val Gly Leu Asn Ser Phe Val Val Gly Ser Gln
2150         2155             2160

Leu Pro Cys Asp Pro Glu Pro Asp Thr Glu Val Leu Ala Ser Met
2165         2170             2175

Leu Thr Asp Pro Ser His Ile Thr Ala Glu Ala Ala Ala Arg Arg
2180         2185             2190

Leu Ala Arg Gly Ser Pro Pro Ser Gln Ala Ser Ser Ser Ala Ser
2195         2200             2205

Gln Leu Ser Ala Pro Ser Leu Lys Ala Thr Cys Thr Thr His Lys
2210         2215             2220

Val Ala Tyr Asp Cys Asp Met Val Asp Ala Asn Leu Phe Met Gly
2225         2230             2235

Gly Asp Val Thr Arg Ile Glu Ser Asn Ser Lys Val Val Ile Leu
2240         2245             2250

Asp Ser Leu Asp Ser Met Thr Glu Val Glu Asp Arg Glu Pro
2255         2260             2265

Ser Ile Pro Ser Glu Tyr Leu Ile Arg Arg Arg Lys Phe Pro Pro
2270         2275             2280

Ala Leu Pro Pro Trp Ala Arg Pro Asp Tyr Asn Pro Pro Val Val
2285         2290             2295

Glu Thr Trp Lys Arg Pro Asp Tyr Glu Pro Pro Thr Val Leu Gly
2300         2305             2310

Cys Ala Leu Pro Pro Thr Pro Gln Ala Pro Val Pro Pro Pro Arg
2315         2320             2325

Arg Arg Arg Ala Lys Val Leu Thr Gln Asp Asn Val Glu Gly Val
2330         2335             2340

Leu Lys Glu Met Ala Asp Lys Val Leu Ser Pro Leu Arg Asp Cys

```
              2345                2350                2355
Asn Asp Ser Gly His Ser Thr Gly Ala Asp Thr Gly Ala Asp Ser
              2360                2365                2370

Val Gln Gln Pro Pro Asp Glu Thr Ala Ala Ser Glu Ala Gly Ser
              2375                2380                2385

Leu Ser Ser Met Pro Pro Leu Glu Gly Glu Pro Gly Asp Pro Asp
              2390                2395                2400

Leu Glu Phe Glu Pro Ala Gly Ser Ala Pro Pro Ser Glu Gly Glu
              2405                2410                2415

Cys Glu Val Ile Asp Ser Asp Ser Lys Ser Trp Ser Thr Val Ser
              2420                2425                2430

Asp Gln Glu Asp Ser Ile Ile Cys Cys Ser Met Ser Tyr Ser Trp
              2435                2440                2445

Thr Gly Ala Leu Ile Thr Pro Cys Gly Pro Glu Glu Glu Lys Leu
              2450                2455                2460

Pro Ile Asn Pro Leu Ser Asn Ser Leu Met Arg Phe His Asn Lys
              2465                2470                2475

Val Tyr Ser Thr Thr Ser Arg Ser Ala Ser Gln Arg Ala Lys Lys
              2480                2485                2490

Val Thr Phe Asp Arg Val Gln Val Leu Asp Lys His Tyr Asp Ser
              2495                2500                2505

Val Leu Gln Asp Val Lys Arg Ala Ala Ser Lys Val Ser Ala Arg
              2510                2515                2520

Leu Leu Ser Ile Glu Glu Ala Cys Ala Leu Thr Pro Pro His Ser
              2525                2530                2535

Ala Lys Ser Arg Tyr Gly Phe Gly Ala Lys Glu Val Arg Ser Leu
              2540                2545                2550

Ser Arg Arg Ala Val Asn His Ile Gln Ser Val Trp Glu Asp Leu
              2555                2560                2565

Leu Glu Asp Gln His Thr Pro Ile Glu Thr Thr Ile Met Ala Lys
              2570                2575                2580

Asn Glu Val Phe Cys Val Asp Pro Ala Lys Gly Gly Lys Lys Ser
              2585                2590                2595

Ala Arg Leu Ile Val Tyr Pro Asp Leu Gly Val Arg Val Cys Glu
              2600                2605                2610

Lys Met Ala Leu Tyr Asp Ile Ala Gln Lys Leu Pro Lys Ala Ile
              2615                2620                2625

Met Gly Pro Ser Tyr Gly Phe Gln Tyr Ser Pro Ala Glu Arg Val
              2630                2635                2640

Asp Phe Leu Leu Lys Ala Trp Gly Ser Lys Lys Asp Pro Met Gly
              2645                2650                2655

Phe Ser Tyr Asp Thr Arg Cys Phe Asp Ser Thr Val Thr Glu Arg
              2660                2665                2670

Asp Ile Arg Thr Glu Glu Ser Ile Tyr Gln Ala Cys Ser Leu Pro
              2675                2680                2685

Gln Glu Ala Arg Val Ala Ile His Ser Leu Thr Glu Arg Leu Tyr
              2690                2695                2700

Val Gly Gly Pro Met Leu Asn Ser Lys Gly Gln Ser Cys Gly Tyr
              2705                2710                2715

Arg Arg Cys Arg Ala Ser Gly Val Phe Thr Thr Ser Met Gly Asn
              2720                2725                2730

Thr Met Thr Cys Tyr Ile Lys Ala Leu Ala Ala Cys Gln Ala Ala
              2735                2740                2745
```

```
Gly Ile Val Asp Pro Val Met Leu Val Cys Gly Asp Asp Leu Val
        2750                2755                2760

Val Ile Ser Glu Ser Gln Gly Asn Asp Glu Asp Glu Arg Asn Leu
        2765                2770                2775

Arg Ala Phe Thr Glu Ala Met Thr Arg Tyr Ser Ala Pro Pro Gly
        2780                2785                2790

Asp Leu Pro Arg Pro Glu Tyr Asp Leu Glu Leu Ile Thr Ser Cys
        2795                2800                2805

Ser Ser Asn Val Ser Val Ala Leu Asp Pro Arg Gly Arg Arg Arg
        2810                2815                2820

Tyr Tyr Leu Thr Arg Asp Pro Thr Thr Pro Ile Ser Arg Ala Ala
        2825                2830                2835

Trp Glu Thr Val Arg His Ser Pro Val Asn Ser Trp Leu Gly Asn
        2840                2845                2850

Ile Ile Gln Tyr Ala Pro Thr Ile Trp Val Arg Met Val Ile Met
        2855                2860                2865

Thr His Phe Phe Ser Ile Leu Leu Ala Gln Asp Thr Leu Asn Gln
        2870                2875                2880

Asn Leu Asn Phe Glu Met Tyr Gly Ala Val Tyr Ser Val Asn Pro
        2885                2890                2895

Leu Asp Leu Pro Ala Ile Ile Glu Arg Leu His Gly Leu Asp Ala
        2900                2905                2910

Phe Ser Leu His Thr Tyr Ser Pro His Glu Leu Ser Arg Val Ala
        2915                2920                2925

Ala Thr Leu Arg Lys Leu Gly Ala Pro Pro Leu Arg Ala Trp Lys
        2930                2935                2940

Ser Arg Ala Arg Ala Val Arg Ala Ser Leu Ile Ala Gln Gly Gly
        2945                2950                2955

Lys Ala Ala Ile Cys Gly Arg Tyr Leu Phe Asn Trp Ala Val Lys
        2960                2965                2970

Thr Lys Leu Lys Leu Thr Pro Leu Pro Glu Ala Ser Arg Leu Asp
        2975                2980                2985

Leu Ser Gly Trp Phe Thr Val Gly Ala Gly Gly Gly Asp Ile Phe
        2990                2995                3000

His Ser Val Ser His Ala Arg Pro Arg Leu Leu Leu Leu Cys Leu
        3005                3010                3015

Leu Leu Leu Ser Val Gly Val Gly Ile Phe Leu Leu Pro Ala Arg
        3020                3025                3030

<210> SEQ ID NO 17
<211> LENGTH: 3033
<212> TYPE: PRT
<213> ORGANISM: Hepatitis C virus

<400> SEQUENCE: 17

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
```

```
            65                  70                  75                  80
Tyr Pro Trp Pro Leu Tyr Gly Asn Glu Gly Cys Gly Trp Ala Gly Trp
                        85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
            115                 120                 125

Gly Phe Ala Asp Leu Met Gly Tyr Ile Pro Val Val Gly Ala Pro Val
130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Glu Val Arg Asn Ile Ser Ser Gly Tyr Tyr Ala Thr Asn Asp Cys Ser
                195                 200                 205

Asn Ser Ile Thr Trp Gln Leu Thr Asn Ala Val Leu His Leu Pro
210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Val Met Ala Ala Thr Ile Cys
            260                 265                 270

Ser Ala Leu Tyr Val Gly Asp Val Cys Gly Ala Val Met Ile Val Ser
            275                 280                 285

Gln Ala Phe Ile Leu Ser Pro Glu Arg His Asn Phe Thr Gln Glu Cys
            290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Val Leu Ala Tyr
                325                 330                 335

Ala Ala Arg Val Pro Glu Leu Val Leu Glu Val Val Phe Gly Gly His
            340                 345                 350

Trp Gly Val Val Phe Gly Leu Ala Tyr Phe Ser Met Gln Gly Ala Trp
            355                 360                 365

Ala Lys Val Met Ala Ile Leu Leu Leu Val Ala Gly Val Asp Ala His
            370                 375                 380

Thr Tyr Ser Thr Gly Ala Arg Ala Gly Gln Ala Ala Ser Gly Leu Thr
385                 390                 395                 400

Ser Leu Phe Ser Val Gly Ser Arg Gln Arg Leu Ser Leu Ile His Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Leu Tyr Val Asn Asn Phe Asn
            435                 440                 445

Ser Ser Gly Cys Pro Glu Arg Met Ser Ser Cys Arg Ala Leu Asp Asp
450                 455                 460

Phe Arg Ile Gly Trp Gly Thr Leu Glu Tyr Glu Thr Asn Val Thr Asn
465                 470                 475                 480

Asp Glu Asp Met Arg Pro Tyr Cys Trp His Tyr Pro Pro Lys Pro Cys
                485                 490                 495
```

-continued

```
Gly Ile Val Pro Ala Gly Thr Val Cys Gly Pro Val Tyr Cys Phe Thr
            500                 505                 510

Pro Ser Pro Val Val Gly Thr Asp Lys Gln Gly Val Pro Thr
        515                 520                 525

Tyr Asn Trp Gly Glu Asn Glu Thr Asp Val Phe Leu Leu Asn Ser Thr
    530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

Tyr Asn Gly Thr Leu Asp Leu Leu Cys Pro Thr Asp Cys Phe Arg Lys
            580                 585                 590

His Pro Glu Thr Thr Tyr Leu Arg Cys Gly Ser Gly Pro Trp Leu Thr
        595                 600                 605

Pro Arg Cys Leu Val Asp Tyr Pro Tyr Arg Leu Trp His Tyr Pro Cys
    610                 615                 620

Thr Val Asn Phe Thr Ile Phe Lys Val Arg Met Tyr Val Gly Gly Val
625                 630                 635                 640

Glu His Arg Leu Ser Ala Ala Cys Asn Phe Thr Arg Gly Asp Arg Cys
                645                 650                 655

Asn Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
        675                 680                 685

Leu Ser Thr Gly Leu Leu His Leu His Gln Asn Ile Val Asp Val Gln
    690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
            740                 745                 750

Glu Lys Leu Ile Ile Leu His Ser Ala Ser Ala Ala Ser Ala Asn Gly
        755                 760                 765

Pro Leu Trp Phe Phe Ile Phe Phe Ile Ala Ala Trp Tyr Leu Lys Gly
    770                 775                 780

Arg Val Val Pro Met Ala Thr Tyr Ser Val Leu Gly Leu Trp Ser Phe
785                 790                 795                 800

Phe Leu Leu Val Leu Ala Leu Pro Gln Gln Ala Tyr Ala Leu Asp Ala
                805                 810                 815

Val Glu Gln Gly Glu Leu Gly Leu Val Leu Leu Gly Val Ile Ser Ile
            820                 825                 830

Phe Thr Leu Thr Pro Ala Tyr Lys Thr Leu Leu Ser Arg Ser Val Trp
        835                 840                 845

Trp Leu Ser Tyr Met Leu Val Leu Ala Glu Ala Gln Ile Gln Gln Trp
    850                 855                 860

Val Pro Pro Leu Glu Ala Arg Gly Gly Arg Asp Gly Ile Ile Trp Val
865                 870                 875                 880

Ala Val Ile Leu Arg Pro Cys Leu Val Phe Glu Ile Thr Lys Trp Leu
                885                 890                 895

Leu Ala Val Leu Gly Pro Ala Tyr Leu Leu Arg Ala Ser Leu Leu Arg
            900                 905                 910
```

```
Val Pro Tyr Phe Val Arg Ala His Ala Leu Leu Arg Leu Cys Ala Leu
        915                 920                 925

Val Arg His Leu Ala Gly Ala Arg Tyr Ile Gln Met Leu Leu Ile Thr
930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
                965                 970                 975

Pro Val Val Phe Ser Pro Met Glu Lys Lys Val Ile Val Trp Gly Ala
            980                 985                 990

Glu Thr Val Ala Cys Gly Asp Ile Leu His Gly Leu Pro Val Ser Ala
            995                 1000                1005

Arg Leu Gly Arg Glu Ile Leu Leu Gly Pro Ala Asp Gly Tyr Thr
    1010                1015                1020

Ser Lys Gly Trp Lys Leu Leu Ala Pro Ile Thr Ala Tyr Thr Gln
    1025                1030                1035

Gln Thr Arg Gly Leu Leu Gly Ala Ile Val Val Ser Leu Thr Gly
    1040                1045                1050

Arg Asp Lys Asn Glu Gln Ala Gly Gln Val Gln Val Leu Ser Ser
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Pro Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Asp Pro Cys Thr
    1115                1120                1125

Cys Gly Ala Val Asp Leu Tyr Leu Val Thr Arg Asn Ala Asp Val
    1130                1135                1140

Ile Pro Val Arg Arg Arg Asp Asp Arg Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Ser Arg Gly His Ala Val Gly Leu Phe Arg Ala Ala Val
    1175                1180                1185

Cys Thr Arg Gly Val Ala Lys Ser Ile Asp Phe Ile Pro Val Glu
    1190                1195                1200

Ser Leu Asp Val Ala Ala Arg Ser Pro Ser Phe Ser Asp Asn Ser
    1205                1210                1215

Thr Pro Pro Ala Val Pro Gln Ser Tyr Gln Val Gly Tyr Leu His
    1220                1225                1230

Ala Pro Thr Gly Ser Gly Lys Ser Thr Lys Val Pro Ala Ala Tyr
    1235                1240                1245

Ala Ser Gln Gly Tyr Lys Val Leu Val Leu Asn Pro Ser Val Ala
    1250                1255                1260

Ala Thr Leu Gly Phe Gly Ala Tyr Met Ser Lys Ala His Gly Ile
    1265                1270                1275

Asn Pro Asn Ile Arg Thr Gly Val Arg Thr Val Thr Thr Gly Asp
    1280                1285                1290

Pro Ile Thr Tyr Ser Thr Tyr Gly Lys Phe Leu Ala Asp Gly Gly
    1295                1300                1305

Cys Ser Ala Gly Ala Tyr Asp Ile Ile Ile Cys Asp Glu Cys His
```

-continued

```
                1310                1315                1320
Ser Val Asp Ala Thr Thr Ile Leu Gly Ile Gly Thr Val Leu Asp
    1325                1330                1335

Gln Ala Glu Thr Ala Gly Ala Arg Leu Val Val Leu Ala Thr Ala
    1340                1345                1350

Thr Pro Pro Gly Thr Val Thr Thr Pro His Ser Asn Ile Glu Glu
    1355                1360                1365

Val Ala Leu Gly His Glu Gly Glu Ile Pro Phe Tyr Gly Lys Ala
    1370                1375                1380

Ile Pro Leu Ala Tyr Ile Lys Gly Gly Arg His Leu Ile Phe Cys
    1385                1390                1395

His Ser Lys Lys Lys Cys Asp Glu Leu Ala Ala Leu Arg Gly
    1400                1405                1410

Met Gly Val Asn Ala Val Ala Tyr Tyr Arg Gly Leu Asp Val Ser
    1415                1420                1425

Val Ile Pro Leu Gln Gly Asp Val Val Val Ala Thr Asp Ala
    1430                1435                1440

Leu Met Thr Gly Phe Thr Gly Asp Phe Asp Ser Val Ile Asp Cys
    1445                1450                1455

Asn Val Ala Val Thr Gln Ile Val Asp Leu Ser Leu Asp Pro Thr
    1460                1465                1470

Phe Thr Ile Thr Thr Gln Thr Val Pro Gln Asp Ala Val Ser Arg
    1475                1480                1485

Ser Gln Arg Arg Gly Arg Thr Gly Arg Gly Arg Leu Gly Ile Tyr
    1490                1495                1500

Arg Tyr Val Ser Ser Gly Glu Arg Pro Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ala Glu Thr Thr Val Arg Leu Arg Ala Tyr Leu Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Gly Gly Asp Asn Phe Ala Tyr Leu Thr Ala Tyr
    1580                1585                1590

Gln Ala Thr Val Cys Ala Arg Ala Arg Ala Pro Pro Pro Ser Trp
    1595                1600                1605

Asp Leu Met Trp Lys Cys Leu Thr Arg Leu Lys Pro Thr Leu Asn
    1610                1615                1620

Gly Pro Thr Pro Leu Leu Tyr Arg Leu Gly Ala Val Thr Asn Glu
    1625                1630                1635

Val Thr Leu Thr His Pro Val Thr Lys Tyr Ile Ala Thr Cys Met
    1640                1645                1650

Gln Ala Asp Leu Glu Ile Met Thr Ser Thr Trp Val Leu Ala Gly
    1655                1660                1665

Gly Val Leu Ala Ala Val Ala Ser Tyr Cys Leu Ala Thr Gly Cys
    1670                1675                1680

Val Ser Ile Ile Gly Arg Leu His Leu Asn Asp Arg Val Val Val
    1685                1690                1695

Ala Pro Asp Lys Glu Ile Leu Tyr Glu Ala Phe Asp Glu Met Glu
    1700                1705                1710
```

```
Glu Cys Ala Ser Lys Ala Ala Leu Ile Glu Glu Gly Gln Arg Met
    1715            1720                1725

Ala Glu Met Leu Lys Thr Lys Ile Gln Gly Leu Leu Gln Gln Ala
    1730            1735                1740

Thr Arg Gln Ala Gln Asp Ile Gln Pro Ala Ile Gln Ser Ser Trp
    1745            1750                1755

Pro Lys Leu Glu Gln Phe Trp Ala Lys His Met Trp Asn Phe Ile
    1760            1765                1770

Ser Gly Ile Gln Tyr Leu Ala Gly Leu Ser Thr Leu Pro Gly Asn
    1775            1780                1785

Pro Ala Val Ala Ser Met Met Ala Phe Ser Ala Ala Leu Thr Ser
    1790            1795                1800

Pro Leu Pro Thr Ser Thr Thr Ile Leu Leu Asn Ile Met Gly Gly
    1805            1810                1815

Trp Leu Ala Ser Gln Ile Ala Pro Pro Ala Gly Ala Thr Gly Phe
    1820            1825                1830

Val Val Ser Gly Leu Val Gly Ala Ala Val Gly Ser Ile Gly Leu
    1835            1840                1845

Gly Lys Ile Leu Val Asp Val Leu Ala Gly Tyr Gly Ala Gly Ile
    1850            1855                1860

Ser Gly Ala Leu Val Ala Phe Lys Ile Met Ser Gly Glu Lys Pro
    1865            1870                1875

Thr Val Glu Asp Val Val Asn Leu Leu Pro Ala Ile Leu Ser Pro
    1880            1885                1890

Gly Ala Leu Val Val Gly Val Ile Cys Ala Ala Ile Leu Arg Arg
    1895            1900                1905

His Ile Gly Gln Gly Glu Gly Ala Val Gln Trp Met Asn Arg Leu
    1910            1915                1920

Ile Ala Phe Ala Ser Arg Gly Asn His Val Ala Pro Thr His Tyr
    1925            1930                1935

Val Ala Glu Ser Asp Ala Ser Gln Arg Val Thr Gln Val Leu Ser
    1940            1945                1950

Ser Leu Thr Ile Thr Ser Leu Leu Arg Arg Leu His Ala Trp Ile
    1955            1960                1965

Thr Glu Asp Cys Pro Val Pro Cys Ser Gly Ser Trp Leu Arg Asp
    1970            1975                1980

Ile Trp Asp Trp Val Cys Ser Ile Leu Thr Asp Phe Lys Asn Trp
    1985            1990                1995

Leu Ser Ser Lys Leu Leu Pro Lys Leu Pro Gly Leu Pro Phe Ile
    2000            2005                2010

Ser Cys Gln Lys Gly Tyr Arg Gly Val Trp Ala Gly Thr Gly Val
    2015            2020                2025

Met Thr Thr Arg Cys Pro Cys Gly Ala Thr Ile Ser Gly His Val
    2030            2035                2040

Arg Met Gly Thr Met Lys Ile Thr Gly Pro Lys Thr Cys Leu Asn
    2045            2050                2055

Met Trp Gln Gly Ser Phe Pro Ile Asn Cys Tyr Thr Glu Gly Pro
    2060            2065                2070

Cys Val Pro Lys Pro Pro Asn Tyr Lys Thr Ala Ile Trp Arg
    2075            2080                2085

Val Ala Ala Ser Glu Tyr Val Glu Ile Thr Gln His Gly Ser Phe
    2090            2095                2100
```

-continued

Ser Tyr Val Thr Gly Leu Thr Asn Asp Asn Leu Lys Val Pro Cys
2105                     2110                2115

Gln Val Pro Ala Pro Glu Phe Phe Ser Trp Val Asp Gly Val Gln
2120                     2125                2130

Ile His Arg Phe Ala Pro Thr Pro Gly Pro Phe Phe Arg Asp Glu
2135                     2140                2145

Val Thr Phe Thr Val Gly Leu Asn Ser Phe Val Val Gly Ser Gln
2150                     2155                2160

Leu Pro Cys Asp Pro Glu Pro Asp Thr Glu Val Leu Ala Ser Met
2165                     2170                2175

Leu Thr Asp Pro Ser His Ile Thr Ala Glu Ala Ala Ala Arg Arg
2180                     2185                2190

Leu Ala Arg Gly Ser Pro Pro Ser Gln Ala Ser Ser Ser Ala Ser
2195                     2200                2205

Gln Leu Ser Ala Pro Ser Leu Lys Ala Thr Cys Thr Thr His Lys
2210                     2215                2220

Val Ala Tyr Asp Cys Asp Met Val Asp Ala Asn Leu Phe Met Gly
2225                     2230                2235

Gly Asp Val Thr Arg Ile Glu Ser Asn Ser Lys Val Val Ile Leu
2240                     2245                2250

Asp Ser Leu Asp Ser Met Thr Glu Val Glu Asp Asp Arg Glu Pro
2255                     2260                2265

Ser Ile Pro Ser Glu Tyr Leu Ile Arg Arg Arg Lys Phe Pro Pro
2270                     2275                2280

Ala Leu Pro Pro Trp Ala Arg Pro Asp Tyr Asn Pro Pro Val Val
2285                     2290                2295

Glu Thr Trp Lys Arg Pro Asp Tyr Glu Pro Pro Thr Val Leu Gly
2300                     2305                2310

Cys Ala Leu Pro Pro Thr Pro Gln Ala Pro Val Pro Pro Pro Arg
2315                     2320                2325

Arg Arg Arg Ala Lys Val Leu Thr Gln Asp Asn Val Glu Gly Val
2330                     2335                2340

Leu Lys Glu Met Ala Asp Lys Val Leu Ser Pro Leu Arg Asp Cys
2345                     2350                2355

Asn Asp Ser Gly His Ser Thr Gly Ala Asp Thr Gly Ala Asp Ser
2360                     2365                2370

Val Gln Gln Pro Pro Asp Glu Thr Ala Ala Ser Glu Ala Gly Ser
2375                     2380                2385

Leu Ser Ser Met Pro Pro Leu Glu Gly Glu Pro Gly Asp Pro Asp
2390                     2395                2400

Leu Glu Phe Glu Pro Ala Gly Ser Ala Pro Pro Ser Glu Gly Glu
2405                     2410                2415

Cys Glu Val Ile Asp Ser Asp Ser Lys Ser Trp Ser Thr Val Ser
2420                     2425                2430

Asp Gln Glu Asp Ser Ile Ile Cys Cys Ser Met Ser Tyr Ser Trp
2435                     2440                2445

Thr Gly Ala Leu Ile Thr Pro Cys Gly Pro Glu Glu Glu Lys Leu
2450                     2455                2460

Pro Ile Asn Pro Leu Ser Asn Ser Leu Met Arg Phe His Asn Lys
2465                     2470                2475

Val Tyr Ser Thr Thr Ser Arg Ser Ala Ser Gln Arg Ala Lys Lys
2480                     2485                2490

Val Thr Phe Asp Arg Val Gln Val Leu Asp Lys His Tyr Asp Ser

```
              2495                2500                2505

Val Leu Gln Asp Val Lys Arg Ala Ala Ser Lys Val Ser Ala Arg
    2510                2515                2520

Leu Leu Ser Ile Glu Glu Ala Cys Ala Leu Thr Pro Pro His Ser
    2525                2530                2535

Ala Lys Ser Arg Tyr Gly Phe Gly Ala Lys Glu Val Arg Ser Leu
    2540                2545                2550

Ser Arg Arg Ala Val Asn His Ile Gln Ser Val Trp Glu Asp Leu
    2555                2560                2565

Leu Glu Asp Gln His Thr Pro Ile Glu Thr Thr Ile Met Ala Lys
    2570                2575                2580

Asn Glu Val Phe Cys Val Asp Pro Ala Lys Gly Gly Lys Lys Ser
    2585                2590                2595

Ala Arg Leu Ile Val Tyr Pro Asp Leu Gly Val Arg Val Cys Glu
    2600                2605                2610

Lys Met Ala Leu Tyr Asp Ile Ala Gln Lys Leu Pro Lys Ala Ile
    2615                2620                2625

Met Gly Pro Ser Tyr Gly Phe Gln Tyr Ser Pro Ala Glu Arg Val
    2630                2635                2640

Asp Phe Leu Leu Lys Ala Trp Gly Ser Lys Lys Asp Pro Met Gly
    2645                2650                2655

Phe Ser Tyr Asp Thr Arg Cys Phe Asp Ser Thr Val Thr Glu Arg
    2660                2665                2670

Asp Ile Arg Thr Glu Glu Ser Ile Tyr Gln Ala Cys Ser Leu Pro
    2675                2680                2685

Gln Glu Ala Arg Val Ala Ile His Ser Leu Thr Glu Arg Leu Tyr
    2690                2695                2700

Val Gly Gly Pro Met Leu Asn Ser Lys Gly Gln Ser Cys Gly Tyr
    2705                2710                2715

Arg Arg Cys Arg Ala Ser Gly Val Phe Thr Thr Ser Met Gly Asn
    2720                2725                2730

Thr Met Thr Cys Tyr Ile Lys Ala Leu Ala Ala Cys Gln Ala Ala
    2735                2740                2745

Gly Ile Val Asp Pro Val Met Leu Val Cys Gly Asp Asp Leu Val
    2750                2755                2760

Val Ile Ser Glu Ser Gln Gly Asn Asp Glu Asp Glu Arg Asn Leu
    2765                2770                2775

Arg Ala Phe Thr Glu Ala Met Thr Arg Tyr Ser Ala Pro Pro Gly
    2780                2785                2790

Asp Leu Pro Arg Pro Glu Tyr Asp Leu Glu Leu Ile Thr Ser Cys
    2795                2800                2805

Ser Ser Asn Val Ser Val Ala Leu Asp Pro Arg Gly Arg Arg Arg
    2810                2815                2820

Tyr Tyr Leu Thr Arg Asp Pro Thr Thr Pro Ile Ser Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Val Arg Met Val Ile Met
    2855                2860                2865

Thr His Phe Phe Ser Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895
```

```
Leu Asp Leu Pro Ala Ile Ile Glu Arg Leu His Gly Leu Asp Ala
        2900                2905                2910

Phe Ser Leu His Thr Tyr Ser Pro His Glu Leu Ser Arg Val Ala
        2915                2920                2925

Ala Thr Leu Arg Lys Leu Gly Ala Pro Pro Leu Arg Ala Trp Lys
        2930                2935                2940

Ser Arg Ala Arg Ala Val Arg Ala Ser Leu Ile Ala Gln Gly Gly
        2945                2950                2955

Lys Ala Ala Ile Cys Gly Arg Tyr Leu Phe Asn Trp Ala Val Lys
        2960                2965                2970

Thr Lys Leu Lys Leu Thr Pro Leu Pro Glu Ala Ser Arg Leu Asp
        2975                2980                2985

Leu Ser Gly Trp Phe Thr Val Gly Ala Gly Gly Gly Gly Ile Phe
        2990                2995                3000

His Ser Val Ser His Ala Arg Pro Arg Leu Leu Leu Leu Cys Leu
        3005                3010                3015

Leu Leu Leu Ser Val Gly Val Gly Ile Phe Leu Leu Pro Ala Arg
        3020                3025                3030

<210> SEQ ID NO 18
<211> LENGTH: 3033
<212> TYPE: PRT
<213> ORGANISM: Hepatitis C virus

<400> SEQUENCE: 18

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Glu Val Arg Asn Ile Ser Ser Gly Tyr Tyr Ala Thr Asn Asp Cys Ser
        195                 200                 205

Asn Asn Ser Ile Thr Trp Gln Leu Thr Asn Ala Val Leu His Leu Pro
    210                 215                 220

Gly Cys Val Pro Cys Glu Asn Asp Asn Gly Thr Leu Arg Cys Trp Ile
```

```
              225           230           235           240
        Gln Val Thr Pro Asn Val Ala Val Lys His Arg Gly Ala Leu Thr His
                         245               250               255
        Asn Leu Arg Thr His Val Asp Val Val Met Ala Ala Thr Ile Cys
                     260               265               270
        Ser Ala Leu Tyr Val Gly Asp Val Cys Gly Ala Val Met Ile Val Ser
                     275               280               285
        Gln Ala Phe Ile Leu Ser Pro Glu Arg His Asn Phe Thr Gln Glu Cys
                 290               295               300
        Asn Cys Ser Ile Tyr Gln Gly His Ile Thr Gly His Arg Met Ala Trp
        305               310               315               320
        Asp Met Met Leu Asn Trp Ser Pro Thr Leu Thr Met Val Leu Ala Tyr
                             325               330               335
        Ala Ala Arg Val Pro Glu Leu Val Leu Glu Val Phe Gly Gly His
                         340               345               350
        Trp Gly Val Val Phe Gly Leu Ala Tyr Phe Ser Met Gln Gly Ala Trp
                         355               360               365
        Ala Lys Val Met Ala Ile Leu Leu Val Ala Gly Val Asp Ala His
                 370               375               380
        Thr Tyr Ser Thr Gly Ala Arg Ala Gly Gln Ala Ala Ser Gly Leu Thr
        385               390               395               400
        Ser Leu Phe Ser Val Gly Ser Arg Gln Arg Leu Ser Leu Ile His Thr
                         405               410               415
        Asn Gly Ser Trp His Ile Asn Arg Thr Ala Leu Asn Cys Asn Asp Ser
                         420               425               430
        Leu His Thr Gly Phe Ile Ala Ser Leu Leu Tyr Val Asn Asn Phe Asn
                     435               440               445
        Ser Ser Gly Cys Pro Glu Arg Met Ser Ser Cys Arg Ala Leu Asp Asp
                 450               455               460
        Phe Arg Ile Gly Trp Gly Thr Leu Glu Tyr Glu Thr Asn Val Thr Asn
        465               470               475               480
        Asp Glu Asp Met Arg Pro Tyr Cys Trp His Tyr Pro Pro Lys Pro Cys
                         485               490               495
        Gly Ile Val Pro Ala Gly Thr Val Cys Gly Pro Val Tyr Cys Phe Thr
                         500               505               510
        Pro Ser Pro Val Val Gly Thr Thr Asp Lys Gln Gly Val Pro Thr
                     515               520               525
        Tyr Asn Trp Gly Glu Asn Glu Thr Asp Val Phe Leu Leu Asn Ser Thr
            530               535               540
        Arg Pro Pro Gln Gly Ala Trp Phe Gly Cys Thr Trp Met Asn Gly Thr
        545               550               555               560
        Gly Phe Thr Lys Thr Cys Gly Ala Pro Pro Cys Arg Ile Arg Arg Asp
                         565               570               575
        Tyr Asn Gly Thr Leu Asp Leu Leu Cys Pro Thr Asp Cys Phe Arg Lys
                     580               585               590
        His Pro Glu Thr Thr Tyr Leu Arg Cys Gly Ser Gly Pro Trp Leu Thr
                 595               600               605
        Pro Arg Cys Leu Val Asp Tyr Pro Tyr Arg Leu Trp His Tyr Pro Cys
        610               615               620
        Thr Val Asn Phe Thr Ile Phe Lys Val Arg Met Tyr Val Gly Gly Val
        625               630               635               640
        Glu His Arg Leu Ser Ala Ala Cys Asn Phe Thr Arg Gly Asp Arg Cys
                     645               650               655
```

```
Asn Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
            690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
            740                 745                 750

Glu Lys Leu Ile Ile Leu His Ser Ala Ser Ala Ala Ser Ala Asn Gly
            755                 760                 765

Pro Leu Trp Phe Phe Ile Phe Phe Ile Ala Ala Trp Tyr Leu Lys Gly
            770                 775                 780

Arg Val Val Pro Met Ala Thr Tyr Ser Val Leu Gly Leu Trp Ser Phe
785                 790                 795                 800

Phe Leu Leu Val Leu Ala Leu Pro Gln Gln Ala Tyr Ala Leu Asp Ala
                805                 810                 815

Val Glu Gln Gly Glu Leu Gly Leu Val Leu Leu Gly Val Ile Ser Ile
            820                 825                 830

Phe Thr Leu Thr Pro Ala Tyr Lys Thr Leu Leu Ser Arg Ser Val Trp
            835                 840                 845

Trp Leu Ser Tyr Met Leu Val Leu Ala Glu Ala Gln Ile Gln Gln Trp
            850                 855                 860

Val Pro Pro Leu Glu Ala Arg Gly Gly Arg Asp Gly Ile Ile Trp Val
865                 870                 875                 880

Ala Val Ile Leu Arg Pro Cys Leu Val Phe Glu Ile Thr Lys Trp Leu
                885                 890                 895

Leu Ala Val Leu Gly Pro Ala Tyr Leu Leu Arg Ala Ser Leu Leu Arg
            900                 905                 910

Val Pro Tyr Phe Val Arg Ala His Ala Leu Leu Arg Leu Cys Ala Leu
            915                 920                 925

Val Arg His Leu Ala Gly Ala Arg Tyr Ile Gln Met Leu Leu Ile Thr
            930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
            965                 970                 975

Pro Val Phe Ser Pro Met Glu Lys Lys Val Ile Val Trp Gly Ala
            980                 985                 990

Glu Thr Val Ala Cys Gly Asp Ile Leu His Gly Leu Pro Val Ser Ala
            995                 1000                1005

Arg Leu Gly Arg Glu Ile Leu Leu Gly Pro Ala Asp Gly Tyr Thr
        1010                1015                1020

Ser Lys Gly Trp Lys Leu Leu Ala Pro Ile Thr Ala Tyr Thr Gln
        1025                1030                1035

Gln Thr Arg Gly Leu Leu Gly Ala Ile Val Val Ser Leu Thr Gly
        1040                1045                1050

Arg Asp Lys Asn Glu Gln Ala Gly Gln Val Gln Val Leu Ser Ser
        1055                1060                1065
```

-continued

```
Val Thr Gln Ser Phe Leu Gly Thr Ser Ile Ser Gly Val Leu Trp
1070                1075                1080

Thr Val Tyr His Gly Ala Gly Asn Lys Thr Leu Ala Gly Pro Arg
1085                1090                1095

Gly Pro Val Thr Gln Met Tyr Ser Ser Ala Glu Gly Asp Leu Val
1100                1105                1110

Gly Trp Pro Ser Pro Pro Gly Thr Lys Ser Leu Asp Pro Cys Thr
1115                1120                1125

Cys Gly Ala Val Asp Leu Tyr Leu Val Thr Arg Asn Ala Asp Val
1130                1135                1140

Ile Pro Val Arg Arg Asp Asp Arg Arg Gly Ala Leu Leu Ser
1145                1150                1155

Pro Arg Pro Leu Ser Thr Leu Lys Gly Ser Ser Gly Pro Val
1160                1165                1170

Leu Cys Ser Arg Gly His Ala Val Gly Leu Phe Arg Ala Ala Val
1175                1180                1185

Cys Thr Arg Gly Val Ala Lys Ser Ile Asp Phe Ile Pro Val Glu
1190                1195                1200

Ser Leu Asp Val Ala Ala Arg Ser Pro Ser Phe Ser Asp Asn Ser
1205                1210                1215

Thr Pro Pro Ala Val Pro Gln Ser Tyr Gln Val Gly Tyr Leu His
1220                1225                1230

Ala Pro Thr Gly Ser Gly Lys Ser Thr Lys Val Pro Ala Ala Tyr
1235                1240                1245

Ala Ser Gln Gly Tyr Lys Val Leu Val Leu Asn Pro Ser Val Ala
1250                1255                1260

Ala Thr Leu Gly Phe Gly Ala Tyr Met Ser Lys Ala His Gly Ile
1265                1270                1275

Asn Pro Asn Ile Arg Thr Gly Val Arg Thr Val Thr Thr Gly Asp
1280                1285                1290

Pro Ile Thr Tyr Ser Thr Tyr Gly Lys Phe Leu Ala Asp Gly Gly
1295                1300                1305

Cys Ser Ala Gly Ala Tyr Asp Ile Ile Ile Cys Asp Glu Cys His
1310                1315                1320

Ser Val Asp Ala Thr Thr Ile Leu Gly Ile Gly Thr Val Leu Asp
1325                1330                1335

Gln Ala Glu Thr Ala Gly Ala Arg Leu Val Val Leu Ala Thr Ala
1340                1345                1350

Thr Pro Pro Gly Thr Val Thr Thr Pro His Ser Asn Ile Glu Glu
1355                1360                1365

Val Ala Leu Gly His Glu Gly Glu Ile Pro Phe Tyr Gly Lys Ala
1370                1375                1380

Ile Pro Leu Ala Tyr Ile Lys Gly Gly Arg His Leu Ile Phe Cys
1385                1390                1395

His Ser Lys Lys Lys Cys Asp Glu Leu Ala Ala Ala Leu Arg Gly
1400                1405                1410

Met Gly Val Asn Ala Val Ala Tyr Tyr Arg Gly Leu Asp Val Ser
1415                1420                1425

Val Ile Pro Leu Gln Gly Asp Val Val Val Val Ala Thr Asp Ala
1430                1435                1440

Leu Met Thr Gly Phe Thr Gly Asp Phe Asp Ser Val Ile Asp Cys
1445                1450                1455

Asn Val Ala Val Thr Gln Ile Val Asp Leu Ser Leu Asp Pro Thr
```

-continued

```
              1460                1465                1470

Phe Thr Ile Thr Thr Gln Thr Val Pro Gln Asp Ala Val Ser Arg
    1475                1480                1485

Ser Gln Arg Arg Gly Arg Thr Gly Arg Gly Arg Leu Gly Ile Tyr
    1490                1495                1500

Arg Tyr Val Ser Ser Gly Glu Arg Pro Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ala Glu Thr Thr Val Arg Leu Arg Ala Tyr Leu Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Gly Gly Asp Asn Phe Ala Tyr Leu Thr Ala Tyr
    1580                1585                1590

Gln Ala Thr Val Cys Ala Arg Ala Arg Ala Pro Pro Pro Ser Trp
    1595                1600                1605

Asp Leu Met Trp Lys Cys Leu Thr Arg Leu Lys Pro Thr Leu Asn
    1610                1615                1620

Gly Pro Thr Pro Leu Leu Tyr Arg Leu Gly Ala Val Thr Asn Glu
    1625                1630                1635

Val Thr Leu Thr His Pro Val Thr Lys Tyr Ile Ala Thr Cys Met
    1640                1645                1650

Gln Ala Asp Leu Glu Ile Met Thr Ser Thr Trp Val Leu Ala Gly
    1655                1660                1665

Gly Val Leu Ala Ala Val Ala Ser Tyr Cys Leu Ala Thr Gly Cys
    1670                1675                1680

Val Ser Ile Ile Gly Arg Leu His Leu Asn Asp Arg Val Val Val
    1685                1690                1695

Ala Pro Asp Lys Glu Ile Leu Tyr Glu Ala Phe Asp Glu Met Glu
    1700                1705                1710

Glu Cys Ala Ser Lys Ala Ala Leu Ile Glu Glu Gly Gln Arg Met
    1715                1720                1725

Ala Glu Met Leu Lys Thr Lys Ile Gln Gly Leu Leu Gln Gln Ala
    1730                1735                1740

Thr Arg Gln Ala Gln Asp Ile Gln Pro Ala Ile Gln Ser Ser Trp
    1745                1750                1755

Pro Lys Leu Glu Gln Phe Trp Ala Lys His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Pro Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Ile Leu Val Asp Val Leu Ala Gly Tyr Gly Ala Gly Ile
    1850                1855                1860
```

```
Ser Gly Ala Leu Val Ala Phe Lys Ile Met Ser Gly Glu Lys Pro
    1865            1870            1875

Thr Val Glu Asp Val Val Asn Leu Leu Pro Ala Ile Leu Ser Pro
    1880            1885            1890

Gly Ala Leu Val Val Gly Val Ile Cys Ala Ala Ile Leu Arg Arg
    1895            1900            1905

His Ile Gly Gln Gly Glu Gly Ala Val Gln Trp Met Asn Arg Leu
    1910            1915            1920

Ile Ala Phe Ala Ser Arg Gly Asn His Val Ala Pro Thr His Tyr
    1925            1930            1935

Val Ala Glu Ser Asp Ala Ser Gln Arg Val Thr Gln Ala Leu Ser
    1940            1945            1950

Ser Leu Thr Ile Thr Ser Leu Leu Arg Arg Leu His Ala Trp Ile
    1955            1960            1965

Thr Glu Asp Cys Pro Val Pro Cys Ser Gly Ser Trp Leu Arg Asp
    1970            1975            1980

Ile Trp Asp Trp Val Cys Ser Ile Leu Thr Asp Phe Lys Asn Trp
    1985            1990            1995

Leu Ser Ser Lys Leu Leu Pro Lys Leu Pro Gly Leu Pro Phe Ile
    2000            2005            2010

Ser Cys Gln Lys Gly Tyr Arg Gly Val Trp Ala Gly Thr Gly Val
    2015            2020            2025

Met Thr Thr Arg Cys Pro Cys Gly Ala Thr Ile Ser Gly His Val
    2030            2035            2040

Arg Met Gly Thr Met Lys Ile Thr Gly Pro Lys Thr Cys Leu Asn
    2045            2050            2055

Met Trp Gln Gly Ser Phe Pro Ile Asn Cys Tyr Thr Glu Gly Pro
    2060            2065            2070

Cys Val Pro Lys Pro Pro Asn Tyr Lys Thr Ala Ile Trp Arg
    2075            2080            2085

Val Ala Ala Ser Glu Tyr Val Glu Ile Thr Gln His Gly Ser Phe
    2090            2095            2100

Ser Tyr Val Thr Gly Leu Thr Asn Asp Asn Leu Lys Val Pro Cys
    2105            2110            2115

Gln Val Pro Ala Pro Glu Phe Phe Ser Trp Val Asp Gly Val Gln
    2120            2125            2130

Ile His Arg Phe Ala Pro Thr Pro Gly Pro Phe Phe Arg Asp Glu
    2135            2140            2145

Val Thr Phe Thr Val Gly Leu Asn Ser Phe Val Val Gly Ser Gln
    2150            2155            2160

Leu Pro Cys Asp Pro Glu Pro Asp Thr Glu Val Leu Ala Ser Met
    2165            2170            2175

Leu Thr Asp Pro Ser His Ile Thr Ala Glu Ala Ala Ala Arg Arg
    2180            2185            2190

Leu Ala Arg Gly Ser Pro Pro Ser Gln Ala Ser Ser Ser Ala Ser
    2195            2200            2205

Gln Leu Ser Ala Pro Ser Leu Lys Ala Thr Cys Thr Thr His Lys
    2210            2215            2220

Val Ala Tyr Asp Cys Asp Met Val Asp Ala Asn Leu Phe Met Gly
    2225            2230            2235

Gly Asp Val Thr Arg Ile Glu Ser Asn Ser Lys Val Val Ile Leu
    2240            2245            2250
```

```
Asp Ser Leu Asp Ser Met Thr Glu Val Glu Asp Arg Glu Pro
    2255            2260            2265

Ser Ile Pro Ser Glu Tyr Leu Ile Arg Arg Lys Phe Pro Pro
    2270            2275            2280

Ala Leu Pro Pro Trp Ala Arg Pro Asp Tyr Asn Pro Val Val
    2285            2290            2295

Glu Thr Trp Lys Arg Pro Asp Tyr Glu Pro Pro Thr Val Leu Gly
    2300            2305            2310

Cys Ala Leu Pro Pro Thr Pro Gln Ala Pro Val Pro Pro Pro Arg
    2315            2320            2325

Arg Arg Arg Ala Lys Val Leu Thr Gln Asp Asn Val Glu Gly Val
    2330            2335            2340

Leu Lys Glu Met Ala Asp Lys Val Leu Ser Pro Leu Arg Asp Cys
    2345            2350            2355

Asn Asp Ser Gly His Ser Thr Gly Ala Asp Thr Gly Ala Asp Ser
    2360            2365            2370

Val Gln Gln Pro Pro Asp Glu Thr Ala Ala Ser Glu Ala Gly Ser
    2375            2380            2385

Leu Ser Ser Met Pro Pro Leu Glu Gly Glu Pro Gly Asp Pro Asp
    2390            2395            2400

Leu Glu Phe Glu Pro Ala Gly Ser Ala Pro Pro Ser Glu Gly Glu
    2405            2410            2415

Cys Glu Val Ile Asp Ser Asp Ser Lys Ser Trp Ser Thr Val Ser
    2420            2425            2430

Asp Gln Glu Asp Ser Ile Ile Cys Cys Ser Met Ser Tyr Ser Trp
    2435            2440            2445

Thr Gly Ala Leu Ile Thr Pro Cys Gly Pro Glu Glu Glu Lys Leu
    2450            2455            2460

Pro Ile Asn Pro Leu Ser Asn Ser Leu Met Arg Phe His Asn Lys
    2465            2470            2475

Val Tyr Ser Thr Thr Ser Arg Ser Ala Ser Gln Arg Ala Lys Lys
    2480            2485            2490

Val Thr Phe Asp Arg Val Gln Val Leu Asp Lys His Tyr Asp Ser
    2495            2500            2505

Val Leu Gln Asp Val Lys Arg Ala Ala Ser Lys Val Ser Ala Arg
    2510            2515            2520

Leu Leu Ser Ile Glu Glu Ala Cys Ala Leu Thr Pro Pro His Ser
    2525            2530            2535

Ala Lys Ser Arg Tyr Gly Phe Gly Ala Lys Glu Val Arg Ser Leu
    2540            2545            2550

Ser Arg Arg Ala Val Asn His Ile Gln Ser Val Trp Glu Asp Leu
    2555            2560            2565

Leu Glu Asp Gln His Thr Pro Ile Glu Thr Thr Ile Met Ala Lys
    2570            2575            2580

Asn Glu Val Phe Cys Val Asp Pro Ala Lys Gly Gly Lys Lys Ser
    2585            2590            2595

Ala Arg Leu Ile Val Tyr Pro Asp Leu Gly Val Arg Val Cys Glu
    2600            2605            2610

Lys Met Ala Leu Tyr Asp Ile Ala Gln Lys Leu Pro Lys Ala Ile
    2615            2620            2625

Met Gly Pro Ser Tyr Gly Phe Gln Tyr Ser Pro Ala Glu Arg Val
    2630            2635            2640

Asp Phe Leu Leu Lys Ala Trp Gly Ser Lys Lys Asp Pro Met Gly
```

-continued

```
                2645                2650                2655

Phe Ser Tyr Asp Thr Arg Cys Phe Asp Ser Thr Val Thr Glu Arg
    2660                2665                2670

Asp Ile Arg Thr Glu Glu Ser Ile Tyr Gln Ala Cys Ser Leu Pro
    2675                2680                2685

Gln Glu Ala Arg Val Ala Ile His Ser Leu Thr Glu Arg Leu Tyr
    2690                2695                2700

Val Gly Gly Pro Met Leu Asn Ser Lys Gly Gln Ser Cys Gly Tyr
    2705                2710                2715

Arg Arg Cys Arg Ala Ser Gly Val Phe Thr Thr Ser Met Gly Asn
    2720                2725                2730

Thr Met Thr Cys Tyr Ile Lys Ala Leu Ala Ala Cys Gln Ala Ala
    2735                2740                2745

Gly Ile Val Asp Pro Val Met Leu Val Cys Gly Asp Asp Leu Val
    2750                2755                2760

Val Ile Ser Glu Ser Gln Gly Asn Asp Glu Asp Arg Asn Leu
    2765                2770                2775

Arg Ala Phe Thr Glu Ala Met Thr Arg Tyr Ser Ala Pro Pro Gly
    2780                2785                2790

Asp Leu Pro Arg Pro Glu Tyr Asp Leu Glu Leu Ile Thr Ser Cys
    2795                2800                2805

Ser Ser Asn Val Ser Val Ala Leu Asp Pro Arg Gly Arg Arg Arg
    2810                2815                2820

Tyr Tyr Leu Thr Arg Asp Pro Thr Thr Pro Ile Ser Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Val Arg Met Val Ile Met
    2855                2860                2865

Thr His Phe Phe Ser Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895

Leu Asp Leu Pro Ala Ile Ile Glu Arg Leu His Gly Leu Asp Ala
    2900                2905                2910

Phe Ser Leu His Thr Tyr Ser Pro His Glu Leu Ser Arg Val Ala
    2915                2920                2925

Ala Thr Leu Arg Lys Leu Gly Ala Pro Pro Leu Arg Ala Trp Lys
    2930                2935                2940

Ser Arg Ala Arg Ala Val Arg Ala Ser Leu Ile Ala Gln Gly Gly
    2945                2950                2955

Lys Ala Ala Ile Cys Gly Arg Tyr Leu Phe Asn Trp Ala Val Lys
    2960                2965                2970

Thr Lys Leu Lys Leu Thr Pro Leu Pro Glu Ala Ser Arg Leu Asp
    2975                2980                2985

Leu Ser Gly Trp Phe Thr Val Gly Ala Gly Gly Gly Ile Phe
    2990                2995                3000

His Ser Val Ser His Ala Arg Pro Arg Leu Leu Leu Leu Cys Leu
    3005                3010                3015

Leu Leu Leu Ser Val Gly Val Gly Ile Phe Leu Leu Pro Ala Arg
    3020                3025                3030
```

<210> SEQ ID NO 19

```
<211> LENGTH: 3033
<212> TYPE: PRT
<213> ORGANISM: Hepatitis C virus

<400> SEQUENCE: 19

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
            115                 120                 125

Gly Phe Ala Asp Leu Met Gly Tyr Ile Pro Val Val Gly Ala Pro Val
130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Glu Val Arg Asn Ile Ser Ser Gly Tyr Tyr Ala Thr Asn Asp Cys Ser
            195                 200                 205

Asn Asn Ser Ile Thr Trp Gln Leu Thr Asn Ala Val Leu His Leu Pro
210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Val Met Ala Ala Thr Ile Cys
            260                 265                 270

Ser Ala Leu Tyr Val Gly Asp Val Cys Gly Ala Val Met Ile Val Ser
            275                 280                 285

Gln Ala Phe Ile Leu Ser Pro Glu Arg His Asn Phe Thr Gln Glu Cys
290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Val Leu Ala Tyr
                325                 330                 335

Ala Ala Arg Val Pro Glu Leu Val Leu Glu Val Phe Gly Gly His
            340                 345                 350

Trp Gly Val Val Phe Gly Leu Ala Tyr Phe Ser Met Gln Gly Ala Trp
            355                 360                 365

Ala Lys Val Met Ala Ile Leu Leu Leu Val Ala Gly Val Asp Ala His
370                 375                 380

Thr Tyr Ser Thr Gly Ala Arg Ala Gly Gln Ala Ala Ser Gly Leu Thr
```

```
            385                 390                 395                 400
        Ser Leu Phe Ser Val Gly Ser Arg Gln Arg Leu Ser Leu Ile His Thr
                        405                 410                 415
        Asn Gly Ser Trp His Ile Asn Arg Thr Ala Leu Asn Cys Asn Asp Ser
                        420                 425                 430
        Leu His Thr Gly Phe Ile Ala Ser Leu Leu Tyr Val Asn Asn Phe Asn
                        435                 440                 445
        Ser Ser Gly Cys Pro Glu Arg Met Ser Ser Cys Arg Ala Leu Asp Asp
                        450                 455                 460
        Phe Arg Ile Gly Trp Gly Thr Leu Glu Tyr Glu Thr Asn Val Thr Asn
        465                 470                 475                 480
        Asp Glu Asp Met Arg Pro Tyr Cys Trp His Tyr Pro Pro Lys Pro Cys
                            485                 490                 495
        Gly Ile Val Pro Ala Gly Thr Val Cys Gly Pro Val Tyr Cys Phe Thr
                        500                 505                 510
        Pro Ser Pro Val Val Gly Thr Thr Asp Lys Gln Gly Val Pro Thr
                        515                 520                 525
        Tyr Asn Trp Gly Glu Asn Glu Thr Asp Val Phe Leu Leu Asn Ser Thr
                        530                 535                 540
        Arg Pro Pro Gln Gly Ala Trp Phe Gly Cys Thr Trp Met Asn Gly Thr
        545                 550                 555                 560
        Gly Phe Thr Lys Thr Cys Gly Ala Pro Pro Cys Arg Ile Arg Arg Asp
                        565                 570                 575
        Tyr Asn Gly Thr Leu Asp Leu Leu Cys Pro Thr Asp Cys Phe Arg Lys
                        580                 585                 590
        His Pro Glu Thr Thr Tyr Leu Arg Cys Gly Ser Gly Pro Trp Leu Thr
                        595                 600                 605
        Pro Arg Cys Leu Val Asp Tyr Pro Tyr Arg Leu Trp His Tyr Pro Cys
                        610                 615                 620
        Thr Val Asn Phe Thr Ile Phe Lys Val Arg Met Tyr Val Gly Gly Val
        625                 630                 635                 640
        Glu His Arg Leu Ser Ala Ala Cys Asn Phe Thr Arg Gly Asp Arg Cys
                        645                 650                 655
        Asn Leu Glu Asp Arg Asp Arg Gly Gln Gln Ser Pro Leu Leu His Ser
                        660                 665                 670
        Thr Thr Glu Trp Ala Val Leu Pro Cys Ser Phe Ser Asp Leu Pro Ala
                        675                 680                 685
        Leu Ser Thr Gly Leu Leu His Leu His Gln Asn Ile Val Asp Val Gln
        690                 695                 700
        Tyr Leu Tyr Gly Leu Ser Pro Ala Ile Thr Arg Tyr Ile Val Lys Trp
        705                 710                 715                 720
        Glu Trp Val Val Leu Leu Phe Leu Leu Leu Ala Asp Ala Arg Val Cys
                        725                 730                 735
        Ala Cys Leu Trp Met Leu Ile Ile Leu Gly Gln Ala Glu Ala Ala Leu
                        740                 745                 750
        Glu Lys Leu Ile Ile Leu His Ser Ala Ser Ala Ala Ser Ala Asn Gly
                        755                 760                 765
        Pro Leu Trp Phe Phe Ile Phe Phe Ile Ala Ala Trp Tyr Leu Lys Gly
                        770                 775                 780
        Arg Val Val Pro Met Ala Thr Tyr Ser Val Leu Gly Leu Trp Ser Phe
        785                 790                 795                 800
        Phe Leu Leu Val Leu Ala Leu Pro Gln Gln Ala Tyr Ala Leu Asp Ala
                        805                 810                 815
```

```
Val Glu Gln Gly Glu Leu Gly Leu Val Leu Leu Gly Val Ile Ser Ile
            820                 825                 830

Phe Thr Leu Thr Pro Ala Tyr Lys Thr Leu Leu Ser Arg Ser Val Trp
            835                 840                 845

Trp Leu Ser Tyr Met Leu Val Leu Ala Glu Ala Gln Ile Gln Gln Trp
            850                 855                 860

Val Pro Pro Leu Glu Ala Arg Gly Gly Arg Asp Gly Ile Ile Trp Val
865                 870                 875                 880

Ala Val Ile Leu Arg Pro Cys Leu Val Phe Glu Ile Thr Lys Trp Leu
                    885                 890                 895

Leu Ala Val Leu Gly Pro Ala Tyr Leu Arg Ala Ser Leu Leu Arg
                900                 905                 910

Val Pro Tyr Phe Val Arg Ala His Ala Leu Leu Arg Leu Cys Ala Leu
                    915                 920                 925

Val Arg His Leu Ala Gly Ala Arg Tyr Ile Gln Met Leu Leu Ile Thr
            930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
                    965                 970                 975

Pro Val Val Phe Ser Pro Met Glu Lys Lys Val Ile Val Trp Gly Ala
                980                 985                 990

Glu Thr Val Ala Cys Gly Asp Ile Leu His Gly Leu Pro Val Ser Ala
            995                 1000                1005

Arg Leu Gly Arg Glu Ile Leu Leu Gly Pro Ala Asp Gly Tyr Thr
    1010                1015                1020

Ser Lys Gly Trp Lys Leu Leu Ala Pro Ile Thr Ala Tyr Thr Gln
    1025                1030                1035

Gln Thr Arg Gly Leu Leu Gly Ala Ile Val Val Ser Leu Thr Gly
    1040                1045                1050

Arg Asp Lys Asn Glu Gln Ala Gly Gln Val Gln Val Leu Ser Ser
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Pro Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Asp Pro Cys Thr
    1115                1120                1125

Cys Gly Ala Val Asp Leu Tyr Leu Val Thr Arg Asn Ala Asp Val
    1130                1135                1140

Ile Pro Val Arg Arg Arg Asp Asp Arg Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Ser Arg Gly His Ala Val Gly Leu Phe Arg Ala Ala Val
    1175                1180                1185

Cys Thr Arg Gly Val Ala Lys Ser Ile Asp Phe Ile Pro Val Glu
    1190                1195                1200

Ser Leu Asp Val Ala Ala Arg Ser Pro Ser Phe Ser Asp Asn Ser
    1205                1210                1215
```

```
Thr Pro Pro Ala Val Pro Gln Ser Tyr Gln Val Gly Tyr Leu His
    1220            1225            1230

Ala Pro Thr Gly Ser Gly Lys Ser Thr Lys Val Pro Ala Ala Tyr
    1235            1240            1245

Ala Ser Gln Gly Tyr Lys Val Leu Val Leu Asn Pro Ser Val Ala
    1250            1255            1260

Ala Thr Leu Gly Phe Gly Ala Tyr Met Ser Lys Ala His Gly Ile
    1265            1270            1275

Asn Pro Asn Ile Arg Thr Gly Val Arg Thr Val Thr Thr Gly Asp
    1280            1285            1290

Pro Ile Thr Tyr Ser Thr Tyr Gly Lys Phe Leu Ala Asp Gly Gly
    1295            1300            1305

Cys Ser Ala Gly Ala Tyr Asp Ile Ile Ile Cys Asp Glu Cys His
    1310            1315            1320

Ser Val Asp Ala Thr Thr Ile Leu Gly Ile Gly Thr Val Leu Asp
    1325            1330            1335

Gln Ala Glu Thr Ala Gly Ala Arg Leu Val Val Leu Ala Thr Ala
    1340            1345            1350

Thr Pro Pro Gly Thr Val Thr Thr Pro His Ser Asn Ile Glu Glu
    1355            1360            1365

Val Ala Leu Gly His Glu Gly Glu Ile Pro Phe Tyr Gly Lys Ala
    1370            1375            1380

Ile Pro Leu Ala Tyr Ile Lys Gly Gly Arg His Leu Ile Phe Cys
    1385            1390            1395

His Ser Lys Lys Lys Cys Asp Glu Leu Ala Ala Ala Leu Arg Gly
    1400            1405            1410

Met Gly Val Asn Ala Val Ala Tyr Tyr Arg Gly Leu Asp Val Ser
    1415            1420            1425

Val Ile Pro Leu Gln Gly Asp Val Val Val Ala Thr Asp Ala
    1430            1435            1440

Leu Met Thr Gly Phe Thr Gly Asp Phe Asp Ser Val Ile Asp Cys
    1445            1450            1455

Asn Val Ala Val Thr Gln Ile Val Asp Leu Ser Leu Asp Pro Thr
    1460            1465            1470

Phe Thr Ile Thr Thr Gln Thr Val Pro Gln Asp Ala Val Ser Arg
    1475            1480            1485

Ser Gln Arg Arg Gly Arg Thr Gly Arg Gly Arg Leu Gly Ile Tyr
    1490            1495            1500

Arg Tyr Val Ser Ser Gly Glu Arg Pro Ser Gly Met Phe Asp Ser
    1505            1510            1515

Val Val Leu Cys Glu Cys Tyr Asp Ala Gly Ala Ala Trp Tyr Glu
    1520            1525            1530

Leu Thr Pro Ala Glu Thr Thr Val Arg Leu Arg Ala Tyr Leu Asn
    1535            1540            1545

Thr Pro Gly Leu Pro Val Cys Gln Asp His Leu Glu Phe Trp Glu
    1550            1555            1560

Ala Val Phe Thr Gly Leu Thr His Ile Asp Ala His Phe Leu Ser
    1565            1570            1575

Gln Thr Lys Gln Gly Gly Asp Asn Phe Ala Tyr Leu Thr Ala Tyr
    1580            1585            1590

Gln Ala Thr Val Cys Ala Arg Ala Arg Ala Pro Pro Pro Ser Trp
    1595            1600            1605

Asp Leu Met Trp Lys Cys Leu Thr Arg Leu Lys Pro Thr Leu Asn
```

-continued

```
            1610                1615                1620
Gly Pro Thr Pro Leu Leu Tyr Arg Leu Gly Ala Val Thr Asn Glu
        1625                1630                1635
Val Thr Leu Thr His Pro Val Thr Lys Tyr Ile Ala Thr Cys Met
        1640                1645                1650
Gln Ala Asp Leu Glu Ile Met Thr Ser Thr Trp Val Leu Ala Gly
        1655                1660                1665
Gly Val Leu Ala Ala Val Ala Ser Tyr Cys Leu Ala Thr Gly Cys
        1670                1675                1680
Val Ser Ile Ile Gly Arg Leu His Leu Asn Asp Arg Val Val Val
        1685                1690                1695
Ala Pro Asp Lys Glu Ile Leu Tyr Glu Ala Phe Asp Glu Met Glu
        1700                1705                1710
Glu Cys Ala Ser Lys Ala Ala Leu Ile Glu Glu Gly Gln Arg Met
        1715                1720                1725
Ala Glu Met Leu Lys Thr Lys Ile Gln Gly Leu Leu Gln Gln Ala
        1730                1735                1740
Thr Arg Gln Ala Gln Asp Ile Gln Pro Ala Ile Gln Ser Ser Trp
        1745                1750                1755
Pro Lys Leu Glu Gln Phe Trp Ala Lys His Met Trp Asn Phe Ile
        1760                1765                1770
Ser Gly Ile Gln Tyr Leu Ala Gly Leu Ser Thr Leu Pro Gly Asn
        1775                1780                1785
Pro Ala Val Ala Ser Met Met Ala Phe Ser Ala Ala Leu Thr Ser
        1790                1795                1800
Pro Leu Pro Thr Ser Thr Thr Ile Leu Leu Asn Ile Met Gly Gly
        1805                1810                1815
Trp Leu Ala Ser Gln Ile Ala Pro Pro Ala Gly Ala Thr Gly Phe
        1820                1825                1830
Val Val Ser Gly Leu Val Gly Ala Ala Val Gly Ser Ile Gly Leu
        1835                1840                1845
Gly Lys Ile Leu Val Asp Val Leu Ala Gly Tyr Gly Ala Gly Ile
        1850                1855                1860
Ser Gly Ala Leu Val Ala Phe Lys Ile Met Ser Gly Glu Lys Pro
        1865                1870                1875
Thr Val Glu Asp Val Val Asn Leu Leu Pro Ala Ile Leu Ser Pro
        1880                1885                1890
Gly Ala Leu Val Val Gly Val Ile Cys Ala Ala Ile Leu Arg Arg
        1895                1900                1905
His Ile Gly Gln Gly Glu Gly Ala Val Gln Trp Met Asn Arg Leu
        1910                1915                1920
Ile Ala Phe Ala Ser Arg Gly Asn His Val Ala Pro Thr His Tyr
        1925                1930                1935
Val Ala Glu Ser Asp Ala Ser Gln Arg Val Thr Gln Ala Leu Ser
        1940                1945                1950
Ser Leu Thr Ile Thr Ser Leu Leu Arg Arg Leu His Ala Trp Ile
        1955                1960                1965
Thr Glu Asp Cys Pro Val Pro Cys Ser Gly Ser Trp Leu Arg Asp
        1970                1975                1980
Ile Trp Asp Trp Val Cys Ser Ile Leu Thr Asp Phe Lys Asn Trp
        1985                1990                1995
Leu Ser Ser Lys Leu Leu Pro Lys Leu Pro Gly Leu Pro Phe Ile
        2000                2005                2010
```

Ser Cys Gln Lys Gly Tyr Arg Gly Val Trp Ala Gly Thr Gly Val
2015                2020                2025

Met Thr Thr Arg Cys Pro Cys Gly Ala Thr Ile Ser Gly His Val
2030                2035                2040

Arg Met Gly Thr Met Lys Ile Thr Gly Pro Lys Thr Cys Leu Asn
2045                2050                2055

Met Trp Gln Gly Ser Phe Pro Ile Asn Cys Tyr Thr Glu Gly Pro
2060                2065                2070

Cys Val Pro Lys Pro Pro Asn Tyr Lys Thr Ala Ile Trp Arg
2075                2080                2085

Val Ala Ala Ser Glu Tyr Val Glu Ile Thr Gln His Gly Ser Phe
2090                2095                2100

Ser Tyr Val Thr Gly Leu Thr Asn Asp Asn Leu Lys Val Pro Cys
2105                2110                2115

Gln Val Pro Ala Pro Glu Phe Phe Ser Trp Val Asp Gly Val Gln
2120                2125                2130

Ile His Arg Phe Ala Pro Thr Pro Gly Pro Phe Phe Arg Asp Glu
2135                2140                2145

Val Thr Phe Thr Val Gly Leu Asn Ser Phe Val Val Gly Ser Gln
2150                2155                2160

Leu Pro Cys Asp Pro Glu Pro Asp Thr Glu Val Leu Ala Ser Met
2165                2170                2175

Leu Thr Asp Pro Ser His Ile Thr Ala Glu Ala Ala Ala Arg Arg
2180                2185                2190

Leu Ala Arg Gly Ser Pro Pro Ser Gln Ala Ser Ser Ser Ala Ser
2195                2200                2205

Gln Leu Ser Ala Pro Ser Leu Lys Ala Thr Cys Thr Thr His Lys
2210                2215                2220

Val Ala Tyr Asp Cys Asp Met Val Asp Ala Asn Leu Phe Met Gly
2225                2230                2235

Gly Asp Val Thr Arg Ile Glu Ser Asn Ser Lys Val Val Ile Leu
2240                2245                2250

Asp Ser Leu Asp Ser Met Thr Glu Val Glu Asp Asp Arg Glu Pro
2255                2260                2265

Ser Ile Pro Ser Glu Tyr Leu Ile Arg Arg Arg Lys Phe Pro Pro
2270                2275                2280

Ala Leu Pro Pro Trp Ala Arg Pro Asp Tyr Asn Pro Pro Val Val
2285                2290                2295

Glu Thr Trp Lys Arg Pro Asp Tyr Glu Pro Pro Thr Val Leu Gly
2300                2305                2310

Cys Ala Leu Pro Pro Thr Pro Gln Ala Pro Val Pro Pro Pro Arg
2315                2320                2325

Arg Arg Arg Ala Lys Val Leu Thr Gln Asp Asn Val Glu Gly Val
2330                2335                2340

Leu Lys Glu Met Ala Asp Lys Val Leu Ser Pro Leu Arg Asp Cys
2345                2350                2355

Asn Asp Ser Gly His Ser Thr Gly Ala Asp Thr Gly Ala Asp Ser
2360                2365                2370

Val Gln Gln Pro Pro Asp Glu Thr Ala Ala Ser Glu Ala Gly Ser
2375                2380                2385

Leu Ser Ser Met Pro Pro Leu Glu Gly Glu Pro Gly Asp Pro Asp
2390                2395                2400

```
Leu Glu Phe Glu Pro Ala Gly Ser Ala Pro Ser Glu Gly Glu
    2405                2410            2415

Cys Glu Val Ile Asp Ser Asp Lys Ser Trp Ser Thr Val Ser
    2420                2425            2430

Asp Gln Glu Asp Ser Thr Ile Cys Cys Ser Met Ser Tyr Ser Trp
    2435                2440            2445

Thr Gly Ala Leu Ile Thr Pro Cys Gly Pro Glu Glu Glu Lys Leu
    2450                2455            2460

Pro Ile Asn Pro Leu Ser Asn Ser Leu Met Arg Phe His Asn Lys
    2465                2470            2475

Val Tyr Ser Thr Thr Ser Arg Ser Ala Ser Gln Arg Ala Lys Lys
    2480                2485            2490

Val Thr Phe Asp Arg Val Gln Val Leu Asp Lys His Tyr Asp Ser
    2495                2500            2505

Val Leu Gln Asp Val Lys Arg Ala Ala Ser Lys Val Ser Ala Arg
    2510                2515            2520

Leu Leu Ser Ile Glu Glu Ala Cys Ala Leu Thr Pro Pro His Ser
    2525                2530            2535

Ala Lys Ser Arg Tyr Gly Phe Gly Ala Lys Glu Val Arg Ser Leu
    2540                2545            2550

Ser Arg Arg Ala Val Asn His Ile Gln Ser Val Trp Glu Asp Leu
    2555                2560            2565

Leu Glu Asp Gln His Thr Pro Ile Glu Thr Thr Ile Met Ala Lys
    2570                2575            2580

Asn Glu Val Phe Cys Val Asp Pro Ala Lys Gly Gly Lys Lys Ser
    2585                2590            2595

Ala Arg Leu Ile Val Tyr Pro Asp Leu Gly Val Arg Val Cys Glu
    2600                2605            2610

Lys Met Ala Leu Tyr Asp Ile Ala Gln Lys Leu Pro Lys Ala Ile
    2615                2620            2625

Met Gly Pro Ser Tyr Gly Phe Gln Tyr Ser Pro Ala Glu Arg Val
    2630                2635            2640

Asp Phe Leu Leu Lys Ala Trp Gly Ser Lys Lys Asp Pro Met Gly
    2645                2650            2655

Phe Ser Tyr Asp Thr Arg Cys Phe Asp Ser Thr Val Thr Glu Arg
    2660                2665            2670

Asp Ile Arg Thr Glu Glu Ser Ile Tyr Gln Ala Cys Ser Leu Pro
    2675                2680            2685

Gln Glu Ala Arg Val Ala Ile His Ser Leu Thr Glu Arg Leu Tyr
    2690                2695            2700

Val Gly Gly Pro Met Leu Asn Ser Lys Gly Gln Ser Cys Gly Tyr
    2705                2710            2715

Arg Arg Cys Arg Ala Ser Gly Val Phe Thr Thr Ser Met Gly Asn
    2720                2725            2730

Thr Met Thr Cys Tyr Ile Lys Ala Leu Ala Ala Cys Gln Ala Ala
    2735                2740            2745

Gly Ile Val Asp Pro Val Met Leu Val Cys Gly Asp Asp Leu Val
    2750                2755            2760

Val Ile Ser Glu Ser Gln Gly Asn Asp Glu Asp Glu Arg Asn Leu
    2765                2770            2775

Arg Ala Phe Thr Glu Ala Met Thr Arg Tyr Ser Ala Pro Pro Gly
    2780                2785            2790

Asp Leu Pro Arg Pro Glu Tyr Asp Leu Glu Leu Ile Thr Ser Cys
```

```
                    2795                2800                2805

Ser Ser Asn Val Ser Val Ala Leu Asp Pro Arg Gly Arg Arg Arg
    2810                2815                2820

Tyr Tyr Leu Thr Arg Asp Pro Thr Thr Pro Ile Ser Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Val Arg Met Val Ile Met
    2855                2860                2865

Thr His Phe Phe Ser Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895

Leu Asp Leu Pro Ala Ile Ile Glu Arg Leu His Gly Leu Asp Ala
    2900                2905                2910

Phe Ser Leu His Thr Tyr Ser Pro His Glu Leu Ser Arg Val Ala
    2915                2920                2925

Ala Thr Leu Arg Lys Leu Gly Ala Pro Pro Leu Arg Ala Trp Lys
    2930                2935                2940

Ser Arg Ala Arg Ala Val Arg Ala Ser Leu Ile Ala Gln Gly Gly
    2945                2950                2955

Lys Ala Ala Ile Cys Gly Arg Tyr Leu Phe Asn Trp Ala Val Lys
    2960                2965                2970

Thr Lys Leu Lys Leu Thr Pro Leu Pro Glu Ala Ser Arg Leu Asp
    2975                2980                2985

Leu Ser Gly Trp Phe Thr Val Gly Ala Gly Gly Gly Ile Phe
    2990                2995                3000

His Ser Val Ser His Ala Arg Pro Arg Leu Leu Leu Cys Leu
    3005                3010                3015

Leu Leu Leu Ser Val Gly Val Gly Ile Phe Leu Leu Pro Ala Arg
    3020                3025                3030

<210> SEQ ID NO 20
<211> LENGTH: 3033
<212> TYPE: PRT
<213> ORGANISM: Hepatitis C virus

<400> SEQUENCE: 20

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
        115                 120                 125
```

```
Gly Phe Ala Asp Leu Met Gly Tyr Ile Pro Val Val Gly Ala Pro Val
130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
                180                 185                 190

Glu Val Arg Asn Ile Ser Ser Gly Tyr Tyr Ala Thr Asn Asp Cys Ser
            195                 200                 205

Asn Asn Ser Ile Thr Trp Gln Leu Thr Asn Ala Val Leu His Leu Pro
210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Val Met Ala Ala Thr Ile Cys
                260                 265                 270

Ser Ala Leu Tyr Val Gly Asp Val Cys Gly Ala Val Met Ile Val Ser
            275                 280                 285

Gln Ala Phe Ile Leu Ser Pro Glu Arg His Asn Phe Thr Gln Glu Cys
290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Val Leu Ala Tyr
                325                 330                 335

Ala Ala Arg Val Pro Glu Leu Val Leu Glu Val Val Phe Gly Gly His
            340                 345                 350

Trp Gly Val Val Phe Gly Leu Ala Tyr Phe Ser Met Gln Gly Ala Trp
            355                 360                 365

Ala Lys Val Met Ala Ile Leu Leu Leu Val Ala Gly Val Asp Ala His
370                 375                 380

Thr Tyr Ser Thr Gly Ala Arg Ala Gly Gln Ala Ala Ser Gly Leu Thr
385                 390                 395                 400

Ser Leu Phe Ser Val Gly Ser Arg Gln Arg Leu Ser Leu Ile His Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Leu Tyr Val Asn Asn Phe Asn
                435                 440                 445

Ser Ser Gly Cys Pro Glu Arg Met Ser Ser Cys Arg Ala Leu Asp Asp
450                 455                 460

Phe Arg Ile Gly Trp Gly Thr Leu Glu Tyr Glu Thr Asn Val Thr Asn
465                 470                 475                 480

Asp Glu Asp Met Arg Pro Tyr Cys Trp His Tyr Pro Pro Lys Pro Cys
                485                 490                 495

Gly Ile Val Pro Ala Gly Thr Val Cys Gly Pro Val Tyr Cys Phe Thr
                500                 505                 510

Pro Ser Pro Val Val Gly Thr Thr Asp Lys Gln Gly Val Pro Thr
            515                 520                 525

Tyr Asn Trp Gly Glu Asn Glu Thr Asp Val Phe Leu Leu Asn Ser Thr
530                 535                 540

Arg Pro Pro Gln Gly Ala Trp Phe Gly Cys Thr Trp Met Asn Gly Thr
```

```
            545                 550                 555                 560
        Gly Phe Thr Lys Thr Cys Gly Ala Pro Pro Cys Arg Ile Arg Arg Asp
                        565                 570                 575

Tyr Asn Gly Thr Leu Asp Leu Leu Cys Pro Thr Asp Cys Phe Arg Lys
                        580                 585                 590

His Pro Glu Thr Thr Tyr Leu Arg Cys Gly Ser Gly Pro Trp Leu Thr
                        595                 600                 605

Pro Arg Cys Leu Val Asp Tyr Pro Tyr Arg Leu Trp His Tyr Pro Cys
                610                 615                 620

Thr Val Asn Phe Thr Ile Phe Lys Val Arg Met Tyr Val Gly Gly Val
        625                 630                 635                 640

Glu His Arg Leu Ser Ala Ala Cys Asn Phe Thr Arg Gly Asp Arg Cys
                        645                 650                 655

Asn Leu Glu Asp Arg Asp Arg Gly Gln Gln Ser Pro Leu Leu His Ser
                        660                 665                 670

Thr Thr Glu Trp Ala Val Leu Pro Cys Ser Phe Ser Asp Leu Pro Ala
                        675                 680                 685

Leu Ser Thr Gly Leu Leu His Leu His Gln Asn Ile Val Asp Val Gln
                        690                 695                 700

Tyr Leu Tyr Gly Leu Ser Pro Ala Ile Thr Arg Tyr Ile Val Lys Trp
        705                 710                 715                 720

Glu Trp Val Val Leu Leu Phe Leu Leu Ala Asp Ala Arg Val Cys
                        725                 730                 735

Ala Cys Leu Trp Met Leu Ile Ile Leu Gly Gln Ala Glu Ala Ala Leu
                        740                 745                 750

Glu Lys Leu Ile Ile Leu His Ser Ala Ser Ala Ala Ser Ala Asn Gly
                        755                 760                 765

Pro Leu Trp Phe Phe Ile Phe Phe Ile Ala Ala Trp Tyr Leu Lys Gly
                        770                 775                 780

Arg Val Val Pro Met Ala Thr Tyr Ser Val Leu Gly Leu Trp Ser Phe
        785                 790                 795                 800

Phe Leu Leu Val Leu Ala Leu Pro Gln Gln Ala Tyr Ala Leu Asp Ala
                        805                 810                 815

Val Glu Gln Gly Glu Leu Gly Leu Val Leu Leu Gly Val Ile Ser Ile
                        820                 825                 830

Phe Thr Leu Thr Pro Ala Tyr Lys Thr Leu Leu Ser Arg Ser Val Trp
                        835                 840                 845

Trp Leu Ser Tyr Met Leu Val Leu Ala Glu Ala Gln Ile Gln Gln Trp
                        850                 855                 860

Val Pro Pro Leu Glu Ala Arg Gly Gly Arg Asp Gly Ile Ile Trp Val
        865                 870                 875                 880

Ala Val Ile Leu Arg Pro Cys Leu Val Phe Glu Ile Thr Lys Trp Leu
                        885                 890                 895

Leu Ala Val Leu Gly Pro Ala Tyr Leu Leu Arg Ala Ser Leu Leu Arg
                        900                 905                 910

Val Pro Tyr Phe Val Arg Ala His Ala Leu Leu Arg Leu Cys Ala Leu
                        915                 920                 925

Val Arg His Leu Ala Gly Ala Arg Tyr Ile Gln Met Leu Leu Ile Thr
                        930                 935                 940

Ile Gly Arg Trp Thr Gly Thr Tyr Ile Tyr Asp His Leu Ser Pro Leu
        945                 950                 955                 960

Ser Thr Trp Ala Ala Gln Gly Leu Arg Asp Leu Ala Val Ala Val Glu
                        965                 970                 975
```

```
Pro Val Val Phe Ser Pro Met Glu Lys Lys Val Ile Val Trp Gly Ala
            980                 985                 990

Glu Thr Val Ala Cys Gly Asp Ile Leu His Gly Leu Pro Val Ser Ala
        995                 1000                1005

Arg Leu Gly Arg Glu Ile Leu Leu Gly Pro Ala Asp Gly Tyr Thr
    1010                1015                1020

Ser Lys Gly Trp Lys Leu Leu Ala Pro Ile Thr Ala Tyr Thr Gln
    1025                1030                1035

Gln Thr Arg Gly Leu Leu Gly Ala Ile Val Ser Leu Thr Gly
    1040                1045                1050

Arg Asp Lys Asn Glu Gln Ala Gly Gln Val Gln Val Leu Ser Ser
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Pro Arg
    1085                1090                1095

Gly Pro Val Thr Gln Met Tyr Ser Ser Ala Glu Gly Asp Leu Val
    1100                1105                1110

Gly Trp Pro Ser Pro Gly Thr Lys Ser Leu Asp Pro Cys Thr
    1115                1120                1125

Cys Gly Ala Val Asp Leu Tyr Leu Val Thr Arg Asn Ala Asp Val
    1130                1135                1140

Ile Pro Val Arg Arg Arg Asp Arg Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Ser Arg Gly His Ala Val Gly Leu Phe Arg Ala Ala Val
    1175                1180                1185

Cys Thr Arg Gly Val Ala Lys Ser Ile Asp Phe Ile Pro Val Glu
    1190                1195                1200

Ser Leu Asp Val Ala Ala Arg Ser Pro Ser Phe Ser Asp Asn Ser
    1205                1210                1215

Thr Pro Pro Ala Val Pro Gln Ser Tyr Gln Val Gly Tyr Leu His
    1220                1225                1230

Ala Pro Thr Gly Ser Gly Lys Ser Thr Lys Val Pro Ala Ala Tyr
    1235                1240                1245

Ala Ser Gln Gly Tyr Lys Val Leu Val Leu Asn Pro Ser Val Ala
    1250                1255                1260

Ala Thr Leu Gly Phe Gly Ala Tyr Met Ser Lys Ala His Gly Ile
    1265                1270                1275

Asn Pro Asn Ile Arg Thr Gly Val Arg Thr Val Thr Thr Gly Asp
    1280                1285                1290

Pro Ile Thr Tyr Ser Thr Tyr Gly Lys Phe Leu Ala Asp Gly Gly
    1295                1300                1305

Cys Ser Ala Gly Ala Tyr Asp Ile Ile Ile Cys Asp Glu Cys His
    1310                1315                1320

Ser Val Asp Ala Thr Thr Ile Leu Gly Ile Gly Thr Val Leu Asp
    1325                1330                1335

Gln Ala Glu Thr Ala Gly Ala Arg Leu Val Val Leu Ala Thr Ala
    1340                1345                1350

Thr Pro Pro Gly Thr Val Thr Thr Pro His Ser Asn Ile Glu Glu
    1355                1360                1365
```

-continued

```
Val Ala Leu Gly His Glu Gly Glu Ile Pro Phe Tyr Gly Lys Ala
    1370                1375                1380

Ile Pro Leu Ala Tyr Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Val Asn Ala Val Ala Tyr Tyr Arg Gly Leu Asp Val Ser
    1415                1420                1425

Val Ile Pro Leu Gln Gly Asp Val Val Val Ala Thr Asp Ala
    1430                1435                1440

Leu Met Thr Gly Phe Thr Gly Asp Phe Asp Ser Val Ile Asp Cys
    1445                1450                1455

Asn Val Ala Val Thr Gln Ile Val Asp Leu Ser Leu Asp Pro Thr
    1460                1465                1470

Phe Thr Ile Thr Thr Gln Thr Val Pro Gln Asp Ala Val Ser Arg
    1475                1480                1485

Ser Gln Arg Arg Gly Arg Thr Gly Arg Gly Arg Leu Gly Ile Tyr
    1490                1495                1500

Arg Tyr Val Ser Ser Gly Glu Arg Pro Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ala Glu Thr Thr Val Arg Leu Arg Ala Tyr Leu Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Gly Gly Asp Asn Phe Ala Tyr Leu Thr Ala Tyr
    1580                1585                1590

Gln Ala Thr Val Cys Ala Arg Ala Arg Ala Pro Pro Pro Ser Trp
    1595                1600                1605

Asp Leu Met Trp Lys Cys Leu Thr Arg Leu Lys Pro Thr Leu Asn
    1610                1615                1620

Gly Pro Thr Pro Leu Leu Tyr Arg Leu Gly Ala Val Thr Asn Glu
    1625                1630                1635

Val Thr Leu Thr His Pro Val Thr Lys Tyr Ile Ala Thr Cys Met
    1640                1645                1650

Gln Ala Asp Leu Glu Ile Met Thr Ser Thr Trp Val Leu Ala Gly
    1655                1660                1665

Gly Val Leu Ala Ala Val Ala Ser Tyr Cys Leu Ala Thr Gly Cys
    1670                1675                1680

Val Ser Ile Ile Gly Arg Leu His Leu Asn Asp Arg Val Val Val
    1685                1690                1695

Ala Pro Asp Lys Glu Ile Leu Tyr Glu Ala Phe Asp Glu Met Glu
    1700                1705                1710

Glu Cys Ala Ser Lys Ala Ala Leu Ile Glu Glu Gly Gln Arg Met
    1715                1720                1725

Ala Glu Met Leu Lys Thr Lys Ile Gln Gly Leu Leu Gln Gln Ala
    1730                1735                1740

Thr Arg Gln Ala Gln Asp Ile Gln Pro Ala Ile Gln Ser Ser Trp
    1745                1750                1755

Pro Lys Leu Glu Gln Phe Trp Ala Lys His Met Trp Asn Phe Ile
```

```
                1760                1765                1770
Ser Gly Ile Gln Tyr Leu Ala Gly Leu Ser Thr Leu Pro Gly Asn
    1775                1780                1785
Pro Ala Val Ala Ser Met Met Ala Phe Ser Ala Ala Leu Thr Ser
    1790                1795                1800
Pro Leu Pro Thr Ser Thr Thr Ile Leu Leu Asn Ile Met Gly Gly
    1805                1810                1815
Trp Leu Ala Ser Gln Ile Ala Pro Pro Ala Gly Ala Thr Gly Phe
    1820                1825                1830
Val Val Ser Gly Leu Val Gly Ala Ala Val Gly Ser Ile Gly Leu
    1835                1840                1845
Gly Lys Ile Leu Val Asp Val Leu Ala Gly Tyr Gly Ala Gly Ile
    1850                1855                1860
Ser Gly Ala Leu Val Ala Phe Lys Ile Met Ser Gly Glu Lys Pro
    1865                1870                1875
Thr Val Glu Asp Val Val Asn Leu Leu Pro Ala Ile Leu Ser Pro
    1880                1885                1890
Gly Ala Leu Val Val Gly Val Ile Cys Ala Ala Ile Leu Arg Arg
    1895                1900                1905
His Ile Gly Gln Gly Glu Gly Ala Val Gln Trp Met Asn Arg Leu
    1910                1915                1920
Ile Ala Phe Ala Ser Arg Gly Asn His Val Ala Pro Thr His Tyr
    1925                1930                1935
Val Ala Glu Ser Asp Ala Ser Gln Arg Val Thr Gln Ala Leu Ser
    1940                1945                1950
Ser Leu Thr Ile Thr Ser Leu Leu Arg Arg Leu His Ala Trp Ile
    1955                1960                1965
Thr Glu Asp Cys Pro Val Pro Cys Ser Gly Ser Trp Leu Arg Asp
    1970                1975                1980
Ile Trp Asp Trp Val Cys Ser Ile Leu Thr Asp Phe Lys Asn Trp
    1985                1990                1995
Leu Ser Ser Lys Leu Leu Pro Lys Leu Pro Gly Leu Pro Phe Ile
    2000                2005                2010
Ser Cys Gln Lys Gly Tyr Arg Gly Val Trp Ala Gly Thr Gly Val
    2015                2020                2025
Met Thr Thr Arg Cys Pro Cys Gly Ala Thr Ile Ser Gly His Val
    2030                2035                2040
Arg Met Gly Thr Met Lys Ile Thr Gly Pro Lys Thr Cys Leu Asn
    2045                2050                2055
Met Trp Gln Gly Ser Phe Pro Ile Asn Cys Tyr Thr Glu Gly Pro
    2060                2065                2070
Cys Val Pro Lys Pro Pro Asn Tyr Lys Thr Ala Ile Trp Arg
    2075                2080                2085
Val Ala Ala Ser Glu Tyr Val Glu Ile Thr Gln His Gly Ser Phe
    2090                2095                2100
Ser Tyr Val Thr Gly Leu Thr Asn Asp Asn Leu Lys Val Pro Cys
    2105                2110                2115
Gln Val Pro Ala Pro Glu Phe Phe Ser Trp Val Asp Gly Val Gln
    2120                2125                2130
Ile His Arg Phe Ala Pro Thr Pro Gly Pro Phe Phe Arg Asp Glu
    2135                2140                2145
Val Thr Phe Thr Val Gly Leu Asn Ser Phe Val Val Gly Ser Gln
    2150                2155                2160
```

```
Leu Pro Cys Asp Pro Glu Pro Asp Thr Glu Val Leu Ala Ser Met
2165                 2170                2175

Leu Thr Asp Pro Ser His Ile Thr Ala Glu Ala Ala Ala Arg Arg
2180                 2185                2190

Leu Ala Arg Gly Ser Pro Pro Ser Gln Ala Ser Ser Ser Ala Ser
2195                 2200                2205

Gln Leu Ser Ala Pro Ser Leu Lys Ala Thr Cys Thr Thr His Lys
2210                 2215                2220

Val Ala Tyr Asp Cys Asp Met Val Asp Ala Asn Leu Phe Met Gly
2225                 2230                2235

Gly Asp Val Thr Arg Ile Glu Ser Asn Ser Lys Val Val Ile Leu
2240                 2245                2250

Asp Ser Leu Asp Ser Met Thr Glu Val Glu Asp Arg Glu Pro
2255                 2260                2265

Ser Ile Pro Ser Glu Tyr Leu Ile Arg Arg Lys Phe Pro Pro
2270                 2275                2280

Ala Leu Pro Pro Trp Ala Arg Pro Asp Tyr Asn Pro Pro Val Val
2285                 2290                2295

Glu Thr Trp Lys Arg Pro Asp Tyr Glu Pro Pro Thr Val Leu Gly
2300                 2305                2310

Cys Ala Leu Pro Pro Thr Pro Gln Ala Pro Val Pro Pro Pro Arg
2315                 2320                2325

Arg Arg Arg Ala Lys Val Leu Thr Gln Asp Asn Val Glu Gly Val
2330                 2335                2340

Leu Lys Glu Met Ala Asp Lys Val Leu Ser Pro Leu Arg Asp Cys
2345                 2350                2355

Asn Asp Ser Gly His Ser Thr Gly Ala Asp Thr Gly Ala Asp Ser
2360                 2365                2370

Val Gln Gln Pro Pro Asp Glu Thr Ala Ala Ser Glu Ala Gly Ser
2375                 2380                2385

Leu Ser Ser Met Pro Pro Leu Glu Gly Glu Pro Gly Asp Pro Asp
2390                 2395                2400

Leu Glu Phe Glu Pro Ala Gly Ser Ala Pro Pro Ser Glu Gly Glu
2405                 2410                2415

Cys Glu Val Ile Asp Ser Asp Ser Lys Ser Trp Ser Thr Val Ser
2420                 2425                2430

Asp Gln Glu Asp Ser Ile Ile Cys Cys Ser Met Ser Tyr Ser Trp
2435                 2440                2445

Thr Gly Ala Leu Ile Thr Pro Cys Gly Pro Glu Glu Glu Lys Leu
2450                 2455                2460

Pro Ile Asn Pro Leu Ser Asn Ser Leu Met Arg Phe His Asn Lys
2465                 2470                2475

Val Tyr Ser Thr Thr Ser Arg Ser Ala Ser Gln Arg Ala Lys Lys
2480                 2485                2490

Val Thr Phe Asp Arg Val Gln Val Leu Asp Lys His Tyr Asp Ser
2495                 2500                2505

Val Leu Gln Asp Val Lys Arg Ala Ala Ser Lys Val Ser Ala Arg
2510                 2515                2520

Leu Leu Ser Ile Glu Glu Ala Cys Ala Leu Thr Pro Pro His Ser
2525                 2530                2535

Ala Lys Ser Arg Tyr Gly Phe Gly Ala Lys Glu Val Arg Ser Leu
2540                 2545                2550
```

```
Ser Arg Arg Ala Val Asn His Ile Gln Ser Val Trp Glu Asp Leu
2555                2560                2565

Leu Glu Asp Gln His Thr Pro Ile Glu Thr Thr Ile Met Ala Lys
2570                2575                2580

Asn Glu Val Phe Cys Val Asp Pro Ala Lys Gly Gly Lys Lys Ser
2585                2590                2595

Ala Arg Leu Ile Val Tyr Pro Asp Leu Gly Val Arg Val Cys Glu
2600                2605                2610

Lys Met Ala Leu Tyr Asp Ile Ala Gln Lys Leu Pro Lys Ala Ile
2615                2620                2625

Met Gly Pro Ser Tyr Gly Phe Gln Tyr Ser Pro Ala Glu Arg Val
2630                2635                2640

Asp Phe Leu Leu Lys Ala Trp Gly Ser Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro
2675                2680                2685

Gln Glu Ala Arg Val Ala Ile His Ser Leu Thr Glu Arg Leu Tyr
2690                2695                2700

Val Gly Gly Pro Met Leu Asn Ser Lys Gly Gln Ser Cys Gly Tyr
2705                2710                2715

Arg Arg Cys Arg Ala Ser Gly Val Phe Thr Thr Ser Met Gly Asn
2720                2725                2730

Thr Met Thr Cys Tyr Ile Lys Ala Leu Ala Ala Cys Gln Ala Ala
2735                2740                2745

Gly Ile Val Asp Pro Val Met Leu Val Cys Gly Asp Asp Leu Val
2750                2755                2760

Val Ile Ser Glu Ser Gln Gly Asn Asp Glu Asp Glu Arg Asn Leu
2765                2770                2775

Arg Ala Phe Thr Glu Ala Met Thr Arg Tyr Ser Ala Pro Pro Gly
2780                2785                2790

Asp Leu Pro Arg Pro Glu Tyr Asp Leu Glu Leu Ile Thr Ser Cys
2795                2800                2805

Ser Ser Asn Val Ser Val Ala Leu Asp Pro Arg Gly Arg Arg Arg
2810                2815                2820

Tyr Tyr Leu Thr Arg Asp Pro Thr Thr Pro Ile Ser Arg Ala Ala
2825                2830                2835

Trp Glu Thr Val Arg His Ser Pro Val Asn Ser Trp Leu Gly Asn
2840                2845                2850

Ile Ile Gln Tyr Ala Pro Thr Ile Trp Val Arg Met Val Ile Met
2855                2860                2865

Thr His Phe Phe Ser Ile Leu Leu Ala Gln Asp Thr Leu Asn Gln
2870                2875                2880

Asn Leu Asn Phe Glu Met Tyr Gly Ala Val Tyr Ser Val Asn Pro
2885                2890                2895

Leu Asp Leu Pro Ala Ile Ile Glu Arg Leu His Gly Leu Asp Ala
2900                2905                2910

Phe Ser Leu His Thr Tyr Ser Pro His Glu Leu Ser Arg Val Ala
2915                2920                2925

Ala Thr Leu Arg Lys Leu Gly Ala Pro Pro Leu Arg Ala Trp Lys
2930                2935                2940

Ser Arg Ala Arg Ala Val Arg Ala Ser Leu Ile Ala Gln Gly Gly
```

-continued

```
                2945                2950                2955
Lys Ala Ala Ile Cys Gly Arg Tyr Leu Phe Asn Trp Ala Val Lys
        2960                2965                2970
Thr Lys Leu Lys Leu Thr Pro Leu Pro Glu Ala Ser Arg Leu Asp
    2975                2980                2985
Leu Ser Gly Trp Phe Thr Val Gly Ala Gly Gly Gly Ile Phe
        2990                2995                3000
His Ser Val Ser His Ala Arg Pro Arg Leu Leu Leu Cys Leu
    3005                3010                3015
Leu Leu Phe Ser Val Gly Val Gly Ile Phe Leu Leu Pro Ala Arg
        3020                3025                3030

<210> SEQ ID NO 21
<211> LENGTH: 3033
<212> TYPE: PRT
<213> ORGANISM: Hepatitis C virus

<400> SEQUENCE: 21

Met Ser Thr Asn Pro Lys Pro Gln Arg Lys Thr Lys Arg Asn Thr Asn
1               5                   10                  15
Arg Arg Pro Gln Asp Val Lys Phe Pro Gly Gly Gly Gln Ile Val Gly
            20                  25                  30
Gly Val Tyr Leu Leu Pro Arg Arg Gly Pro Arg Leu Gly Val Arg Ala
        35                  40                  45
Thr Arg Lys Thr Ser Glu Arg Ser Gln Pro Arg Gly Arg Arg Gln Pro
    50                  55                  60
Ile Pro Lys Asp Arg Arg Ser Thr Gly Lys Ser Trp Gly Lys Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Thr Trp Gly Pro Thr Asp Pro
            100                 105                 110
Arg His Arg Ser Arg Asn Leu Gly Lys Val Ile Asp Thr Ile Thr Cys
        115                 120                 125
Gly Phe Ala Asp Leu Met Gly Tyr Ile Pro Val Val Gly Ala Pro Val
    130                 135                 140
Gly Gly Val Ala Arg Ala Leu Ala His Gly Val Arg Val Leu Glu Asp
145                 150                 155                 160
Gly Ile Asn Tyr Ala Thr Gly Asn Leu Pro Gly Cys Ser Phe Ser Ile
                165                 170                 175
Phe Leu Leu Ala Leu Leu Ser Cys Ile Thr Val Pro Val Ser Ala Val
            180                 185                 190
Glu Val Arg Asn Ile Ser Ser Gly Tyr Tyr Ala Thr Asn Asp Cys Ser
        195                 200                 205
Asn Asn Ser Ile Thr Trp Gln Leu Thr Asn Ala Val Leu His Leu Pro
    210                 215                 220
Gly Cys Val Pro Cys Glu Asn Asp Asn Gly Thr Leu Arg Cys Trp Ile
225                 230                 235                 240
Gln Val Thr Pro Asn Val Ala Val Lys His Arg Gly Ala Leu Thr His
                245                 250                 255
Asn Leu Arg Thr His Val Asp Val Val Met Ala Ala Thr Ile Cys
            260                 265                 270
Ser Ala Leu Tyr Val Gly Asp Val Cys Gly Ala Val Met Ile Val Ser
        275                 280                 285
```

```
Gln Ala Phe Ile Leu Ser Pro Glu Arg His Asn Phe Thr Gln Glu Cys
    290                 295                 300
Asn Cys Ser Ile Tyr Gln Gly His Ile Thr Gly His Arg Met Ala Trp
305                 310                 315                 320
Asp Met Met Leu Asn Trp Ser Pro Thr Leu Thr Met Val Leu Ala Tyr
                325                 330                 335
Ala Ala Arg Val Pro Glu Leu Val Leu Glu Val Val Phe Gly Gly His
            340                 345                 350
Trp Gly Val Val Phe Gly Leu Ala Tyr Phe Ser Met Gln Gly Ala Trp
                355                 360                 365
Ala Lys Val Met Ala Ile Leu Leu Leu Val Ala Gly Val Asp Ala His
    370                 375                 380
Thr Tyr Ser Thr Gly Ala Arg Ala Gly Gln Ala Ala Ser Gly Leu Thr
385                 390                 395                 400
Ser Leu Phe Ser Val Gly Ser Arg Gln Arg Leu Ser Leu Ile His Thr
                405                 410                 415
Asn Gly Ser Trp His Ile Asn Arg Thr Ala Leu Asn Cys Asn Asp Ser
            420                 425                 430
Leu His Thr Gly Phe Ile Ala Ser Leu Leu Tyr Val Asn Asn Phe Asn
    435                 440                 445
Ser Ser Gly Cys Pro Glu Arg Met Ser Ser Cys Arg Ala Leu Asp Asp
450                 455                 460
Phe Arg Ile Gly Trp Gly Thr Leu Glu Tyr Glu Thr Asn Val Thr Asn
465                 470                 475                 480
Asp Glu Asp Met Arg Pro Tyr Cys Trp His Tyr Pro Pro Lys Pro Cys
                485                 490                 495
Gly Ile Val Pro Ala Gly Thr Val Cys Gly Pro Val Tyr Cys Phe Thr
            500                 505                 510
Pro Ser Pro Val Val Gly Thr Thr Asp Lys Gln Gly Val Pro Thr
    515                 520                 525
Tyr Asn Trp Gly Glu Asn Glu Thr Asp Val Phe Leu Leu Asn Ser Thr
530                 535                 540
Arg Pro Pro Gln Gly Ala Trp Phe Gly Cys Thr Trp Met Asn Gly Thr
545                 550                 555                 560
Gly Phe Thr Lys Thr Cys Gly Ala Pro Pro Cys Arg Ile Arg Arg Asp
                565                 570                 575
Tyr Asn Gly Thr Leu Asp Leu Leu Cys Pro Thr Asp Cys Phe Arg Lys
            580                 585                 590
His Pro Glu Thr Thr Tyr Leu Arg Cys Gly Ser Gly Pro Trp Leu Thr
    595                 600                 605
Pro Arg Cys Leu Val Asp Tyr Pro Tyr Arg Leu Trp His Tyr Pro Cys
610                 615                 620
Thr Val Asn Phe Thr Ile Phe Lys Val Arg Met Tyr Val Gly Gly Val
625                 630                 635                 640
Glu His Arg Leu Ser Ala Ala Cys Asn Phe Thr Arg Gly Asp Arg Cys
                645                 650                 655
Asn Leu Glu Asp Arg Asp Arg Gly Gln Gln Ser Pro Leu Leu His Ser
            660                 665                 670
Thr Thr Glu Trp Ala Val Leu Pro Cys Ser Phe Ser Asp Leu Pro Ala
    675                 680                 685
Leu Ser Thr Gly Leu Leu His Leu His Gln Asn Ile Val Asp Val Gln
    690                 695                 700
Tyr Leu Tyr Gly Leu Ser Pro Ala Ile Thr Arg Tyr Ile Val Lys Trp
```

-continued

```
            705                 710                 715                 720
         Glu Trp Val Val Leu Leu Phe Leu Leu Ala Asp Ala Arg Val Cys
                         725                 730                 735
         Ala Cys Leu Trp Met Leu Ile Ile Leu Gly Gln Ala Glu Ala Leu
                         740                 745                 750
         Glu Lys Leu Ile Ile Leu His Ser Ala Ser Ala Ala Ser Ala Asn Gly
                         755                 760                 765
         Pro Leu Trp Phe Phe Ile Phe Phe Ile Ala Ala Trp Tyr Leu Lys Gly
                         770                 775                 780
         Arg Val Val Pro Met Ala Thr Tyr Ser Val Leu Gly Leu Trp Ser Phe
         785                 790                 795                 800
         Phe Leu Leu Val Leu Ala Leu Pro Gln Gln Ala Tyr Ala Leu Asp Ala
                         805                 810                 815
         Val Glu Gln Gly Glu Leu Gly Leu Val Leu Gly Val Ile Ser Ile
                         820                 825                 830
         Phe Thr Leu Thr Pro Ala Tyr Lys Thr Leu Leu Ser Arg Ser Val Trp
                         835                 840                 845
         Trp Leu Ser Tyr Met Leu Val Leu Ala Glu Ala Gln Ile Gln Gln Trp
         850                 855                 860
         Val Pro Pro Leu Glu Ala Arg Gly Gly Arg Asp Gly Ile Ile Trp Val
         865                 870                 875                 880
         Ala Val Ile Leu Arg Pro Cys Leu Val Phe Glu Ile Thr Lys Trp Leu
                         885                 890                 895
         Leu Ala Val Leu Gly Pro Ala Tyr Leu Leu Arg Ala Ser Leu Leu Arg
                         900                 905                 910
         Val Pro Tyr Phe Val Arg Ala His Ala Leu Leu Arg Leu Cys Ala Leu
                         915                 920                 925
         Val Arg His Leu Ala Gly Ala Arg Tyr Ile Gln Met Leu Leu Ile Thr
                         930                 935                 940
         Ile Gly Arg Trp Thr Gly Thr Tyr Ile Tyr Asp His Leu Ser Pro Leu
         945                 950                 955                 960
         Ser Thr Trp Ala Ala Gln Gly Leu Arg Asp Leu Ala Val Ala Val Glu
                         965                 970                 975
         Pro Val Val Phe Ser Pro Met Glu Lys Lys Val Ile Val Trp Gly Ala
                         980                 985                 990
         Glu Thr Val Ala Cys Gly Asp Ile Leu His Gly Leu Pro Val Ser Ala
                         995                 1000                1005
         Arg Leu Gly Arg Glu Ile Leu Leu Gly Pro Ala Asp Gly Tyr Thr
         1010                1015                1020
         Ser Lys Gly Trp Lys Leu Leu Ala Pro Ile Thr Ala Tyr Thr Gln
         1025                1030                1035
         Gln Thr Arg Gly Leu Leu Gly Ala Ile Val Val Ser Leu Thr Gly
         1040                1045                1050
         Arg Asp Lys Asn Glu Gln Ala Gly Gln Val Gln Val Leu Ser Ser
         1055                1060                1065
         Val Thr Gln Ser Phe Leu Gly Thr Ser Ile Ser Gly Val Leu Trp
         1070                1075                1080
         Thr Val Tyr His Gly Ala Gly Asn Lys Thr Leu Ala Gly Pro Arg
         1085                1090                1095
         Gly Pro Val Thr Gln Met Tyr Ser Ser Ala Glu Gly Asp Leu Val
         1100                1105                1110
         Gly Trp Pro Ser Pro Pro Gly Thr Lys Ser Leu Asp Pro Cys Thr
         1115                1120                1125
```

```
Cys Gly Ala Val Asp Leu Tyr Leu Val Thr Arg Asn Ala Asp Val
1130                1135                1140

Ile Pro Val Arg Arg Asp Arg Arg Gly Ala Leu Leu Ser
1145                1150                1155

Pro Arg Pro Leu Ser Thr Leu Lys Gly Ser Ser Gly Gly Pro Val
1160                1165                1170

Leu Cys Ser Arg Gly His Ala Val Gly Leu Phe Arg Ala Ala Val
1175                1180                1185

Cys Thr Arg Gly Val Ala Lys Ser Ile Asp Phe Ile Pro Val Glu
1190                1195                1200

Ser Leu Asp Val Ala Ala Arg Ser Pro Ser Phe Ser Asp Asn Ser
1205                1210                1215

Thr Pro Pro Ala Val Pro Gln Ser Tyr Gln Val Gly Tyr Leu His
1220                1225                1230

Ala Pro Thr Gly Ser Gly Lys Ser Thr Lys Val Pro Ala Ala Tyr
1235                1240                1245

Ala Ser Gln Gly Tyr Lys Val Leu Val Leu Asn Pro Ser Val Ala
1250                1255                1260

Ala Thr Leu Gly Phe Gly Ala Tyr Met Ser Lys Ala His Gly Ile
1265                1270                1275

Asn Pro Asn Ile Arg Thr Gly Val Arg Thr Val Thr Thr Gly Asp
1280                1285                1290

Pro Ile Thr Tyr Ser Thr Tyr Gly Lys Phe Leu Ala Asp Gly Gly
1295                1300                1305

Cys Ser Ala Gly Ala Tyr Asp Ile Ile Ile Cys Asp Glu Cys His
1310                1315                1320

Ser Val Asp Ala Thr Thr Ile Leu Gly Ile Gly Thr Val Leu Asp
1325                1330                1335

Gln Ala Glu Thr Ala Gly Ala Arg Leu Val Val Leu Ala Thr Ala
1340                1345                1350

Thr Pro Pro Gly Thr Val Thr Thr Pro His Ser Asn Ile Glu Glu
1355                1360                1365

Val Ala Leu Gly His Glu Gly Glu Ile Pro Phe Tyr Gly Lys Ala
1370                1375                1380

Ile Pro Leu Ala Tyr Ile Lys Gly Gly Arg His Leu Ile Phe Cys
1385                1390                1395

His Ser Lys Lys Lys Cys Asp Glu Leu Ala Ala Ala Leu Arg Gly
1400                1405                1410

Met Gly Val Asn Ala Val Ala Tyr Tyr Arg Gly Leu Asp Val Ser
1415                1420                1425

Val Ile Pro Leu Gln Gly Asp Val Val Val Val Ala Thr Asp Ala
1430                1435                1440

Leu Met Thr Gly Phe Thr Gly Asp Phe Asp Ser Val Ile Asp Cys
1445                1450                1455

Asn Val Ala Val Thr Gln Ile Val Asp Leu Ser Leu Asp Pro Thr
1460                1465                1470

Phe Thr Ile Thr Thr Gln Thr Val Pro Gln Asp Ala Val Ser Arg
1475                1480                1485

Ser Gln Arg Arg Gly Arg Thr Gly Arg Gly Arg Leu Gly Ile Tyr
1490                1495                1500

Arg Tyr Val Ser Ser Gly Glu Arg Pro Ser Gly Met Phe Asp Ser
1505                1510                1515
```

```
Val Val Leu Cys Glu Cys Tyr Asp Ala Gly Ala Ala Trp Tyr Glu
1520                1525                1530

Leu Thr Pro Ala Glu Thr Thr Val Arg Leu Arg Ala Tyr Leu Asn
1535                1540                1545

Thr Pro Gly Leu Pro Val Cys Gln Asp His Leu Glu Phe Trp Glu
1550                1555                1560

Ala Val Phe Thr Gly Leu Thr His Ile Asp Ala His Phe Leu Ser
1565                1570                1575

Gln Thr Lys Gln Gly Gly Asp Asn Phe Ala Tyr Leu Thr Ala Tyr
1580                1585                1590

Gln Ala Thr Val Cys Ala Arg Ala Arg Ala Pro Pro Pro Ser Trp
1595                1600                1605

Asp Leu Met Trp Lys Cys Leu Thr Arg Leu Lys Pro Thr Leu Asn
1610                1615                1620

Gly Pro Thr Pro Leu Leu Tyr Arg Leu Gly Ala Val Thr Asn Glu
1625                1630                1635

Val Thr Leu Thr His Pro Val Thr Lys Tyr Ile Ala Thr Cys Met
1640                1645                1650

Gln Ala Asp Leu Glu Ile Met Thr Ser Thr Trp Val Leu Ala Gly
1655                1660                1665

Gly Val Leu Ala Ala Val Ala Ser Tyr Cys Leu Ala Thr Gly Cys
1670                1675                1680

Val Ser Ile Ile Gly Arg Leu His Leu Asn Asp Arg Val Val Val
1685                1690                1695

Ala Pro Asp Lys Glu Ile Leu Tyr Glu Ala Phe Asp Glu Met Glu
1700                1705                1710

Glu Cys Ala Ser Lys Ala Ala Leu Ile Glu Glu Gly Gln Arg Met
1715                1720                1725

Ala Glu Met Leu Lys Thr Lys Ile Gln Gly Leu Leu Gln Gln Ala
1730                1735                1740

Thr Arg Gln Ala Gln Asp Ile Gln Pro Ala Ile Gln Ser Ser Trp
1745                1750                1755

Pro Lys Leu Glu Gln Phe Trp Ala Lys His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Pro Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Ile Leu Val Asp Val Leu Ala Gly Tyr Gly Ala Gly Ile
1850                1855                1860

Ser Gly Ala Leu Val Ala Phe Lys Ile Met Ser Gly Glu Lys Pro
1865                1870                1875

Thr Val Glu Asp Val Val Asn Leu Leu Pro Ala Ile Leu Ser Pro
1880                1885                1890

Gly Ala Leu Val Val Gly Val Ile Cys Ala Ala Ile Leu Arg Arg
1895                1900                1905

His Ile Gly Gln Gly Glu Gly Ala Val Gln Trp Met Asn Arg Leu
```

-continued

```
              1910                1915                1920

Ile  Ala  Phe  Ala  Ser  Arg  Gly  Asn  His  Val  Ala  Pro  Thr  His  Tyr
         1925                1930                1935

Val  Ala  Glu  Ser  Asp  Ala  Ser  Gln  Arg  Val  Thr  Gln  Ala  Leu  Ser
         1940                1945                1950

Ser  Leu  Thr  Ile  Thr  Ser  Leu  Leu  Arg  Arg  Leu  His  Ala  Trp  Ile
         1955                1960                1965

Thr  Glu  Asp  Cys  Pro  Val  Pro  Cys  Ser  Gly  Ser  Trp  Leu  Arg  Asp
         1970                1975                1980

Ile  Trp  Asp  Trp  Val  Cys  Ser  Ile  Leu  Thr  Asp  Phe  Lys  Asn  Trp
         1985                1990                1995

Leu  Ser  Ser  Lys  Leu  Leu  Pro  Lys  Leu  Pro  Gly  Leu  Pro  Phe  Ile
         2000                2005                2010

Ser  Cys  Gln  Lys  Gly  Tyr  Arg  Gly  Val  Trp  Ala  Gly  Thr  Gly  Val
         2015                2020                2025

Met  Thr  Thr  Arg  Cys  Pro  Cys  Gly  Ala  Thr  Ile  Ser  Gly  His  Val
         2030                2035                2040

Arg  Met  Gly  Thr  Met  Lys  Ile  Thr  Gly  Pro  Lys  Thr  Cys  Leu  Asn
         2045                2050                2055

Met  Trp  Gln  Gly  Ser  Phe  Pro  Ile  Asn  Cys  Tyr  Thr  Glu  Gly  Pro
         2060                2065                2070

Cys  Val  Pro  Lys  Pro  Pro  Asn  Tyr  Lys  Thr  Ala  Ile  Trp  Arg
         2075                2080                2085

Val  Ala  Ala  Ser  Glu  Tyr  Val  Glu  Ile  Thr  Gln  His  Gly  Ser  Phe
         2090                2095                2100

Ser  Tyr  Val  Thr  Gly  Leu  Thr  Asn  Asp  Asn  Leu  Lys  Val  Pro  Cys
         2105                2110                2115

Gln  Val  Pro  Ala  Pro  Glu  Phe  Phe  Ser  Trp  Val  Asp  Gly  Val  Gln
         2120                2125                2130

Ile  His  Arg  Phe  Ala  Pro  Thr  Pro  Gly  Pro  Phe  Phe  Arg  Asp  Glu
         2135                2140                2145

Val  Thr  Phe  Thr  Val  Gly  Leu  Asn  Ser  Phe  Val  Val  Gly  Ser  Gln
         2150                2155                2160

Leu  Pro  Cys  Asp  Pro  Glu  Pro  Asp  Thr  Glu  Val  Leu  Ala  Ser  Met
         2165                2170                2175

Leu  Thr  Asp  Pro  Ser  His  Ile  Thr  Ala  Glu  Ala  Ala  Arg  Arg
         2180                2185                2190

Leu  Ala  Arg  Gly  Ser  Pro  Pro  Ser  Gln  Ala  Ser  Ser  Ser  Ala  Ser
         2195                2200                2205

Gln  Leu  Ser  Ala  Pro  Ser  Leu  Lys  Ala  Thr  Cys  Thr  Thr  His  Lys
         2210                2215                2220

Val  Ala  Tyr  Asp  Cys  Asp  Met  Val  Asp  Ala  Asn  Leu  Phe  Met  Gly
         2225                2230                2235

Gly  Asp  Val  Thr  Arg  Ile  Glu  Ser  Asn  Ser  Lys  Val  Val  Ile  Leu
         2240                2245                2250

Asp  Ser  Leu  Asp  Ser  Met  Thr  Glu  Val  Glu  Asp  Asp  Arg  Glu  Pro
         2255                2260                2265

Ser  Ile  Pro  Ser  Glu  Tyr  Leu  Ile  Arg  Arg  Arg  Lys  Phe  Pro  Pro
         2270                2275                2280

Ala  Leu  Pro  Pro  Trp  Ala  Arg  Pro  Asp  Tyr  Asn  Pro  Pro  Val  Val
         2285                2290                2295

Glu  Thr  Trp  Lys  Arg  Pro  Asp  Tyr  Glu  Pro  Pro  Thr  Val  Leu  Gly
         2300                2305                2310
```

```
Cys Ala Leu Pro Pro Thr Pro Gln Ala Pro Val Pro Pro Pro Arg
    2315            2320                2325

Arg Arg Arg Ala Lys Val Leu Thr Gln Asp Asn Val Glu Gly Val
    2330            2335                2340

Leu Lys Glu Met Ala Asp Lys Val Leu Ser Pro Leu Arg Asp Cys
    2345            2350                2355

Asn Asp Ser Gly His Ser Thr Gly Ala Asp Thr Gly Ala Asp Ser
    2360            2365                2370

Val Gln Gln Pro Pro Asp Glu Thr Ala Ala Ser Glu Ala Gly Ser
    2375            2380                2385

Leu Ser Ser Met Pro Pro Leu Glu Gly Glu Pro Gly Asp Pro Asp
    2390            2395                2400

Leu Glu Phe Glu Pro Ala Gly Ser Ala Pro Pro Ser Glu Gly Glu
    2405            2410                2415

Cys Glu Val Ile Asp Ser Asp Ser Lys Ser Trp Ser Thr Val Ser
    2420            2425                2430

Asp Gln Glu Asp Ser Ile Thr Cys Cys Ser Met Ser Tyr Ser Trp
    2435            2440                2445

Thr Gly Ala Leu Ile Thr Pro Cys Gly Pro Glu Glu Glu Lys Leu
    2450            2455                2460

Pro Ile Asn Pro Leu Ser Asn Ser Leu Met Arg Phe His Asn Lys
    2465            2470                2475

Val Tyr Ser Thr Thr Ser Arg Ser Ala Ser Gln Arg Ala Lys Lys
    2480            2485                2490

Val Thr Phe Asp Arg Val Gln Val Leu Asp Lys His Tyr Asp Ser
    2495            2500                2505

Val Leu Gln Asp Val Lys Arg Ala Ala Ser Lys Val Ser Ala Arg
    2510            2515                2520

Leu Leu Ser Ile Glu Glu Ala Cys Ala Leu Thr Pro Pro His Ser
    2525            2530                2535

Ala Lys Ser Arg Tyr Gly Phe Gly Ala Lys Glu Val Arg Ser Leu
    2540            2545                2550

Ser Arg Arg Ala Val Asn His Ile Gln Ser Val Trp Glu Asp Leu
    2555            2560                2565

Leu Glu Asp Gln His Thr Pro Ile Glu Thr Thr Ile Met Ala Lys
    2570            2575                2580

Asn Glu Val Phe Cys Val Asp Pro Ala Lys Gly Gly Lys Lys Ser
    2585            2590                2595

Ala Arg Leu Ile Val Tyr Pro Asp Leu Gly Val Arg Val Cys Glu
    2600            2605                2610

Lys Met Ala Leu Tyr Asp Ile Ala Gln Lys Leu Pro Lys Ala Ile
    2615            2620                2625

Met Gly Pro Ser Tyr Gly Phe Gln Tyr Ser Pro Ala Glu Arg Val
    2630            2635                2640

Asp Phe Leu Leu Lys Ala Trp Gly Ser Lys Lys Asp Pro Met Gly
    2645            2650                2655

Phe Ser Tyr Asp Thr Arg Cys Phe Asp Ser Thr Val Thr Glu Arg
    2660            2665                2670

Asp Ile Arg Thr Glu Glu Ser Ile Tyr Gln Ala Cys Ser Leu Pro
    2675            2680                2685

Gln Glu Ala Arg Val Ala Ile His Ser Leu Thr Glu Arg Leu Tyr
    2690            2695                2700
```

Val Gly Gly Pro Met Leu Asn Ser Lys Gly Gln Ser Cys Gly Tyr
2705               2710                  2715

Arg Arg Cys Arg Ala Ser Gly Val Phe Thr Thr Ser Met Gly Asn
2720               2725                  2730

Thr Met Thr Cys Tyr Ile Lys Ala Leu Ala Ala Cys Gln Ala Ala
2735               2740                  2745

Gly Ile Val Asp Pro Val Met Leu Val Cys Gly Asp Asp Leu Val
2750               2755                  2760

Val Ile Ser Glu Ser Gln Gly Asn Asp Glu Asp Glu Arg Asn Leu
2765               2770                  2775

Arg Ala Phe Thr Glu Ala Met Thr Arg Tyr Ser Ala Pro Pro Gly
2780               2785                  2790

Asp Leu Pro Arg Pro Glu Tyr Asp Leu Glu Leu Ile Thr Ser Cys
2795               2800                  2805

Ser Ser Asn Val Ser Val Ala Leu Asp Pro Arg Gly Arg Arg Arg
2810               2815                  2820

Tyr Tyr Leu Thr Arg Asp Pro Thr Thr Pro Ile Ser Arg Ala Ala
2825               2830                  2835

Trp Glu Thr Val Arg His Ser Pro Val Asn Ser Trp Leu Gly Asn
2840               2845                  2850

Ile Ile Gln Tyr Ala Pro Thr Ile Trp Val Arg Met Val Ile Met
2855               2860                  2865

Thr His Phe Phe Ser Ile Leu Leu Ala Gln Asp Thr Leu Asn Gln
2870               2875                  2880

Asn Leu Asn Phe Glu Met Tyr Gly Ala Val Tyr Ser Val Asn Pro
2885               2890                  2895

Leu Asp Leu Pro Ala Ile Ile Glu Arg Leu His Gly Leu Asp Ala
2900               2905                  2910

Phe Ser Leu His Thr Tyr Ser Pro His Glu Leu Ser Arg Val Ala
2915               2920                  2925

Ala Thr Leu Arg Lys Leu Gly Ala Pro Pro Leu Arg Ala Trp Lys
2930               2935                  2940

Ser Arg Ala Arg Ala Val Arg Ala Ser Leu Ile Ala Gln Gly Gly
2945               2950                  2955

Lys Ala Ala Ile Cys Gly Arg Tyr Leu Phe Asn Trp Ala Val Lys
2960               2965                  2970

Thr Lys Leu Lys Leu Thr Pro Leu Pro Glu Ala Ser Arg Leu Asp
2975               2980                  2985

Leu Ser Gly Trp Phe Thr Val Gly Ala Gly Gly Gly Ile Phe
2990               2995                  3000

His Ser Val Ser His Ala Arg Pro Arg Leu Leu Leu Leu Cys Leu
3005               3010                  3015

Leu Leu Phe Ser Val Gly Val Gly Ile Phe Leu Leu Pro Ala Arg
3020               3025                  3030

<210> SEQ ID NO 22
<211> LENGTH: 3033
<212> TYPE: PRT
<213> ORGANISM: Hepatitis C virus

<400> SEQUENCE: 22

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

```
Gly Val Tyr Leu Leu Pro Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Thr Trp Gly Pro Thr Asp Pro
                100                 105                 110

Arg His Arg Ser Arg Asn Leu Gly Lys Val Ile Asp Thr Ile Thr Cys
                115                 120                 125

Gly Phe Ala Asp Leu Met Gly Tyr Ile Pro Val Val Gly Ala Pro Val
        130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
                180                 185                 190

Glu Val Arg Asn Ile Ser Ser Gly Tyr Tyr Ala Thr Asn Asp Cys Ser
        195                 200                 205

Asn Asn Ser Ile Thr Trp Gln Leu Thr Asn Ala Val Leu His Leu Pro
        210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Val Met Ala Ala Thr Ile Cys
                260                 265                 270

Ser Ala Leu Tyr Val Gly Asp Val Cys Gly Ala Val Met Ile Val Ser
        275                 280                 285

Gln Ala Phe Ile Leu Ser Pro Glu Arg His Asn Phe Thr Gln Glu Cys
        290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Val Leu Ala Tyr
                325                 330                 335

Ala Ala Arg Val Pro Glu Leu Val Leu Glu Val Val Phe Gly Gly His
                340                 345                 350

Trp Gly Val Val Phe Gly Leu Ala Tyr Phe Ser Met Gln Gly Ala Trp
        355                 360                 365

Ala Lys Val Met Ala Ile Leu Leu Leu Val Ala Gly Val Asp Ala His
        370                 375                 380

Thr Tyr Ser Thr Gly Ala Arg Ala Gly Gln Ala Ala Ser Gly Leu Thr
385                 390                 395                 400

Ser Leu Phe Ser Val Gly Ser Arg Gln Arg Leu Ser Leu Ile His Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Leu Tyr Val Asn Asn Phe Asn
        435                 440                 445
```

```
Ser Ser Gly Cys Pro Glu Arg Met Ser Ser Cys Arg Ala Leu Asp Asp
450                 455                 460

Phe Arg Ile Gly Trp Gly Thr Leu Glu Tyr Glu Thr Asn Val Thr Asn
465                 470                 475                 480

Asp Glu Asp Met Arg Pro Tyr Cys Trp His Tyr Pro Pro Lys Pro Cys
            485                 490                 495

Gly Ile Val Pro Ala Gly Thr Val Cys Gly Pro Val Tyr Cys Phe Thr
            500                 505                 510

Pro Ser Pro Val Val Gly Thr Asp Lys Gln Gly Val Pro Thr
        515                 520                 525

Tyr Asn Trp Gly Glu Asn Glu Thr Asp Val Phe Leu Leu Asn Ser Thr
530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
            565                 570                 575

Tyr Asn Gly Thr Leu Asp Leu Leu Cys Pro Thr Asp Cys Phe Arg Lys
            580                 585                 590

His Pro Glu Thr Thr Tyr Leu Arg Cys Gly Ser Gly Pro Trp Leu Thr
            595                 600                 605

Pro Arg Cys Leu Val Asp Tyr Pro Tyr Arg Leu Trp His Tyr Pro Cys
        610                 615                 620

Thr Val Asn Phe Thr Ile Phe Lys Val Arg Met Tyr Val Gly Gly Val
625                 630                 635                 640

Glu His Arg Leu Ser Ala Ala Cys Asn Phe Thr Arg Gly Asp Arg Cys
                645                 650                 655

Asn Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
        675                 680                 685

Leu Ser Thr Gly Leu Leu His Leu His Gln Asn Ile Val Asp Val Gln
    690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
            725                 730                 735

Ala Cys Leu Trp Met Leu Ile Ile Leu Gly Gln Ala Glu Ala Ala Leu
            740                 745                 750

Glu Lys Leu Ile Ile Leu His Ser Ala Ser Ala Ala Ser Ala Asn Gly
            755                 760                 765

Pro Leu Trp Phe Phe Ile Phe Phe Ile Ala Ala Trp Tyr Leu Lys Gly
        770                 775                 780

Arg Val Val Pro Met Ala Thr Tyr Ser Val Leu Gly Leu Trp Ser Phe
785                 790                 795                 800

Phe Leu Leu Val Leu Ala Leu Pro Gln Gln Ala Tyr Ala Leu Asp Ala
                805                 810                 815

Val Glu Gln Gly Glu Leu Gly Leu Val Leu Leu Gly Val Ile Ser Ile
            820                 825                 830

Phe Thr Leu Thr Pro Ala Tyr Lys Thr Leu Leu Ser Arg Ser Val Trp
        835                 840                 845

Trp Leu Ser Tyr Met Leu Val Leu Ala Glu Ala Gln Ile Gln Gln Trp
    850                 855                 860

Val Pro Pro Leu Glu Ala Arg Gly Gly Arg Asp Gly Ile Ile Trp Val
```

```
              865                 870                 875                 880
Ala Val Ile Pro Arg Pro Cys Leu Val Phe Glu Ile Thr Lys Trp Leu
                    885                 890                 895
Leu Ala Val Leu Gly Pro Ala Tyr Leu Leu Arg Ala Ser Leu Leu Arg
                900                 905                 910
Val Pro Tyr Phe Val Arg Ala His Ala Leu Leu Arg Leu Cys Ala Leu
                915                 920                 925
Val Arg His Leu Ala Gly Ala Arg Tyr Ile Gln Met Leu Leu Ile Thr
            930                 935                 940
Ile Gly Arg Trp Thr Gly Thr Tyr Ile Tyr Asp His Leu Ser Pro Leu
945                 950                 955                 960
Ser Thr Trp Ala Ala Gln Gly Leu Arg Asp Leu Ala Val Ala Val Glu
                    965                 970                 975
Pro Val Val Phe Ser Pro Met Glu Lys Lys Val Ile Val Trp Gly Ala
                980                 985                 990
Glu Thr Val Ala Cys Gly Asp Ile Leu His Gly Leu Pro Val Ser Ala
                    995                1000                1005
Arg Leu Gly Arg Glu Ile Leu Leu Gly Pro Ala Asp Gly Tyr Thr
           1010                1015                1020
Ser Lys Gly Trp Lys Leu Leu Ala Pro Ile Thr Ala Tyr Thr Gln
           1025                1030                1035
Gln Thr Arg Gly Leu Leu Gly Ala Ile Val Val Ser Leu Thr Gly
           1040                1045                1050
Arg Asp Lys Asn Glu Gln Ala Gly Gln Val Gln Val Leu Ser Ser
           1055                1060                1065
Val Thr Gln Ser Phe Leu Gly Thr Ser Ile Ser Gly Val Leu Trp
           1070                1075                1080
Thr Val Tyr His Gly Ala Gly Asn Lys Thr Leu Ala Gly Pro Arg
           1085                1090                1095
Gly Pro Val Thr Gln Met Tyr Ser Ser Ala Glu Gly Asp Leu Val
           1100                1105                1110
Gly Trp Pro Ser Pro Pro Gly Thr Lys Ser Leu Asp Pro Cys Thr
           1115                1120                1125
Cys Gly Ala Val Asp Leu Tyr Leu Val Thr Arg Asn Ala Asp Val
           1130                1135                1140
Ile Pro Val Arg Arg Arg Asp Asp Arg Arg Gly Ala Leu Leu Ser
           1145                1150                1155
Pro Arg Pro Leu Ser Thr Leu Lys Gly Ser Ser Gly Gly Pro Val
           1160                1165                1170
Leu Cys Ser Arg Gly His Ala Val Gly Leu Phe Arg Ala Ala Val
           1175                1180                1185
Cys Thr Arg Gly Val Ala Lys Ser Ile Asp Phe Ile Pro Val Glu
           1190                1195                1200
Ser Leu Asp Val Ala Ala Arg Ser Pro Ser Phe Ser Asp Asn Ser
           1205                1210                1215
Thr Pro Pro Ala Val Pro Gln Ser Tyr Gln Val Gly Tyr Leu His
           1220                1225                1230
Ala Pro Thr Gly Ser Gly Lys Ser Thr Lys Val Pro Ala Ala Tyr
           1235                1240                1245
Ala Ser Gln Gly Tyr Lys Val Leu Val Leu Asn Pro Ser Val Ala
           1250                1255                1260
Ala Thr Leu Gly Phe Gly Ala Tyr Met Ser Lys Ala His Gly Ile
           1265                1270                1275
```

-continued

```
Asn Pro Asn Ile Arg Thr Gly Val Arg Thr Val Thr Thr Gly Asp
    1280            1285                1290
Pro Ile Thr Tyr Ser Thr Tyr Gly Lys Phe Leu Ala Asp Gly Gly
    1295            1300                1305
Cys Ser Ala Gly Ala Tyr Asp Ile Ile Cys Asp Glu Cys His
    1310            1315                1320
Ser Val Asp Ala Thr Thr Ile Leu Gly Ile Gly Thr Val Leu Asp
    1325            1330                1335
Gln Ala Glu Thr Ala Gly Ala Arg Leu Val Val Leu Ala Thr Ala
    1340            1345                1350
Thr Pro Pro Gly Thr Val Thr Thr Pro His Ser Asn Ile Glu Glu
    1355            1360                1365
Val Ala Leu Gly His Glu Gly Glu Ile Pro Phe Tyr Gly Lys Ala
    1370            1375                1380
Ile Pro Leu Ala Tyr Ile Lys Gly Gly Arg His Leu Ile Phe Cys
    1385            1390                1395
His Ser Lys Lys Lys Cys Asp Glu Leu Ala Ala Ala Leu Arg Gly
    1400            1405                1410
Met Gly Val Asn Ala Val Ala Tyr Tyr Arg Gly Leu Asp Val Ser
    1415            1420                1425
Val Ile Pro Leu Gln Gly Asp Val Val Val Ala Thr Asp Ala
    1430            1435                1440
Leu Met Thr Gly Phe Thr Gly Asp Phe Asp Ser Val Ile Asp Cys
    1445            1450                1455
Asn Val Ala Val Thr Gln Ile Val Asp Leu Ser Leu Asp Pro Thr
    1460            1465                1470
Phe Thr Ile Thr Thr Gln Thr Val Pro Gln Asp Ala Val Ser Arg
    1475            1480                1485
Ser Gln Arg Arg Gly Arg Thr Gly Arg Gly Arg Leu Gly Ile Tyr
    1490            1495                1500
Arg Tyr Val Ser Ser Gly Glu Arg Pro Ser Gly Met Phe Asp Ser
    1505            1510                1515
Val Val Leu Cys Glu Cys Tyr Asp Ala Gly Ala Ala Trp Tyr Glu
    1520            1525                1530
Leu Thr Pro Ala Glu Thr Thr Val Arg Leu Arg Ala Tyr Leu Asn
    1535            1540                1545
Thr Pro Gly Leu Pro Val Cys Gln Asp His Leu Glu Phe Trp Glu
    1550            1555                1560
Ala Val Phe Thr Gly Leu Thr His Ile Asp Ala His Phe Leu Ser
    1565            1570                1575
Gln Thr Lys Gln Gly Gly Asp Asn Phe Ala Tyr Leu Thr Ala Tyr
    1580            1585                1590
Gln Ala Thr Val Cys Ala Arg Ala Arg Ala Pro Pro Pro Ser Trp
    1595            1600                1605
Asp Leu Met Trp Lys Cys Leu Thr Arg Leu Lys Pro Thr Leu Asn
    1610            1615                1620
Gly Pro Thr Pro Leu Leu Tyr Arg Leu Gly Ala Val Thr Asn Glu
    1625            1630                1635
Val Thr Leu Thr His Pro Val Thr Lys Tyr Ile Ala Thr Cys Met
    1640            1645                1650
Gln Ala Asp Leu Glu Ile Met Thr Ser Thr Trp Val Leu Ala Gly
    1655            1660                1665
```

```
Gly Val Leu Ala Ala Val Ala Ser Tyr Cys Leu Ala Thr Gly Cys
    1670                1675                1680

Val Ser Ile Ile Gly Arg Leu His Leu Asn Asp Arg Val Val Val
    1685                1690                1695

Ala Pro Asp Lys Glu Ile Leu Tyr Glu Ala Phe Asp Glu Met Glu
    1700                1705                1710

Glu Cys Ala Ser Lys Ala Ala Leu Ile Glu Glu Gly Gln Arg Met
    1715                1720                1725

Ala Glu Met Leu Lys Thr Lys Ile Gln Gly Leu Leu Gln Gln Ala
    1730                1735                1740

Thr Arg Gln Ala Gln Asp Ile Gln Pro Ala Ile Gln Ser Ser Trp
    1745                1750                1755

Pro Lys Leu Glu Gln Phe Trp Ala Lys His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Pro Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Ile Leu Val Asp Val Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Thr Val Glu Asp Val Val Asn Leu Leu Pro Ala Ile Leu Ser Pro
    1880                1885                1890

Gly Ala Leu Val Val Gly Val Ile Cys Ala Ala Ile Leu Arg Arg
    1895                1900                1905

His Ile Gly Gln Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Ala Glu Ser Asp Ala Ser Gln Arg Val Thr Gln Ala Leu Ser
    1940                1945                1950

Ser Leu Thr Ile Thr Ser Leu Leu Arg Arg Leu His Ala Trp Ile
    1955                1960                1965

Thr Glu Asp Cys Pro Val Pro Cys Ser Gly Ser Trp Leu Arg Asp
    1970                1975                1980

Ile Trp Asp Trp Val Cys Ser Ile Leu Thr Asp Phe Lys Asn Trp
    1985                1990                1995

Leu Ser Ser Lys Leu Leu Pro Lys Leu Pro Gly Leu Pro Phe Ile
    2000                2005                2010

Ser Cys Gln Lys Gly Tyr Arg Gly Val Trp Ala Gly Thr Gly Val
    2015                2020                2025

Met Thr Thr Arg Cys Pro Cys Gly Ala Thr Ile Ser Gly His Val
    2030                2035                2040

Arg Met Gly Thr Met Lys Ile Thr Gly Pro Lys Thr Cys Leu Asn
    2045                2050                2055

Met Trp Gln Gly Ser Phe Pro Ile Asn Cys Tyr Thr Glu Gly Pro
```

```
               2060                2065                2070
Cys Val Pro Lys Pro Pro Asn Tyr Lys Thr Ala Ile Trp Arg
    2075                2080                2085
Val Ala Ala Ser Glu Tyr Val Glu Ile Thr Gln His Gly Ser Phe
    2090                2095                2100
Ser Tyr Val Thr Gly Leu Thr Asn Asp Asn Leu Lys Val Pro Cys
    2105                2110                2115
Gln Val Pro Ala Pro Glu Phe Phe Ser Trp Val Asp Gly Val Gln
    2120                2125                2130
Ile His Arg Phe Ala Pro Thr Pro Gly Pro Phe Phe Arg Asp Glu
    2135                2140                2145
Val Thr Phe Thr Val Gly Leu Asn Ser Phe Val Val Gly Ser Gln
    2150                2155                2160
Leu Pro Cys Asp Pro Glu Pro Asp Thr Glu Val Leu Ala Ser Met
    2165                2170                2175
Leu Thr Asp Pro Ser His Ile Thr Ala Glu Ala Ala Ala Arg Arg
    2180                2185                2190
Leu Ala Arg Gly Ser Pro Pro Ser Gln Ala Ser Ser Ser Ala Ser
    2195                2200                2205
Gln Leu Ser Ala Pro Ser Leu Lys Ala Thr Cys Thr Thr His Lys
    2210                2215                2220
Val Ala Tyr Asp Cys Asp Met Val Asp Ala Asn Leu Phe Met Gly
    2225                2230                2235
Gly Asp Val Thr Arg Ile Glu Ser Asn Ser Lys Val Val Ile Leu
    2240                2245                2250
Asp Ser Leu Asp Ser Met Thr Glu Val Glu Asp Asp Arg Glu Pro
    2255                2260                2265
Ser Ile Pro Ser Glu Tyr Leu Ile Arg Arg Arg Lys Phe Pro Pro
    2270                2275                2280
Ala Leu Pro Pro Trp Ala Arg Pro Asp Tyr Asn Pro Pro Val Val
    2285                2290                2295
Glu Thr Trp Lys Arg Pro Asp Tyr Glu Pro Pro Thr Val Leu Gly
    2300                2305                2310
Cys Ala Leu Pro Pro Thr Pro Gln Ala Pro Val Pro Pro Pro Arg
    2315                2320                2325
Arg Arg Arg Ala Lys Val Leu Thr Gln Asp Asn Val Glu Gly Val
    2330                2335                2340
Leu Lys Glu Met Ala Asp Lys Val Leu Ser Pro Leu Arg Asp Cys
    2345                2350                2355
Asn Asp Ser Gly His Ser Thr Gly Ala Asp Thr Gly Ala Asp Ser
    2360                2365                2370
Val Gln Gln Pro Pro Asp Glu Thr Ala Ala Ser Glu Ala Gly Ser
    2375                2380                2385
Leu Ser Ser Met Pro Pro Leu Glu Gly Glu Pro Gly Asp Pro Asp
    2390                2395                2400
Leu Glu Phe Glu Pro Ala Gly Ser Ala Pro Pro Ser Glu Gly Glu
    2405                2410                2415
Cys Glu Val Ile Asp Ser Asp Ser Lys Ser Trp Ser Thr Val Ser
    2420                2425                2430
Asp Gln Glu Asp Ser Ile Thr Cys Cys Ser Met Ser Tyr Ser Trp
    2435                2440                2445
Thr Gly Ala Leu Ile Thr Pro Cys Gly Pro Glu Glu Glu Lys Leu
    2450                2455                2460
```

```
Pro Ile Asn Pro Leu Ser Asn Ser Leu Met Arg Phe His Asn Lys
    2465            2470                2475

Val Tyr Ser Thr Thr Ser Arg Ser Ala Ser Gln Arg Ala Lys Lys
    2480            2485                2490

Val Thr Phe Asp Arg Val Gln Val Leu Asp Lys His Tyr Asp Ser
    2495            2500                2505

Val Leu Gln Asp Val Lys Arg Ala Ala Ser Lys Val Ser Ala Arg
    2510            2515                2520

Leu Leu Ser Ile Glu Glu Ala Cys Ala Leu Thr Pro Pro His Ser
    2525            2530                2535

Ala Lys Ser Arg Tyr Gly Phe Gly Ala Lys Glu Val Arg Ser Leu
    2540            2545                2550

Ser Arg Arg Ala Val Asn His Ile Gln Ser Val Trp Glu Asp Leu
    2555            2560                2565

Leu Glu Asp Gln His Thr Pro Ile Glu Thr Thr Ile Met Ala Lys
    2570            2575                2580

Asn Glu Val Phe Cys Val Asp Pro Ala Lys Gly Gly Lys Lys Ser
    2585            2590                2595

Ala Arg Leu Ile Val Tyr Pro Asp Leu Gly Val Arg Val Cys Glu
    2600            2605                2610

Lys Met Ala Leu Tyr Asp Ile Ala Gln Lys Leu Pro Lys Ala Ile
    2615            2620                2625

Met Gly Pro Ser Tyr Gly Phe Gln Tyr Ser Pro Ala Glu Arg Val
    2630            2635                2640

Asp Phe Leu Leu Lys Ala Trp Gly Ser Lys Lys Asp Pro Met Gly
    2645            2650                2655

Phe Ser Tyr Asp Thr Arg Cys Phe Asp Ser Thr Val Thr Glu Arg
    2660            2665                2670

Asp Ile Arg Thr Glu Glu Ser Ile Tyr Gln Ala Cys Ser Leu Pro
    2675            2680                2685

Gln Glu Ala Arg Val Ala Ile His Ser Leu Thr Glu Arg Leu Tyr
    2690            2695                2700

Val Gly Gly Pro Met Leu Asn Ser Lys Gly Gln Ser Cys Gly Tyr
    2705            2710                2715

Arg Arg Cys Arg Ala Ser Gly Val Phe Thr Thr Ser Met Gly Asn
    2720            2725                2730

Thr Met Thr Cys Tyr Ile Lys Ala Leu Ala Ala Cys Gln Ala Ala
    2735            2740                2745

Gly Ile Val Asp Pro Val Met Leu Val Cys Gly Asp Asp Leu Val
    2750            2755                2760

Val Ile Ser Glu Ser Gln Gly Asn Asp Glu Asp Glu Arg Asn Leu
    2765            2770                2775

Arg Ala Phe Thr Glu Ala Met Thr Arg Tyr Ser Ala Pro Pro Gly
    2780            2785                2790

Asp Leu Pro Arg Pro Glu Tyr Asp Leu Glu Leu Ile Thr Ser Cys
    2795            2800                2805

Ser Ser Asn Val Ser Val Ala Leu Asp Pro Arg Gly Arg Arg Arg
    2810            2815                2820

Tyr Tyr Leu Thr Arg Asp Pro Thr Thr Pro Ile Ser Arg Ala Ala
    2825            2830                2835

Trp Glu Thr Val Arg His Ser Pro Val Asn Ser Trp Leu Gly Asn
    2840            2845                2850
```

-continued

```
Ile Ile Gln Tyr Ala Pro Thr Ile Trp Val Arg Met Val Ile Met
2855                2860                2865

Thr His Phe Phe Ser Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895

Leu Asp Leu Pro Ala Ile Ile Glu Arg Leu His Gly Leu Asp Ala
2900                2905                2910

Phe Ser Leu His Thr Tyr Ser Pro His Glu Leu Ser Arg Val Ala
2915                2920                2925

Ala Thr Leu Arg Lys Leu Gly Ala Pro Pro Leu Arg Ala Trp Lys
2930                2935                2940

Ser Arg Ala Arg Ala Val Arg Ala Ser Leu Ile Ala Gln Gly Gly
2945                2950                2955

Lys Ala Ala Ile Cys Gly Arg Tyr Leu Phe Asn Trp Ala Val Lys
2960                2965                2970

Thr Lys Leu Lys Leu Thr Pro Leu Pro Glu Ala Ser Arg Leu Asp
2975                2980                2985

Leu Ser Gly Trp Phe Thr Val Gly Ala Gly Gly Gly Ile Phe
2990                2995                3000

His Ser Val Ser His Ala Arg Pro Arg Leu Leu Leu Cys Leu
3005                3010                3015

Leu Leu Phe Ser Val Gly Val Gly Ile Phe Leu Leu Pro Ala Arg
3020                3025                3030
```

<210> SEQ ID NO 23
<211> LENGTH: 3033
<212> TYPE: PRT
<213> ORGANISM: Hepatitis C virus

<400> SEQUENCE: 23

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190
```

```
Glu Val Arg Asn Ile Ser Ser Gly Tyr Tyr Ala Thr Asn Asp Cys Ser
    195                 200                 205

Asn Asn Ser Ile Thr Trp Gln Leu Thr Asn Ala Val Leu His Leu Pro
    210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Val Met Ala Ala Thr Ile Cys
            260                 265                 270

Ser Ala Leu Tyr Val Gly Asp Val Cys Gly Ala Val Met Ile Val Ser
            275                 280                 285

Gln Ala Phe Ile Leu Ser Pro Glu Arg His Asn Phe Thr Gln Glu Cys
        290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Val Leu Ala Tyr
                325                 330                 335

Ala Ala Arg Val Pro Glu Leu Val Leu Glu Val Val Phe Gly Gly His
                340                 345                 350

Trp Gly Val Val Phe Gly Leu Ala Tyr Phe Ser Met Gln Gly Ala Trp
        355                 360                 365

Ala Lys Val Met Ala Ile Leu Leu Leu Val Ala Gly Val Asp Ala His
        370                 375                 380

Thr Tyr Ser Thr Gly Ala Arg Ala Gly Gln Ala Ser Gly Leu Thr
385                 390                 395                 400

Ser Leu Phe Ser Val Gly Ser Arg Gln Arg Leu Ser Leu Ile His Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Leu Tyr Val Asn Asn Phe Asn
        435                 440                 445

Ser Ser Gly Cys Pro Glu Arg Met Ser Ser Cys Arg Ala Leu Asp Asp
450                 455                 460

Phe Arg Ile Gly Trp Gly Thr Leu Glu Tyr Glu Thr Asn Val Thr Asn
465                 470                 475                 480

Asp Glu Asp Met Arg Pro Tyr Cys Trp His Tyr Pro Pro Lys Pro Cys
                485                 490                 495

Gly Ile Val Pro Ala Gly Thr Val Cys Gly Pro Val Tyr Cys Phe Thr
                500                 505                 510

Pro Ser Pro Val Val Gly Thr Thr Asp Lys Gln Gly Val Pro Thr
        515                 520                 525

Tyr Asn Trp Gly Glu Asn Glu Thr Asp Val Phe Leu Leu Asn Ser Thr
        530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

Tyr Asn Gly Thr Leu Asp Leu Leu Cys Pro Thr Asp Cys Phe Arg Lys
            580                 585                 590

His Pro Glu Thr Thr Tyr Leu Arg Cys Gly Ser Gly Pro Trp Leu Thr
            595                 600                 605
```

```
Pro Arg Cys Leu Val Asp Tyr Pro Tyr Arg Leu Trp His Tyr Pro Cys
610                 615                 620

Thr Val Asn Phe Thr Ile Phe Lys Val Arg Met Tyr Val Gly Gly Val
625                 630                 635                 640

Glu His Arg Leu Ser Ala Ala Cys Asn Phe Thr Arg Gly Asp Arg Cys
            645                 650                 655

Asn Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
                740                 745                 750

Glu Lys Leu Ile Ile Ser His Ser Ala Ser Ala Ser Ala Asn Gly
            755                 760                 765

Pro Leu Trp Phe Phe Ile Phe Phe Ile Ala Ala Trp Tyr Leu Lys Gly
770                 775                 780

Arg Val Val Pro Met Ala Thr Tyr Ser Val Leu Gly Leu Trp Ser Phe
785                 790                 795                 800

Phe Leu Leu Val Leu Ala Leu Pro Gln Gln Ala Tyr Ala Leu Asp Ala
                805                 810                 815

Val Glu Gln Gly Glu Leu Gly Leu Val Leu Leu Gly Val Ile Ser Ile
            820                 825                 830

Phe Thr Leu Thr Pro Ala Tyr Lys Thr Leu Leu Ser Arg Ser Val Trp
            835                 840                 845

Trp Leu Ser Tyr Met Leu Val Leu Ala Glu Ala Gln Ile Gln Gln Trp
850                 855                 860

Val Pro Pro Leu Glu Ala Arg Gly Gly Arg Asp Gly Ile Ile Trp Val
865                 870                 875                 880

Ala Val Ile Leu Arg Pro Cys Leu Val Phe Glu Ile Thr Lys Trp Leu
                885                 890                 895

Leu Ala Val Leu Gly Pro Ala Tyr Leu Leu Arg Ala Ser Leu Leu Arg
            900                 905                 910

Val Pro Tyr Phe Val Arg Ala His Ala Leu Leu Arg Leu Cys Ala Leu
            915                 920                 925

Val Arg His Leu Ala Gly Ala Arg Tyr Ile Gln Met Leu Leu Ile Thr
930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
            965                 970                 975

Pro Val Val Phe Ser Pro Met Glu Lys Lys Val Ile Val Trp Gly Ala
            980                 985                 990

Glu Thr Val Ala Cys Gly Asp Ile Leu His Gly Leu Pro Val Ser Ala
            995                 1000                1005

Arg Leu Gly Arg Glu Ile Leu Leu Gly Pro Ala Asp Gly Tyr Thr
    1010                1015                1020

Ser Lys Gly Trp Lys Leu Leu Ala Pro Ile Thr Ala Tyr Thr Gln
```

-continued

```
              1025                1030                1035
Gln Thr Arg Gly Leu Leu Gly Ala Ile Val Val Ser Leu Thr Gly
              1040                1045                1050
Arg Asp Lys Asn Glu Gln Ala Gly Gln Val Gln Val Leu Ser Ser
              1055                1060                1065
Val Thr Gln Ser Phe Leu Gly Thr Ser Ile Ser Gly Val Leu Trp
              1070                1075                1080
Thr Val Tyr His Gly Ala Gly Asn Lys Thr Leu Ala Gly Pro Arg
              1085                1090                1095
Gly Pro Val Thr Gln Met Tyr Ser Ser Ala Glu Gly Asp Leu Val
              1100                1105                1110
Gly Trp Pro Ser Pro Pro Gly Thr Lys Ser Leu Asp Pro Cys Thr
              1115                1120                1125
Cys Gly Ala Val Asp Leu Tyr Leu Val Thr Arg Asn Ala Asp Val
              1130                1135                1140
Ile Pro Val Arg Arg Arg Asp Asp Arg Arg Gly Ala Leu Leu Ser
              1145                1150                1155
Pro Arg Pro Leu Ser Thr Leu Lys Gly Ser Ser Gly Gly Pro Val
              1160                1165                1170
Leu Cys Ser Arg Gly His Ala Val Gly Leu Phe Arg Ala Ala Val
              1175                1180                1185
Cys Thr Arg Gly Val Ala Lys Ser Ile Asp Phe Ile Pro Val Glu
              1190                1195                1200
Ser Leu Asp Val Ala Ala Arg Ser Pro Ser Phe Ser Asp Asn Ser
              1205                1210                1215
Thr Pro Pro Ala Val Pro Gln Ser Tyr Gln Val Gly Tyr Leu His
              1220                1225                1230
Ala Pro Thr Gly Ser Gly Lys Ser Thr Lys Val Pro Ala Ala Tyr
              1235                1240                1245
Ala Ser Gln Gly Tyr Lys Val Leu Val Leu Asn Pro Ser Val Ala
              1250                1255                1260
Ala Thr Leu Gly Phe Gly Ala Tyr Met Ser Lys Ala His Gly Ile
              1265                1270                1275
Asn Pro Asn Ile Arg Thr Gly Val Arg Thr Val Thr Thr Gly Asp
              1280                1285                1290
Pro Ile Thr Tyr Ser Thr Tyr Gly Lys Phe Leu Ala Asp Gly Gly
              1295                1300                1305
Cys Ser Ala Gly Ala Tyr Asp Ile Ile Ile Cys Asp Glu Cys His
              1310                1315                1320
Ser Val Asp Ala Thr Thr Ile Leu Gly Ile Gly Thr Val Leu Asp
              1325                1330                1335
Gln Ala Glu Thr Ala Gly Ala Arg Leu Val Val Leu Ala Thr Ala
              1340                1345                1350
Thr Pro Pro Gly Thr Val Thr Thr Pro His Ser Asn Ile Glu Glu
              1355                1360                1365
Val Ala Leu Gly His Glu Gly Glu Ile Pro Phe Tyr Gly Lys Ala
              1370                1375                1380
Ile Pro Leu Ala Tyr Ile Lys Gly Gly Arg His Leu Ile Phe Cys
              1385                1390                1395
His Ser Lys Lys Lys Cys Asp Glu Leu Ala Ala Ala Leu Arg Gly
              1400                1405                1410
Met Gly Val Asn Ala Val Ala Tyr Tyr Arg Gly Leu Asp Val Ser
              1415                1420                1425
```

```
Val Ile Pro Leu Gln Gly Asp Val Val Val Ala Thr Asp Ala
    1430            1435            1440

Leu Met Thr Gly Phe Thr Gly Asp Phe Asp Ser Val Ile Asp Cys
    1445            1450            1455

Asn Val Ala Val Thr Gln Ile Val Asp Leu Ser Leu Asp Pro Thr
    1460            1465            1470

Phe Thr Ile Thr Thr Gln Thr Val Pro Gln Asp Ala Val Ser Arg
    1475            1480            1485

Ser Gln Arg Arg Gly Arg Thr Gly Arg Gly Arg Leu Gly Ile Tyr
    1490            1495            1500

Arg Tyr Val Ser Ser Gly Glu Arg Pro Ser Gly Met Phe Asp Ser
    1505            1510            1515

Val Val Leu Cys Glu Cys Tyr Asp Ala Gly Ala Ala Trp Tyr Glu
    1520            1525            1530

Leu Thr Pro Ala Glu Thr Thr Val Arg Leu Arg Ala Tyr Leu Asn
    1535            1540            1545

Thr Pro Gly Leu Pro Val Cys Gln Asp His Leu Glu Phe Trp Glu
    1550            1555            1560

Ala Val Phe Thr Gly Leu Thr His Ile Asp Ala His Phe Leu Ser
    1565            1570            1575

Gln Thr Lys Gln Gly Gly Asp Asn Phe Ala Tyr Leu Thr Ala Tyr
    1580            1585            1590

Gln Ala Thr Val Cys Ala Arg Ala Arg Ala Pro Pro Pro Ser Trp
    1595            1600            1605

Asp Leu Met Trp Lys Cys Leu Thr Arg Leu Lys Pro Thr Leu Asn
    1610            1615            1620

Gly Pro Thr Pro Leu Leu Tyr Arg Leu Gly Ala Val Thr Asn Glu
    1625            1630            1635

Val Thr Leu Thr His Pro Val Thr Lys Tyr Ile Ala Thr Cys Met
    1640            1645            1650

Gln Ala Asp Leu Glu Ile Met Thr Ser Thr Trp Val Leu Ala Gly
    1655            1660            1665

Gly Val Leu Ala Ala Val Ala Ser Tyr Cys Leu Ala Thr Gly Cys
    1670            1675            1680

Val Ser Ile Ile Gly Arg Leu His Leu Asn Asp Arg Val Val Val
    1685            1690            1695

Ala Pro Asp Lys Glu Ile Leu Tyr Glu Ala Phe Asp Glu Met Glu
    1700            1705            1710

Glu Cys Ala Ser Lys Ala Ala Leu Ile Glu Glu Gly Gln Arg Met
    1715            1720            1725

Ala Glu Met Leu Lys Thr Lys Ile Gln Gly Leu Leu Gln Gln Ala
    1730            1735            1740

Thr Arg Gln Ala Gln Asp Ile Gln Pro Ala Ile Gln Ser Ser Trp
    1745            1750            1755

Pro Lys Leu Glu Gln Phe Trp Ala Lys His Met Trp Asn Phe Ile
    1760            1765            1770

Ser Gly Ile Gln Tyr Leu Ala Gly Leu Ser Thr Leu Pro Gly Asn
    1775            1780            1785

Pro Thr Val Ala Ser Met Met Ala Phe Ser Ala Ala Leu Thr Ser
    1790            1795            1800

Pro Leu Pro Thr Ser Thr Thr Ile Leu Leu Asn Ile Met Gly Gly
    1805            1810            1815
```

-continued

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Ile Leu Val Asp Val Leu Ala Gly Tyr Gly Ala Gly Ile
1850                1855                1860

Ser Gly Ala Leu Val Ala Phe Lys Ile Met Ser Gly Glu Lys Pro
1865                1870                1875

Thr Val Glu Asp Val Val Asn Leu Leu Pro Ala Ile Leu Ser Pro
1880                1885                1890

Gly Ala Leu Val Val Gly Val Ile Cys Ala Ala Ile Leu Arg Arg
1895                1900                1905

His Ile Gly Gln Gly Glu Gly Ala Val Gln Trp Met Asn Arg Leu
1910                1915                1920

Ile Ala Phe Ala Ser Arg Gly Asn His Val Ala Pro Thr His Tyr
1925                1930                1935

Val Ala Glu Ser Asp Ala Ser Gln Arg Val Thr Gln Ala Leu Ser
1940                1945                1950

Ser Leu Thr Ile Thr Ser Leu Leu Arg Arg Leu His Ala Trp Ile
1955                1960                1965

Thr Glu Asp Cys Pro Val Pro Cys Ser Gly Ser Trp Leu Arg Asp
1970                1975                1980

Ile Trp Asp Trp Val Cys Ser Ile Leu Thr Asp Phe Lys Asn Trp
1985                1990                1995

Leu Ser Ser Lys Leu Leu Pro Lys Leu Pro Gly Leu Pro Phe Ile
2000                2005                2010

Ser Cys Gln Lys Gly Tyr Arg Gly Val Trp Ala Gly Thr Gly Val
2015                2020                2025

Met Thr Thr Arg Cys Pro Cys Gly Ala Thr Ile Ser Gly His Val
2030                2035                2040

Arg Met Gly Thr Met Lys Ile Thr Gly Pro Lys Thr Cys Leu Asn
2045                2050                2055

Met Trp Gln Gly Ser Phe Pro Ile Asn Cys Tyr Thr Glu Gly Pro
2060                2065                2070

Cys Val Pro Lys Pro Pro Pro Asn Tyr Lys Thr Ala Ile Trp Arg
2075                2080                2085

Val Ala Ala Ser Glu Tyr Val Glu Ile Thr Gln His Gly Ser Phe
2090                2095                2100

Ser Tyr Val Thr Gly Leu Thr Asn Asp Asn Leu Lys Val Pro Cys
2105                2110                2115

Gln Val Pro Ala Pro Glu Phe Phe Ser Trp Val Asp Gly Val Gln
2120                2125                2130

Ile His Arg Phe Ala Pro Thr Pro Gly Pro Phe Phe Arg Asp Glu
2135                2140                2145

Val Thr Phe Thr Val Gly Leu Asn Ser Phe Val Val Gly Ser Gln
2150                2155                2160

Leu Pro Cys Asp Pro Glu Pro Asp Thr Glu Val Leu Ala Ser Met
2165                2170                2175

Leu Thr Asp Pro Ser His Ile Thr Ala Glu Ala Ala Ala Arg Arg
2180                2185                2190

Leu Ala Arg Gly Ser Pro Pro Ser Gln Ala Ser Ser Ser Ala Ser
2195                2200                2205

Gln Leu Ser Ala Pro Ser Leu Lys Ala Thr Cys Thr Thr His Lys

```
                2210                    2215                    2220

Val Ala Tyr Asp Cys Asp Met Val Asp Ala Asn Leu Phe Met Gly
    2225                    2230                2235

Gly Asp Val Thr Arg Ile Glu Ser Asn Ser Lys Val Val Ile Leu
    2240                    2245                2250

Asp Ser Leu Asp Ser Met Thr Glu Val Glu Asp Arg Glu Pro
    2255                    2260                2265

Ser Ile Pro Ser Glu Tyr Leu Ile Arg Arg Lys Phe Pro Pro
    2270                    2275                2280

Ala Leu Pro Pro Trp Ala Arg Pro Asp Tyr Asn Pro Pro Val Val
    2285                    2290                2295

Glu Thr Trp Lys Arg Pro Asp Tyr Glu Pro Pro Thr Val Leu Gly
    2300                    2305                2310

Cys Ala Leu Pro Pro Thr Pro Gln Ala Pro Val Pro Pro Pro Arg
    2315                    2320                2325

Arg Arg Arg Ala Lys Val Leu Thr Gln Asp Asn Val Glu Gly Val
    2330                    2335                2340

Leu Lys Glu Met Ala Asp Lys Val Leu Ser Pro Leu Arg Asp Cys
    2345                    2350                2355

Asn Asp Ser Gly His Ser Thr Gly Ala Asp Thr Gly Ala Asp Ser
    2360                    2365                2370

Val Gln Gln Pro Pro Asp Glu Thr Ala Ala Ser Glu Ala Gly Ser
    2375                    2380                2385

Leu Ser Ser Met Pro Pro Leu Glu Gly Glu Pro Gly Asp Pro Asp
    2390                    2395                2400

Leu Glu Phe Glu Pro Ala Gly Ser Ala Pro Pro Ser Glu Gly Glu
    2405                    2410                2415

Cys Glu Val Ile Asp Ser Asp Ser Lys Ser Trp Ser Thr Val Ser
    2420                    2425                2430

Asp Gln Glu Asp Ser Thr Ile Cys Cys Ser Met Ser Tyr Ser Trp
    2435                    2440                2445

Thr Gly Ala Leu Ile Thr Pro Cys Gly Pro Glu Glu Glu Lys Leu
    2450                    2455                2460

Pro Ile Asn Pro Leu Ser Asn Ser Leu Met Arg Phe His Asn Lys
    2465                    2470                2475

Val Tyr Ser Thr Thr Ser Arg Ser Ala Ser Gln Arg Ala Lys Lys
    2480                    2485                2490

Val Thr Phe Asp Arg Val Gln Val Leu Asp Lys His Tyr Asp Ser
    2495                    2500                2505

Val Leu Gln Asp Val Lys Arg Ala Ala Ser Lys Val Ser Ala Arg
    2510                    2515                2520

Leu Leu Ser Ile Glu Glu Ala Cys Ala Leu Thr Pro Pro His Ser
    2525                    2530                2535

Ala Lys Ser Arg Tyr Gly Phe Gly Ala Lys Glu Val Arg Ser Leu
    2540                    2545                2550

Ser Arg Arg Ala Val Asn His Ile Gln Ser Val Trp Glu Asp Leu
    2555                    2560                2565

Leu Glu Asp Gln His Thr Pro Ile Glu Thr Thr Ile Met Ala Lys
    2570                    2575                2580

Asn Glu Val Phe Cys Val Asp Pro Ala Lys Gly Gly Lys Lys Ser
    2585                    2590                2595

Ala Arg Leu Ile Val Tyr Pro Asp Leu Gly Val Arg Val Cys Glu
    2600                    2605                2610
```

```
Lys Met Ala Leu Tyr Asp Ile Ala Gln Lys Leu Pro Lys Ala Ile
2615                2620                    2625

Met Gly Pro Ser Tyr Gly Phe Gln Tyr Ser Pro Ala Glu Arg Val
2630                2635                    2640

Asp Phe Leu Leu Lys Ala Trp Gly Ser Lys Asp Pro Met Gly
2645                2650                    2655

Phe Ser Tyr Asp Thr Arg Cys Phe Asp Ser Thr Val Thr Glu Arg
2660                2665                    2670

Asp Ile Arg Thr Glu Glu Ser Ile Tyr Gln Ala Cys Ser Leu Pro
2675                2680                    2685

Gln Glu Ala Arg Val Ala Ile His Ser Leu Thr Glu Arg Leu Tyr
2690                2695                    2700

Val Gly Gly Pro Met Leu Asn Ser Lys Gly Gln Ser Cys Gly Tyr
2705                2710                    2715

Arg Arg Cys Arg Ala Ser Gly Val Phe Thr Thr Ser Met Gly Asn
2720                2725                    2730

Thr Met Thr Cys Tyr Ile Lys Ala Leu Ala Ala Cys Gln Ala Ala
2735                2740                    2745

Gly Ile Val Asp Pro Val Met Leu Val Cys Gly Asp Asp Leu Val
2750                2755                    2760

Val Ile Ser Glu Ser Gln Gly Asn Asp Glu Asp Glu Arg Asn Leu
2765                2770                    2775

Arg Ala Phe Thr Glu Ala Met Thr Arg Tyr Ser Ala Pro Pro Gly
2780                2785                    2790

Asp Leu Pro Arg Pro Glu Tyr Asp Leu Glu Leu Ile Thr Ser Cys
2795                2800                    2805

Ser Ser Asn Val Ser Val Ala Leu Asp Pro Arg Gly Arg Arg Arg
2810                2815                    2820

Tyr Tyr Leu Thr Arg Asp Pro Thr Thr Pro Ile Ser Arg Ala Ala
2825                2830                    2835

Trp Glu Thr Val Arg His Ser Pro Val Asn Ser Trp Leu Gly Asn
2840                2845                    2850

Ile Ile Gln Tyr Ala Pro Thr Ile Trp Val Arg Met Val Ile Met
2855                2860                    2865

Thr His Phe Phe Ser Ile Leu Leu Ala Gln Asp Thr Leu Asn Gln
2870                2875                    2880

Asn Leu Asn Phe Glu Met Tyr Gly Ala Val Tyr Ser Val Asn Pro
2885                2890                    2895

Leu Asp Leu Pro Ala Ile Ile Glu Arg Leu His Gly Leu Asp Ala
2900                2905                    2910

Phe Ser Leu His Thr Tyr Ser Pro His Glu Leu Ser Arg Val Ala
2915                2920                    2925

Ala Thr Leu Arg Lys Leu Gly Ala Pro Pro Leu Arg Ala Trp Lys
2930                2935                    2940

Ser Arg Ala Arg Ala Val Arg Ala Ser Leu Ile Ala Gln Gly Gly
2945                2950                    2955

Lys Ala Ala Ile Cys Gly Arg Tyr Leu Phe Asn Trp Ala Val Lys
2960                2965                    2970

Thr Lys Leu Lys Leu Thr Pro Leu Pro Glu Ala Ser Arg Leu Asp
2975                2980                    2985

Leu Ser Gly Trp Phe Thr Val Gly Ala Gly Gly Gly Gly Ile Phe
2990                2995                    3000
```

His Ser Val Ser His Ala Arg Pro Arg Leu Leu Leu Leu Cys Leu
    3005                3010                3015

Leu Leu Leu Ser Val Gly Val Gly Ile Phe Leu Leu Pro Ala Arg
    3020                3025                3030

<210> SEQ ID NO 24
<211> LENGTH: 3033
<212> TYPE: PRT
<213> ORGANISM: Hepatitis C virus

<400> SEQUENCE: 24

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Glu Val Arg Asn Ile Ser Ser Gly Tyr Tyr Ala Thr Asn Asp Cys Ser
        195                 200                 205

Asn Asn Ser Ile Thr Trp Gln Leu Thr Asn Ala Val Leu His Leu Pro
    210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Val Met Ala Ala Thr Ile Cys
            260                 265                 270

Ser Ala Leu Tyr Val Gly Asp Val Cys Gly Ala Val Met Ile Val Ser
        275                 280                 285

Gln Ala Phe Ile Leu Ser Pro Glu Arg His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Val Leu Ala Tyr
                325                 330                 335

Ala Ala Arg Val Pro Glu Leu Val Leu Glu Val Val Phe Gly Gly His
            340                 345                 350

```
Trp Gly Val Val Phe Gly Leu Ala Tyr Phe Ser Met Gln Gly Ala Trp
        355                 360                 365

Ala Lys Val Met Ala Ile Leu Leu Val Ala Gly Val Asp Ala His
        370                 375                 380

Thr Tyr Ser Thr Gly Ala Arg Ala Gly Gln Ala Ala Ser Gly Leu Thr
385                 390                 395                 400

Ser Leu Phe Ser Val Gly Ser Arg Gln Arg Leu Ser Leu Ile His Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Leu Tyr Val Asn Asn Phe Asn
            435                 440                 445

Ser Ser Gly Cys Pro Glu Arg Met Ser Ser Cys Arg Ala Leu Asp Asp
        450                 455                 460

Phe Arg Ile Gly Trp Gly Thr Leu Glu Tyr Glu Thr Asn Val Thr Asn
465                 470                 475                 480

Asp Glu Asp Met Arg Pro Tyr Cys Trp His Tyr Pro Lys Pro Cys
                485                 490                 495

Gly Ile Val Pro Ala Gly Thr Val Cys Gly Pro Val Tyr Cys Phe Thr
            500                 505                 510

Pro Ser Pro Val Val Val Gly Thr Thr Asp Lys Gln Gly Val Pro Thr
            515                 520                 525

Tyr Asn Trp Gly Glu Asn Glu Thr Asp Val Phe Leu Leu Asn Ser Thr
            530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

Tyr Asn Gly Thr Leu Asp Leu Leu Cys Pro Thr Asp Cys Phe Arg Lys
            580                 585                 590

His Pro Glu Thr Thr Tyr Leu Arg Cys Gly Ser Gly Pro Trp Leu Thr
            595                 600                 605

Pro Arg Cys Leu Val Asp Tyr Pro Tyr Arg Leu Trp His Tyr Pro Cys
        610                 615                 620

Thr Val Asn Phe Thr Ile Phe Lys Val Arg Met Tyr Val Gly Gly Val
625                 630                 635                 640

Glu His Arg Leu Ser Ala Ala Cys Asn Phe Thr Arg Gly Asp Arg Cys
                645                 650                 655

Asn Leu Glu Asp Arg Asp Arg Gly Gln Ser Pro Leu Leu His Ser
                660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
        690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
                740                 745                 750

Glu Lys Leu Ile Ile Ser His Ser Ala Ser Ala Ala Ser Ala Asn Gly
            755                 760                 765
```

```
Pro Leu Trp Phe Phe Ile Phe Phe Ile Ala Ala Trp Tyr Leu Lys Gly
770                 775                 780

Arg Val Val Pro Met Ala Thr Tyr Ser Val Leu Gly Leu Trp Ser Phe
785                 790                 795                 800

Phe Leu Leu Val Leu Ala Leu Pro Gln Gln Ala Tyr Ala Leu Asp Ala
                805                 810                 815

Val Glu Gln Gly Glu Leu Gly Leu Val Leu Leu Gly Val Ile Ser Ile
                820                 825                 830

Phe Thr Leu Thr Pro Ala Tyr Lys Thr Leu Leu Ser Arg Ser Val Trp
        835                 840                 845

Trp Leu Ser Tyr Met Leu Val Leu Ala Glu Ala Gln Ile Gln Gln Trp
850                 855                 860

Val Pro Pro Leu Glu Ala Arg Gly Gly Arg Asp Gly Ile Ile Trp Val
865                 870                 875                 880

Ala Val Ile Leu Arg Pro Cys Leu Val Phe Glu Ile Thr Lys Trp Leu
                885                 890                 895

Leu Ala Val Leu Gly Pro Ala Tyr Leu Leu Arg Ala Ser Leu Leu Arg
                900                 905                 910

Val Pro Tyr Phe Val Arg Ala His Ala Leu Leu Arg Leu Cys Ala Leu
            915                 920                 925

Val Arg His Leu Ala Gly Ala Arg Tyr Ile Gln Met Leu Leu Ile Thr
930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
                965                 970                 975

Pro Val Val Phe Ser Pro Met Glu Lys Lys Val Ile Val Trp Gly Ala
                980                 985                 990

Glu Thr Val Ala Cys Gly Asp Ile Leu His Gly Leu Pro Val Ser Ala
            995                 1000                1005

Arg Leu Gly Arg Glu Ile Leu Leu Gly Pro Ala Asp Gly Tyr Thr
    1010                1015                1020

Ser Lys Gly Trp Lys Leu Leu Ala Pro Ile Thr Ala Tyr Thr Gln
    1025                1030                1035

Gln Thr Arg Gly Leu Leu Gly Ala Ile Val Val Ser Leu Thr Gly
    1040                1045                1050

Arg Asp Lys Asn Glu Gln Ala Gly Gln Val Gln Val Leu Ser Ser
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Pro Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Asp Pro Cys Thr
    1115                1120                1125

Cys Gly Ala Val Asp Leu Tyr Leu Val Thr Arg Asn Ala Asp Val
    1130                1135                1140

Ile Pro Val Arg Arg Arg Asp Asp Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Ser Arg Gly His Ala Val Gly Leu Phe Arg Ala Ala Val
```

-continued

```
            1175                1180                1185
Cys Thr Arg Gly Val Ala Lys Ser Ile Asp Phe Ile Pro Val Glu
    1190                1195                1200

Ser Leu Asp Val Ala Ala Arg Ser Pro Ser Phe Ser Asp Asn Ser
    1205                1210                1215

Thr Pro Pro Ala Val Pro Gln Ser Tyr Gln Val Gly Tyr Leu His
    1220                1225                1230

Ala Pro Thr Gly Ser Gly Lys Ser Thr Lys Val Pro Ala Ala Tyr
    1235                1240                1245

Ala Ser Gln Gly Tyr Lys Val Leu Val Leu Asn Pro Ser Val Ala
    1250                1255                1260

Ala Thr Leu Gly Phe Gly Ala Tyr Met Ser Lys Ala His Gly Ile
    1265                1270                1275

Asn Pro Asn Ile Arg Thr Gly Val Arg Thr Val Thr Thr Gly Asp
    1280                1285                1290

Pro Ile Thr Tyr Ser Thr Tyr Gly Lys Phe Leu Ala Asp Gly Gly
    1295                1300                1305

Cys Ser Ala Gly Ala Tyr Asp Ile Ile Ile Cys Asp Glu Cys His
    1310                1315                1320

Ser Val Asp Ala Thr Thr Ile Leu Gly Ile Gly Thr Val Leu Asp
    1325                1330                1335

Gln Ala Glu Thr Ala Gly Ala Arg Leu Val Val Leu Ala Thr Ala
    1340                1345                1350

Thr Pro Pro Gly Thr Val Thr Thr Pro His Ser Asn Ile Glu Glu
    1355                1360                1365

Val Ala Leu Gly His Glu Gly Glu Ile Pro Phe Tyr Gly Lys Ala
    1370                1375                1380

Ile Pro Leu Ala Tyr Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Val Asn Ala Val Ala Tyr Tyr Arg Gly Leu Asp Val Ser
    1415                1420                1425

Val Ile Pro Leu Gln Gly Asp Val Val Val Val Ala Thr Asp Ala
    1430                1435                1440

Leu Met Thr Gly Phe Thr Gly Asp Phe Asp Ser Val Ile Asp Cys
    1445                1450                1455

Asn Val Ala Val Thr Gln Ile Val Asp Leu Ser Leu Asp Pro Thr
    1460                1465                1470

Phe Thr Ile Thr Thr Gln Thr Val Pro Gln Asp Ala Val Ser Arg
    1475                1480                1485

Ser Gln Arg Arg Gly Arg Thr Gly Arg Gly Arg Leu Gly Ile Tyr
    1490                1495                1500

Arg Tyr Val Ser Ser Gly Glu Arg Pro Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ala Glu Thr Thr Val Arg Leu Arg Ala Tyr Leu Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575
```

```
Gln Thr Lys Gln Gly Gly Asp Asn Phe Ala Tyr Leu Thr Ala Tyr
    1580                1585                1590

Gln Ala Thr Val Cys Ala Arg Ala Arg Ala Pro Pro Pro Ser Trp
    1595                1600                1605

Asp Leu Met Trp Lys Cys Leu Thr Arg Leu Lys Pro Thr Leu Asn
    1610                1615                1620

Gly Pro Thr Pro Leu Leu Tyr Arg Leu Gly Ala Val Thr Asn Glu
    1625                1630                1635

Val Thr Leu Thr His Pro Val Thr Lys Tyr Ile Ala Thr Cys Met
    1640                1645                1650

Gln Ala Asp Leu Glu Ile Met Thr Ser Thr Trp Val Leu Ala Gly
    1655                1660                1665

Gly Val Leu Ala Ala Val Ala Ser Tyr Cys Leu Ala Thr Gly Cys
    1670                1675                1680

Val Ser Ile Ile Gly Arg Leu His Leu Asn Asp Arg Val Val Val
    1685                1690                1695

Ala Pro Asp Lys Glu Ile Leu Tyr Glu Ala Phe Asp Glu Met Glu
    1700                1705                1710

Glu Cys Ala Ser Lys Ala Ala Leu Ile Glu Glu Gly Gln Arg Met
    1715                1720                1725

Ala Glu Met Leu Lys Thr Lys Ile Gln Gly Leu Leu Gln Gln Ala
    1730                1735                1740

Thr Arg Gln Ala Gln Asp Ile Gln Pro Ala Ile Gln Ser Ser Trp
    1745                1750                1755

Pro Lys Leu Glu Gln Phe Trp Ala Lys His Met Trp Asn Phe Ile
    1760                1765                1770

Ser Gly Ile Gln Tyr Leu Ala Gly Leu Ser Thr Leu Pro Gly Asn
    1775                1780                1785

Pro Thr Val Ala Ser Met Met Ala Phe Ser Ala Ala Leu Thr Ser
    1790                1795                1800

Pro Leu Pro Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Ile Leu Val Asp Val Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Thr Val Glu Asp Val Val Asn Leu Leu Pro Ala Ile Leu Ser Pro
    1880                1885                1890

Gly Ala Leu Val Val Gly Val Ile Cys Ala Ala Ile Leu Arg Arg
    1895                1900                1905

His Ile Gly Gln Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Ala Glu Ser Asp Ala Ser Gln Arg Val Thr Gln Ala Leu Ser
    1940                1945                1950

Ser Leu Thr Ile Thr Ser Leu Leu Arg Arg Leu His Ala Trp Ile
    1955                1960                1965
```

-continued

```
Thr Glu Asp Cys Pro Val Pro Cys Ser Gly Ser Trp Leu Arg Asp
1970                1975                1980

Ile Trp Asp Trp Val Cys Ser Ile Leu Thr Asp Phe Lys Asn Trp
1985                1990                1995

Leu Ser Ser Lys Leu Leu Pro Lys Leu Pro Gly Leu Pro Phe Ile
2000                2005                2010

Ser Cys Gln Lys Gly Tyr Arg Gly Val Trp Ala Gly Thr Gly Val
2015                2020                2025

Met Thr Thr Arg Cys Pro Cys Gly Ala Thr Ile Ser Gly His Val
2030                2035                2040

Arg Met Gly Thr Met Lys Ile Thr Gly Pro Lys Thr Cys Leu Asn
2045                2050                2055

Met Trp Gln Gly Ser Phe Pro Ile Asn Cys Tyr Thr Glu Gly Pro
2060                2065                2070

Cys Val Pro Lys Pro Pro Pro Asn Tyr Lys Thr Ala Ile Trp Arg
2075                2080                2085

Val Ala Ala Ser Glu Tyr Val Glu Ile Thr Gln His Gly Ser Phe
2090                2095                2100

Ser Tyr Val Thr Gly Leu Thr Asn Asp Asn Leu Lys Val Pro Cys
2105                2110                2115

Gln Val Pro Ala Pro Glu Phe Phe Ser Trp Val Asp Gly Val Gln
2120                2125                2130

Ile His Arg Phe Ala Pro Thr Pro Gly Pro Phe Phe Arg Asp Glu
2135                2140                2145

Val Thr Phe Thr Val Gly Leu Asn Ser Phe Val Val Gly Ser Gln
2150                2155                2160

Leu Pro Cys Asp Pro Glu Pro Asp Thr Glu Val Leu Ala Ser Met
2165                2170                2175

Leu Thr Asp Pro Ser His Ile Thr Ala Glu Ala Ala Ala Arg Arg
2180                2185                2190

Leu Ala Arg Gly Ser Pro Pro Ser Gln Ala Ser Ser Ser Ala Ser
2195                2200                2205

Gln Leu Ser Ala Pro Ser Leu Lys Ala Thr Cys Thr Thr His Lys
2210                2215                2220

Val Ala Tyr Asp Cys Asp Met Val Asp Ala Asn Leu Phe Met Gly
2225                2230                2235

Gly Asp Val Thr Arg Ile Glu Ser Asn Ser Lys Val Val Ile Leu
2240                2245                2250

Asp Ser Leu Asp Ser Met Thr Glu Val Glu Asp Arg Glu Pro
2255                2260                2265

Ser Ile Pro Ser Glu Tyr Leu Ile Arg Arg Arg Lys Phe Pro Pro
2270                2275                2280

Ala Leu Pro Pro Trp Ala Arg Pro Asp Tyr Asn Pro Pro Val Val
2285                2290                2295

Glu Thr Trp Lys Arg Pro Asp Tyr Glu Pro Pro Thr Val Leu Gly
2300                2305                2310

Cys Ala Leu Pro Pro Thr Pro Gln Ala Pro Val Pro Pro Pro Arg
2315                2320                2325

Arg Arg Arg Ala Lys Val Leu Thr Gln Asp Asn Val Glu Gly Val
2330                2335                2340

Leu Lys Glu Met Ala Asp Lys Val Leu Ser Pro Leu Arg Asp Cys
2345                2350                2355

Asn Asp Ser Gly His Ser Thr Gly Ala Asp Thr Gly Ala Asp Ser
```

-continued

```
            2360                2365                2370
Val Gln Gln Pro Pro Asp Glu Thr Ala Ala Ser Glu Ala Gly Ser
            2375                2380                2385
Leu Ser Ser Met Pro Pro Leu Glu Gly Glu Pro Gly Asp Pro Asp
            2390                2395                2400
Leu Glu Phe Glu Pro Ala Gly Ser Ala Pro Pro Ser Glu Gly Glu
            2405                2410                2415
Cys Glu Val Ile Asp Ser Asp Ser Lys Ser Trp Ser Thr Val Ser
            2420                2425                2430
Asp Gln Glu Asp Ser Thr Ile Cys Cys Ser Met Ser Tyr Ser Trp
            2435                2440                2445
Thr Gly Ala Leu Ile Thr Pro Cys Gly Pro Glu Glu Glu Lys Leu
            2450                2455                2460
Pro Ile Asn Pro Leu Ser Asn Ser Leu Met Arg Phe His Asn Lys
            2465                2470                2475
Val Tyr Ser Thr Thr Ser Arg Ser Ala Ser Gln Arg Ala Lys Lys
            2480                2485                2490
Val Thr Phe Asp Arg Val Gln Val Leu Asp Lys His Tyr Asp Ser
            2495                2500                2505
Val Leu Gln Asp Val Lys Arg Ala Ala Ser Lys Val Ser Ala Arg
            2510                2515                2520
Leu Leu Ser Ile Glu Glu Ala Cys Ala Leu Thr Pro Pro His Ser
            2525                2530                2535
Ala Lys Ser Arg Tyr Gly Phe Gly Ala Lys Glu Val Arg Ser Leu
            2540                2545                2550
Ser Arg Arg Ala Val Asn His Ile Gln Ser Val Trp Glu Asp Leu
            2555                2560                2565
Leu Glu Asp Gln His Thr Pro Ile Glu Thr Thr Ile Met Ala Lys
            2570                2575                2580
Asn Glu Val Phe Cys Val Asp Pro Ala Lys Gly Gly Lys Lys Ser
            2585                2590                2595
Ala Arg Leu Ile Val Tyr Pro Asp Leu Gly Val Arg Val Cys Glu
            2600                2605                2610
Lys Met Ala Leu Tyr Asp Ile Ala Gln Lys Leu Pro Lys Ala Ile
            2615                2620                2625
Met Gly Pro Ser Tyr Gly Phe Gln Tyr Ser Pro Ala Glu Arg Val
            2630                2635                2640
Asp Phe Leu Leu Lys Ala Trp Gly Ser Lys Lys Asp Pro Met Gly
            2645                2650                2655
Phe Ser Tyr Asp Thr Arg Cys Phe Asp Ser Thr Val Thr Glu Arg
            2660                2665                2670
Asp Ile Arg Thr Glu Glu Ser Ile Tyr Gln Ala Cys Ser Leu Pro
            2675                2680                2685
Gln Glu Ala Arg Val Ala Ile His Ser Leu Thr Glu Arg Leu Tyr
            2690                2695                2700
Val Gly Gly Pro Met Leu Asn Ser Lys Gly Gln Ser Cys Gly Tyr
            2705                2710                2715
Arg Arg Cys Arg Ala Ser Gly Val Phe Thr Thr Ser Met Gly Asn
            2720                2725                2730
Thr Met Thr Cys Tyr Ile Lys Ala Leu Ala Ala Cys Gln Ala Ala
            2735                2740                2745
Gly Ile Val Asp Pro Val Met Leu Val Cys Gly Asp Asp Leu Val
            2750                2755                2760
```

```
Val Ile Ser Glu Ser Gln Gly Asn Asp Glu Asp Glu Arg Asn Leu
        2765                2770                2775

Arg Ala Phe Thr Glu Ala Met Thr Arg Tyr Ser Ala Pro Pro Gly
    2780                2785                2790

Asp Leu Pro Arg Pro Glu Tyr Asp Leu Glu Leu Ile Thr Ser Cys
    2795                2800                2805

Ser Ser Asn Val Ser Val Ala Leu Asp Pro Arg Gly Arg Arg Arg
    2810                2815                2820

Tyr Tyr Leu Thr Arg Asp Pro Thr Thr Pro Ile Ser Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Val Arg Met Val Ile Met
    2855                2860                2865

Thr His Phe Phe Ser Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895

Leu Asp Leu Pro Ala Ile Ile Glu Arg Leu His Gly Leu Asp Ala
    2900                2905                2910

Phe Ser Leu His Thr Tyr Ser Pro His Glu Leu Ser Arg Val Ala
    2915                2920                2925

Ala Thr Leu Arg Lys Leu Gly Ala Pro Pro Leu Arg Ala Trp Lys
    2930                2935                2940

Ser Arg Ala Arg Ala Val Arg Ala Ser Leu Ile Ala Gln Gly Gly
    2945                2950                2955

Lys Ala Ala Ile Cys Gly Arg Tyr Leu Phe Asn Trp Ala Val Lys
    2960                2965                2970

Thr Lys Leu Lys Leu Thr Pro Leu Pro Glu Ala Ser Arg Leu Asp
    2975                2980                2985

Leu Ser Gly Trp Phe Thr Val Gly Ala Gly Gly Gly Ile Phe
    2990                2995                3000

His Ser Val Ser His Ala Arg Pro Arg Leu Leu Leu Leu Cys Leu
    3005                3010                3015

Leu Leu Phe Ser Val Gly Val Gly Ile Phe Leu Leu Pro Ala Arg
    3020                3025                3030

<210> SEQ ID NO 25
<211> LENGTH: 3033
<212> TYPE: PRT
<213> ORGANISM: Hepatitis C virus

<400> SEQUENCE: 25

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
```

```
                    85                  90                  95
Leu Leu Ser Pro Arg Gly Ser Arg Pro Thr Trp Gly Pro Thr Asp Pro
                100                 105                 110

Arg His Arg Ser Arg Asn Leu Gly Arg Val Ile Asp Thr Ile Thr Cys
                115                 120                 125

Gly Phe Ala Asp Leu Met Gly Tyr Ile Pro Val Val Gly Ala Pro Val
                130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Phe Thr Val Pro Val Ser Ala Val
                180                 185                 190

Glu Val Arg Asn Ile Ser Ser Ser Tyr Tyr Ala Thr Asn Asp Cys Ser
                195                 200                 205

Asn Ser Ser Ile Thr Trp Gln Leu Ala Asp Ala Val Leu His Leu Pro
                210                 215                 220

Gly Cys Val Pro Cys Glu Asn Asn Gly Thr Pro Arg Cys Trp Ile
225                 230                 235                 240

Gln Val Thr Pro Asn Val Ala Val Lys Tyr Arg Gly Ala Leu Thr His
                245                 250                 255

Ser Leu Arg Thr His Ile Asp Val Ile Val Met Ala Ala Thr Val Cys
                260                 265                 270

Ser Ala Leu Tyr Val Gly Asp Val Cys Gly Ala Val Met Ile Val Ser
                275                 280                 285

Gln Ala Phe Ile Val Ser Pro Gln Phe His Asn Phe Thr Gln Glu Cys
                290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Ile Leu Ala Tyr
                325                 330                 335

Ala Thr Arg Val Pro Glu Leu Ala Leu Glu Ile Val Phe Gly Gly His
                340                 345                 350

Trp Gly Val Val Phe Gly Leu Ala Tyr Phe Ser Leu Gln Gly Ala Trp
                355                 360                 365

Ala Lys Val Val Ala Ile Leu Leu Leu Val Ala Gly Val Asp Ala His
                370                 375                 380

Thr Gln Leu Thr Gly Thr Asn Val Gly Arg Thr Thr Ala Gly Phe Ala
385                 390                 395                 400

Ser Leu Phe Ala Pro Gly Ala Arg Gln Glu Ile Ser Leu Ile Asn Thr
                405                 410                 415

Asn Gly Ser Trp His Val Asn Arg Thr Ala Leu Asn Cys Asn Asp Ser
                420                 425                 430

Leu Asn Thr Gly Phe Leu Thr Ala Leu Phe Tyr Arg Asn Lys Phe Asn
                435                 440                 445

Ser Ser Gly Cys Pro Glu Arg Leu Ser Ser Cys Arg Glu Leu Asp Asp
                450                 455                 460

Phe Arg Ile Gly Trp Gly Thr Val Glu Tyr Glu Thr Val Thr Asn
465                 470                 475                 480

Asp Glu Asp Met Arg Pro Tyr Cys Trp His Tyr Pro Pro Lys Pro Cys
                485                 490                 495

Gly Ile Val Ser Ala Lys Thr Val Cys Gly Pro Val Tyr Cys Phe Thr
                500                 505                 510
```

```
Pro Ser Pro Val Val Gly Thr Thr Asp Arg Leu Gly Ala Pro Thr
    515                 520                 525

Tyr Asn Trp Gly Ile Asn Glu Thr Asp Val Phe Leu Leu Asn Ser Thr
    530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

His Asn Ser Thr Leu Asp Leu Leu Cys Pro Thr Asp Cys Phe Arg Lys
            580                 585                 590

His Pro Asp Thr Thr Tyr Leu Lys Cys Gly Ala Gly Pro Trp Leu Thr
        595                 600                 605

Pro Lys Cys Leu Ile Asp Tyr Pro Tyr Arg Leu Trp His Tyr Pro Cys
    610                 615                 620

Thr Val Asn Phe Thr Ile Phe Lys Val Arg Met Tyr Val Gly Gly Val
625                 630                 635                 640

Glu His Arg Leu Asp Ala Ala Cys Asn Phe Thr Arg Gly Asp Arg Cys
                645                 650                 655

Arg Leu Glu Asp Arg Asp Arg Gly Gln Gln Thr Pro Leu Leu His Ser
            660                 665                 670

Thr Thr Glu Trp Ala Ile Leu Pro Cys Thr Phe Ser Asp Leu Pro Ala
        675                 680                 685

Leu Ser Thr Gly Leu Leu His Leu His Gln Asn Thr Val Asp Val Gln
    690                 695                 700

Tyr Leu Tyr Gly Leu Thr Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
            740                 745                 750

Glu Lys Leu Ile Ile Leu His Ser Ala Ser Ala Ala Ser Ala Asn Gly
        755                 760                 765

Pro Leu Trp Phe Phe Ile Phe Phe Ile Ala Ala Trp Tyr Leu Lys Gly
    770                 775                 780

Arg Val Val Pro Ala Ala Thr Tyr Ser Val Leu Gly Leu Trp Ser Phe
785                 790                 795                 800

Leu Leu Leu Val Leu Ala Leu Pro Gln Gln Ala Tyr Ala Leu Asp Ala
                805                 810                 815

Thr Glu Gln Gly Glu Leu Gly Leu Val Met Leu Val Val Leu Ser Ile
            820                 825                 830

Phe Thr Leu Thr Pro Ala Tyr Lys Thr Leu Leu Ser Arg Ser Val Trp
        835                 840                 845

Trp Leu Ser Tyr Met Leu Val Leu Ala Glu Ala Gln Val Gln Gln Trp
    850                 855                 860

Val Pro Pro Leu Glu Ala Arg Gly Gly Arg Asp Gly Ile Ile Trp Ala
865                 870                 875                 880

Ala Val Ile Leu His Pro Arg Leu Val Phe Glu Ile Thr Lys Trp Leu
                885                 890                 895

Leu Ala Ile Leu Gly Pro Ala Tyr Phe Leu Lys Ala Ser Leu Leu Arg
            900                 905                 910

Val Pro Tyr Phe Val Arg Ala His Ala Leu Leu Arg Met Cys Thr Leu
        915                 920                 925
```

```
Val Arg His Leu Ala Gly Ala Lys Tyr Ile Gln Met Leu Leu Ile Thr
930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
                965                 970                 975

Pro Val Val Phe Ser Pro Met Glu Lys Lys Val Ile Val Trp Gly Ala
                980                 985                 990

Glu Thr Ala Ala Cys Gly Asp Ile Leu His Gly Leu Pro Val Ser Ala
                995                 1000                1005

Arg Leu Gly Arg Glu Val Leu Leu Gly Pro Ala Asp Gly Tyr Thr
    1010                1015                1020

Ser Lys Gly Trp Lys Leu Leu Ala Pro Ile Thr Ala Tyr Thr Gln
    1025                1030                1035

Gln Thr Arg Gly Leu Leu Gly Ser Ile Val Val Cys Leu Thr Gly
    1040                1045                1050

Arg Asp Lys Asn Glu Gln Ala Gly His Val Gln Val Leu Ser Ser
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Pro Lys
    1085                1090                1095

Gly Pro Ile Thr Gln Met Tyr Thr Ser Ala Glu Gly Asp Leu Val
    1100                1105                1110

Gly Trp Pro Ser Pro Pro Gly Thr Lys Ser Leu Asp Pro Cys Thr
    1115                1120                1125

Cys Gly Ala Val Asp Leu Tyr Leu Val Thr Arg Asn Ala Asp Val
    1130                1135                1140

Ile Pro Val Arg Arg Lys Asp Asp Arg Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Pro Arg Gly His Ala Val Gly Leu Phe Arg Ala Ala Leu
    1175                1180                1185

Cys Ala Arg Gly Val Ala Lys Ser Ile Asp Phe Ile Pro Val Glu
    1190                1195                1200

Ser Leu Asp Ile Val Ala Arg Ser Pro Ser Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Ala Ala Tyr
    1235                1240                1245

Ala Ser Gln Gly Tyr Lys Val Leu Val Leu Asn Pro Ser Val Ala
    1250                1255                1260

Ala Thr Leu Gly Phe Gly Ala Tyr Met Ser Lys Ala His Gly Ile
    1265                1270                1275

Asn Pro Asn Ile Arg Thr Gly Val Arg Thr Val Thr Thr Gly Asp
    1280                1285                1290

Pro Ile Thr Tyr Ser Thr Tyr Gly Lys Phe Leu Ala Asp Gly Gly
    1295                1300                1305

Cys Ser Ala Gly Ala Tyr Asp Ile Ile Ile Cys Asp Glu Cys His
    1310                1315                1320

Ala Val Asp Ala Thr Thr Ile Leu Gly Ile Gly Thr Val Leu Asp
```

```
            1325                1330                1335

Gln Ala Glu Thr Ala Gly Ala Arg Leu Val Val Leu Ala Thr Ala
        1340                1345                1350

Thr Pro Pro Gly Thr Val Thr Thr Pro His Ser Asn Ile Glu Glu
        1355                1360                1365

Val Ala Leu Gly His Glu Gly Glu Ile Pro Phe Tyr Gly Lys Ala
        1370                1375                1380

Ile Pro Leu Ala Phe Ile Lys Gly Gly Arg His Leu Ile Phe Cys
        1385                1390                1395

His Ser Lys Lys Lys Cys Asp Glu Val Ala Ala Leu Arg Ser
        1400                1405                1410

Val Gly Val Asn Ala Val Ala Tyr Tyr Arg Gly Leu Asp Val Ser
        1415                1420                1425

Val Ile Pro Thr Gln Gly Asp Val Val Val Ala Thr Asp Ala
        1430                1435                1440

Leu Met Thr Gly Tyr Thr Gly Asp Phe Asp Ser Val Ile Asp Cys
        1445                1450                1455

Asn Val Ala Val Thr Gln Ile Val Asp Leu Ser Leu Asp Pro Thr
        1460                1465                1470

Phe Thr Ile Thr Thr Gln Thr Val Pro Gln Asp Ala Val Ser Arg
        1475                1480                1485

Ser Gln Arg Arg Gly Arg Thr Gly Arg Gly Arg Leu Gly Ile Tyr
        1490                1495                1500

Arg Tyr Val Ser Ser Gly Glu Arg Pro Ser Gly Met Phe Asp Ser
        1505                1510                1515

Val Val Leu Cys Glu Cys Tyr Asp Ala Gly Ala Ala Trp Tyr Glu
        1520                1525                1530

Leu Thr Pro Ala Glu Thr Thr Val Arg Leu Arg Ala Tyr Phe Asn
        1535                1540                1545

Thr Pro Gly Leu Pro Val Cys Gln Asp His Leu Glu Phe Trp Glu
        1550                1555                1560

Ala Val Phe Thr Gly Leu Thr His Ile Asp Ala His Phe Leu Ser
        1565                1570                1575

Gln Thr Lys Gln Gly Gly Asp Asn Phe Ala Tyr Leu Thr Ala Tyr
        1580                1585                1590

Gln Ala Thr Val Cys Ala Arg Ala Lys Ala Pro Pro Pro Ser Trp
        1595                1600                1605

Asp Val Met Trp Lys Cys Leu Thr Arg Leu Lys Pro Thr Leu Thr
        1610                1615                1620

Gly Pro Thr Pro Leu Leu Tyr Arg Leu Gly Ala Val Thr Asn Glu
        1625                1630                1635

Ile Thr Leu Thr His Pro Val Thr Lys Tyr Ile Ala Thr Cys Met
        1640                1645                1650

Gln Ala Asp Leu Glu Ile Met Thr Ser Thr Trp Val Leu Ala Gly
        1655                1660                1665

Gly Val Leu Ala Ala Val Ala Ser Tyr Cys Leu Ala Thr Gly Cys
        1670                1675                1680

Ile Ser Ile Ile Gly Arg Leu His Leu Asn Asp Arg Val Val Val
        1685                1690                1695

Ala Pro Asp Lys Glu Ile Leu Tyr Glu Ala Phe Asp Glu Met Glu
        1700                1705                1710

Glu Cys Ala Ser Lys Ala Ala Leu Ile Glu Glu Gly His Arg Met
        1715                1720                1725
```

-continued

```
Ala Glu Met Leu Lys Ser Lys Ile Gln Gly Leu Leu Gln Gln Ala
    1730                1735                1740

Thr Lys Gln Ala Gln Asp Ile Gln Pro Ala Ile Gln Ser Ser Trp
    1745                1750                1755

Pro Lys Leu Glu Gln Phe Trp Ala Lys His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Pro Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Ile Leu Val Asp Val Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Ser Val Glu Asp Val Val Asn Leu Leu Pro Ala Ile Leu Ser Pro
    1880                1885                1890

Gly Ala Leu Val Val Gly Val Ile Cys Ala Ala Ile Leu Arg Arg
    1895                1900                1905

His Val Gly Gln Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Ala Glu Ser Asp Ala Ser Gln Arg Val Thr Gln Val Leu Ser
    1940                1945                1950

Ser Leu Thr Ile Thr Ser Leu Leu Arg Arg Leu His Ala Trp Ile
    1955                1960                1965

Thr Glu Asp Cys Pro Val Pro Cys Ser Gly Ser Trp Leu Arg Asp
    1970                1975                1980

Ile Trp Asp Trp Val Cys Ser Ile Leu Thr Asp Phe Lys Asn Trp
    1985                1990                1995

Leu Ser Ser Lys Leu Leu Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Ser Cys Gly Ala Asn Ile Ser Gly His Val
    2030                2035                2040

Arg Met Gly Thr Met Lys Ile Thr Gly Pro Lys Thr Cys Leu Asn
    2045                2050                2055

Leu Trp Gln Gly Thr Phe Pro Ile Asn Cys Tyr Thr Glu Gly Pro
    2060                2065                2070

Cys Val Pro Lys Pro Pro Pro Asn Tyr Lys Thr Ala Ile Trp Arg
    2075                2080                2085

Val Ala Ala Ser Glu Tyr Val Glu Ile Thr Gln His Gly Ser Phe
    2090                2095                2100

Ser Tyr Val Thr Gly Leu Thr Ser Asp Asn Leu Lys Val Pro Cys
    2105                2110                2115
```

-continued

```
Gln Val Pro Ala Pro Glu Phe Phe Ser Trp Val Asp Gly Val Gln
2120                2125                2130

Ile His Arg Phe Ala Pro Thr Pro Gly Pro Phe Phe Arg Asp Glu
2135                2140                2145

Val Thr Phe Ser Val Gly Leu Asn Ser Phe Val Val Gly Ser Gln
2150                2155                2160

Leu Pro Cys Asp Pro Glu Pro Asp Thr Glu Val Leu Ala Ser Met
2165                2170                2175

Leu Thr Asp Pro Ser His Ile Thr Ala Glu Ala Ala Ala Arg Arg
2180                2185                2190

Leu Ala Arg Gly Ser Pro Pro Ser Gln Ala Ser Ser Ser Ala Ser
2195                2200                2205

Gln Leu Ser Ala Pro Ser Leu Lys Ala Thr Cys Thr Thr His Lys
2210                2215                2220

Met Ala Tyr Asp Cys Asp Met Val Asp Ala Asn Leu Phe Met Gly
2225                2230                2235

Gly Asp Val Thr Arg Ile Glu Ser Asn Ser Lys Val Ile Val Leu
2240                2245                2250

Asp Ser Leu Asp Ser Met Thr Glu Ala Glu Asp Asp Arg Glu Pro
2255                2260                2265

Ser Ile Pro Ser Glu Tyr Leu Ile Arg Arg Lys Phe Pro Pro
2270                2275                2280

Ala Leu Pro Pro Trp Ala Arg Pro Asp Tyr Asn Pro Pro Val Ile
2285                2290                2295

Glu Thr Trp Lys Arg Pro Gly Tyr Glu Pro Pro Thr Val Leu Gly
2300                2305                2310

Cys Ala Leu Pro Pro Thr Pro Gln Ala Pro Val Pro Pro Pro Arg
2315                2320                2325

Arg Arg Arg Ala Lys Val Leu Thr Gln Asp Asn Val Glu Gly Val
2330                2335                2340

Leu Lys Glu Met Ala Asp Lys Val Leu Ser Pro Leu Gln Asp Tyr
2345                2350                2355

Asn Asp Ser Gly His Ser Thr Gly Val Gly Thr Gly Gly Asp Ser
2360                2365                2370

Val Gln Glu Pro Ser Asp Glu Thr Ala Ala Ser Glu Val Gly Ser
2375                2380                2385

Leu Ser Ser Met Pro Pro Leu Glu Gly Glu Pro Gly Asp Pro Asp
2390                2395                2400

Leu Glu Phe Glu Pro Ala Arg Ser Ala Pro Pro Ser Glu Gly Glu
2405                2410                2415

Cys Glu Val Val Asp Ser Asp Ser Lys Ser Trp Ser Thr Val Ser
2420                2425                2430

Asp Gln Glu Asp Ser Ile Val Cys Cys Ser Met Ser Tyr Ser Trp
2435                2440                2445

Thr Gly Ala Leu Ile Thr Pro Cys Gly Pro Glu Glu Glu Lys Leu
2450                2455                2460

Pro Ile Asn Pro Leu Ser Asn Ser Leu Met Arg Phe His Asn Lys
2465                2470                2475

Val Tyr Ser Thr Thr Ser Arg Ser Ala Ala Leu Arg Ala Lys Lys
2480                2485                2490

Val Thr Phe Asp Arg Val Gln Ile Leu Asp Thr Tyr Tyr Asp Ser
2495                2500                2505

Val Leu Gln Asp Val Lys Arg Ala Ala Ser Lys Val Ser Ala Arg
```

-continued

```
                    2510                2515                2520

Leu Leu Ser Val Glu Glu Ala Cys Ala Leu Thr Pro Pro His Ser
    2525                2530                2535

Ala Arg Ser Arg Tyr Gly Phe Gly Ala Lys Glu Val Arg Ser Leu
    2540                2545                2550

Ser Arg Arg Ala Val Asn His Ile Gln Ser Val Trp Glu Asp Leu
    2555                2560                2565

Leu Glu Asp Gln Asn Thr Pro Ile Glu Thr Thr Ile Met Ala Lys
    2570                2575                2580

Asn Glu Val Phe Cys Val Asp Pro Ala Lys Gly Lys Lys Ala
    2585                2590                2595

Ala Arg Leu Ile Val Tyr Pro Asp Leu Gly Val Arg Val Cys Glu
    2600                2605                2610

Lys Met Ala Leu Tyr Asp Ile Ala Gln Lys Leu Pro Lys Ala Ile
    2615                2620                2625

Met Gly Pro Ser Tyr Gly Phe Gln Tyr Ser Pro Ala Glu Arg Val
    2630                2635                2640

Asp Phe Leu Leu Lys Ala Trp Gly Ser Lys Lys Asp Pro Met Gly
    2645                2650                2655

Phe Ser Tyr Asp Thr Arg Cys Phe Asp Ser Thr Val Thr Glu Arg
    2660                2665                2670

Asp Ile Arg Thr Glu Glu Ser Ile Tyr Gln Ala Cys Ser Leu Pro
    2675                2680                2685

Gln Glu Ala Arg Thr Val Ile His Ser Leu Thr Glu Arg Leu Tyr
    2690                2695                2700

Val Gly Gly Pro Met Leu Asn Ser Lys Gly Gln Ser Cys Gly Tyr
    2705                2710                2715

Arg Arg Cys Arg Ala Ser Gly Val Phe Thr Thr Ser Met Gly Asn
    2720                2725                2730

Thr Met Thr Cys Tyr Ile Lys Ala Leu Ala Ala Cys Lys Ala Ala
    2735                2740                2745

Gly Ile Val Asp Pro Val Met Leu Val Cys Gly Asp Asp Leu Val
    2750                2755                2760

Val Ile Ser Glu Ser Gln Gly Asn Glu Glu Asp Glu Arg Asn Leu
    2765                2770                2775

Arg Ala Phe Thr Glu Ala Met Thr Arg Tyr Ser Ala Pro Pro Gly
    2780                2785                2790

Asp Leu Pro Arg Pro Glu Tyr Asp Leu Glu Leu Ile Thr Ser Cys
    2795                2800                2805

Ser Ser Asn Val Ser Val Ala Leu Asp Pro Arg Gly Arg Arg Arg
    2810                2815                2820

Tyr Tyr Leu Thr Arg Asp Pro Ile Thr Pro Ile Ser Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Val Arg Met Val Ile Met
    2855                2860                2865

Thr His Phe Phe Ala Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895

Leu Asp Leu Pro Ala Ile Ile Glu Arg Leu His Gly Leu Asp Ala
    2900                2905                2910
```

-continued

```
Phe Ser Leu His Thr Tyr Ser Pro Thr Glu Leu Thr Arg Val Ala
    2915                2920                2925

Ala Ala Leu Arg Lys Leu Gly Ala Pro Pro Leu Arg Ala Trp Lys
    2930                2935                2940

Ser Arg Ala Arg Ala Val Arg Ala Ser Leu Leu Ala Gln Gly Gly
    2945                2950                2955

Arg Ala Ala Ile Cys Gly Arg Tyr Leu Phe Asn Trp Ala Val Lys
    2960                2965                2970

Thr Lys Leu Lys Leu Thr Pro Leu Pro Glu Ala Ser Arg Leu Asp
    2975                2980                2985

Leu Ser Arg Trp Phe Thr Val Gly Ala Gly Gly Gly Ile Phe
    2990                2995                3000

His Ser Val Ser His Ala Arg Pro Arg Leu Leu Leu Leu Cys Leu
    3005                3010                3015

Leu Leu Leu Ser Val Gly Val Gly Ile Phe Leu Leu Pro Ala Arg
    3020                3025                3030

<210> SEQ ID NO 26
<211> LENGTH: 3033
<212> TYPE: PRT
<213> ORGANISM: Hepatitis C virus

<400> SEQUENCE: 26

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Phe Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Ser Ser Ile Thr Trp Gln Leu Ala Asp Ala Val Leu His Leu Pro
    210                 215                 220

Gly Cys Val Pro Cys Glu Asn Asn Gly Thr Pro Arg Cys Trp Ile
225                 230                 235                 240

Gln Val Thr Pro Asn Val Ala Val Lys Tyr Arg Gly Ala Leu Thr His
```

-continued

```
                245                 250                 255
Ser Leu Arg Thr His Ile Asp Val Ile Val Met Ala Ala Thr Val Cys
            260                 265                 270
Ser Ala Leu Tyr Val Gly Asp Val Cys Gly Ala Val Met Ile Val Ser
        275                 280                 285
Gln Ala Phe Ile Val Ser Pro Gln Phe His Asn Phe Thr Gln Glu Cys
    290                 295                 300
Asn Cys Ser Ile Tyr Gln Gly His Ile Thr Gly His Arg Met Ala Trp
305                 310                 315                 320
Asp Met Met Leu Asn Trp Ser Pro Thr Leu Thr Met Ile Leu Ala Tyr
                325                 330                 335
Ala Thr Arg Val Pro Glu Leu Ala Leu Glu Ile Val Phe Gly Gly His
            340                 345                 350
Trp Gly Val Val Phe Gly Leu Ala Tyr Phe Ser Leu Gln Gly Ala Trp
        355                 360                 365
Ala Lys Val Val Ala Ile Leu Leu Leu Val Ala Gly Val Asp Ala His
    370                 375                 380
Thr Gln Leu Thr Gly Thr Asn Val Gly Arg Thr Thr Ala Gly Phe Ala
385                 390                 395                 400
Ser Leu Phe Ala Pro Gly Ala Arg Gln Glu Ile Ser Leu Ile Asn Thr
                405                 410                 415
Asn Gly Ser Trp His Val Asn Arg Thr Ala Leu Asn Cys Asn Asp Ser
            420                 425                 430
Leu Asn Thr Gly Phe Leu Thr Ala Leu Phe Tyr Arg Asn Lys Phe Asn
        435                 440                 445
Ser Ser Gly Cys Pro Glu Arg Leu Ser Ser Cys Arg Glu Leu Asp Asp
    450                 455                 460
Phe Arg Ile Gly Trp Gly Thr Val Glu Tyr Glu Thr Val Val Thr Asn
465                 470                 475                 480
Asp Glu Asp Met Arg Pro Tyr Cys Trp His Tyr Pro Pro Lys Pro Cys
                485                 490                 495
Gly Ile Val Ser Ala Lys Thr Val Cys Gly Pro Val Tyr Cys Phe Thr
            500                 505                 510
Pro Ser Pro Val Val Val Gly Thr Thr Asp Arg Leu Gly Ala Pro Thr
        515                 520                 525
Tyr Asn Trp Gly Ile Asn Glu Thr Asp Val Phe Leu Leu Asn Ser Thr
    530                 535                 540
Arg Pro Pro Gln Gly Ala Trp Phe Gly Cys Thr Trp Met Asn Gly Thr
545                 550                 555                 560
Gly Phe Thr Lys Thr Cys Gly Ala Pro Pro Cys Arg Ile Arg Arg Asp
                565                 570                 575
His Asn Ser Thr Leu Asp Leu Leu Cys Pro Thr Asp Cys Phe Arg Lys
            580                 585                 590
His Pro Asp Thr Thr Tyr Leu Lys Cys Gly Ala Gly Pro Trp Leu Thr
        595                 600                 605
Pro Lys Cys Leu Ile Asp Tyr Pro Tyr Arg Leu Trp His Tyr Pro Cys
    610                 615                 620
Thr Val Asn Phe Thr Ile Phe Lys Val Arg Met Tyr Val Gly Gly Val
625                 630                 635                 640
Glu His Arg Leu Asp Ala Ala Cys Asn Phe Thr Arg Gly Asp Arg Cys
                645                 650                 655
Arg Leu Glu Asp Arg Asp Arg Gly Gln Gln Thr Pro Leu Leu His Ser
            660                 665                 670
```

```
Thr Thr Glu Trp Ala Ile Leu Pro Cys Thr Phe Ser Asp Leu Pro Ala
        675                 680                 685

Leu Ser Thr Gly Leu Leu His Leu His Gln Asn Thr Val Asp Val Gln
690                 695                 700

Tyr Leu Tyr Gly Leu Thr Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
                740                 745                 750

Glu Lys Leu Ile Ile Leu His Ser Ala Ser Ala Ala Ser Ala Asn Gly
                755                 760                 765

Pro Leu Trp Phe Phe Ile Phe Phe Ile Ala Ala Trp Tyr Leu Lys Gly
770                 775                 780

Arg Val Val Pro Ala Ala Thr Tyr Ser Val Leu Gly Leu Trp Ser Phe
785                 790                 795                 800

Leu Leu Leu Val Leu Ala Leu Pro Gln Gln Ala Tyr Ala Leu Asp Ala
                805                 810                 815

Thr Glu Gln Gly Glu Leu Gly Leu Val Met Leu Val Val Leu Ser Ile
                820                 825                 830

Phe Thr Leu Thr Pro Ala Tyr Lys Thr Leu Leu Ser Arg Ser Val Trp
        835                 840                 845

Trp Leu Ser Tyr Met Leu Val Leu Ala Glu Ala Gln Val Gln Gln Trp
        850                 855                 860

Val Pro Pro Leu Glu Ala Arg Gly Gly Arg Asp Gly Ile Ile Trp Ala
865                 870                 875                 880

Ala Val Ile Leu His Pro Arg Leu Val Phe Glu Ile Thr Lys Trp Leu
                885                 890                 895

Leu Ala Ile Leu Gly Pro Ala Tyr Phe Leu Lys Ala Ser Leu Leu Arg
                900                 905                 910

Val Pro Tyr Phe Val Arg Ala His Ala Leu Leu Arg Met Cys Thr Leu
                915                 920                 925

Val Arg His Leu Ala Gly Ala Lys Tyr Ile Gln Met Leu Leu Ile Thr
        930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
                965                 970                 975

Pro Val Val Phe Ser Pro Met Glu Lys Lys Val Ile Val Trp Gly Ala
                980                 985                 990

Glu Thr Ala Ala Cys Gly Asp Ile Leu His Gly Leu Pro Val Ser Ala
        995                 1000                1005

Arg Leu Gly Arg Glu Val Leu Leu Gly Pro Ala Asp Gly Tyr Thr
        1010                1015                1020

Ser Lys Gly Trp Lys Leu Leu Ala Pro Ile Thr Ala Tyr Thr Gln
        1025                1030                1035

Gln Thr Arg Gly Leu Leu Gly Ser Ile Val Val Cys Leu Thr Gly
        1040                1045                1050

Arg Asp Lys Asn Glu Gln Ala Gly His Val Gln Val Leu Ser Ser
        1055                1060                1065

Val Thr Gln Ser Phe Leu Gly Thr Ser Ile Ser Gly Val Leu Trp
        1070                1075                1080
```

```
Thr Val Tyr His Gly Ala Gly Asn Lys Thr Leu Ala Gly Pro Lys
1085                1090                1095

Gly Pro Ile Thr Gln Met Tyr Thr Ser Ala Glu Gly Asp Leu Val
1100                1105                1110

Gly Trp Pro Ser Pro Pro Gly Thr Lys Ser Leu Asp Pro Cys Thr
1115                1120                1125

Cys Gly Ala Val Asp Leu Tyr Leu Val Thr Arg Asn Ala Asp Val
1130                1135                1140

Ile Pro Val Arg Arg Lys Asp Asp Arg Gly Ala Leu Leu Ser
1145                1150                1155

Pro Arg Pro Leu Ser Thr Leu Lys Gly Ser Ser Gly Gly Pro Val
1160                1165                1170

Leu Cys Pro Arg Gly His Ala Val Gly Leu Phe Arg Ala Ala Leu
1175                1180                1185

Cys Ala Arg Gly Val Ala Lys Ser Ile Asp Phe Ile Pro Val Glu
1190                1195                1200

Ser Leu Asp Ile Val Ala Arg Ser Pro Ser Phe Ser Asp Asn Ser
1205                1210                1215

Thr Pro Pro Ala Val Pro Gln Thr Tyr Gln Val Gly Tyr Leu His
1220                1225                1230

Ala Pro Thr Gly Ser Gly Lys Ser Thr Lys Val Pro Ala Ala Tyr
1235                1240                1245

Ala Ser Gln Gly Tyr Lys Val Leu Val Leu Asn Pro Ser Val Ala
1250                1255                1260

Ala Thr Leu Gly Phe Gly Ala Tyr Met Ser Lys Ala His Gly Ile
1265                1270                1275

Asn Pro Asn Ile Arg Thr Gly Val Arg Thr Val Thr Thr Gly Asp
1280                1285                1290

Pro Ile Thr Tyr Ser Thr Tyr Gly Lys Phe Leu Ala Asp Gly Gly
1295                1300                1305

Cys Ser Ala Gly Ala Tyr Asp Ile Ile Ile Cys Asp Glu Cys His
1310                1315                1320

Ala Val Asp Ala Thr Thr Ile Leu Gly Ile Gly Thr Val Leu Asp
1325                1330                1335

Gln Ala Glu Thr Ala Gly Ala Arg Leu Val Val Leu Ala Thr Ala
1340                1345                1350

Thr Pro Pro Gly Thr Val Thr Thr Pro His Ser Asn Ile Glu Glu
1355                1360                1365

Val Ala Leu Gly His Glu Gly Glu Ile Pro Phe Tyr Gly Lys Ala
1370                1375                1380

Ile Pro Leu Ala Phe Ile Lys Gly Gly Arg His Leu Ile Phe Cys
1385                1390                1395

His Ser Lys Lys Lys Cys Asp Glu Val Ala Ala Leu Arg Ser
1400                1405                1410

Val Gly Val Asn Ala Val Ala Tyr Tyr Arg Gly Leu Asp Val Ser
1415                1420                1425

Val Ile Pro Thr Gln Gly Asp Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Ile Val Asp Leu Ser Leu Asp Pro Thr
1460                1465                1470

Phe Thr Ile Thr Thr Gln Thr Val Pro Gln Asp Ala Val Ser Arg
```

-continued

```
              1475              1480              1485

Ser Gln Arg Arg Gly Arg Thr Gly Arg Gly Arg Leu Gly Ile Tyr
              1490              1495              1500

Arg Tyr Val Ser Ser Gly Glu Arg Pro Ser Gly Met Phe Asp Ser
              1505              1510              1515

Val Val Leu Cys Glu Cys Tyr Asp Ala Gly Ala Ala Trp Tyr Glu
              1520              1525              1530

Leu Thr Pro Ala Glu Thr Thr Val Arg Leu Arg Ala Tyr Phe Asn
              1535              1540              1545

Thr Pro Gly Leu Pro Val Cys Gln Asp His Leu Glu Phe Trp Glu
              1550              1555              1560

Ala Val Phe Thr Gly Leu Thr His Ile Asp Ala His Phe Leu Ser
              1565              1570              1575

Gln Thr Lys Gln Gly Gly Asp Asn Phe Ala Tyr Leu Thr Ala Tyr
              1580              1585              1590

Gln Ala Thr Val Cys Ala Arg Ala Lys Ala Pro Pro Ser Trp
              1595              1600              1605

Asp Val Met Trp Lys Cys Leu Thr Arg Leu Lys Pro Thr Leu Thr
              1610              1615              1620

Gly Pro Thr Pro Leu Leu Tyr Arg Leu Gly Ala Val Thr Asn Glu
              1625              1630              1635

Ile Thr Leu Thr His Pro Val Thr Lys Tyr Ile Ala Thr Cys Met
              1640              1645              1650

Gln Ala Asp Leu Glu Ile Met Thr Ser Thr Trp Val Leu Ala Gly
              1655              1660              1665

Gly Val Leu Ala Ala Val Ala Ser Tyr Cys Leu Ala Thr Gly Cys
              1670              1675              1680

Ile Ser Ile Ile Gly Arg Leu His Leu Asn Asp Arg Val Val Val
              1685              1690              1695

Ala Pro Asp Lys Glu Ile Leu Tyr Glu Ala Phe Asp Glu Met Glu
              1700              1705              1710

Glu Cys Ala Ser Lys Ala Ala Leu Ile Glu Glu Gly His Arg Met
              1715              1720              1725

Ala Glu Met Leu Lys Ser Lys Ile Gln Gly Leu Leu Gln Gln Ala
              1730              1735              1740

Thr Lys Gln Ala Gln Asp Ile Gln Pro Ala Ile Gln Ser Ser Trp
              1745              1750              1755

Pro Lys Leu Glu Gln Phe Trp Ala Lys His Met Trp Asn Phe Ile
              1760              1765              1770

Ser Gly Ile Gln Tyr Leu Ala Gly Leu Ser Thr Leu Pro Gly Asn
              1775              1780              1785

Pro Ala Val Ala Ser Met Met Ala Phe Ser Ala Ala Leu Thr Ser
              1790              1795              1800

Pro Leu Pro Thr Ser Thr Thr Ile Leu Leu Asn Ile Met Gly Gly
              1805              1810              1815

Trp Leu Ala Ser Gln Ile Ala Pro Pro Ala Gly Ala Thr Gly Phe
              1820              1825              1830

Val Val Ser Gly Leu Val Gly Ala Ala Val Gly Ser Ile Gly Leu
              1835              1840              1845

Gly Lys Ile Leu Val Asp Val Leu Ala Gly Tyr Gly Ala Gly Ile
              1850              1855              1860

Ser Gly Ala Leu Val Ala Phe Lys Ile Met Ser Gly Glu Lys Pro
              1865              1870              1875
```

-continued

```
Ser Val Glu Asp Val Val Asn Leu Leu Pro Ala Ile Leu Ser Pro
    1880            1885                1890

Gly Ala Leu Val Val Gly Val Ile Cys Ala Ala Ile Leu Arg Arg
    1895            1900                1905

His Val Gly Gln Gly Glu Gly Ala Val Gln Trp Met Asn Arg Leu
    1910            1915                1920

Ile Ala Phe Ala Ser Arg Gly Asn His Val Ala Pro Thr His Tyr
    1925            1930                1935

Val Ala Glu Ser Asp Ala Ser Gln Arg Val Thr Gln Ala Leu Ser
    1940            1945                1950

Ser Leu Thr Ile Thr Ser Leu Leu Arg Arg Leu His Ala Trp Ile
    1955            1960                1965

Thr Glu Asp Cys Pro Val Pro Cys Ser Gly Ser Trp Leu Arg Asp
    1970            1975                1980

Ile Trp Asp Trp Val Cys Ser Ile Leu Thr Asp Phe Lys Asn Trp
    1985            1990                1995

Leu Ser Ser Lys Leu Leu Pro Lys Leu Pro Gly Leu Pro Phe Ile
    2000            2005                2010

Ser Cys Gln Lys Gly Tyr Lys Gly Val Trp Ala Gly Thr Gly Ile
    2015            2020                2025

Met Thr Thr Arg Cys Ser Cys Gly Ala Asn Ile Ser Gly His Val
    2030            2035                2040

Arg Met Gly Thr Met Lys Ile Thr Gly Pro Lys Thr Cys Leu Asn
    2045            2050                2055

Leu Trp Gln Gly Thr Phe Pro Ile Asn Cys Tyr Thr Glu Gly Pro
    2060            2065                2070

Cys Val Pro Lys Pro Pro Pro Asn Tyr Lys Thr Ala Ile Trp Arg
    2075            2080                2085

Val Ala Ala Ser Glu Tyr Val Glu Ile Thr Gln His Gly Ser Phe
    2090            2095                2100

Ser Tyr Val Thr Gly Leu Thr Ser Asp Asn Leu Lys Val Pro Cys
    2105            2110                2115

Gln Val Pro Ala Pro Glu Phe Phe Ser Trp Val Asp Gly Val Gln
    2120            2125                2130

Ile His Arg Phe Ala Pro Thr Pro Gly Pro Phe Phe Arg Asp Glu
    2135            2140                2145

Val Thr Phe Ser Val Gly Leu Asn Ser Phe Val Val Gly Ser Gln
    2150            2155                2160

Leu Pro Cys Asp Pro Glu Pro Asp Thr Glu Val Leu Ala Ser Met
    2165            2170                2175

Leu Thr Asp Pro Ser His Ile Thr Ala Glu Ala Ala Arg Arg
    2180            2185                2190

Leu Ala Arg Gly Ser Pro Pro Ser Gln Ala Ser Ser Ser Ala Ser
    2195            2200                2205

Gln Leu Ser Ala Pro Ser Leu Lys Ala Thr Cys Thr Thr His Lys
    2210            2215                2220

Met Ala Tyr Asp Cys Asp Met Val Asp Ala Asn Leu Phe Met Gly
    2225            2230                2235

Gly Asp Val Thr Arg Ile Glu Ser Asn Ser Lys Val Ile Val Leu
    2240            2245                2250

Asp Ser Leu Asp Ser Met Thr Glu Ala Glu Asp Asp Arg Glu Pro
    2255            2260                2265
```

```
Ser Ile Pro Ser Glu Tyr Leu Ile Arg Arg Lys Lys Phe Pro Pro
    2270            2275            2280

Ala Leu Pro Pro Trp Ala Arg Pro Asp Tyr Asn Pro Pro Val Ile
    2285            2290            2295

Glu Thr Trp Lys Arg Pro Gly Tyr Glu Pro Pro Thr Val Leu Gly
    2300            2305            2310

Cys Ala Leu Pro Pro Thr Pro Gln Ala Pro Val Pro Pro Pro Arg
    2315            2320            2325

Arg Arg Arg Ala Lys Val Leu Thr Gln Asp Asn Val Glu Gly Val
    2330            2335            2340

Leu Lys Glu Met Ala Asp Lys Val Leu Ser Pro Leu Gln Asp Tyr
    2345            2350            2355

Asn Asp Ser Gly His Ser Thr Gly Val Gly Thr Gly Gly Asp Ser
    2360            2365            2370

Val Gln Glu Pro Ser Asp Glu Thr Ala Ala Ser Glu Val Gly Ser
    2375            2380            2385

Leu Ser Ser Met Pro Pro Leu Glu Gly Glu Pro Gly Asp Pro Asp
    2390            2395            2400

Leu Glu Phe Glu Pro Ala Arg Ser Ala Pro Pro Ser Glu Gly Glu
    2405            2410            2415

Cys Glu Val Val Asp Ser Asp Ser Lys Ser Trp Ser Thr Val Ser
    2420            2425            2430

Asp Gln Glu Asp Ser Ile Val Cys Cys Ser Met Ser Tyr Ser Trp
    2435            2440            2445

Thr Gly Ala Leu Ile Thr Pro Cys Gly Pro Glu Glu Glu Lys Leu
    2450            2455            2460

Pro Ile Asn Pro Leu Ser Asn Ser Leu Met Arg Phe His Asn Lys
    2465            2470            2475

Val Tyr Ser Thr Thr Ser Arg Ser Ala Ala Leu Arg Ala Lys Lys
    2480            2485            2490

Val Thr Phe Asp Arg Val Gln Ile Leu Asp Thr Tyr Tyr Asp Ser
    2495            2500            2505

Val Leu Gln Asp Val Lys Arg Ala Ala Ser Lys Val Ser Ala Arg
    2510            2515            2520

Leu Leu Ser Val Glu Glu Ala Cys Ala Leu Thr Pro Pro His Ser
    2525            2530            2535

Ala Arg Ser Arg Tyr Gly Phe Gly Ala Lys Glu Val Arg Ser Leu
    2540            2545            2550

Ser Arg Arg Ala Val Asn His Ile Gln Ser Val Trp Glu Asp Leu
    2555            2560            2565

Leu Glu Asp Gln Asn Thr Pro Ile Glu Thr Thr Ile Met Ala Lys
    2570            2575            2580

Asn Glu Val Phe Cys Val Asp Pro Ala Lys Gly Gly Lys Lys Ala
    2585            2590            2595

Ala Arg Leu Ile Val Tyr Pro Asp Leu Gly Val Arg Val Cys Glu
    2600            2605            2610

Lys Met Ala Leu Tyr Asp Ile Ala Gln Lys Leu Pro Lys Ala Ile
    2615            2620            2625

Met Gly Pro Ser Tyr Gly Phe Gln Tyr Ser Pro Ala Glu Arg Val
    2630            2635            2640

Asp Phe Leu Leu Lys Ala Trp Gly Ser Lys Lys Asp Pro Met Gly
    2645            2650            2655

Phe Ser Tyr Asp Thr Arg Cys Phe Asp Ser Thr Val Thr Glu Arg
```

```
                    2660                2665                2670

Asp Ile Arg Thr Glu Glu Ser Ile Tyr Gln Ala Cys Ser Leu Pro
                2675                2680                2685

Gln Glu Ala Arg Thr Val Ile His Ser Leu Thr Glu Arg Leu Tyr
            2690                2695                2700

Val Gly Gly Pro Met Leu Asn Ser Lys Gly Gln Ser Cys Gly Tyr
        2705                2710                2715

Arg Arg Cys Arg Ala Ser Gly Val Phe Thr Thr Ser Met Gly Asn
    2720                2725                2730

Thr Met Thr Cys Tyr Ile Lys Ala Leu Ala Ala Cys Lys Ala Ala
    2735                2740                2745

Gly Ile Val Asp Pro Val Met Leu Val Cys Gly Asp Asp Leu Val
    2750                2755                2760

Val Ile Ser Glu Ser Gln Gly Asn Glu Glu Asp Glu Arg Asn Leu
    2765                2770                2775

Arg Ala Phe Thr Glu Ala Met Thr Arg Tyr Ser Ala Pro Pro Gly
    2780                2785                2790

Asp Leu Pro Arg Pro Glu Tyr Asp Leu Glu Leu Ile Thr Ser Cys
    2795                2800                2805

Ser Ser Asn Val Ser Val Ala Leu Asp Pro Arg Gly Arg Arg Arg
    2810                2815                2820

Tyr Tyr Leu Thr Arg Asp Pro Ile Thr Pro Ile Ser Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Val Arg Met Val Ile Met
    2855                2860                2865

Thr His Phe Phe Ala Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895

Leu Asp Leu Pro Ala Ile Ile Glu Arg Leu His Gly Leu Asp Ala
    2900                2905                2910

Phe Ser Leu His Thr Tyr Ser Pro Thr Glu Leu Thr Arg Val Ala
    2915                2920                2925

Ala Ala Leu Arg Lys Leu Gly Ala Pro Pro Leu Arg Ala Trp Lys
    2930                2935                2940

Ser Arg Ala Arg Ala Val Arg Ala Ser Leu Leu Ala Gln Gly Gly
    2945                2950                2955

Arg Ala Ala Ile Cys Gly Arg Tyr Leu Phe Asn Trp Ala Val Lys
    2960                2965                2970

Thr Lys Leu Lys Leu Thr Pro Leu Pro Glu Ala Ser Arg Leu Asp
    2975                2980                2985

Leu Ser Arg Trp Phe Thr Val Gly Ala Gly Gly Gly Gly Ile Phe
    2990                2995                3000

His Ser Val Ser His Ala Arg Pro Arg Leu Leu Leu Leu Cys Leu
    3005                3010                3015

Leu Leu Leu Ser Val Gly Val Gly Ile Phe Leu Leu Pro Ala Arg
    3020                3025                3030

<210> SEQ ID NO 27
<211> LENGTH: 3033
<212> TYPE: PRT
<213> ORGANISM: Hepatitis C virus
```

<400> SEQUENCE: 27

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Thr Trp Gly Pro Thr Asp Pro
                100                 105                 110

Arg His Arg Ser Arg Asn Leu Gly Arg Val Ile Asp Thr Ile Thr Cys
             115                 120                 125

Gly Phe Ala Asp Leu Met Gly Tyr Ile Pro Val Val Gly Ala Pro Val
         130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                 165                 170                 175

Phe Leu Leu Ala Leu Leu Ser Cys Phe Thr Val Pro Val Ser Ala Val
                180                 185                 190

Glu Val Arg Asn Ile Ser Ser Ser Tyr Tyr Ala Thr Asn Asp Cys Ser
             195                 200                 205

Asn Ser Ser Ile Thr Trp Gln Leu Ala Asp Ala Val Leu His Leu Pro
         210                 215                 220

Gly Cys Val Pro Cys Glu Asn Asn Asn Gly Thr Pro Arg Cys Trp Ile
225                 230                 235                 240

Gln Val Thr Pro Asn Val Ala Val Lys Tyr Arg Gly Ala Leu Thr His
                 245                 250                 255

Ser Leu Arg Thr His Ile Asp Val Ile Val Met Ala Ala Thr Val Cys
                260                 265                 270

Ser Ala Leu Tyr Val Gly Asp Val Cys Gly Ala Val Met Ile Val Ser
             275                 280                 285

Gln Ala Phe Ile Val Ser Pro Gln Phe His Asn Phe Thr Gln Glu Cys
         290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Ile Leu Ala Tyr
                 325                 330                 335

Ala Thr Arg Val Pro Glu Leu Ala Leu Glu Ile Val Phe Gly Ser His
             340                 345                 350

Trp Gly Val Val Phe Gly Leu Ala Tyr Phe Ser Leu Gln Gly Ala Trp
         355                 360                 365

Ala Lys Val Val Ala Ile Leu Leu Val Ala Gly Val Asp Ala His
         370                 375                 380

Thr Gln Leu Thr Gly Thr Asn Val Gly Arg Thr Thr Ala Gly Phe Ala
385                 390                 395                 400

Ser Leu Phe Ala Pro Gly Ala Arg Gln Glu Ile Ser Leu Ile Asn Thr

```
                405                 410                 415
Asn Gly Ser Trp His Val Asn Arg Thr Ala Leu Asn Cys Asn Asp Ser
            420                 425                 430

Leu Asn Thr Gly Phe Leu Thr Ala Leu Phe Tyr Arg Asn Lys Phe Asn
            435                 440                 445

Ser Ser Gly Cys Pro Glu Arg Leu Ser Ser Cys Arg Glu Leu Asp Asp
            450                 455                 460

Phe Arg Ile Gly Trp Gly Thr Val Glu Tyr Glu Thr Val Val Thr Asn
465                 470                 475                 480

Asp Glu Asp Met Arg Pro Tyr Cys Trp His Tyr Pro Pro Lys Pro Cys
                485                 490                 495

Gly Ile Val Ser Ala Lys Thr Val Cys Gly Pro Val Tyr Cys Phe Thr
            500                 505                 510

Pro Ser Pro Val Val Gly Thr Thr Asp Arg Leu Gly Ala Pro Thr
            515                 520                 525

Tyr Asn Trp Gly Ile Asn Glu Thr Asp Val Phe Leu Leu Asn Ser Thr
            530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

His Asn Ser Thr Leu Asp Leu Leu Cys Pro Thr Asp Cys Phe Arg Lys
            580                 585                 590

His Pro Asp Thr Thr Tyr Leu Lys Cys Gly Ala Gly Pro Trp Leu Thr
            595                 600                 605

Pro Lys Cys Leu Ile Asp Tyr Pro Tyr Arg Leu Trp His Tyr Pro Cys
            610                 615                 620

Thr Val Asn Phe Thr Ile Phe Lys Val Arg Met Tyr Val Gly Gly Val
625                 630                 635                 640

Glu His Arg Leu Asp Ala Ala Cys Asn Phe Thr Arg Gly Asp Arg Cys
                645                 650                 655

Arg Leu Glu Asp Arg Asp Arg Gly Gln Gln Thr Pro Leu Leu His Ser
            660                 665                 670

Thr Thr Glu Trp Ala Ile Leu Pro Cys Thr Phe Ser Asp Leu Pro Ala
            675                 680                 685

Leu Ser Thr Gly Leu Leu His Leu His Gln Asn Thr Val Asp Val Gln
            690                 695                 700

Tyr Leu Tyr Gly Leu Thr Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
            740                 745                 750

Glu Lys Leu Ile Ile Leu His Ser Ala Ser Ala Ala Ser Ala Asn Gly
            755                 760                 765

Pro Leu Trp Phe Phe Ile Phe Phe Ile Ala Ala Trp Tyr Leu Lys Gly
            770                 775                 780

Arg Val Val Pro Ala Ala Thr Asn Ser Val Leu Gly Leu Trp Ser Phe
785                 790                 795                 800

Leu Leu Leu Val Leu Ala Leu Pro Gln Gln Ala Tyr Ala Leu Asp Ala
                805                 810                 815

Thr Glu Gln Gly Glu Leu Gly Leu Val Met Leu Val Val Leu Ser Ile
            820                 825                 830
```

Phe Thr Leu Thr Pro Ala Tyr Lys Thr Leu Leu Ser Arg Ser Val Trp
    835                 840                 845

Trp Leu Ser Tyr Met Leu Val Leu Ala Glu Ala Gln Val Gln Gln Trp
    850                 855                 860

Val Pro Pro Leu Glu Ala Arg Gly Gly Arg Asp Gly Ile Ile Trp Ala
865                 870                 875                 880

Ala Val Ile Leu His Pro Arg Leu Val Phe Glu Ile Thr Lys Trp Leu
            885                 890                 895

Leu Ala Ile Leu Gly Pro Ala Tyr Phe Leu Lys Ala Ser Leu Leu Arg
                900                 905                 910

Val Pro Tyr Phe Val Arg Ala His Ala Leu Leu Arg Met Cys Thr Leu
                915                 920                 925

Val Arg His Leu Ala Gly Ala Lys Tyr Ile Gln Met Leu Leu Ile Thr
    930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
            965                 970                 975

Pro Val Val Phe Ser Pro Met Glu Lys Lys Val Ile Val Trp Gly Val
                980                 985                 990

Glu Thr Ala Ala Cys Gly Asp Ile Leu His Gly Leu Pro Val Ser Ala
                995                 1000                1005

Arg Leu Gly Arg Glu Val Leu Leu Gly Pro Ala Asp Gly Tyr Thr
    1010                1015                1020

Ser Lys Gly Trp Lys Leu Leu Ala Pro Ile Thr Ala Tyr Thr Gln
    1025                1030                1035

Gln Thr Arg Gly Leu Leu Gly Ser Ile Val Val Cys Leu Thr Gly
    1040                1045                1050

Arg Asp Lys Asn Glu Gln Ala Gly His Val Gln Val Leu Ser Ser
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Pro Lys
    1085                1090                1095

Gly Pro Ile Thr Gln Met Tyr Thr Ser Ala Glu Gly Asp Leu Val
    1100                1105                1110

Gly Trp Pro Ser Pro Pro Gly Thr Lys Ser Leu Asp Pro Cys Thr
    1115                1120                1125

Cys Gly Ala Val Asp Leu Tyr Leu Val Thr Arg Asn Ala Asp Val
    1130                1135                1140

Ile Pro Val Arg Arg Lys Asp Asp Arg Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Pro Arg Gly His Ala Val Gly Leu Phe Arg Ala Ala Leu
    1175                1180                1185

Cys Ala Arg Gly Val Ala Lys Ser Ile Asp Phe Ile Pro Val Glu
    1190                1195                1200

Ser Leu Asp Ile Val Ala Arg Ser Pro Ser Phe Ser Asp Asn Ser
    1205                1210                1215

Thr Pro Pro Ala Val Pro Gln Thr Tyr Gln Val Gly Tyr Leu His
    1220                1225                1230

```
Ala Pro Thr Gly Ser Gly Lys Ser Thr Lys Val Pro Ala Ala Tyr
1235                1240                1245

Ala Ser Gln Gly Tyr Lys Val Leu Val Leu Asn Pro Ser Val Ala
1250                1255                1260

Ala Thr Leu Gly Phe Gly Ala Tyr Met Ser Lys Ala His Gly Ile
1265                1270                1275

Asn Pro Asn Ile Arg Thr Gly Val Arg Thr Val Thr Thr Gly Asp
1280                1285                1290

Pro Ile Thr Tyr Ser Thr Tyr Gly Lys Phe Leu Ala Asp Gly Gly
1295                1300                1305

Cys Ser Ala Gly Ala Tyr Asp Ile Ile Ile Cys Asp Glu Cys His
1310                1315                1320

Ala Val Asp Ala Thr Thr Ile Leu Gly Ile Gly Thr Val Leu Asp
1325                1330                1335

Gln Ala Glu Thr Ala Gly Ala Arg Leu Val Val Leu Ala Thr Ala
1340                1345                1350

Thr Pro Pro Gly Thr Val Thr Thr Pro His Ser Asn Ile Glu Glu
1355                1360                1365

Val Ala Leu Gly His Glu Gly Glu Ile Pro Phe Tyr Gly Lys Ala
1370                1375                1380

Ile Pro Leu Ala Phe Ile Lys Gly Gly Arg His Leu Ile Phe Cys
1385                1390                1395

His Ser Lys Lys Lys Cys Asp Glu Val Ala Ala Leu Arg Ser
1400                1405                1410

Val Gly Val Asn Ala Val Ala Tyr Tyr Arg Gly Leu Asp Val Ser
1415                1420                1425

Val Ile Pro Thr Gln Gly Asp Val Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Ile Val Asp Leu Ser Leu Asp Pro Thr
1460                1465                1470

Phe Thr Ile Thr Thr Gln Thr Val Pro Gln Asp Ala Val Ser Arg
1475                1480                1485

Ser Gln Arg Arg Gly Arg Thr Gly Arg Gly Arg Leu Gly Ile Tyr
1490                1495                1500

Arg Tyr Val Ser Ser Gly Glu Arg Pro Ser Gly Met Phe Asp Ser
1505                1510                1515

Val Val Leu Cys Glu Cys Tyr Asp Ala Gly Ala Ala Trp Tyr Glu
1520                1525                1530

Leu Thr Pro Ala Glu Thr Thr Val Arg Leu Arg Ala Tyr Phe Asn
1535                1540                1545

Thr Pro Gly Leu Pro Val Cys Gln Asp His Leu Glu Phe Trp Glu
1550                1555                1560

Ala Val Phe Thr Gly Leu Thr His Ile Asp Ala His Phe Leu Ser
1565                1570                1575

Gln Thr Lys Gln Gly Gly Asp Asn Phe Ala Tyr Leu Thr Ala Tyr
1580                1585                1590

Gln Ala Thr Val Cys Ala Arg Ala Lys Ala Pro Pro Pro Ser Trp
1595                1600                1605

Asp Val Met Trp Lys Cys Leu Thr Arg Leu Lys Pro Thr Leu Thr
1610                1615                1620

Gly Pro Thr Pro Leu Leu Tyr Arg Leu Gly Ala Val Thr Asn Glu
```

-continued

```
            1625                1630                1635

Ile Thr Leu Thr His Pro Val Thr Lys Tyr Ile Ala Thr Cys Met
            1640                1645                1650

Gln Ala Asp Leu Glu Ile Met Thr Ser Thr Trp Val Leu Ala Gly
            1655                1660                1665

Gly Val Leu Ala Ala Val Ala Ser Tyr Cys Leu Ala Thr Gly Cys
            1670                1675                1680

Ile Ser Ile Ile Gly Arg Leu His Leu Asn Asp Arg Val Val Val
            1685                1690                1695

Ala Pro Asp Lys Glu Ile Leu Tyr Glu Ala Phe Asp Glu Met Glu
            1700                1705                1710

Glu Cys Ala Ser Lys Ala Ala Leu Ile Glu Glu Gly His Arg Met
            1715                1720                1725

Ala Glu Met Leu Lys Ser Lys Ile Gln Gly Leu Leu Gln Gln Ala
            1730                1735                1740

Thr Lys Gln Ala Gln Asp Ile Gln Pro Ala Ile Gln Ser Ser Trp
            1745                1750                1755

Pro Lys Leu Glu Gln Phe Trp Ala Lys His Met Trp Asn Phe Ile
            1760                1765                1770

Ser Gly Ile Gln Tyr Leu Ala Gly Leu Ser Thr Leu Pro Gly Asn
            1775                1780                1785

Pro Ala Val Ala Ser Met Met Ala Phe Ser Ala Ala Leu Thr Ser
            1790                1795                1800

Pro Leu Pro Thr Ser Thr Thr Ile Leu Leu Asn Ile Met Gly Gly
            1805                1810                1815

Trp Leu Ala Ser Gln Val Ala Pro Pro Ala Gly Ala Thr Gly Phe
            1820                1825                1830

Val Val Ser Gly Leu Val Gly Ala Ala Val Gly Ser Ile Gly Leu
            1835                1840                1845

Gly Lys Ile Leu Val Asp Val Leu Ala Gly Tyr Gly Ala Gly Ile
            1850                1855                1860

Ser Gly Ala Leu Val Ala Phe Lys Ile Met Ser Gly Glu Lys Pro
            1865                1870                1875

Ser Val Glu Asp Val Val Asn Leu Leu Pro Ala Ile Leu Ser Pro
            1880                1885                1890

Gly Ala Leu Val Val Gly Val Ile Cys Ala Ala Ile Leu Arg Arg
            1895                1900                1905

His Val Gly Gln Gly Glu Gly Ala Val Gln Trp Met Asn Arg Leu
            1910                1915                1920

Ile Ala Phe Ala Ser Arg Gly Ser His Val Ala Pro Thr His Tyr
            1925                1930                1935

Val Ala Glu Ser Asp Ala Ser Gln Arg Val Thr Gln Ala Leu Ser
            1940                1945                1950

Ser Leu Thr Ile Thr Ser Leu Leu Arg Arg Leu His Ala Trp Ile
            1955                1960                1965

Thr Glu Asp Cys Pro Val Pro Cys Ser Gly Ser Trp Leu Arg Asp
            1970                1975                1980

Ile Trp Asp Trp Val Cys Ser Ile Leu Thr Asp Phe Lys Asn Trp
            1985                1990                1995

Leu Ser Ser Lys Leu Leu Pro Lys Leu Pro Gly Leu Pro Phe Ile
            2000                2005                2010

Ser Cys Gln Lys Gly Tyr Lys Gly Val Trp Ala Gly Thr Gly Ile
            2015                2020                2025
```

-continued

Met Thr Thr Arg Cys Ser Cys Gly Ala Asn Ile Ser Gly His Val
         2030              2035              2040

Arg Met Gly Thr Met Lys Ile Thr Gly Pro Lys Thr Cys Leu Asn
         2045              2050              2055

Leu Trp Gln Gly Thr Phe Pro Ile Asn Cys Tyr Thr Glu Gly Pro
         2060              2065              2070

Cys Val Pro Lys Pro Pro Asn Tyr Lys Thr Ala Ile Trp Arg
         2075              2080              2085

Val Ala Ala Ser Glu Tyr Val Glu Ile Thr Gln His Gly Ser Phe
         2090              2095              2100

Ser Tyr Val Thr Gly Leu Thr Ser Asp Asn Leu Lys Val Pro Cys
         2105              2110              2115

Gln Val Pro Ala Pro Glu Phe Phe Ser Trp Val Asp Gly Val Gln
         2120              2125              2130

Ile His Arg Phe Ala Pro Thr Pro Gly Pro Phe Phe Arg Asp Glu
         2135              2140              2145

Val Thr Phe Ser Val Gly Leu Asn Ser Phe Val Val Gly Ser Gln
         2150              2155              2160

Leu Pro Cys Asp Pro Glu Pro Asp Thr Glu Val Leu Ala Ser Met
         2165              2170              2175

Leu Thr Asp Pro Ser His Ile Thr Ala Glu Ala Ala Arg Arg
         2180              2185              2190

Leu Ala Arg Gly Ser Pro Pro Ser Gln Ala Ser Ser Ser Ala Ser
         2195              2200              2205

Gln Leu Ser Ala Pro Ser Leu Lys Ala Thr Cys Thr Thr His Lys
         2210              2215              2220

Met Ala Tyr Asp Cys Asp Met Val Asp Ala Asn Leu Phe Met Gly
         2225              2230              2235

Gly Asp Val Thr Arg Ile Glu Ser Asn Ser Lys Val Ile Val Leu
         2240              2245              2250

Asp Ser Leu Asp Ser Met Thr Glu Ala Glu Asp Arg Glu Pro
         2255              2260              2265

Ser Ile Pro Ser Glu Tyr Leu Ile Arg Arg Lys Lys Phe Pro Pro
         2270              2275              2280

Ala Leu Pro Pro Trp Ala Arg Pro Asp Tyr Asn Pro Pro Val Ile
         2285              2290              2295

Glu Thr Trp Lys Arg Pro Gly Tyr Glu Pro Pro Thr Val Leu Gly
         2300              2305              2310

Cys Ala Leu Pro Pro Thr Pro Gln Ala Pro Val Pro Pro Pro Arg
         2315              2320              2325

Arg Arg Arg Ala Lys Val Leu Thr Gln Asp Asn Val Glu Gly Val
         2330              2335              2340

Leu Lys Glu Met Ala Asp Lys Val Leu Ser Pro Leu Gln Asp Tyr
         2345              2350              2355

Asn Asp Ser Gly His Ser Thr Gly Val Gly Thr Gly Gly Asp Ser
         2360              2365              2370

Val Gln Glu Pro Ser Asp Glu Thr Ala Ala Ser Glu Val Gly Ser
         2375              2380              2385

Leu Ser Ser Met Pro Pro Leu Glu Gly Glu Pro Gly Asp Pro Asp
         2390              2395              2400

Leu Glu Phe Glu Pro Ala Arg Ser Ala Pro Pro Ser Glu Gly Glu
         2405              2410              2415

```
Cys Glu Val Val Asp Ser Asp Ser Lys Ser Trp Ser Thr Val Ser
    2420                2425                2430

Asn Gln Glu Asp Ser Ile Val Cys Cys Ser Met Ser Tyr Ser Trp
    2435                2440                2445

Thr Gly Ala Leu Ile Thr Pro Cys Gly Pro Glu Glu Glu Lys Leu
    2450                2455                2460

Pro Ile Asn Pro Leu Ser Asn Ser Leu Met Arg Phe His Asn Lys
    2465                2470                2475

Val Tyr Ser Thr Thr Ser Arg Ser Ala Ala Leu Arg Ala Lys Lys
    2480                2485                2490

Val Thr Phe Asp Arg Val Gln Ile Leu Asp Thr Tyr Tyr Asp Ser
    2495                2500                2505

Val Leu Gln Asp Val Lys Arg Ala Ala Ser Lys Val Ser Ala Arg
    2510                2515                2520

Leu Leu Ser Val Glu Glu Ala Cys Ala Leu Thr Pro Pro His Ser
    2525                2530                2535

Ala Arg Ser Arg Tyr Gly Phe Gly Ala Lys Glu Val Arg Ser Leu
    2540                2545                2550

Ser Arg Arg Ala Val Asn His Ile Gln Ser Val Trp Glu Asp Leu
    2555                2560                2565

Leu Glu Asp Gln Asn Thr Pro Ile Glu Thr Thr Ile Met Ala Lys
    2570                2575                2580

Asn Glu Val Phe Cys Val Asp Pro Ala Lys Gly Gly Lys Lys Ala
    2585                2590                2595

Ala Arg Leu Ile Val Tyr Pro Asp Leu Gly Val Arg Val Cys Glu
    2600                2605                2610

Lys Met Ala Leu Tyr Asp Ile Ala Gln Lys Leu Pro Lys Ala Ile
    2615                2620                2625

Met Gly Pro Ser Tyr Gly Phe Gln Tyr Ser Pro Ala Glu Arg Val
    2630                2635                2640

Asp Phe Leu Leu Lys Ala Trp Gly Ser Lys Lys Asp Pro Met Gly
    2645                2650                2655

Phe Ser Tyr Asp Thr Arg Cys Phe Asp Ser Thr Val Thr Glu Arg
    2660                2665                2670

Asp Ile Arg Thr Glu Glu Ser Ile Tyr Gln Ala Cys Ser Leu Pro
    2675                2680                2685

Gln Glu Ala Arg Thr Val Ile His Ser Leu Thr Glu Arg Leu Tyr
    2690                2695                2700

Val Gly Gly Pro Met Leu Asn Ser Lys Gly Gln Ser Cys Gly Tyr
    2705                2710                2715

Arg Arg Cys Arg Ala Ser Gly Val Phe Thr Thr Ser Met Gly Asn
    2720                2725                2730

Thr Met Thr Cys Tyr Ile Lys Ala Leu Ala Ala Cys Lys Ala Ala
    2735                2740                2745

Gly Ile Val Asp Pro Val Met Leu Val Cys Gly Asp Asp Leu Val
    2750                2755                2760

Val Ile Ser Glu Ser Gln Gly Asn Glu Glu Asp Glu Arg Asn Leu
    2765                2770                2775

Arg Ala Phe Thr Glu Ala Met Thr Arg Tyr Ser Ala Pro Pro Gly
    2780                2785                2790

Asp Leu Pro Arg Pro Glu Tyr Asp Leu Glu Leu Ile Thr Ser Cys
    2795                2800                2805

Ser Ser Asn Val Ser Val Ala Leu Asp Pro Arg Gly Arg Arg Arg
```

```
            2810               2815               2820

Tyr Tyr Leu Thr Arg Asp Pro Ile Thr Pro Ile Ser Arg Ala Ala
    2825               2830               2835

Trp Glu Thr Val Arg His Ser Pro Val Asn Ser Trp Leu Gly Asn
    2840               2845               2850

Ile Ile Gln Tyr Ala Pro Thr Ile Trp Val Arg Met Val Ile Met
    2855               2860               2865

Thr His Phe Phe Ala Ile Leu Leu Ala Gln Asp Thr Leu Asn Gln
    2870               2875               2880

Asn Leu Asn Phe Glu Met Tyr Gly Ala Val Tyr Ser Val Asn Pro
    2885               2890               2895

Leu Asp Leu Pro Ala Ile Ile Glu Arg Leu His Gly Leu Asp Ala
    2900               2905               2910

Phe Ser Leu His Thr Tyr Ser Pro Thr Glu Leu Thr Arg Val Ala
    2915               2920               2925

Ala Ala Leu Arg Lys Leu Gly Ala Pro Pro Leu Arg Ala Trp Lys
    2930               2935               2940

Ser Arg Ala Arg Ala Val Arg Ala Ser Leu Leu Ala Gln Gly Gly
    2945               2950               2955

Arg Ala Ala Ile Cys Gly Arg Tyr Leu Phe Asn Trp Ala Val Lys
    2960               2965               2970

Thr Lys Leu Lys Leu Thr Pro Leu Pro Glu Ala Ser Arg Leu Asp
    2975               2980               2985

Leu Ser Arg Trp Phe Thr Val Gly Ala Gly Gly Gly Ile Phe
    2990               2995               3000

His Ser Val Ser His Ala Arg Pro Arg Leu Leu Leu Cys Leu
    3005               3010               3015

Leu Leu Leu Ser Val Gly Val Gly Ile Phe Leu Leu Pro Ala Arg
    3020               3025               3030

<210> SEQ ID NO 28
<211> LENGTH: 3033
<212> TYPE: PRT
<213> ORGANISM: Hepatitis C virus

<400> SEQUENCE: 28

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140
```

```
Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
            165                 170                 175

Phe Leu Leu Ala Leu Leu Ser Cys Phe Thr Val Pro Val Ser Ala Val
                180                 185                 190

Glu Val Arg Asn Ile Ser Ser Tyr Tyr Ala Thr Asn Asp Cys Ser
        195                 200                 205

Asn Ser Ser Ile Thr Trp Gln Leu Ala Asp Ala Val Leu His Leu Pro
        210                 215                 220

Gly Cys Val Pro Cys Glu Asn Asn Gly Thr Pro Arg Cys Trp Ile
225                 230                 235                 240

Gln Val Thr Pro Asn Val Ala Val Lys Tyr Arg Gly Ala Leu Thr His
                245                 250                 255

Ser Leu Arg Thr His Ile Asp Val Ile Val Met Ala Ala Thr Val Cys
            260                 265                 270

Ser Ala Leu Tyr Val Gly Asp Val Cys Gly Ala Val Met Ile Val Ser
                275                 280                 285

Gln Ala Phe Ile Val Ser Pro Gln Phe His Asn Phe Thr Gln Glu Cys
290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Ile Leu Ala Tyr
                325                 330                 335

Ala Thr Arg Val Pro Glu Leu Ala Leu Glu Ile Val Phe Gly Ser His
            340                 345                 350

Trp Gly Val Val Phe Gly Leu Ala Tyr Phe Ser Leu Gln Gly Ala Trp
            355                 360                 365

Ala Lys Val Val Ala Ile Leu Leu Leu Val Ala Gly Val Asp Ala His
        370                 375                 380

Thr Gln Leu Thr Gly Thr Asn Val Gly Arg Thr Thr Ala Gly Phe Ala
385                 390                 395                 400

Ser Leu Phe Ala Pro Gly Ala Arg Gln Glu Ile Ser Leu Ile Asn Thr
                405                 410                 415

Asn Gly Ser Trp His Val Asn Arg Thr Ala Leu Asn Cys Asn Asp Ser
            420                 425                 430

Leu Asn Thr Gly Phe Leu Thr Ala Leu Phe Tyr Arg Asn Lys Phe Asn
        435                 440                 445

Ser Ser Gly Cys Pro Glu Arg Leu Ser Ser Cys Arg Glu Leu Asp Asp
450                 455                 460

Phe Arg Ile Gly Trp Gly Thr Val Glu Tyr Glu Thr Val Val Thr Asn
465                 470                 475                 480

Asp Glu Asp Met Arg Pro Tyr Cys Trp His Tyr Pro Lys Pro Cys
                485                 490                 495

Gly Ile Val Ser Ala Lys Thr Val Cys Gly Pro Val Tyr Cys Phe Thr
            500                 505                 510

Pro Ser Pro Val Val Val Gly Thr Thr Asp Arg Leu Gly Ala Pro Thr
                515                 520                 525

Tyr Asn Trp Gly Ile Asn Glu Thr Asp Val Phe Leu Leu Asn Ser Thr
            530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
```

```
              565                 570                 575
His Asn Ser Thr Leu Asp Leu Cys Pro Thr Asp Cys Phe Arg Lys
            580                 585                 590
His Pro Asp Thr Thr Tyr Leu Lys Cys Gly Ala Gly Pro Trp Leu Thr
            595                 600                 605
Pro Lys Cys Leu Ile Asp Tyr Pro Tyr Arg Leu Trp His Tyr Pro Cys
610                 615                 620
Thr Val Asn Phe Thr Ile Phe Lys Val Arg Met Tyr Val Gly Val
625                 630                 635                 640
Glu His Arg Leu Asp Ala Ala Cys Asn Phe Thr Arg Gly Asp Arg Cys
                645                 650                 655
Arg Leu Glu Asp Arg Asp Arg Gly Gln Gln Thr Pro Leu Leu His Ser
            660                 665                 670
Thr Thr Glu Trp Ala Ile Leu Pro Cys Thr Phe Ser Asp Leu Pro Ala
            675                 680                 685
Leu Ser Thr Gly Leu Leu His Leu His Gln Asn Thr Val Asp Val Gln
            690                 695                 700
Tyr Leu Tyr Gly Leu Thr Pro Ala Ile Thr Arg Tyr Ile Val Lys Trp
705                 710                 715                 720
Glu Trp Val Val Leu Leu Phe Leu Leu Leu Ala Asp Ala Arg Val Cys
                725                 730                 735
Ala Cys Leu Trp Met Leu Ile Ile Leu Gly Gln Ala Glu Ala Leu
            740                 745                 750
Glu Lys Leu Ile Ile Leu His Ser Ala Ser Ala Ala Ser Ala Asn Gly
            755                 760                 765
Pro Leu Trp Phe Phe Ile Phe Phe Ile Ala Ala Trp Tyr Leu Lys Gly
            770                 775                 780
Arg Val Val Pro Ala Ala Thr Asn Ser Val Leu Gly Leu Trp Ser Phe
785                 790                 795                 800
Leu Leu Leu Val Leu Ala Leu Pro Gln Gln Ala Tyr Ala Leu Asp Ala
                805                 810                 815
Thr Glu Gln Gly Glu Leu Gly Leu Val Met Leu Val Val Leu Ser Ile
            820                 825                 830
Phe Thr Leu Thr Pro Ala Tyr Lys Thr Leu Leu Ser Arg Ser Val Trp
            835                 840                 845
Trp Leu Ser Tyr Met Leu Val Leu Ala Glu Ala Gln Val Gln Gln Trp
            850                 855                 860
Val Pro Pro Leu Glu Ala Arg Gly Gly Arg Asp Gly Ile Ile Trp Ala
865                 870                 875                 880
Ala Val Ile Leu His Pro Arg Leu Val Phe Glu Ile Thr Lys Trp Leu
                885                 890                 895
Leu Ala Ile Leu Gly Pro Ala Tyr Phe Leu Lys Ala Ser Leu Leu Arg
            900                 905                 910
Val Pro Tyr Phe Val Arg Ala His Ala Leu Leu Arg Met Cys Thr Leu
            915                 920                 925
Val Arg His Leu Ala Gly Ala Lys Tyr Ile Gln Met Leu Leu Ile Thr
            930                 935                 940
Ile Gly Arg Trp Thr Gly Thr Tyr Ile Tyr Asp His Leu Ser Pro Leu
945                 950                 955                 960
Ser Thr Trp Ala Ala Gln Gly Leu Arg Asp Leu Ala Val Ala Val Glu
                965                 970                 975
Pro Val Val Phe Ser Pro Met Glu Lys Lys Val Ile Val Trp Gly Val
            980                 985                 990
```

-continued

```
Glu Thr Ala Ala Cys Gly Asp Ile Leu His Gly Leu Pro Val Ser Ala
    995                 1000                1005

Arg Leu Gly Arg Glu Val Leu Leu Gly Pro Ala Asp Gly Tyr Thr
   1010                1015                1020

Ser Lys Gly Trp Lys Leu Leu Ala Pro Ile Thr Ala Tyr Thr Gln
   1025                1030                1035

Gln Thr Arg Gly Leu Leu Gly Ser Ile Val Val Cys Leu Thr Gly
   1040                1045                1050

Arg Asp Lys Asn Glu Gln Ala Gly His Val Gln Val Leu Ser Ser
   1055                1060                1065

Val Thr Gln Ser Phe Leu Gly Thr Ser Ile Ser Gly Val Leu Trp
   1070                1075                1080

Thr Val Tyr His Gly Ala Gly Asn Lys Thr Leu Ala Gly Pro Lys
   1085                1090                1095

Gly Pro Ile Thr Gln Met Tyr Thr Ser Ala Glu Gly Asp Leu Val
   1100                1105                1110

Gly Trp Pro Ser Pro Pro Gly Thr Lys Ser Leu Asp Pro Cys Thr
   1115                1120                1125

Cys Gly Ala Val Asp Leu Tyr Leu Val Thr Arg Asn Ala Asp Val
   1130                1135                1140

Ile Pro Val Arg Arg Lys Asp Asp Arg Arg Gly Ala Leu Leu Ser
   1145                1150                1155

Pro Arg Pro Leu Ser Thr Leu Lys Gly Ser Ser Gly Gly Pro Val
   1160                1165                1170

Leu Cys Pro Arg Gly His Ala Val Gly Leu Phe Arg Ala Ala Leu
   1175                1180                1185

Cys Ala Arg Gly Val Ala Lys Ser Ile Asp Phe Ile Pro Val Glu
   1190                1195                1200

Ser Leu Asp Ile Val Ala Arg Ser Pro Ser Phe Ser Asp Asn Ser
   1205                1210                1215

Thr Pro Pro Ala Val Pro Gln Thr Tyr Gln Val Gly Tyr Leu His
   1220                1225                1230

Ala Pro Thr Gly Ser Gly Lys Ser Thr Lys Val Pro Ala Ala Tyr
   1235                1240                1245

Ala Ser Gln Gly Tyr Lys Val Leu Val Leu Asn Pro Ser Val Ala
   1250                1255                1260

Ala Thr Leu Gly Phe Gly Ala Tyr Met Ser Lys Ala His Gly Ile
   1265                1270                1275

Asn Pro Asn Ile Arg Thr Gly Val Arg Thr Val Thr Thr Gly Asp
   1280                1285                1290

Pro Ile Thr Tyr Ser Thr Tyr Gly Lys Phe Leu Ala Asp Gly Gly
   1295                1300                1305

Cys Ser Ala Gly Ala Tyr Asp Ile Ile Cys Asp Glu Cys His
   1310                1315                1320

Ala Val Asp Ala Thr Thr Ile Leu Gly Ile Gly Thr Val Leu Asp
   1325                1330                1335

Gln Ala Glu Thr Ala Gly Ala Arg Leu Val Val Leu Ala Thr Ala
   1340                1345                1350

Thr Pro Pro Gly Thr Val Thr Thr Pro His Ser Asn Ile Glu Glu
   1355                1360                1365

Val Ala Leu Gly His Glu Gly Glu Ile Pro Phe Tyr Gly Lys Ala
   1370                1375                1380
```

-continued

```
Ile Pro Leu Ala Phe Ile Lys Gly Gly Arg His Leu Ile Phe Cys
    1385                1390                1395

His Ser Lys Lys Lys Cys Asp Glu Val Ala Ala Ala Leu Arg Ser
    1400                1405                1410

Val Gly Val Asn Ala Val Ala Tyr Tyr Arg Gly Leu Asp Val Ser
    1415                1420                1425

Val Ile Pro Thr Gln Gly Asp Val Val Val Ala Thr Asp Ala
    1430                1435                1440

Leu Met Thr Gly Tyr Thr Gly Asp Phe Asp Ser Val Ile Asp Cys
    1445                1450                1455

Asn Val Ala Val Thr Gln Ile Val Asp Leu Ser Leu Asp Pro Thr
    1460                1465                1470

Phe Thr Ile Thr Thr Gln Thr Val Pro Gln Asp Ala Val Ser Arg
    1475                1480                1485

Ser Gln Arg Arg Gly Arg Thr Gly Arg Gly Arg Leu Gly Ile Tyr
    1490                1495                1500

Arg Tyr Val Ser Ser Gly Glu Arg Pro Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ala Glu Thr Thr Val Arg Leu Arg Ala Tyr Phe Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Gly Gly Asp Asn Phe Ala Tyr Leu Thr Ala Tyr
    1580                1585                1590

Gln Ala Thr Val Cys Ala Arg Ala Lys Ala Pro Pro Pro Ser Trp
    1595                1600                1605

Asp Val Met Trp Lys Cys Leu Thr Arg Leu Lys Pro Thr Leu Thr
    1610                1615                1620

Gly Pro Thr Pro Leu Leu Tyr Arg Leu Gly Ala Val Thr Asn Glu
    1625                1630                1635

Ile Thr Leu Thr His Pro Val Thr Lys Tyr Ile Ala Thr Cys Met
    1640                1645                1650

Gln Ala Asp Leu Glu Ile Met Thr Ser Thr Trp Val Leu Ala Gly
    1655                1660                1665

Gly Val Leu Ala Ala Val Ala Ser Tyr Cys Leu Ala Thr Gly Cys
    1670                1675                1680

Ile Ser Ile Ile Gly Arg Leu His Leu Asn Asp Arg Val Val Val
    1685                1690                1695

Ala Pro Asp Lys Glu Ile Leu Tyr Glu Ala Phe Asp Glu Met Glu
    1700                1705                1710

Glu Cys Ala Ser Lys Ala Ala Leu Ile Glu Glu Gly His Arg Met
    1715                1720                1725

Ala Glu Met Leu Lys Ser Lys Ile Gln Gly Leu Leu Gln Gln Ala
    1730                1735                1740

Thr Lys Gln Ala Gln Asp Ile Gln Pro Ala Ile Gln Ser Ser Trp
    1745                1750                1755

Pro Lys Leu Glu Gln Phe Trp Ala Lys His Met Trp Asn Phe Ile
    1760                1765                1770

Ser Gly Ile Gln Tyr Leu Ala Gly Leu Ser Thr Leu Pro Gly Asn
```

```
                    1775                1780                1785

Pro Ala Val Ala Ser Met Met Ala Phe Ser Ala Ala Leu Thr Ser
        1790                1795                1800

Pro Leu Pro Thr Ser Thr Thr Ile Leu Leu Asn Ile Met Gly Gly
        1805                1810                1815

Trp Leu Ala Ser Gln Val Ala Pro Pro Ala Gly Ala Thr Gly Phe
        1820                1825                1830

Val Val Ser Gly Leu Val Gly Ala Ala Val Gly Ser Ile Gly Leu
        1835                1840                1845

Gly Lys Ile Leu Val Asp Val Leu Ala Gly Tyr Gly Ala Gly Ile
        1850                1855                1860

Ser Gly Ala Leu Val Ala Phe Lys Ile Met Ser Gly Glu Lys Pro
        1865                1870                1875

Ser Val Glu Asp Val Val Asn Leu Leu Pro Ala Ile Leu Ser Pro
        1880                1885                1890

Gly Ala Leu Val Val Gly Val Ile Cys Ala Ala Ile Leu Arg Arg
        1895                1900                1905

His Val Gly Gln Gly Glu Gly Ala Val Gln Trp Met Asn Arg Leu
        1910                1915                1920

Ile Ala Phe Ala Ser Arg Gly Thr His Val Ala Pro Thr His Tyr
        1925                1930                1935

Val Ala Glu Ser Asp Ala Ser Gln Arg Val Thr Gln Ala Leu Ser
        1940                1945                1950

Ser Leu Thr Ile Thr Ser Leu Leu Arg Arg Leu His Ala Trp Ile
        1955                1960                1965

Thr Glu Asp Cys Pro Val Pro Cys Ser Gly Ser Trp Leu Arg Asp
        1970                1975                1980

Ile Trp Asp Trp Val Cys Ser Ile Leu Thr Asp Phe Lys Asn Trp
        1985                1990                1995

Leu Ser Ser Lys Leu Leu Pro Lys Leu Pro Gly Leu Pro Phe Ile
        2000                2005                2010

Ser Cys Gln Lys Gly Tyr Lys Gly Val Trp Ala Gly Thr Gly Ile
        2015                2020                2025

Met Thr Thr Arg Cys Ser Cys Gly Ala Asn Ile Ser Gly His Val
        2030                2035                2040

Arg Met Gly Thr Met Lys Ile Thr Gly Pro Lys Thr Cys Leu Asn
        2045                2050                2055

Leu Trp Gln Gly Thr Phe Pro Ile Asn Cys Tyr Thr Glu Gly Pro
        2060                2065                2070

Cys Val Pro Lys Pro Pro Pro Asn Tyr Lys Thr Ala Ile Trp Arg
        2075                2080                2085

Val Ala Ala Ser Glu Tyr Val Glu Ile Thr Gln His Gly Ser Phe
        2090                2095                2100

Ser Tyr Val Thr Gly Leu Thr Ser Asp Asn Leu Lys Val Pro Cys
        2105                2110                2115

Gln Val Pro Ala Pro Glu Phe Phe Ser Trp Val Asp Gly Val Gln
        2120                2125                2130

Ile His Arg Phe Ala Pro Thr Pro Gly Pro Phe Phe Arg Asp Glu
        2135                2140                2145

Val Thr Phe Ser Val Gly Leu Asn Ser Phe Val Val Gly Ser Gln
        2150                2155                2160

Leu Pro Cys Asp Pro Glu Pro Asp Thr Glu Val Leu Ala Ser Met
        2165                2170                2175
```

```
Leu Thr Asp Pro Ser His Ile Thr Ala Glu Ala Ala Ala Arg Arg
    2180            2185                2190

Leu Ala Arg Gly Ser Pro Pro Ser Gln Ala Ser Ser Ser Ala Ser
    2195            2200                2205

Gln Leu Ser Ala Pro Ser Leu Lys Ala Thr Cys Thr Thr His Lys
    2210            2215                2220

Met Ala Tyr Asp Cys Asp Met Val Asp Ala Asn Leu Phe Met Gly
    2225            2230                2235

Gly Asp Val Thr Arg Ile Glu Ser Asn Ser Lys Val Ile Val Leu
    2240            2245                2250

Asp Ser Leu Asp Ser Met Thr Glu Ala Glu Asp Arg Glu Pro
    2255            2260                2265

Ser Ile Pro Ser Glu Tyr Leu Ile Arg Arg Lys Phe Pro Pro
    2270            2275                2280

Ala Leu Pro Pro Trp Ala Arg Pro Asp Tyr Asn Pro Pro Val Ile
    2285            2290                2295

Glu Thr Trp Lys Arg Pro Gly Tyr Glu Pro Pro Thr Val Leu Gly
    2300            2305                2310

Cys Ala Leu Pro Pro Thr Pro Gln Ala Pro Val Pro Pro Pro Arg
    2315            2320                2325

Arg Arg Arg Ala Lys Val Leu Thr Gln Asp Asn Val Glu Gly Val
    2330            2335                2340

Leu Lys Glu Met Ala Asp Lys Val Leu Ser Pro Leu Gln Asp Tyr
    2345            2350                2355

Asn Asp Ser Gly His Ser Thr Gly Val Gly Thr Gly Gly Asp Ser
    2360            2365                2370

Val Gln Glu Pro Ser Asp Glu Thr Ala Ala Ser Glu Val Gly Ser
    2375            2380                2385

Leu Ser Ser Met Pro Pro Leu Glu Gly Glu Pro Gly Asp Pro Asp
    2390            2395                2400

Leu Glu Phe Glu Pro Ala Arg Ser Ala Pro Pro Ser Glu Gly Glu
    2405            2410                2415

Cys Glu Val Val Asp Ser Asp Ser Lys Ser Trp Ser Thr Val Ser
    2420            2425                2430

Asn Gln Glu Asp Ser Ile Val Cys Cys Ser Met Ser Tyr Ser Trp
    2435            2440                2445

Thr Gly Ala Leu Ile Thr Pro Cys Gly Pro Glu Glu Glu Lys Leu
    2450            2455                2460

Pro Ile Asn Pro Leu Ser Asn Ser Leu Met Arg Phe His Asn Lys
    2465            2470                2475

Val Tyr Ser Thr Thr Ser Arg Ser Ala Ala Leu Arg Ala Lys Lys
    2480            2485                2490

Val Thr Phe Asp Arg Val Gln Ile Leu Asp Thr Tyr Tyr Asp Ser
    2495            2500                2505

Val Leu Gln Asp Val Lys Arg Ala Ala Ser Lys Val Ser Ala Arg
    2510            2515                2520

Leu Leu Ser Val Glu Glu Ala Cys Ala Leu Thr Pro Pro His Ser
    2525            2530                2535

Ala Arg Ser Arg Tyr Gly Phe Gly Ala Lys Glu Val Arg Ser Leu
    2540            2545                2550

Ser Arg Arg Ala Val Asn His Ile Gln Ser Val Trp Glu Asp Leu
    2555            2560                2565
```

```
Leu Glu Asp Gln Asn Thr Pro Ile Glu Thr Thr Ile Met Ala Lys
2570                2575                2580

Asn Glu Val Phe Cys Val Asp Pro Ala Lys Gly Gly Lys Lys Ala
2585                2590                2595

Ala Arg Leu Ile Val Tyr Pro Asp Leu Gly Val Arg Val Cys Glu
2600                2605                2610

Lys Met Ala Leu Tyr Asp Ile Ala Gln Lys Leu Pro Lys Ala Ile
2615                2620                2625

Met Gly Pro Ser Tyr Gly Phe Gln Tyr Ser Pro Ala Glu Arg Val
2630                2635                2640

Asp Phe Leu Leu Lys Ala Trp Gly Ser Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro
2675                2680                2685

Gln Glu Ala Arg Thr Val Ile His Ser Leu Thr Glu Arg Leu Tyr
2690                2695                2700

Val Gly Gly Pro Met Leu Asn Ser Lys Gly Gln Ser Cys Gly Tyr
2705                2710                2715

Arg Arg Cys Arg Ala Ser Gly Val Phe Thr Thr Ser Met Gly Asn
2720                2725                2730

Thr Met Thr Cys Tyr Ile Lys Ala Leu Ala Ala Cys Lys Ala Ala
2735                2740                2745

Gly Ile Val Asp Pro Val Met Leu Val Cys Gly Asp Asp Leu Val
2750                2755                2760

Val Ile Ser Glu Ser Gln Gly Asn Glu Glu Asp Glu Arg Asn Leu
2765                2770                2775

Arg Ala Phe Thr Glu Ala Met Thr Arg Tyr Ser Ala Pro Pro Gly
2780                2785                2790

Asp Leu Pro Arg Pro Glu Tyr Asp Leu Glu Leu Ile Thr Ser Cys
2795                2800                2805

Ser Ser Asn Val Ser Val Ala Leu Asp Pro Arg Gly Arg Arg Arg
2810                2815                2820

Tyr Tyr Leu Thr Arg Asp Pro Ile Thr Pro Ile Ser Arg Ala Ala
2825                2830                2835

Trp Glu Thr Val Arg His Ser Pro Val Asn Ser Trp Leu Gly Asn
2840                2845                2850

Ile Ile Gln Tyr Ala Pro Thr Ile Trp Val Arg Met Val Ile Met
2855                2860                2865

Thr His Phe Phe Ala Ile Leu Leu Ala Gln Asp Thr Leu Asn Gln
2870                2875                2880

Asn Leu Asn Phe Glu Met Tyr Gly Ala Val Tyr Ser Val Asn Pro
2885                2890                2895

Leu Asp Leu Pro Ala Ile Ile Glu Arg Leu His Gly Leu Asp Ala
2900                2905                2910

Phe Ser Leu His Thr Tyr Ser Pro Thr Glu Leu Thr Arg Val Ala
2915                2920                2925

Ala Ala Leu Arg Lys Leu Gly Ala Pro Pro Leu Arg Ala Trp Lys
2930                2935                2940

Ser Arg Ala Arg Ala Val Arg Ala Ser Leu Leu Ala Gln Gly Gly
2945                2950                2955

Arg Ala Ala Ile Cys Gly Arg Tyr Leu Phe Asn Trp Ala Val Lys
```

|   |   |   |   |   |   |   |   |   |   |   |   |
|---|---|---|---|---|---|---|---|---|---|---|---|
|   |   |   | 2960 |   |   |   | 2965 |   |   |   | 2970 |

Thr Lys Leu Lys Leu Thr Pro Leu Pro Glu Ala Ser Arg Leu Asp
     2975                   2980                  2985

Leu Ser Arg Trp Phe Thr Val Gly Ala Gly Gly Gly Ile Phe
     2990                   2995                  3000

His Ser Val Ser His Ala Arg Pro Arg Leu Leu Leu Leu Cys Leu
     3005                   3010                  3015

Leu Leu Leu Ser Val Gly Val Gly Ile Phe Leu Leu Pro Ala Arg
     3020                   3025                  3030

<210> SEQ ID NO 29
<211> LENGTH: 3033
<212> TYPE: PRT
<213> ORGANISM: Hepatitis C virus

<400> SEQUENCE: 29

Met Ser Thr Asn Pro Lys Pro Gln Arg Lys Thr Lys Arg Asn Thr Asn
1               5               10              15

Arg Arg Pro Gln Asp Val Lys Phe Pro Gly Gly Gly Gln Ile Val Gly
          20               25              30

Gly Val Tyr Leu Leu Pro Arg Arg Gly Pro Arg Leu Gly Val Arg Ala
        35              40              45

Thr Arg Lys Thr Ser Glu Arg Ser Gln Pro Arg Gly Arg Arg Gln Pro
50              55               60

Ile Pro Lys Asp Arg Arg Ser Thr Gly Lys Ser Trp Gly Lys Pro Gly
65              70              75              80

Tyr Pro Trp Pro Leu Tyr Gly Asn Glu Gly Cys Gly Trp Ala Gly Trp
             85               90              95

Leu Leu Ser Pro Arg Gly Ser Arg Pro Thr Trp Gly Pro Thr Asp Pro
        100             105            110

Arg His Arg Ser Arg Asn Leu Gly Arg Val Ile Asp Thr Ile Thr Cys
          115             120            125

Gly Phe Ala Asp Leu Met Gly Tyr Ile Pro Val Val Gly Ala Pro Val
    130               135            140

Gly Gly Val Ala Arg Ala Leu Ala His Gly Val Arg Val Leu Glu Asp
145            150             155           160

Gly Ile Asn Tyr Ala Thr Gly Asn Leu Pro Gly Cys Ser Phe Ser Ile
          165             170            175

Phe Leu Leu Ala Leu Leu Ser Cys Val Thr Val Pro Val Ser Ala Val
        180             185            190

Glu Val Arg Asn Ile Ser Ser Ser Tyr Tyr Ala Thr Asn Asp Cys Ser
          195             200            205

Asn Asn Ser Ile Thr Trp Gln Leu Thr Asp Ala Val Leu His Leu Pro
    210               215            220

Gly Cys Val Pro Cys Glu Asn Asp Asn Gly Thr Leu His Cys Trp Ile
225            230             235           240

Gln Val Thr Pro Asn Val Ala Val Lys His Arg Gly Ala Leu Thr Arg
          245             250            255

Ser Leu Arg Thr His Val Asp Met Ile Val Met Ala Ala Thr Ala Cys
        260             265            270

Ser Ala Leu Tyr Val Gly Asp Val Cys Gly Ala Val Met Ile Leu Ser
          275             280            285

Gln Ala Phe Leu Val Ser Pro Gln Arg His Asn Phe Thr Gln Glu Cys
    290               295            300

```
Asn Cys Ser Ile Tyr Gln Gly His Ile Thr Gly His Arg Met Ala Trp
305                 310                 315                 320

Asp Met Met Leu Asn Trp Ser Pro Thr Leu Ala Met Ile Leu Ala Tyr
            325                 330                 335

Ala Ala Arg Val Pro Glu Met Val Leu Glu Ile Ile Phe Gly Gly His
        340                 345                 350

Trp Gly Val Val Phe Gly Leu Ala Tyr Phe Ser Met Gln Gly Ala Trp
            355                 360                 365

Ala Lys Val Ile Ala Ile Leu Leu Val Ala Gly Val Asp Ala Thr
    370                 375                 380

Thr Tyr Ser Ser Gly Gln Glu Ala Gly Arg Thr Val Leu Gly Phe Thr
385                 390                 395                 400

Asn Leu Phe Thr Ser Gly Ala Lys Gln Asn Leu Tyr Leu Ile Asn Thr
            405                 410                 415

Asn Gly Ser Trp His Ile Asn Arg Thr Ala Leu Asn Cys Asn Asp Ser
            420                 425                 430

Leu Gln Thr Gly Phe Met Ala Ser Leu Phe Tyr Thr His Arg Phe Asn
        435                 440                 445

Ser Ser Gly Cys Pro Glu Arg Leu Ser Ser Cys Arg Gly Leu Asp Asp
450                 455                 460

Phe Arg Ile Gly Trp Gly Thr Leu Glu Tyr Glu Thr His Val Thr Asn
465                 470                 475                 480

Asp Glu Asp Met Arg Pro Tyr Cys Trp His Tyr Pro Arg Pro Cys
                485                 490                 495

Gly Ile Val Pro Ala Arg Thr Val Cys Gly Pro Val Tyr Cys Phe Thr
            500                 505                 510

Pro Ser Pro Val Val Val Gly Thr Thr Asp Lys Gln Gly Val Pro Thr
            515                 520                 525

Tyr Thr Trp Gly Glu Asn Glu Thr Asp Val Phe Leu Leu Asn Ser Thr
    530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
            565                 570                 575

Tyr Asn Ser Thr Ile Asp Leu Leu Cys Pro Thr Asp Cys Phe Arg Lys
            580                 585                 590

His Pro Asp Ala Thr Tyr Leu Lys Cys Gly Ala Gly Pro Trp Leu Thr
    595                 600                 605

Pro Arg Cys Met Val Asp Tyr Pro Tyr Arg Leu Trp His Tyr Pro Cys
    610                 615                 620

Thr Val Asn Phe Thr Ile Phe Lys Ala Arg Met Tyr Val Gly Gly Val
625                 630                 635                 640

Glu His Arg Phe Ser Ala Ala Cys Asn Phe Thr Arg Gly Asp Arg Cys
            645                 650                 655

Arg Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
        675                 680                 685

Leu Ser Thr Gly Leu Leu His Leu His Gln Asn Ile Val Asp Val Gln
        690                 695                 700

Tyr Leu Tyr Gly Leu Ser Pro Ala Leu Thr Arg Tyr Ile Val Lys Trp
705                 710                 715                 720

Glu Trp Val Ile Leu Leu Phe Leu Leu Leu Ala Asp Ala Arg Ile Cys
```

```
                725                 730                 735
Ala Cys Leu Trp Met Leu Ile Ile Leu Gly Gln Ala Glu Ala Ala Leu
            740                 745                 750
Glu Lys Leu Ile Ile Leu His Ser Ala Ser Ala Ser Ala Asn Gly
            755                 760                 765
Pro Leu Trp Cys Phe Ile Phe Phe Thr Ala Ala Trp Tyr Leu Lys Gly
            770                 775                 780
Arg Val Val Pro Val Ala Thr Tyr Ser Val Leu Gly Leu Trp Ser Phe
785                 790                 795                 800
Leu Leu Leu Val Leu Ala Leu Pro Gln Gln Ala Tyr Ala Leu Asp Ala
                805                 810                 815
Ala Glu Gln Gly Glu Leu Gly Leu Ala Ile Leu Val Ile Ile Ser Ile
                820                 825                 830
Phe Thr Leu Thr Pro Ala Tyr Lys Ile Leu Leu Ser Arg Ser Val Trp
                835                 840                 845
Trp Leu Ser Tyr Met Leu Val Leu Ala Glu Ala Gln Ile Gln Gln Arg
            850                 855                 860
Val Pro Pro Leu Glu Val Arg Gly Gly Arg Asp Gly Ile Ile Trp Val
865                 870                 875                 880
Ala Val Ile Leu His Pro Arg Leu Val Phe Glu Val Thr Lys Trp Leu
                885                 890                 895
Leu Ala Ile Leu Gly Pro Ala Tyr Leu Leu Lys Ala Ser Leu Leu Arg
                900                 905                 910
Ile Pro Tyr Phe Val Arg Ala His Ala Leu Leu Arg Val Cys Thr Leu
            915                 920                 925
Val Lys His Leu Ala Gly Ala Arg Tyr Ile Gln Met Leu Leu Ile Thr
            930                 935                 940
Ile Gly Arg Trp Thr Gly Thr Tyr Ile Tyr Asp His Leu Ser Pro Leu
945                 950                 955                 960
Ser Thr Trp Ala Ala Gln Gly Leu Arg Asp Leu Ala Ile Ala Val Glu
                965                 970                 975
Pro Val Val Phe Ser Pro Met Glu Lys Lys Val Ile Val Trp Gly Ala
            980                 985                 990
Glu Thr Val Ala Cys Gly Asp Ile Leu His Gly Leu Pro Val Ser Ala
            995                 1000                1005
Arg Leu Gly Arg Glu Val Leu Leu Gly Pro Ala Asp Gly Tyr Thr
    1010                1015                1020
Ser Lys Gly Trp Lys Leu Leu Ala Pro Ile Thr Ala Tyr Thr Gln
    1025                1030                1035
Gln Thr Arg Gly Leu Leu Gly Ala Ile Val Val Ser Leu Thr Gly
    1040                1045                1050
Arg Asp Lys Asn Glu Gln Ala Gly Gln Val Gln Val Leu Ser Ser
    1055                1060                1065
Val Thr Gln Thr Phe Leu Gly Thr Ser Ile Ser Gly Val Leu Trp
    1070                1075                1080
Thr Val Tyr His Gly Ala Gly Asn Lys Thr Leu Ala Gly Pro Lys
    1085                1090                1095
Gly Pro Val Thr Gln Met Tyr Thr Ser Ala Glu Gly Asp Leu Val
    1100                1105                1110
Gly Trp Pro Ser Pro Pro Gly Thr Lys Ser Leu Asp Pro Cys Thr
    1115                1120                1125
Cys Gly Ala Val Asp Leu Tyr Leu Val Thr Arg Asn Ala Asp Val
    1130                1135                1140
```

-continued

```
Ile Pro Val Arg Arg Lys Asp Asp Arg Ala Ala Leu Leu Ser
1145                1150                1155

Pro Arg Pro Leu Ser Thr Leu Lys Gly Ser Ser Gly Gly Pro Val
1160                1165                1170

Leu Cys Ser Arg Gly His Ala Val Gly Leu Phe Arg Ala Ala Val
1175                1180                1185

Cys Ala Arg Gly Val Ala Lys Ser Ile Asp Phe Ile Pro Val Glu
1190                1195                1200

Ser Leu Asp Val Thr Thr Arg Thr Pro Ser Phe Ser Asp Tyr Ser
1205                1210                1215

Thr Pro Pro Ala Val Pro Gln Ser Tyr Gln Val Gly Tyr Leu His
1220                1225                1230

Ala Pro Thr Gly Ser Gly Lys Ser Thr Lys Val Pro Ala Ala Tyr
1235                1240                1245

Ala Ser Gln Gly Tyr Lys Val Leu Val Leu Asn Pro Ser Val Ala
1250                1255                1260

Ala Thr Leu Gly Phe Gly Ala Tyr Met Ser Lys Ala His Gly Ile
1265                1270                1275

Asn Pro Asn Ile Arg Thr Gly Val Arg Thr Val Thr Thr Gly Asp
1280                1285                1290

Ser Ile Thr Tyr Ser Thr Tyr Gly Lys Phe Ile Ala Asp Gly Gly
1295                1300                1305

Cys Ala Ala Gly Ala Tyr Asp Ile Ile Ile Cys Asp Glu Cys His
1310                1315                1320

Ser Val Asp Ala Thr Thr Ile Leu Gly Ile Gly Thr Val Leu Asp
1325                1330                1335

Gln Ala Glu Thr Ala Gly Val Arg Leu Val Val Leu Ala Thr Ala
1340                1345                1350

Thr Pro Pro Gly Thr Val Thr Thr Pro His Ser Asn Ile Glu Glu
1355                1360                1365

Val Ala Leu Gly His Glu Gly Glu Ile Pro Phe Tyr Gly Lys Ala
1370                1375                1380

Ile Pro Leu Ala Phe Ile Lys Gly Gly Arg His Leu Ile Phe Cys
1385                1390                1395

His Ser Lys Lys Lys Cys Asp Glu Leu Ala Ala Ala Leu Arg Gly
1400                1405                1410

Met Gly Val Asn Ala Val Ala Tyr Tyr Arg Gly Leu Asp Val Ser
1415                1420                1425

Val Ile Pro Thr Gln Gly Asp Val Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Ser Gln Ile Val Asp Leu Ser Leu Asp Pro Thr
1460                1465                1470

Phe Thr Ile Thr Thr Gln Ile Val Pro Gln Asp Ala Val Ser Arg
1475                1480                1485

Ser Gln Arg Arg Gly Arg Thr Gly Arg Gly Arg Leu Gly Val Tyr
1490                1495                1500

Arg Tyr Val Ser Ser Gly Glu Arg Pro Ser Gly Met Phe Asp Ser
1505                1510                1515

Val Val Leu Cys Glu Cys Tyr Asp Ala Gly Ala Ala Trp Tyr Glu
1520                1525                1530
```

```
Leu Thr Pro Ala Glu Thr Thr Val Arg Leu Arg Ala Tyr Phe Asn
    1535            1540                1545

Thr Pro Gly Leu Pro Val Cys Gln Asp His Leu Glu Phe Trp Glu
1550            1555                1560

Ala Val Phe Thr Gly Leu Thr His Ile Asp Ala His Phe Leu Ser
1565            1570                1575

Gln Thr Lys Gln Gly Gly Glu Asn Phe Ala Tyr Leu Thr Ala Tyr
    1580            1585                1590

Gln Ala Thr Val Cys Ala Arg Ala Lys Ala Pro Pro Pro Ser Trp
    1595            1600                1605

Asp Val Met Trp Lys Cys Leu Thr Arg Leu Lys Pro Thr Leu Thr
    1610            1615                1620

Gly Pro Thr Pro Leu Leu Tyr Arg Leu Gly Ala Val Thr Asn Glu
    1625            1630                1635

Val Thr Leu Thr His Pro Val Thr Lys Tyr Ile Ala Thr Cys Met
1640            1645                1650

Gln Ala Asp Leu Glu Ile Met Thr Ser Ser Trp Val Leu Ala Gly
    1655            1660                1665

Gly Val Leu Ala Ala Val Ala Ser Tyr Cys Leu Ala Thr Gly Cys
    1670            1675                1680

Ile Ser Ile Ile Gly Arg Leu His Leu Asn Asp Arg Val Val Val
    1685            1690                1695

Ala Pro Asp Lys Glu Ile Leu Tyr Glu Ala Phe Asp Glu Met Glu
    1700            1705                1710

Glu Cys Ala Ser Lys Ala Ala Leu Ile Glu Glu Gly Gln Arg Met
    1715            1720                1725

Ala Glu Met Leu Lys Ser Lys Ile Gln Gly Leu Leu Gln Gln Ala
    1730            1735                1740

Thr Arg Gln Ala Gln Asp Ile Gln Pro Ala Ile Gln Ser Ser Trp
    1745            1750                1755

Pro Lys Leu Glu Arg Phe Trp Ala Lys His Met Trp Asn Phe Ile
    1760            1765                1770

Ser Gly Ile Gln Tyr Leu Ala Gly Leu Ser Thr Leu Pro Gly Asn
    1775            1780                1785

Pro Ala Val Ala Ser Met Met Ala Phe Ser Ala Ala Leu Thr Ser
    1790            1795                1800

Pro Leu Pro Thr Ser Thr Thr Ile Leu Leu Asn Ile Met Gly Gly
    1805            1810                1815

Trp Leu Ala Ser Gln Ile Ala Pro Pro Ala Gly Ala Thr Gly Phe
    1820            1825                1830

Val Val Ser Gly Leu Val Gly Ala Ala Val Gly Ser Ile Gly Leu
    1835            1840                1845

Gly Lys Ile Leu Val Asp Val Leu Ala Gly Tyr Gly Ala Gly Ile
    1850            1855                1860

Ser Gly Ala Leu Val Ala Phe Lys Ile Met Ser Gly Glu Lys Pro
    1865            1870                1875

Thr Val Glu Asp Val Val Asn Leu Leu Pro Ala Ile Leu Ser Pro
    1880            1885                1890

Gly Ala Leu Val Val Gly Val Ile Cys Ala Ala Ile Leu Arg Arg
    1895            1900                1905

His Val Gly Gln Gly Glu Gly Ala Val Gln Trp Met Asn Arg Leu
    1910            1915                1920

Ile Ala Phe Ala Ser Arg Gly Asn His Val Ala Pro Thr His Tyr
```

-continued

```
                1925                1930                1935

Val Val Glu Ser Asp Ala Ser Gln Arg Val Thr Gln Val Leu Ser
        1940                1945                1950

Ser Leu Thr Ile Thr Ser Leu Leu Arg Arg Leu His Ala Trp Val
        1955                1960                1965

Thr Glu Asp Cys Pro Val Pro Cys Ser Gly Ser Trp Leu Gln Asp
        1970                1975                1980

Ile Trp Asp Trp Val Cys Ser Ile Leu Thr Asp Phe Lys Asn Trp
        1985                1990                1995

Leu Ser Ser Lys Leu Leu Pro Lys Met Pro Gly Ile Pro Phe Ile
        2000                2005                2010

Ser Cys Gln Lys Gly Tyr Lys Gly Val Trp Ala Gly Thr Gly Val
        2015                2020                2025

Met Thr Thr Arg Cys Pro Cys Gly Ala Asn Ile Ser Gly His Val
        2030                2035                2040

Arg Met Gly Thr Met Lys Ile Thr Gly Pro Lys Thr Cys Leu Asn
        2045                2050                2055

Leu Trp Gln Gly Thr Phe Pro Ile Asn Cys Tyr Thr Glu Gly Pro
        2060                2065                2070

Cys Val Pro Lys Pro Pro Pro Asn Tyr Lys Thr Ala Ile Trp Arg
        2075                2080                2085

Val Ala Ala Ser Glu Tyr Val Glu Val Thr Gln His Gly Ser Phe
        2090                2095                2100

Ser Tyr Val Thr Gly Leu Thr Ser Asp Asn Leu Lys Val Pro Cys
        2105                2110                2115

Gln Val Pro Ala Pro Glu Phe Phe Ser Trp Val Asp Gly Val Gln
        2120                2125                2130

Ile His Arg Phe Ala Pro Val Pro Gly Pro Phe Phe Arg Asp Glu
        2135                2140                2145

Val Thr Phe Thr Val Gly Leu Asn Ser Phe Val Val Gly Ser Gln
        2150                2155                2160

Leu Pro Cys Asp Pro Glu Pro Asp Thr Glu Val Leu Ala Ser Met
        2165                2170                2175

Leu Thr Asp Pro Ser His Ile Thr Ala Glu Ala Ala Ala Arg Arg
        2180                2185                2190

Leu Ala Arg Gly Ser Pro Pro Ser Gln Ala Ser Ser Ser Ala Ser
        2195                2200                2205

Gln Leu Ser Ala Pro Ser Leu Lys Ala Thr Cys Thr Thr His Lys
        2210                2215                2220

Thr Ala Tyr Asp Cys Asp Met Val Asp Ala Asn Leu Phe Met Gly
        2225                2230                2235

Gly Asp Val Thr Arg Ile Glu Ser Asp Ser Lys Val Ile Val Leu
        2240                2245                2250

Asp Ser Leu Asp Ser Met Thr Glu Val Val Asp Asp Arg Glu Pro
        2255                2260                2265

Ser Val Pro Ser Glu Tyr Leu Ile Lys Arg Arg Lys Phe Pro Pro
        2270                2275                2280

Ala Leu Pro Pro Trp Ala Arg Pro Asp Tyr Asn Pro Val Leu Ile
        2285                2290                2295

Glu Thr Trp Lys Arg Pro Gly Tyr Glu Pro Pro Thr Val Leu Gly
        2300                2305                2310

Cys Ala Leu Pro Pro Thr Pro Gln Thr Pro Val Pro Pro Pro Arg
        2315                2320                2325
```

-continued

Arg Arg Arg Ala Lys Val Leu Thr Gln Asp Asn Val Glu Gly Ile
2330                2335                2340

Leu Arg Glu Met Ala Asp Lys Val Leu Ser Pro Leu Gln Asp Asn
2345                2350                2355

Asn Asp Ser Gly His Ser Thr Gly Ala Asp Thr Gly Gly Asp Ile
2360                2365                2370

Val Gln Gln Pro Ser Asp Glu Thr Ala Ala Ser Glu Ala Gly Ser
2375                2380                2385

Leu Ser Ser Met Pro Pro Leu Glu Gly Glu Pro Gly Asp Pro Asp
2390                2395                2400

Leu Glu Phe Glu Pro Val Gly Ser Ala Pro Pro Ser Glu Gly Glu
2405                2410                2415

Cys Glu Val Ile Asp Ser Asp Ser Lys Ser Trp Ser Thr Val Ser
2420                2425                2430

Asp Gln Glu Asp Ser Val Thr Cys Cys Ser Met Ser Tyr Ser Trp
2435                2440                2445

Thr Gly Ala Leu Ile Thr Pro Cys Gly Pro Glu Glu Glu Lys Leu
2450                2455                2460

Pro Ile Asn Pro Leu Ser Asn Ser Leu Met Arg Phe His Asn Lys
2465                2470                2475

Val Tyr Ser Thr Thr Ser Arg Ser Ala Ser Leu Arg Ala Lys Lys
2480                2485                2490

Val Thr Phe Asp Arg Val Gln Val Leu Asp Ala His Tyr Asp Ser
2495                2500                2505

Val Leu Gln Asp Val Lys Arg Ala Ala Ser Lys Val Ser Ala Arg
2510                2515                2520

Leu Leu Thr Val Glu Glu Ala Cys Ala Leu Thr Pro Pro His Ser
2525                2530                2535

Ala Lys Ser Arg Tyr Gly Phe Gly Ala Lys Glu Val Arg Ser Leu
2540                2545                2550

Ser Arg Arg Ala Val Asn His Ile Arg Ser Val Trp Glu Asp Leu
2555                2560                2565

Leu Glu Asp Gln His Thr Pro Ile Asp Thr Thr Ile Met Ala Lys
2570                2575                2580

Asn Glu Val Phe Cys Ile Asp Pro Thr Lys Gly Gly Lys Lys Pro
2585                2590                2595

Ala Arg Leu Ile Val Tyr Pro Asp Leu Gly Val Arg Val Cys Glu
2600                2605                2610

Lys Met Ala Leu Tyr Asp Ile Ala Gln Lys Leu Pro Lys Ala Ile
2615                2620                2625

Met Gly Pro Ser Tyr Gly Phe Gln Tyr Ser Pro Ala Glu Arg Val
2630                2635                2640

Asp Phe Leu Leu Lys Ala Trp Gly Ser Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro
2675                2680                2685

Gln Glu Ala Arg Thr Val Ile His Ser Leu Thr Glu Arg Leu Tyr
2690                2695                2700

Val Gly Gly Pro Met Thr Asn Ser Lys Gly Gln Ser Cys Gly Tyr
2705                2710                2715

```
Arg Arg Cys Arg Ala Ser Gly Val Phe Thr Thr Ser Met Gly Asn
2720                2725                2730

Thr Met Thr Cys Tyr Ile Lys Ala Leu Ala Ala Cys Lys Ala Ala
2735                2740                2745

Gly Ile Val Asp Pro Val Met Leu Val Cys Gly Asp Asp Leu Val
2750                2755                2760

Val Ile Ser Glu Ser Gln Gly Asn Glu Glu Asp Glu Arg Asn Leu
2765                2770                2775

Arg Ala Phe Thr Glu Ala Met Thr Arg Tyr Ser Ala Pro Pro Gly
2780                2785                2790

Asp Leu Pro Arg Pro Glu Tyr Asp Leu Glu Leu Ile Thr Ser Cys
2795                2800                2805

Ser Ser Asn Val Ser Val Ala Leu Asp Ser Arg Gly Arg Arg Arg
2810                2815                2820

Tyr Phe Leu Thr Arg Asp Pro Thr Thr Pro Ile Thr Arg Ala Ala
2825                2830                2835

Trp Glu Thr Val Arg His Ser Pro Val Asn Ser Trp Leu Gly Asn
2840                2845                2850

Ile Ile Gln Tyr Ala Pro Thr Ile Trp Val Arg Met Val Ile Met
2855                2860                2865

Thr His Phe Phe Ser Ile Leu Leu Ala Gln Asp Thr Leu Asn Gln
2870                2875                2880

Asn Leu Asn Phe Glu Met Tyr Gly Ala Val Tyr Ser Val Asn Pro
2885                2890                2895

Leu Asp Leu Pro Ala Ile Ile Glu Arg Leu His Gly Leu Glu Ala
2900                2905                2910

Phe Ser Leu His Thr Tyr Ser Pro Arg Glu Leu Ser Arg Val Ala
2915                2920                2925

Ala Thr Leu Arg Lys Leu Gly Ala Pro Pro Leu Arg Ala Trp Lys
2930                2935                2940

Ser Arg Ala Arg Ala Val Arg Ala Ser Leu Ile Ala Gln Gly Ala
2945                2950                2955

Arg Ala Ala Ile Cys Gly Arg Tyr Leu Phe Asn Trp Ala Val Lys
2960                2965                2970

Thr Lys Leu Lys Leu Thr Pro Leu Pro Glu Ala Ser Arg Leu Asp
2975                2980                2985

Leu Ser Gly Trp Phe Thr Val Gly Ala Gly Gly Gly Ile Tyr
2990                2995                3000

His Ser Val Ser His Ala Arg Pro Arg Leu Leu Leu Leu Cys Leu
3005                3010                3015

Leu Leu Leu Ser Val Gly Val Gly Ile Phe Leu Leu Pro Ala Arg
3020                3025                3030

<210> SEQ ID NO 30
<211> LENGTH: 3033
<212> TYPE: PRT
<213> ORGANISM: Hepatitis C virus

<400> SEQUENCE: 30

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45
```

-continued

```
Thr Arg Lys Thr Ser Glu Arg Ser Gln Pro Arg Gly Arg Gln Pro
     50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Thr Trp Gly Pro Thr Asp Pro
                100                 105                 110

Arg His Arg Ser Arg Asn Leu Gly Arg Val Ile Asp Thr Ile Thr Cys
            115                 120                 125

Gly Phe Ala Asp Leu Met Gly Tyr Ile Pro Val Val Gly Ala Pro Val
        130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
                180                 185                 190

Glu Val Arg Asn Ile Ser Ser Ser Tyr Tyr Ala Thr Asn Asp Cys Ser
            195                 200                 205

Asn Asn Ser Ile Thr Trp Gln Leu Thr Asp Ala Val Leu His Leu Pro
210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270

Ser Ala Leu Tyr Val Gly Asp Val Cys Gly Ala Val Met Ile Leu Ser
        275                 280                 285

Gln Ala Phe Met Val Ser Pro Gln Arg His Asn Phe Thr Gln Glu Cys
290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Ala Met Ile Leu Ala Tyr
                325                 330                 335

Ala Ala Arg Val Pro Glu Met Val Leu Glu Ile Ile Phe Gly Gly His
            340                 345                 350

Trp Gly Val Val Phe Gly Leu Ala Tyr Phe Ser Met Gln Gly Ala Trp
        355                 360                 365

Ala Lys Val Ile Ala Ile Leu Leu Leu Val Ala Gly Val Asp Ala Thr
370                 375                 380

Thr Tyr Ser Ser Gly Gln Glu Ala Gly Arg Thr Val Leu Gly Phe Thr
385                 390                 395                 400

Asn Leu Phe Thr Ser Gly Ala Lys Gln Asn Leu Tyr Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Met Ala Ser Leu Phe Tyr Thr His Arg Phe Asn
        435                 440                 445

Ser Ser Gly Cys Pro Glu Arg Leu Ser Ser Cys Arg Gly Leu Asp Asp
450                 455                 460
```

-continued

Phe Arg Ile Gly Trp Gly Thr Leu Glu Tyr Glu Thr His Val Thr Asn
465                 470                 475                 480

Asp Glu Asp Met Arg Pro Tyr Cys Trp His Tyr Pro Arg Pro Cys
            485                 490                 495

Gly Ile Val Pro Ala Arg Thr Val Cys Gly Pro Val Tyr Cys Phe Thr
                500                 505                 510

Pro Ser Pro Val Val Gly Thr Thr Asp Lys Gln Gly Val Pro Thr
        515                 520                 525

Tyr Thr Trp Gly Glu Asn Glu Thr Asp Val Phe Leu Leu Asn Ser Thr
    530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575

Tyr Asn Ser Thr Ile Asp Leu Leu Cys Pro Thr Asp Cys Phe Arg Lys
            580                 585                 590

His Pro Asp Ala Thr Tyr Leu Lys Cys Gly Ala Gly Pro Trp Leu Thr
        595                 600                 605

Pro Arg Cys Leu Val Asp Tyr Pro Tyr Arg Leu Trp His Tyr Pro Cys
    610                 615                 620

Thr Val Asn Phe Thr Ile Phe Lys Ala Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
        675                 680                 685

Leu Ser Thr Gly Leu Leu His Leu His Gln Asn Ile Val Asp Val Gln
690                 695                 700

Tyr Leu Tyr Gly Leu Ser Pro Ala Leu Thr Arg Tyr Ile Val Lys Trp
705                 710                 715                 720

Glu Trp Val Ile Leu Leu Phe Leu Leu Leu Ala Asp Ala Arg Ile Cys
                725                 730                 735

Ala Cys Leu Trp Met Leu Ile Ile Leu Gly Gln Ala Glu Ala Ala Leu
            740                 745                 750

Glu Lys Leu Ile Ile Ser His Ser Ala Ser Ala Ala Ser Ala Asn Gly
        755                 760                 765

Pro Leu Trp Phe Phe Ile Phe Phe Thr Ala Ala Trp Tyr Leu Lys Gly
770                 775                 780

Arg Val Val Pro Val Ala Thr Tyr Ser Val Leu Gly Leu Trp Ser Phe
785                 790                 795                 800

Leu Leu Leu Val Leu Ala Leu Pro Gln Gln Ala Tyr Ala Leu Asp Ala
                805                 810                 815

Ala Glu Gln Gly Glu Leu Gly Leu Ala Ile Leu Val Ile Ile Ser Ile
            820                 825                 830

Phe Thr Leu Thr Pro Ala Tyr Lys Ile Leu Leu Ser Arg Ser Val Trp
        835                 840                 845

Trp Leu Ser Tyr Met Leu Val Leu Ala Glu Ala Gln Ile Gln Gln Trp
850                 855                 860

Val Pro Pro Leu Glu Val Arg Gly Gly Arg Asp Gly Ile Ile Trp Val
865                 870                 875                 880

Ala Val Ile Leu His Pro Arg Leu Val Phe Glu Val Thr Lys Trp Leu

-continued

```
                885                 890                 895
Leu Ala Ile Leu Gly Pro Ala Tyr Leu Leu Lys Ala Ser Leu Leu Arg
                900                 905                 910
Ile Pro Tyr Phe Val Arg Ala His Ala Leu Leu Arg Val Cys Thr Leu
                915                 920                 925
Val Lys His Leu Ala Gly Ala Arg Tyr Ile Gln Met Leu Leu Ile Thr
                930                 935                 940
Ile Gly Arg Trp Thr Gly Thr Tyr Ile Tyr Asp His Leu Ser Pro Leu
945                 950                 955                 960
Ser Thr Trp Ala Ala Gln Gly Leu Arg Asp Leu Ala Ile Ala Val Glu
                965                 970                 975
Pro Val Val Phe Ser Pro Met Glu Lys Lys Val Ile Val Trp Gly Ala
                980                 985                 990
Glu Thr Val Ala Cys Gly Asp Ile Leu His Gly Leu Pro Val Ser Ala
                995                 1000                1005
Arg Leu Gly Arg Glu Val Leu Leu Gly Pro Ala Asp Gly Tyr Thr
        1010                1015                1020
Ser Lys Gly Trp Lys Leu Leu Ala Pro Ile Thr Ala Tyr Thr Gln
        1025                1030                1035
Gln Thr Arg Gly Leu Leu Gly Ala Ile Val Val Ser Leu Thr Gly
        1040                1045                1050
Arg Asp Lys Asn Glu Gln Ala Gly Gln Val Gln Val Leu Ser Ser
        1055                1060                1065
Val Thr Gln Thr Phe Leu Gly Thr Ser Ile Ser Gly Val Leu Trp
        1070                1075                1080
Thr Val Tyr His Gly Ala Gly Asn Lys Thr Leu Ala Gly Pro Lys
        1085                1090                1095
Gly Pro Val Thr Gln Met Tyr Thr Ser Ala Glu Gly Asp Leu Val
        1100                1105                1110
Gly Trp Pro Ser Pro Pro Gly Thr Lys Ser Leu Asp Pro Cys Thr
        1115                1120                1125
Cys Gly Ala Val Asp Leu Tyr Leu Val Thr Arg Asn Ala Asp Val
        1130                1135                1140
Ile Pro Val Arg Arg Lys Asp Asp Arg Arg Gly Ala Leu Leu Ser
        1145                1150                1155
Pro Arg Pro Leu Ser Thr Leu Lys Gly Ser Ser Gly Gly Pro Val
        1160                1165                1170
Leu Cys Ser Arg Gly His Ala Val Gly Leu Phe Arg Ala Ala Val
        1175                1180                1185
Cys Ala Arg Gly Val Ala Lys Ser Ile Asp Phe Ile Pro Val Glu
        1190                1195                1200
Ser Leu Asp Val Ala Thr Arg Thr Pro Ser Phe Ser Asp Asn Ser
        1205                1210                1215
Thr Pro Pro Ala Val Pro Gln Ser Tyr Gln Val Gly Tyr Leu His
        1220                1225                1230
Ala Pro Thr Gly Ser Gly Lys Ser Thr Lys Val Pro Ala Ala Tyr
        1235                1240                1245
Ala Ser Gln Gly Tyr Lys Val Leu Val Leu Asn Pro Ser Val Ala
        1250                1255                1260
Ala Thr Leu Gly Phe Gly Ala Tyr Met Ser Lys Ala His Gly Ile
        1265                1270                1275
Asn Pro Asn Ile Arg Thr Gly Val Arg Thr Val Thr Thr Gly Asp
        1280                1285                1290
```

-continued

```
Ser Ile Thr Tyr Ser Thr Tyr Gly Lys Phe Ile Ala Asp Gly Gly
    1295                1300                1305

Cys Ala Ala Gly Ala Tyr Asp Ile Ile Ile Cys Asp Glu Cys His
    1310                1315                1320

Ser Val Asp Ala Thr Thr Ile Leu Gly Ile Gly Thr Val Leu Asp
    1325                1330                1335

Gln Ala Glu Thr Ala Gly Val Arg Leu Val Val Leu Ala Thr Ala
    1340                1345                1350

Thr Pro Pro Gly Thr Val Thr Thr Pro His Ser Asn Ile Glu Glu
    1355                1360                1365

Val Ala Leu Gly His Glu Gly Glu Ile Pro Phe Tyr Gly Lys Ala
    1370                1375                1380

Ile Pro Leu Ala Phe Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Val Asn Ala Val Ala Tyr Tyr Arg Gly Leu Asp Val Ser
    1415                1420                1425

Val Ile Pro Thr Gln Gly Asp Val Val Val Val Ala Thr Asp Ala
    1430                1435                1440

Leu Met Thr Gly Tyr Thr Gly Asp Phe Asp Ser Val Ile Asp Cys
    1445                1450                1455

Asn Val Ala Val Ser Gln Ile Val Asp Leu Ser Leu Asp Pro Thr
    1460                1465                1470

Phe Thr Ile Thr Thr Gln Ile Val Pro Gln Asp Ala Val Ser Arg
    1475                1480                1485

Ser Gln Arg Arg Gly Arg Thr Gly Arg Gly Arg Leu Gly Val Tyr
    1490                1495                1500

Arg Tyr Val Ser Ser Gly Glu Arg Pro Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ala Glu Thr Thr Val Arg Leu Arg Ala Tyr Phe Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Gly Gly Glu Asn Phe Ala Tyr Leu Thr Ala Tyr
    1580                1585                1590

Gln Ala Thr Val Cys Ala Arg Ala Lys Ala Pro Pro Pro Ser Trp
    1595                1600                1605

Asp Val Met Trp Lys Cys Leu Thr Arg Leu Lys Pro Thr Leu Thr
    1610                1615                1620

Gly Pro Thr Pro Leu Leu Tyr Arg Leu Gly Ala Val Thr Asn Glu
    1625                1630                1635

Val Thr Leu Thr His Pro Val Thr Lys Tyr Ile Ala Thr Cys Met
    1640                1645                1650

Gln Ala Asp Leu Glu Ile Met Thr Ser Ser Trp Val Leu Ala Gly
    1655                1660                1665

Gly Val Leu Ala Ala Val Ala Ser Tyr Cys Leu Ala Thr Gly Cys
    1670                1675                1680
```

```
Ile Ser Ile Ile Gly Arg Leu His Leu Asn Asp Arg Val Val Val
1685                1690                1695

Ala Pro Asp Lys Glu Ile Leu Tyr Glu Ala Phe Asp Glu Met Glu
1700                1705                1710

Glu Cys Ala Ser Lys Ala Ala Leu Ile Glu Glu Gly Gln Arg Met
1715                1720                1725

Ala Glu Met Leu Lys Ser Lys Ile Gln Gly Leu Leu Gln Gln Ala
1730                1735                1740

Thr Arg Gln Ala Gln Asp Ile Gln Pro Ala Ile Gln Ser Ser Trp
1745                1750                1755

Pro Lys Leu Glu Gln Phe Trp Ala Lys His Met Trp Asn Phe Ile
1760                1765                1770

Ser Gly Ile Gln Tyr Leu Ala Gly Leu Ser Thr Leu Pro Gly Asn
1775                1780                1785

Pro Thr Val Ala Ser Met Met Ala Phe Ser Ala Ala Leu Thr Ser
1790                1795                1800

Pro Leu Pro Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Ile Leu Val Asp Val Leu Ala Gly Tyr Gly Ala Gly Ile
1850                1855                1860

Ser Gly Ala Leu Val Ala Phe Lys Ile Met Ser Gly Glu Lys Pro
1865                1870                1875

Thr Val Glu Asp Val Val Asn Leu Leu Pro Ala Ile Leu Ser Pro
1880                1885                1890

Gly Ala Leu Val Val Gly Val Ile Cys Ala Ala Ile Leu Arg Arg
1895                1900                1905

His Val Gly Gln Gly Glu Gly Ala Val Gln Trp Met Asn Arg Leu
1910                1915                1920

Ile Ala Phe Ala Ser Arg Gly Asn His Val Ala Pro Thr His Tyr
1925                1930                1935

Val Val Glu Ser Asp Ala Ser Gln Arg Val Thr Gln Ala Leu Ser
1940                1945                1950

Ser Leu Thr Ile Thr Ser Leu Leu Arg Arg Leu His Ala Trp Ile
1955                1960                1965

Thr Glu Asp Cys Pro Val Pro Cys Ser Gly Ser Trp Leu Gln Asp
1970                1975                1980

Ile Trp Asp Trp Val Cys Ser Ile Leu Thr Asp Phe Lys Asn Trp
1985                1990                1995

Leu Ser Ser Lys Leu Leu Pro Lys Met Pro Gly Ile Pro Phe Ile
2000                2005                2010

Ser Cys Gln Lys Gly Tyr Lys Gly Val Trp Ala Gly Thr Gly Val
2015                2020                2025

Met Thr Thr Arg Cys Pro Cys Gly Ala Asn Ile Ser Gly His Val
2030                2035                2040

Arg Met Gly Thr Met Lys Ile Thr Gly Pro Lys Thr Cys Leu Asn
2045                2050                2055

Leu Trp Gln Gly Thr Phe Pro Ile Asn Cys Tyr Thr Glu Gly Pro
2060                2065                2070

Cys Val Pro Lys Pro Pro Pro Asn Tyr Lys Thr Ala Ile Trp Arg
```

```
                2075                2080                2085
Val Ala Ala Ser Glu Tyr Val Glu Val Thr Gln His Gly Ser Phe
    2090                2095                2100
Ser Tyr Val Thr Gly Leu Thr Ser Asp Asn Leu Lys Val Pro Cys
    2105                2110                2115
Gln Val Pro Ala Pro Glu Phe Phe Ser Trp Val Asp Gly Val Gln
    2120                2125                2130
Ile His Arg Phe Ala Pro Val Pro Gly Pro Phe Phe Arg Asp Glu
    2135                2140                2145
Val Thr Phe Thr Val Gly Leu Asn Ser Phe Val Val Gly Ser Gln
    2150                2155                2160
Leu Pro Cys Asp Pro Glu Pro Asp Thr Glu Val Leu Ala Ser Met
    2165                2170                2175
Leu Thr Asp Pro Ser His Ile Thr Ala Glu Ala Ala Ala Arg Arg
    2180                2185                2190
Leu Ala Arg Gly Ser Pro Pro Ser Gln Ala Ser Ser Ser Ala Ser
    2195                2200                2205
Gln Leu Ser Ala Pro Ser Leu Lys Ala Thr Cys Thr Thr His Lys
    2210                2215                2220
Thr Ala Tyr Asp Cys Asp Met Val Asp Ala Asn Leu Phe Met Gly
    2225                2230                2235
Gly Asp Val Thr Arg Ile Glu Ser Asp Ser Lys Val Ile Val Leu
    2240                2245                2250
Asp Ser Leu Asp Ser Met Thr Glu Val Glu Asp Arg Glu Pro
    2255                2260                2265
Ser Val Pro Ser Glu Tyr Leu Ile Lys Arg Arg Lys Phe Pro Pro
    2270                2275                2280
Ala Leu Pro Pro Trp Ala Arg Pro Asp Tyr Asn Pro Val Leu Ile
    2285                2290                2295
Glu Thr Trp Lys Arg Pro Gly Tyr Glu Pro Pro Thr Val Leu Gly
    2300                2305                2310
Cys Ala Leu Pro Pro Thr Pro Gln Thr Pro Val Pro Pro Pro Arg
    2315                2320                2325
Arg Arg Arg Ala Lys Val Leu Thr Gln Asp Asn Val Glu Gly Ile
    2330                2335                2340
Leu Arg Glu Met Ala Asp Lys Val Leu Ser Pro Leu Gln Asp Asn
    2345                2350                2355
Asn Asp Ser Gly His Ser Thr Gly Ala Asp Thr Gly Gly Asp Ile
    2360                2365                2370
Val Gln Gln Pro Ser Asp Glu Thr Ala Ala Ser Glu Ala Gly Ser
    2375                2380                2385
Leu Ser Ser Met Pro Pro Leu Glu Gly Glu Pro Gly Asp Pro Asp
    2390                2395                2400
Leu Glu Phe Glu Pro Val Gly Ser Ala Pro Pro Ser Glu Gly Glu
    2405                2410                2415
Cys Glu Val Ile Asp Ser Asp Ser Lys Ser Trp Ser Thr Val Ser
    2420                2425                2430
Asp Gln Glu Asp Ser Val Thr Cys Cys Ser Met Ser Tyr Ser Trp
    2435                2440                2445
Thr Gly Ala Leu Ile Thr Pro Cys Gly Pro Glu Glu Glu Lys Leu
    2450                2455                2460
Pro Ile Asn Pro Leu Ser Asn Ser Leu Met Arg Phe His Asn Lys
    2465                2470                2475
```

```
Val Tyr Ser Thr Thr Ser Arg Ser Ala Ser Leu Arg Ala Lys Lys
    2480            2485                2490

Val Thr Phe Asp Arg Val Gln Val Leu Asp Ala His Tyr Asp Ser
    2495            2500                2505

Val Leu Gln Asp Val Lys Arg Ala Ala Ser Lys Val Ser Ala Arg
    2510            2515                2520

Leu Leu Thr Val Glu Glu Ala Cys Ala Leu Thr Pro Pro His Ser
    2525            2530                2535

Ala Lys Ser Arg Tyr Gly Phe Gly Ala Lys Glu Val Arg Ser Leu
    2540            2545                2550

Ser Arg Arg Ala Val Asn His Ile Arg Ser Val Trp Glu Asp Leu
    2555            2560                2565

Leu Glu Asp Gln His Thr Pro Ile Asp Thr Thr Ile Met Ala Lys
    2570            2575                2580

Asn Glu Val Phe Cys Ile Asp Pro Thr Lys Gly Gly Lys Lys Pro
    2585            2590                2595

Ala Arg Leu Ile Val Tyr Pro Asp Leu Gly Val Arg Val Cys Glu
    2600            2605                2610

Lys Met Ala Leu Tyr Asp Ile Ala Gln Lys Leu Pro Lys Ala Ile
    2615            2620                2625

Met Gly Pro Ser Tyr Gly Phe Gln Tyr Ser Pro Ala Glu Arg Val
    2630            2635                2640

Asp Phe Leu Leu Lys Ala Trp Gly Ser Lys Lys Asp Pro Met Gly
    2645            2650                2655

Phe Ser Tyr Asp Thr Arg Cys Phe Asp Ser Thr Val Thr Glu Arg
    2660            2665                2670

Asp Ile Arg Thr Glu Glu Ser Ile Tyr Gln Ala Cys Ser Leu Pro
    2675            2680                2685

Gln Glu Ala Arg Thr Val Ile His Ser Leu Thr Glu Arg Leu Tyr
    2690            2695                2700

Val Gly Gly Pro Met Thr Asn Ser Lys Gly Gln Ser Cys Gly Tyr
    2705            2710                2715

Arg Arg Cys Arg Ala Ser Gly Val Phe Thr Thr Ser Met Gly Asn
    2720            2725                2730

Thr Met Thr Cys Tyr Ile Lys Ala Leu Ala Ala Cys Lys Ala Ala
    2735            2740                2745

Gly Ile Val Asp Pro Val Met Leu Val Cys Gly Asp Asp Leu Val
    2750            2755                2760

Val Ile Ser Glu Ser Gln Gly Asn Glu Glu Asp Glu Arg Asn Leu
    2765            2770                2775

Arg Ala Phe Thr Glu Ala Met Thr Arg Tyr Ser Ala Pro Pro Gly
    2780            2785                2790

Asp Leu Pro Arg Pro Glu Tyr Asp Leu Glu Leu Ile Thr Ser Cys
    2795            2800                2805

Ser Ser Asn Val Ser Val Ala Leu Asp Ser Arg Gly Arg Arg Arg
    2810            2815                2820

Tyr Phe Leu Thr Arg Asp Pro Thr Thr Pro Ile Thr Arg Ala Ala
    2825            2830                2835

Trp Glu Thr Val Arg His Ser Pro Val Asn Ser Trp Leu Gly Asn
    2840            2845                2850

Ile Ile Gln Tyr Ala Pro Thr Ile Trp Val Arg Met Val Ile Met
    2855            2860                2865
```

```
Thr His Phe Phe Ser Ile Leu Leu Ala Gln Asp Thr Leu Asn Gln
    2870            2875            2880

Asn Leu Asn Phe Glu Met Tyr Gly Ala Val Tyr Ser Val Asn Pro
    2885            2890            2895

Leu Asp Leu Pro Ala Ile Ile Glu Arg Leu His Gly Leu Glu Ala
    2900            2905            2910

Phe Ser Leu His Thr Tyr Ser Pro His Glu Leu Ser Arg Val Ala
    2915            2920            2925

Ala Thr Leu Arg Lys Leu Gly Ala Pro Pro Leu Arg Ala Trp Lys
    2930            2935            2940

Ser Arg Ala Arg Ala Val Arg Ala Ser Leu Ile Ala Gln Gly Ala
    2945            2950            2955

Arg Ala Ala Ile Cys Gly Arg Tyr Leu Phe Asn Trp Ala Val Lys
    2960            2965            2970

Thr Lys Leu Lys Leu Thr Pro Leu Pro Glu Ala Ser Arg Leu Asp
    2975            2980            2985

Leu Ser Gly Trp Phe Thr Val Gly Ala Gly Gly Gly Ile Tyr
    2990            2995            3000

His Ser Val Ser His Ala Arg Pro Arg Leu Leu Leu Cys Leu
    3005            3010            3015

Leu Leu Leu Ser Val Gly Val Gly Ile Phe Leu Leu Pro Ala Arg
    3020            3025            3030
```

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31 gcaaaccctä gctacactcc atag                                          24

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
actgtcttca cgcagaaagc gtctagccat                                    30

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
cggcaaaccc tagctacact cc                                            22

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34

```
acgcagaaag cgtctagcca tggcgttagt                                        30
```

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35

```
atggcatggg acatgatg                                                     18
```

<210> SEQ ID NO 36
<211> LENGTH: 17
<212> TYPE: DNA
<213> ORGANISM: Artificial Sequence
<220> FEATURE:
<223> OTHER INFORMATION: Primer

<400> SEQUENCE: 36

```
ccrggatatc cttggcc                                                      17
```

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37

```
tcaacagctc tggctgccc                                                    19
```

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38

```
atggcatggg acatgatg                                                     18
```

<210> SEQ ID NO 39
<211> LENGTH: 17
<212> TYPE: DNA
<213> ORGANISM: Artificial Sequence
<220> FEATURE:
<223> OTHER INFORMATION: Primer

<400> SEQUENCE: 39

```
gtggacgtgc agtacct                                                      17
```

<210> SEQ ID NO 40
<211> LENGTH: 16
<212> TYPE: DNA
<213> ORGANISM: Artificial Sequence
<220> FEATURE:
<223> OTHER INFORMATION: Primer

<400> SEQUENCE: 40

```
aaggygcgga tgtatg                                                       16
```

<210> SEQ ID NO 41
<211> LENGTH: 17
<212> TYPE: DNA
<213> ORGANISM: Artificial Sequence

```
<220> FEATURE:
<223> OTHER INFORMATION: Primer

<400> SEQUENCE: 41
cccaatggag aagaagg                                                    17

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
tggtggctgt cctacatgct g                                               21

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
caaccctcaa rggatcatc                                                  19

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
cgaaacgctg atgtcattcc                                                 20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
aacgtagagg gagaactggg                                                 20

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
ctcgacgtct ccgttatacc a                                               21

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
ccatcctctt gaacatcatg g                                               21
```

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
ggcctcytac aacaggcc                                                 18

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
atttggaggg tggcagcgt                                                19

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
ccatgaaaat aacrggcccg                                               20

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
tgactccggt cactccactg g                                             21

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
aaccacccac tgtcctaggy                                               20

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
cagaagaatc catatatcag gc                                            22

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
cctatgggtt ccaatactct cc					22

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
cggcaaaccc tagctacact cc					22

<210> SEQ ID NO 56
<211> LENGTH: 3033
<212> TYPE: PRT
<213> ORGANISM: Hepatitis C virus

<400> SEQUENCE: 56

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Phe Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Ser Ser Ile Thr Trp Gln Leu Ala Asp Ala Val Leu His Leu Pro
    210                 215                 220

Gly Cys Val Pro Cys Glu Asn Asn Asn Gly Thr Pro Arg Cys Trp Ile
225                 230                 235                 240

Gln Val Thr Pro Asn Val Ala Val Lys Tyr Arg Gly Ala Leu Thr His
                245                 250                 255

Ser Leu Arg Thr His Ile Asp Val Ile Val Met Ala Ala Thr Val Cys
            260                 265                 270

Ser Ala Leu Tyr Val Gly Asp Val Cys Gly Ala Val Met Ile Val Ser
        275                 280                 285
```

-continued

```
Gln Ala Phe Ile Val Ser Pro Gln Phe His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Thr Met Ile Leu Ala Tyr
                325                 330                 335

Ala Thr Arg Val Pro Glu Leu Ala Leu Glu Ile Val Phe Gly Gly His
            340                 345                 350

Trp Gly Val Val Phe Gly Leu Ala Tyr Phe Ser Leu Gln Gly Ala Trp
        355                 360                 365

Ala Lys Val Val Ala Ile Leu Leu Leu Val Ala Gly Val Asp Ala His
    370                 375                 380

Thr Gln Leu Thr Gly Thr Asn Val Gly Arg Thr Thr Ala Gly Phe Ala
385                 390                 395                 400

Ser Leu Phe Ala Pro Gly Ala Arg Gln Glu Ile Ser Leu Ile Asn Thr
                405                 410                 415

Asn Gly Ser Trp His Val Asn Arg Thr Ala Leu Asn Cys Asn Asp Ser
            420                 425                 430

Leu Asn Thr Gly Phe Leu Thr Ala Leu Phe Tyr Arg Asn Lys Phe Asn
        435                 440                 445

Ser Ser Gly Cys Pro Glu Arg Leu Ser Ser Cys Arg Glu Leu Asp Asp
    450                 455                 460

Phe Arg Ile Gly Trp Gly Thr Val Glu Tyr Glu Thr Val Val Thr Asn
465                 470                 475                 480

Asp Glu Asp Met Arg Pro Tyr Cys Trp His Tyr Pro Pro Lys Pro Cys
                485                 490                 495

Gly Ile Val Ser Ala Lys Thr Val Cys Gly Pro Val Tyr Cys Phe Thr
            500                 505                 510

Pro Ser Pro Val Val Gly Thr Thr Asp Arg Leu Gly Ala Pro Thr
    515                 520                 525

Tyr Asn Trp Gly Ile Asn Glu Thr Asp Val Phe Leu Leu Asn Ser Thr
        530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

His Asn Ser Thr Leu Asp Leu Leu Cys Pro Thr Asp Cys Phe Arg Lys
            580                 585                 590

His Pro Asp Thr Thr Tyr Leu Lys Cys Gly Ala Gly Pro Trp Leu Thr
        595                 600                 605

Pro Lys Cys Leu Ile Asp Tyr Pro Tyr Arg Leu Trp His Tyr Pro Cys
    610                 615                 620

Thr Val Asn Phe Thr Ile Phe Lys Val Arg Met Tyr Val Gly Gly Val
625                 630                 635                 640

Glu His Arg Leu Asp Ala Ala Cys Asn Phe Thr Arg Gly Asp Arg Cys
                645                 650                 655

Arg Leu Glu Asp Arg Asp Arg Gly Gln Gln Thr Pro Leu Leu His Ser
            660                 665                 670

Thr Thr Glu Trp Ala Ile Leu Pro Cys Thr Phe Ser Asp Leu Pro Ala
        675                 680                 685

Leu Ser Thr Gly Leu Leu His Leu His Gln Asn Thr Val Asp Val Gln
    690                 695                 700

Tyr Leu Tyr Gly Leu Thr Pro Ala Ile Thr Arg Tyr Ile Val Lys Trp
```

-continued

```
705                 710                 715                 720
Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala Ala Leu
                740                 745                 750

Glu Lys Leu Ile Ile Leu His Ser Ala Ser Ala Ala Ser Ala Asn Gly
                755                 760                 765

Pro Leu Trp Phe Phe Ile Phe Phe Ile Ala Ala Trp Tyr Leu Lys Gly
                770                 775                 780

Arg Val Val Pro Ala Ala Thr Tyr Ser Val Leu Gly Leu Trp Ser Phe
785                 790                 795                 800

Leu Leu Leu Val Leu Ala Leu Pro Gln Gln Ala Tyr Ala Leu Asp Ala
                805                 810                 815

Thr Glu Gln Gly Glu Leu Gly Leu Val Met Leu Val Val Leu Ser Ile
                820                 825                 830

Phe Thr Leu Thr Pro Ala Tyr Lys Thr Leu Leu Ser Arg Ser Val Trp
                835                 840                 845

Trp Leu Ser Tyr Met Leu Val Leu Ala Glu Ala Gln Val Gln Gln Trp
                850                 855                 860

Val Pro Pro Leu Glu Ala Arg Gly Gly Arg Asp Gly Ile Ile Trp Ala
865                 870                 875                 880

Ala Val Ile Leu His Pro Arg Leu Val Phe Glu Ile Thr Lys Trp Leu
                885                 890                 895

Leu Ala Ile Leu Gly Pro Ala Tyr Phe Leu Lys Ala Ser Leu Leu Arg
                900                 905                 910

Val Pro Tyr Phe Val Arg Ala His Ala Leu Leu Arg Met Cys Thr Leu
                915                 920                 925

Val Arg His Leu Ala Gly Ala Lys Tyr Ile Gln Met Leu Leu Ile Thr
                930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
                965                 970                 975

Pro Val Val Phe Ser Pro Met Glu Lys Lys Val Ile Val Trp Gly Ala
                980                 985                 990

Glu Thr Ala Ala Cys Gly Asp Ile Leu His Gly Leu Pro Val Ser Ala
                995                 1000                1005

Arg Leu Gly Arg Glu Val Leu Leu Gly Pro Ala Asp Gly Tyr Thr
                1010                1015                1020

Ser Lys Gly Trp Lys Leu Leu Ala Pro Ile Thr Ala Tyr Thr Gln
                1025                1030                1035

Gln Thr Arg Gly Leu Leu Gly Ser Ile Val Val Cys Leu Thr Gly
                1040                1045                1050

Arg Asp Lys Asn Glu Gln Ala Gly His Val Gln Val Leu Ser Ser
                1055                1060                1065

Val Thr Gln Ser Phe Leu Gly Thr Ser Ile Ser Gly Val Leu Trp
                1070                1075                1080

Thr Val Tyr His Gly Ala Gly Asn Lys Thr Leu Ala Gly Pro Lys
                1085                1090                1095

Gly Pro Ile Thr Gln Met Tyr Thr Ser Ala Glu Gly Asp Leu Val
                1100                1105                1110

Gly Trp Pro Ser Pro Pro Gly Thr Lys Ser Leu Asp Pro Cys Thr
                1115                1120                1125
```

```
Cys Gly Ala Val Asp Leu Tyr Leu Val Thr Arg Asn Ala Asp Val
1130                1135                1140

Ile Pro Val Arg Arg Lys Asp Asp Arg Gly Ala Leu Leu Ser
1145                1150                1155

Pro Arg Pro Leu Ser Thr Leu Lys Gly Ser Ser Gly Gly Pro Val
1160                1165                1170

Leu Cys Pro Arg Gly His Ala Val Gly Leu Phe Arg Ala Ala Leu
1175                1180                1185

Cys Ala Arg Gly Val Ala Lys Ser Ile Asp Phe Ile Pro Val Glu
1190                1195                1200

Ser Leu Asp Ile Val Ala Arg Ser Pro Ser Phe Ser Asp Asn Ser
1205                1210                1215

Thr Pro Pro Ala Val Pro Gln Thr Tyr Gln Val Gly Tyr Leu His
1220                1225                1230

Ala Pro Thr Gly Ser Gly Lys Ser Thr Lys Val Pro Ala Ala Tyr
1235                1240                1245

Ala Ser Gln Gly Tyr Lys Val Leu Val Leu Asn Pro Ser Val Ala
1250                1255                1260

Ala Thr Leu Gly Phe Gly Ala Tyr Met Ser Lys Ala His Gly Ile
1265                1270                1275

Asn Pro Asn Ile Arg Thr Gly Val Arg Thr Val Thr Thr Gly Asp
1280                1285                1290

Pro Ile Thr Tyr Ser Thr Tyr Gly Lys Phe Leu Ala Asp Gly Gly
1295                1300                1305

Cys Ser Ala Gly Ala Tyr Asp Ile Ile Ile Cys Asp Glu Cys His
1310                1315                1320

Ala Val Asp Ala Thr Thr Ile Leu Gly Ile Gly Thr Val Leu Asp
1325                1330                1335

Gln Ala Glu Thr Ala Gly Ala Arg Leu Val Val Leu Ala Thr Ala
1340                1345                1350

Thr Pro Pro Gly Thr Val Thr Thr Pro His Ser Asn Ile Glu Glu
1355                1360                1365

Val Ala Leu Gly His Glu Gly Glu Ile Pro Phe Tyr Gly Lys Ala
1370                1375                1380

Ile Pro Leu Ala Phe Ile Lys Gly Gly Arg His Leu Ile Phe Cys
1385                1390                1395

His Ser Lys Lys Lys Cys Asp Glu Val Ala Ala Ala Leu Arg Ser
1400                1405                1410

Val Gly Val Asn Ala Val Ala Tyr Tyr Arg Gly Leu Asp Val Ser
1415                1420                1425

Val Ile Pro Thr Gln Gly Asp Val Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Ile Val Asp Phe Ser Leu Asp Pro Thr
1460                1465                1470

Phe Thr Ile Thr Thr Gln Val Pro Gln Asp Ala Val Ser Arg
1475                1480                1485

Ser Gln Arg Arg Gly Arg Thr Gly Arg Gly Arg Leu Gly Ile Tyr
1490                1495                1500

Arg Tyr Val Ser Ser Gly Glu Arg Pro Ser Gly Met Phe Asp Ser
1505                1510                1515
```

```
Val Val Leu Cys Glu Cys Tyr Asp Ala Gly Ala Ala Trp Tyr Glu
1520                1525                1530

Leu Thr Pro Ala Glu Thr Thr Val Arg Leu Arg Ala Tyr Phe Asn
1535                1540                1545

Thr Pro Gly Leu Pro Val Cys Gln Asp His Leu Glu Phe Trp Glu
1550                1555                1560

Ala Val Phe Thr Gly Leu Thr His Ile Asp Ala His Phe Leu Ser
1565                1570                1575

Gln Thr Lys Gln Gly Gly Asp Asn Phe Ala Tyr Leu Thr Ala Tyr
1580                1585                1590

Gln Ala Thr Val Cys Ala Arg Ala Lys Ala Pro Pro Ser Trp
1595                1600                1605

Asp Val Met Trp Lys Cys Leu Thr Arg Leu Lys Pro Thr Leu Thr
1610                1615                1620

Gly Pro Thr Pro Leu Leu Tyr Arg Leu Gly Ala Val Thr Asn Glu
1625                1630                1635

Ile Thr Leu Thr His Pro Val Thr Lys Tyr Ile Ala Thr Cys Met
1640                1645                1650

Gln Ala Asp Leu Glu Ile Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Ile Ser Ile Ile Gly Arg Leu His Leu Asn Asp Arg Val Val Val
1685                1690                1695

Ala Pro Asp Lys Glu Ile Leu Tyr Glu Ala Phe Asp Glu Met Glu
1700                1705                1710

Glu Cys Ala Ser Lys Ala Ala Leu Ile Glu Glu Gly His Arg Met
1715                1720                1725

Ala Glu Met Leu Lys Ser Lys Ile Gln Gly Leu Leu Gln Gln Ala
1730                1735                1740

Thr Lys Gln Ala Gln Asp Ile Gln Pro Ala Ile Gln Ser Ser Trp
1745                1750                1755

Pro Lys Leu Glu Gln Phe Trp Ala Lys His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Pro Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Ile Leu Val Asp Val Leu Ala Gly Tyr Gly Ala Gly Ile
1850                1855                1860

Ser Gly Ala Leu Val Ala Phe Lys Ile Met Ser Gly Glu Lys Pro
1865                1870                1875

Ser Val Glu Asp Val Val Asn Leu Leu Pro Ala Ile Leu Ser Pro
1880                1885                1890

Gly Ala Leu Val Val Gly Val Ile Cys Ala Ala Ile Leu Arg Arg
1895                1900                1905

His Val Gly Gln Gly Glu Gly Ala Val Gln Trp Met Asn Arg Leu
```

-continued

```
            1910                1915                1920
Ile Ala Phe Ala Ser Arg Gly Asn His Val Ala Pro Thr His Tyr
    1925                1930                1935

Val Ala Glu Ser Asp Ala Ser Gln Arg Val Thr Gln Val Leu Ser
    1940                1945                1950

Ser Leu Thr Ile Thr Ser Leu Leu Arg Arg Leu His Ala Trp Ile
    1955                1960                1965

Thr Glu Asp Cys Pro Val Pro Cys Ser Gly Ser Trp Leu Arg Asp
    1970                1975                1980

Ile Trp Asp Trp Val Cys Ser Ile Leu Thr Asp Phe Lys Asn Trp
    1985                1990                1995

Leu Ser Ser Lys Leu Leu Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Ser Cys Gly Ala Asn Ile Ser Gly His Val
    2030                2035                2040

Arg Met Gly Thr Met Lys Ile Thr Gly Pro Lys Thr Cys Leu Asn
    2045                2050                2055

Leu Trp Gln Gly Thr Phe Pro Ile Asn Cys Tyr Thr Glu Gly Pro
    2060                2065                2070

Cys Val Pro Lys Pro Pro Asn Tyr Lys Thr Ala Ile Trp Arg
    2075                2080                2085

Val Ala Ala Ser Glu Tyr Val Glu Ile Thr Gln His Gly Ser Phe
    2090                2095                2100

Ser Tyr Val Thr Gly Leu Thr Ser Asp Asn Leu Lys Val Pro Cys
    2105                2110                2115

Gln Val Pro Ala Pro Glu Phe Phe Ser Trp Val Asp Gly Val Gln
    2120                2125                2130

Ile His Arg Phe Ala Pro Thr Pro Gly Pro Phe Phe Arg Asp Glu
    2135                2140                2145

Val Thr Phe Ser Val Gly Leu Asn Ser Phe Val Val Gly Ser Gln
    2150                2155                2160

Leu Pro Cys Asp Pro Glu Pro Asp Thr Glu Val Leu Ala Ser Met
    2165                2170                2175

Leu Thr Asp Pro Ser His Ile Thr Ala Glu Ala Ala Arg Arg
    2180                2185                2190

Leu Ala Arg Gly Ser Pro Pro Ser Gln Ala Ser Ser Ala Ser
    2195                2200                2205

Gln Leu Ser Ala Pro Ser Leu Lys Ala Thr Cys Thr Thr His Lys
    2210                2215                2220

Met Ala Tyr Asp Cys Asp Met Val Asp Ala Asn Leu Phe Met Gly
    2225                2230                2235

Gly Asp Val Thr Arg Ile Glu Ser Asn Ser Lys Val Ile Val Leu
    2240                2245                2250

Asp Ser Leu Asp Ser Met Thr Glu Ala Glu Asp Arg Glu Pro
    2255                2260                2265

Ser Ile Pro Ser Glu Tyr Leu Ile Arg Arg Lys Lys Phe Pro Pro
    2270                2275                2280

Ala Leu Pro Pro Trp Ala Arg Pro Asp Tyr Asn Pro Pro Val Ile
    2285                2290                2295

Glu Thr Trp Lys Arg Pro Gly Tyr Glu Pro Pro Thr Val Leu Gly
    2300                2305                2310
```

```
Cys Ala Leu Pro Pro Thr Pro Gln Ala Pro Val Pro Pro Pro Arg
2315                2320                2325

Arg Arg Arg Ala Lys Val Leu Thr Gln Asp Asn Val Glu Gly Val
2330                2335                2340

Leu Lys Glu Met Ala Asp Lys Val Leu Ser Pro Leu Gln Asp Tyr
2345                2350                2355

Asn Asp Ser Gly His Ser Thr Gly Val Gly Thr Gly Gly Asp Ser
2360                2365                2370

Val Gln Glu Pro Ser Asp Glu Thr Ala Ala Ser Glu Val Gly Ser
2375                2380                2385

Leu Ser Ser Met Pro Pro Leu Glu Gly Glu Pro Gly Asp Pro Asp
2390                2395                2400

Leu Glu Phe Glu Pro Ala Arg Ser Ala Pro Pro Ser Glu Gly Glu
2405                2410                2415

Cys Glu Val Val Asp Ser Asp Ser Lys Ser Trp Ser Thr Val Ser
2420                2425                2430

Asp Gln Glu Asp Ser Ile Val Cys Cys Ser Met Ser Tyr Ser Trp
2435                2440                2445

Thr Gly Ala Leu Ile Thr Pro Cys Gly Pro Glu Glu Glu Lys Leu
2450                2455                2460

Pro Ile Asn Pro Leu Ser Asn Ser Leu Met Arg Phe His Asn Lys
2465                2470                2475

Val Tyr Ser Thr Thr Ser Arg Ser Ala Ala Leu Arg Ala Lys Lys
2480                2485                2490

Val Thr Phe Asp Arg Val Gln Ile Leu Asp Thr Tyr Tyr Asp Ser
2495                2500                2505

Val Leu Gln Asp Val Lys Arg Ala Ala Ser Lys Val Ser Ala Arg
2510                2515                2520

Leu Leu Ser Val Glu Glu Ala Cys Ala Leu Thr Pro Pro His Ser
2525                2530                2535

Ala Arg Ser Arg Tyr Gly Phe Gly Ala Lys Glu Val Arg Ser Leu
2540                2545                2550

Ser Arg Arg Ala Val Asn His Ile Gln Ser Val Trp Glu Asp Leu
2555                2560                2565

Leu Glu Asp Gln Asn Thr Pro Ile Glu Thr Thr Ile Met Ala Lys
2570                2575                2580

Asn Glu Val Phe Cys Val Asp Pro Ala Lys Gly Gly Lys Lys Ala
2585                2590                2595

Ala Arg Leu Ile Val Tyr Pro Asp Leu Gly Val Arg Val Cys Glu
2600                2605                2610

Lys Met Ala Leu Tyr Asp Ile Ala Gln Lys Leu Pro Lys Ala Ile
2615                2620                2625

Met Gly Pro Ser Tyr Gly Phe Gln Tyr Ser Pro Ala Glu Arg Val
2630                2635                2640

Asp Phe Leu Leu Lys Ala Trp Gly Ser Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro
2675                2680                2685

Gln Glu Ala Arg Thr Val Ile His Ser Leu Thr Glu Arg Leu Tyr
2690                2695                2700
```

```
Val Gly Gly Pro Met Leu Asn Ser Lys Gly Gln Ser Cys Gly Tyr
    2705                2710                2715

Arg Arg Cys Arg Ala Ser Gly Val Phe Thr Thr Ser Met Gly Asn
    2720                2725                2730

Thr Met Thr Cys Tyr Ile Lys Ala Leu Ala Ala Cys Lys Ala Ala
    2735                2740                2745

Gly Ile Val Asp Pro Val Met Leu Val Cys Gly Asp Asp Leu Val
    2750                2755                2760

Val Ile Ser Glu Ser Gln Gly Asn Glu Glu Asp Glu Arg Asn Leu
    2765                2770                2775

Arg Ala Phe Thr Glu Ala Met Thr Arg Tyr Ser Ala Pro Pro Gly
    2780                2785                2790

Asp Leu Pro Arg Pro Glu Tyr Asp Leu Glu Leu Ile Thr Ser Cys
    2795                2800                2805

Ser Ser Asn Val Ser Val Ala Leu Asp Pro Arg Gly Arg Arg Arg
    2810                2815                2820

Tyr Tyr Leu Thr Arg Asp Pro Ile Thr Pro Ile Ser Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Val Arg Met Val Ile Met
    2855                2860                2865

Thr His Phe Phe Ala Ile Leu Leu Ala Gln Asp Thr Leu Asn Gln
    2870                2875                2880

Asn Leu Asn Phe Glu Met Tyr Gly Ala Val Tyr Ser Val Asn Pro
    2885                2890                2895

Leu Asp Leu Pro Ala Ile Ile Glu Arg Leu His Gly Leu Asp Ala
    2900                2905                2910

Phe Ser Leu His Thr Tyr Ser Pro Thr Glu Leu Thr Arg Val Ala
    2915                2920                2925

Ala Ala Leu Arg Lys Leu Gly Ala Pro Pro Leu Arg Ala Trp Lys
    2930                2935                2940

Ser Arg Ala Arg Ala Val Arg Ala Ser Leu Leu Ala Gln Gly Gly
    2945                2950                2955

Arg Ala Ala Ile Cys Gly Arg Tyr Leu Phe Asn Trp Ala Val Lys
    2960                2965                2970

Thr Lys Leu Lys Leu Thr Pro Leu Pro Glu Ala Ser Arg Leu Asp
    2975                2980                2985

Leu Ser Arg Trp Phe Thr Val Gly Ala Gly Gly Asp Ile Phe
    2990                2995                3000

His Ser Val Ser His Ala Arg Pro Arg Leu Leu Leu Leu Cys Leu
    3005                3010                3015

Leu Leu Leu Ser Val Gly Val Gly Ile Phe Leu Leu Pro Ala Arg
    3020                3025                3030
```